United States Patent
Bass, III et al.

(10) Patent No.: US 7,960,552 B2
(45) Date of Patent: Jun. 14, 2011

(54) FARNESOID X RECEPTOR AGONISTS

(75) Inventors: Jonathan York Bass, III, Irvine, CA (US); Justin Caravella, Durham, NC (US); David Norman Deaton, Durham, NC (US); Robert Blount McFadyen, Durham, NC (US); Frank Navas, III, Durham, NC (US); Paul Kenneth Spearing, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 828 days.

(21) Appl. No.: 11/876,906

(22) Filed: Oct. 23, 2007

(65) Prior Publication Data

US 2008/0096921 A1  Apr. 24, 2008

Related U.S. Application Data

(60) Provisional application No. 60/853,886, filed on Oct. 24, 2006, provisional application No. 60/855,337, filed on Oct. 30, 2006, provisional application No. 60/911,954, filed on Apr. 16, 2007.

(51) Int. Cl.
*C07D 401/00* (2006.01)

(52) U.S. Cl. .................................................. 546/167
(58) Field of Classification Search .................. 546/167
See application file for complete search history.

(56) References Cited

U.S. PATENT DOCUMENTS

| 7,705,028 B2 * | 4/2010 | Caldwell et al. .............. 514/378 |
| 2004/0048316 A1 | 3/2004 | Haffner et al. |

FOREIGN PATENT DOCUMENTS

WO  03015771 A1  2/2003

OTHER PUBLICATIONS

West, Solid State Chemistry and Its Applications, John Wiley & Sons, 1984.*
Stayrook et al.;Regulaton of Carbohydrate Metabolism by the Farnesoid X Recepor.; Endocrinology; 2005; 146; 984-991.

* cited by examiner

*Primary Examiner* — Nizal S Chandrakumar
(74) *Attorney, Agent, or Firm* — Robert H. Brik

(57) ABSTRACT

The present invention provides novel substituted isoxazole compounds, pharmaceutical compositions, therapeutic uses and processes for preparing the same.

6 Claims, No Drawings

FARNESOID X RECEPTOR AGONISTS

BACKGROUND OF THE INVENTION

The present invention relates to farnesoid X receptors (FXR, NR1H4). More particularly, the present invention relates to compounds useful as agonists for FXR, pharmaceutical formulations comprising such compounds, and therapeutic use of the same.

FXR is a member of the nuclear receptor class of ligand-activated transcription factors. Physiological concentrations of bile acids bind and activate FXR. [Parks, D. J., et al. 1999 Science 284:1365-1368; Makishima, M., et al. 1999 Science 284:1362-1365] Bile acids are amphipathic molecules that form micelles and emulsify dietary lipids. This property also makes bile acids cytotoxic if sufficient concentrations are achieved and thus mechanisms have evolved to ensure bile acid concentrations are tightly regulated. FXR plays a key role in regulating bile acid homeostasis. [Makishima, M. 2005 J. Pharmacol. Sci. 97:177-183; Kuipers, F., et al. 2004 Rev. Endocrine Metab. Disorders 5:319-326]

FXR is expressed in liver, intestine, kidney, and adrenal. [Kuipers, F., et al. 2004 Rev. Endocrine Metab. Disorders 5:319-326] FXR target genes in hepatocytes include small heterodimer partner (SHP, NR0B2) which encodes an atypical nuclear receptor that represses transcription of genes such as CYP7A1 (encoding cholesterol 7α-hydroxylase), the first and rate limiting step in the conversion of cholesterol to bile acid, CYP8B1 (encoding sterol 12α-hydroxylase) which controls the hydrophobicity of the bile pool and NTCP (encoding the sodium/taurocholate co-transporting polypeptide, SLC10A1) that imports bile acids from the portal and systemic circulation into the hepatocyte. [Goodwin, B., et al. 2000 Mol. Cell. 6:517-526; del Castillo-Olivares, A., et al 2001 Nucleic Acids Res. 29:4035-4042; Denson, L. A., et al. 2001 Gastroenterology 121(1):140-147] Other FXR target genes that are induced in liver include the canalicular transporter BSEP (encoding the bile salt export pump, ABCB11) that transports bile acids from the hepatocyte into the bile, multi-drug resistance P glycoprotein-3 (MDR3) (encoding the canalicular phospholipid flippase, ABCB4) that transports phospholipids from the hepatocyte into the bile and MRP2 (encoding multidrug resistance-related protein-2, ABCC2) that transports conjugated bilirubin, glutathione and glutathione conjugates into bile. [Ananthanarayanan, M., et al. 2001 J. Biol. Chem. 276:28857-28865; Huang, L et al., 2003 J. Biol. Chem. 278:51085-51090; Kast, H. R., et al. 2002 J. Biol. Chem. 277:2908-2915.]

In the intestine FXR also induces expression of SHP which represses transcription of the apical sodium dependent bile acid transporter (ASBT, SLC10A2) gene which encodes the high affinity apical sodium dependent bile acid transporter that moves bile acids from the intestinal lumen into the enterocyte as part of the enterohepatic recycling of bile acids. [Li, H., et al. 2005 Am. J. Physiol. Gastrointest. Liver Physiol. 288:G60-G66] Ileal bile acid binding protein (IBABP) gene expression is also induced by FXR agonists in the enterocyte. [Grober, J. et al., 1999 J. Biol. Chem. 274:29749-29754] The function of this ileal bile acid binding protein remains under investigation.

Cholestasis is a condition of reduced or arrested bile flow. Unresolved cholestasis leads to liver damage such as that seen in primary biliary cirrhosis (PBC) and primary sclerosing cholangitis (PSC), two cholestatic liver diseases. FXR agonists have been shown to protect the liver in rodent models of cholestatic liver disease. [Liu, Y. et al. 2003 J. Clin. Invest. 112:1678-1687; Fiorucci, S., et al. 2005 J. Pharmacol. Exp. Ther. 313:604-612; Pellicciari, R., et al. 2002 J. Med. Chem. 45:3569-3572]

FXR is also expressed in hepatic stellate cells (HSC) which play a role in deposition of extracellular matrix during the fibrotic process. Treatment of cultured HSCs with the FXR agonist 6-ethyl-chenodeoxycholic acid (6EtCDCA) results in decreased expression of fibrotic markers such as α-smooth muscle actin and α1(I)collagen. 6EtCDCA has also been reported to prevent development and promote resolution of hepatic fibrosis in multiple rodent models of this disease. [Fiorucci, S., et al., 2004 Gastroenterology 127:1497-1512; Fiorucci, S., et al., 2005 J. Pharmacol. Exp. Ther. 314:584-595.] According to Fiorucci et al., this anti-fibrotic effect is due to SHP inactivation of Jun and subsequent repression of tissue inhibitor of metalloproteinase 1 (TIMP1) via the activation protein 1 (AP1) binding site on the TIMP1 promoter.

Recently, S. Kliewer presented data at the Digestive Diseases Week (DDW) Conference (2005) organized by the American Association for the study of Liver Disease (AASLD) showing that activation of FXR by the agonist GW4064 resulted in improved mucosal barrier and decreased bacterial overgrowth in a bile duct-ligated mouse model of cholestasis and intestinal bacterial overgrowth. Dr. Kliewer showed data indicating decreased translocation of bacteria to mesenteric lymph nodes in mice treated with GW4064. This effect of GW4064 was lost in FXR null mice. [Inagaki, T., et al. 2006 Proc. Nat. Acad. Sci., U.S.A. 103:3920-3925.]

The FXR agonist GW4064, when administered to mice on a lithogenic diet, prevented the formation of cholesterol crystals in the bile. This effect of the compound was lost in FXR null mice. Moschetta, A., et al. 2004 Nat. Med. 10: 1352-1358.

It has been suggested that GW4064 could improve lipid and glucose homeostasis and insulin sensitivity in rodent diabetic and insulin resistance models. Chen and colleagues [2006 Diabetes 55 suppl. 1: A200] demonstrated that when administered to mice on high-fat diet, GW4064 decrease body weight and body fat mass, serum glucose, insulin, triglyceride, and total cholesterol. GW4064 also corrected glucose intolerance in those animals. In addition, GW4064 decreased serum insulin concentration, improved glucose tolerance and enhanced insulin sensitivity in ob/ob mice [Cariou, B., et al., 2006 J. Biol. Chem. 281:11039-11049]. In another study, it was reported that GW4064 significantly improved hyperglycemia and hyperlipidemia in diabetic db/db mice [Zhang, Y., et al. 2006 Proc. Nat. Acad. Sci., U.S.A. 103:1006-1011].

SUMMARY OF THE INVENTION

As a first aspect, the present invention provides compounds of formula (I):

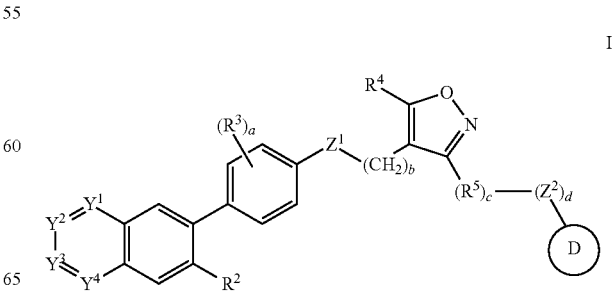

wherein:
each of $Y^1$, $Y^2$, $Y^3$ and $Y^4$ is the same or different and is independently selected from N, CH and C—$R^1$, wherein one or two of $Y^1$, $Y^2$, $Y^3$ and $Y^4$ is N, and at least one of $Y^1$, $Y^2$, $Y^3$ and $Y^4$ is C—$R^1$;
each $R^1$ is the same or different and is independently selected from alkyl, fluoroalkyl, —$CO_2H$, —$C(O)NH_2$, —$CO_2$alkyl, and an acid equivalent group; wherein at least one $R^1$ is —$CO_2H$, —$C(O)NH_2$, —$CO_2$alkyl, or an acid equivalent group;
$R^2$ is H, halo, alkyl or fluoroalkyl;
a is 0, 1 or 2;
each $R^3$ is the same or different and is independently selected from halo, alkyl and fluoroalkyl;
$Z^1$ is —O—, —S— or —N($R^8$)—, wherein $R^8$ is H or alkyl;
b is 1, 2 or 3;
$R^4$ is selected from alkyl, 2,2,2-trifluoroethyl, $C_{3-6}$cycloalkyl, alkenyl, $C_{3-6}$cycloalkenyl and fluoro-substituted $C_{3-6}$cycloalkyl;
c and d are both 0 or c is 1 and d is 0 or 1;
$R^5$ is —$C_{1-3}$alkylene-;
$Z^2$ is —O—, —S(O)$_e$—, or —NH—, wherein e is 0, 1 or 2;
Ring D is $C_{3-6}$cycloalkyl or $C_{3-6}$cycloalkenyl, optionally substituted one, two, or three times with alkyl or fluoroalkyl, or Ring D is a moiety of formula i, ii or iii:

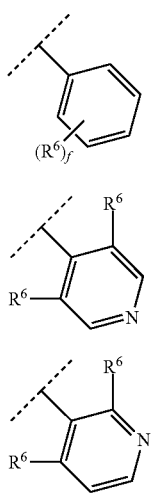

wherein:
f is 1, 2 or 3; and
each $R^6$ is the same or different and is independently selected from halo, alkyl, fluoroalkyl, —O-alkyl, —O-fluoroalkyl, alkyl-OH, and alkenyl;
or a pharmaceutically acceptable salt or solvate thereof.

In a second aspect, the present invention provides a pharmaceutical composition comprising a compound of formula (I). The composition may further comprise a pharmaceutically acceptable carrier or diluent.

In a third aspect, the present invention provides a method for the treatment of a condition mediated by decreased FXR activity in a subject in need thereof. The method comprises administering to the subject a therapeutically effective amount of a compound of formula (I).

In a fourth aspect, the present invention provides a method for the treatment of obesity in a subject in need thereof. The method comprises administering to the subject a therapeutically effective amount of a compound of formula (I).

In a fifth aspect, the present invention provides a method for the treatment of diabetes mellitus in a subject in need thereof. The method comprises administering to the subject a therapeutically effective amount of a compound of formula (I).

In a sixth aspect, the present invention provides a method for the treatment of metabolic syndrome in a subject in need thereof. The method comprises administering to the subject a therapeutically effective amount of a compound of formula (I).

In a seventh aspect, the present invention provides a method for the treatment of cholestatic liver disease in a subject in need thereof. The method comprises administering to the subject a therapeutically effective amount of a compound of formula (I).

In a eighth aspect, the present invention provides a method for the treatment of organ fibrosis in a subject in need thereof. The method comprises administering to the subject a therapeutically effective amount of a compound of formula (I). In one embodiment, the organ fibrosis is liver fibrosis.

In a ninth aspect, the present invention provides a method for the treatment of liver fibrosis in a subject in need thereof. The method comprises administering to the subject a therapeutically effective amount of a compound of formula (I).

In a tenth aspect, the present invention provides a process for preparing a compound of formula (I). The process comprises the steps of:
a) reacting a compound of formula (II)

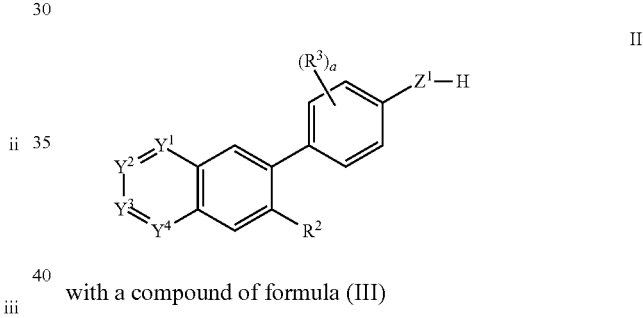

with a compound of formula (III)

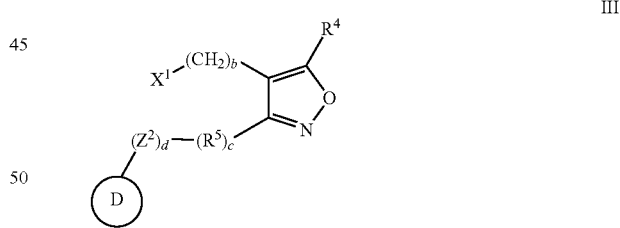

wherein:
$X^1$ is chloride, iodide, bromide, triflate, tosylate, nosylate, besylate or mesylate, (preferably chloro);
each $R^1$ is the same or different and is independently selected from alkyl, fluoroalkyl or
—$CO_2$alkyl; wherein at least one $R^1$ is —$CO_2$alkyl; and
all other variables are as defined above for formula (I)
to prepare a compound of formula (I);
b) optionally converting the compound of formula (I) into a pharmaceutically acceptable salt or solvate thereof,
c) optionally converting the compound of formula (I) or a pharmaceutically acceptable salt or solvate thereof into a different compound of formula (I) or a pharmaceutically acceptable salt or solvate thereof.

In another aspect, the present invention provides another process for preparing a compound of formula (I). This process comprises the steps of:

a) reacting a compound of formula (IV)

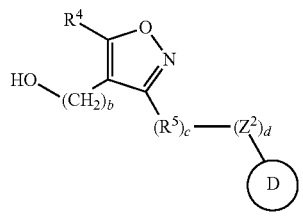

IV with a compound of formula (II) under Mitsunobu reaction conditions

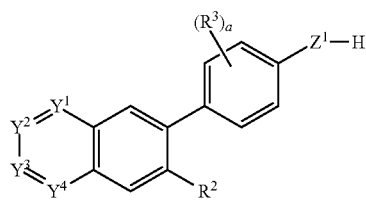

II wherein at least one R¹ is —CO₂alkyl and all other variables are as defined above to prepare a compound of formula (I);

b) optionally converting the compound of formula (I) into a pharmaceutically acceptable salt or solvate thereof, and c) optionally converting the compound of formula (I) or a pharmaceutically acceptable salt or solvate thereof into a different compound of formula (I) or a pharmaceutically acceptable salt or solvate thereof.

In another aspect, the present invention provides another process for preparing a compound of formula (I). This process comprises the steps of:

a) reacting a compound of formula (XLI) under Mitsunobu reaction conditions

XLI

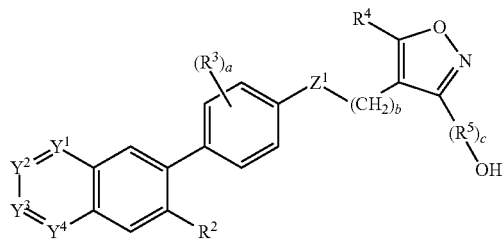

with a compound of formula i-a, ii-a, or iii-a

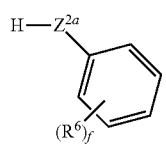

i-a

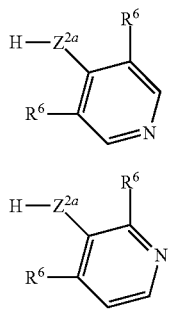

ii-a

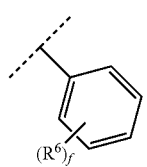

iii-a wherein at least one R¹ is —CO₂alkyl
Z²ᵃ is selected from —O—, —S—, —N(H)—, and N(COCF₃); and
all other variables are as defined above
to prepare a compound of formula (I-A)

I-A

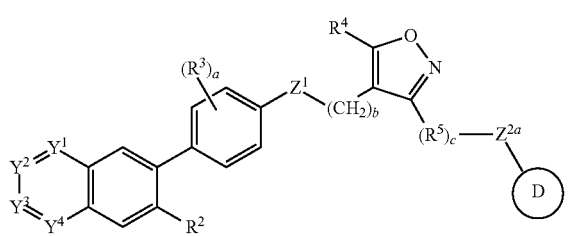

wherein Ring D is a moiety of formula i, ii or iii:

i

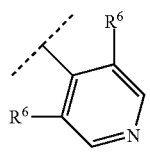

ii iii b) optionally converting the compound of formula (I-A) into a pharmaceutically acceptable salt or solvate thereof, and c) optionally converting the compound of formula (I-A) or a pharmaceutically acceptable salt or solvate thereof into a different compound of formula (I) or a pharmaceutically acceptable salt or solvate thereof.

In another aspect, the present invention provides another process for preparing a compound of formula (I). This process comprises the steps of:

a) reacting a compound of formula (XXV)

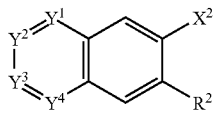

XXV wherein: $X^2$ is chloro, bromo, iodo, or triflate;
and at least one $R^1$ is —$CO_2$alkyl;
with a boronic acid or ester compound of formula (XLV) under Suzuki coupling conditions

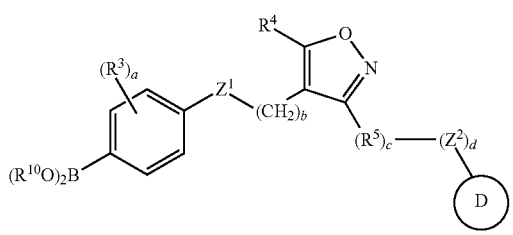

XLV wherein:
$R^{10}$ is H or alkyl; and
all other variables are as defined above
to prepare a compound of formula (I);
b) optionally converting the compound of formula (I) into a pharmaceutically acceptable salt or solvate thereof, and
c) optionally converting the compound of formula (I) or a pharmaceutically acceptable salt or solvate thereof into a different compound of formula (I) or a pharmaceutically acceptable salt or solvate thereof.

In another aspect, the present invention provides another process for preparing a compound of formula (I). The process comprises the steps of:
a) reacting a compound of formula (XXV-5)

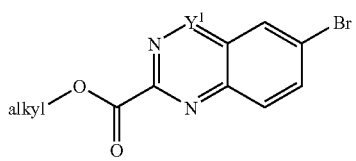

XXV-5 with a boronic acid or ester of compound of formula (XLV) under Suzuki coupling conditions

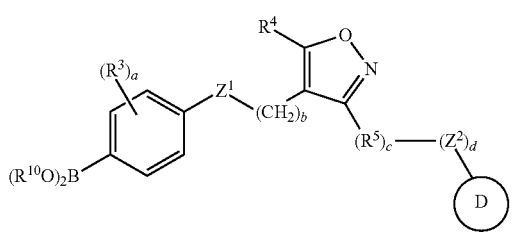

XLV wherein at least one $R^1$ is $C_{1-6}$alkyl or fluoroalkyl;
$R^{10}$ is H or alkyl; and
all other variables are as defined above
to prepare a compound of formula (I) wherein $Y^2$ is N and $Y^4$ is N;
b) optionally converting the compound of formula (I) into a pharmaceutically acceptable salt or solvate thereof, and
c) optionally converting the compound of formula (I) or a pharmaceutically acceptable salt or solvate thereof into a different compound of formula (I) or a pharmaceutically acceptable salt or solvate thereof.

In another aspect, the present invention provides another process for preparing a compound of formula (I). The process comprises the steps of:
a) reacting a compound of formula (XXV-6)

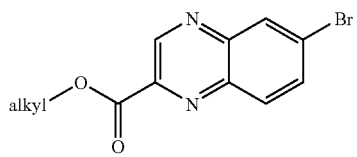

XXV-6 with a boronic acid or ester of compound of formula (XLV) under Suzuki coupling conditions wherein at least one $R^1$ is $C_{1-6}$alkyl or fluoroalkyl;
$R^{10}$ is H or alkyl; and
all other variables are as defined above
to prepare a compound of formula (I) wherein $Y^1$ is N and $Y^4$ is N;
b) optionally converting the compound of formula (I) into a pharmaceutically acceptable salt or solvate thereof, and
c) optionally converting the compound of formula (I) or a pharmaceutically acceptable salt or solvate thereof into a different compound of formula (I) or a pharmaceutically acceptable salt or solvate thereof.

In another aspect, the present invention provides a compound of formula (I) for use in therapy. The present invention also provides a compound of formula (I) for use in the treatment of a condition mediated by decreased FXR activity in a subject; a compound of formula (I) for use in the treatment of obesity in a subject; a compound of formula (I) for use in the treatment of diabetes mellitus in a subject; a compound of formula (I) for use in the treatment of metabolic syndrome in a subject; a compound of formula (I) for use in the treatment of cholestatic liver disease in a subject; a compound of formula (I) for use in the treatment of organ fibrosis in a subject; and a compound of formula (I) for use in the treatment of liver fibrosis in a subject.

In another aspect, the present invention provides the use of a compound of formula (I) for the preparation of a medicament for the treatment of a condition mediated by decreased FXR activity in a subject; the use of a compound of formula (I) for the preparation of a medicament for the treatment of obesity; the use of a compound of formula (I) for the preparation of a medicament for the treatment of diabetes mellitus in a subject; the use of a compound of formula (I) for the preparation of a medicament for the treatment of metabolic syndrome in a subject; the use of a compound of formula (I) for the preparation of a medicament for the treatment of cholestatic liver disease in a subject; the use of a compound of formula (I) for the preparation of a medicament for the treatment of organ fibrosis in a subject; and the use of a compound of formula (I) for the preparation of a medicament for the treatment of liver fibrosis in a subject.

In another aspect, the present invention provides a pharmaceutical composition comprising a compound of formula (I) for use in the treatment of a condition mediated by decreased FXR activity.

Further aspects of the present invention are described in the description of particular embodiments, examples, and claims which follow.

DETAILED DESCRIPTION OF THE PREFERRED EMBODIMENTS

As used herein, "a compound of the invention" or "a compound of formula (I)" or "(I-A)," etc. means a compound of formula (I) (or (I-A)) or a pharmaceutically acceptable salt or solvate thereof. Similarly, with respect to isolatable intermediates such as for example, compounds of formula (II), (III), (IV), (V), (XL), (XLI) and (XLII), the phrase "a compound of formula (number)" means a compound having that formula or a pharmaceutically acceptable salt or solvate thereof.

As used herein, the term "alkyl" refers to aliphatic straight or branched saturated hydrocarbon chains containing 1-8 carbon atoms. Examples of "alkyl" groups as used herein include but are not limited to methyl, ethyl, n-propyl, isopropyl, n-butyl, isobutyl, t-butyl, pentyl, hexyl, octyl and the like.

The term "fluoroalkyl" as used herein refers to an alkyl as defined above substituted with one or more fluoro. In on particular embodiment, fluoroalkyl refers to an alkyl substituted with two or more fluoro. The term "di(fluoroalkyl)" refers to two alkyl as defined above each substituted with one or more fluoro. For example, the term "di(fluoromethyl)" refers to —(CH$_2$F)$_2$.

The term "alkylene" refers to a straight or branched alkyl bridge, i.e., the group -alkyl-, wherein alkyl is as defined above.

As used herein, the term "halo" refers to any halogen atom. i.e., fluorine, chlorine, bromine or iodine.

As used herein, the term "alkenyl" refers to an aliphatic straight or branched unsaturated hydrocarbon chain containing 2-8 carbon atoms and at least one and up to three carbon-carbon double bonds. Examples of "alkenyl" groups as used herein include but are not limited to ethenyl and propenyl.

The term "alkenylene" refers to a straight or branched alkenyl bridge, i.e., the group -alkenyl-, wherein alkenyl is as defined above.

As used herein, the term "cycloalkyl" refers to a non-aromatic monocyclic carbocyclic ring having from 3 to 8 carbon atoms (unless a different number of atoms is specified) and no carbon-carbon double bonds. "Cycloalkyl" includes by way of example cyclopropyl, cyclobutyl, cyclopentyl, cyclohexyl, cycloheptyl and cyclooctyl. Particular cycloalkyl groups include $C_{3-6}$cycloalkyl.

As used herein, the term "cycloalkenyl" refers to a non-aromatic monocyclic carbocyclic ring having from 3 to 8 carbon atoms (unless a different number of atoms is specified) and from 1 to 3 carbon-carbon double bonds. "Cycloalkenyl" includes by way of example cyclopropenyl, cyclobutenyl, cyclopentenyl, cyclohexenyl, cycloheptenyl and cyclooctenyl. Particular cycloalkenyl groups include $C_{3-6}$cycloalkenyl.

As used herein, the term "optionally" means that the subsequently described event(s) may or may not occur, and includes both event(s) that occur and events that do not occur.

The present invention relates to compounds of formula (I):

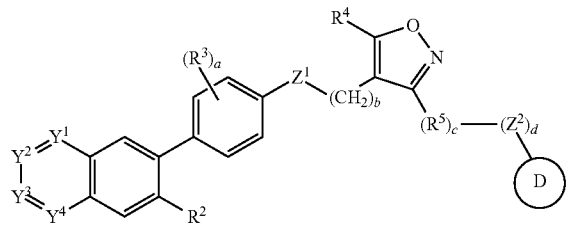

I wherein:
each of $Y^1$, $Y^2$, $Y^3$ and $Y^4$ is the same or different and is independently selected from N, CH and C—$R^1$, wherein one or two of $Y^1$, $Y^2$, $Y^3$ and $Y^4$ is N, and at least one of $Y^1$, $Y^2$, $Y^3$ and $Y^4$ is C—$R^1$;

each $R^1$ is the same or different and is independently selected from alkyl, fluoroalkyl, —CO$_2$H, —C(O)NH$_2$, —CO$_2$alkyl, and an acid equivalent group; wherein at least one $R^1$ is —CO$_2$H, —C(O)NH$_2$, —CO$_2$alkyl, or an acid equivalent group;

$R^2$ is H, halo, alkyl or fluoroalkyl;

a is 0, 1 or 2;

each $R^3$ is the same or different and is independently selected from halo, alkyl and fluoroalkyl;

$Z^1$ is —O—, —S— or —N($R^8$)—, wherein $R^8$ is H or alkyl;

b is 1, 2 or 3

$R^4$ is selected from alkyl, 2,2,2-trifluoroethyl, $C_{3-6}$cycloalkyl, alkenyl, $C_{3-6}$cycloalkenyl and fluoro-substituted $C_{3-6}$cycloalkyl;

c and d are both 0 or c is 1 and d is 0 or 1;

$R^5$ is —$C_{1-3}$alkylene-;

$Z^2$ is —O—, —S(O)$_e$—, or —NH—, wherein e is 0, 1 or 2;

Ring D is $C_{3-6}$cycloalkyl or $C_{3-6}$cycloalkenyl, optionally substituted one, two, or three times with alkyl or fluoroalkyl, or Ring D is a moiety of formula i, ii or iii:

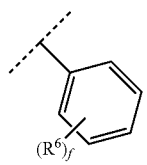

i

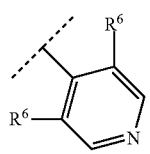

ii

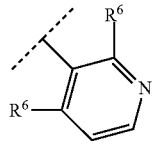

iii wherein:
f is 1, 2 or 3; and
each $R^6$ is the same or different and is independently selected from halo, alkyl, fluoroalkyl, —O-alkyl, —O-fluoroalkyl, alkyl-OH, and alkenyl;

or a pharmaceutically acceptable salt or solvate thereof.

Any one or two of $Y^1$, $Y^2$, $Y^3$ and $Y^4$ may be N. In one particular embodiment only one of $Y^1$, $Y^2$, $Y^3$ and $Y^4$ is N. At least one of $Y^1$, $Y^2$, $Y^3$ and $Y^4$ is C—$R^1$. In a particular embodiment, two of $Y^1$, $Y^2$, $Y^3$ and $Y^4$ are independently C—$R^1$. In another particular embodiment, only one of $Y^1$, $Y^2$, $Y^3$ and $Y^4$ is C—$R^1$. In such embodiment one or two of the other variables $Y^1$, $Y^2$, $Y^3$ and $Y^4$ is N and the remaining other variables $Y^1$, $Y^2$, $Y^3$ and $Y^4$ are CH.

In one embodiment, the compounds of formula (I) are defined wherein $Y^2$ is N and $Y^3$ is C—$R^1$. In one particular version of this embodiment, $Y^1$ and $Y^4$ are selected from CH and C—$R^1$, more particularly both are CH. In another embodiment, the compounds of formula (I) are defined wherein $Y^1$ is N and $Y^3$ is C—$R^1$. In one particular version of this embodiment, $Y^2$ and $Y^4$ are both CH. In another embodiment, the compounds of formula (I) are defined wherein $Y^1$ is N and $Y^4$ is C—$R^1$. In one particular version of this embodiment, $Y^2$ and $Y^3$ are CH. In another embodiment, the compounds of formula (I) are defined wherein $Y^3$ is N and $Y^4$ is C—$R^1$. In another embodiment, the compounds of formula (I) are defined wherein $Y^4$ is N and $Y^2$ is C—$R^1$. In one particular version of this embodiment, $Y^1$ is CH and $Y^3$ is C—$R^1$. In one preferred embodiment, the compounds of formula (I) are defined wherein $Y^4$ is N and $Y^3$ is C—$R^1$. In such embodiment, $Y^1$ and $Y^2$ are preferably selected from CH and C—$R^1$, more particularly CH.

In an additional embodiment, the compounds of formula (I) are defined wherein $Y^2$ and $Y^4$ are N. In one particular version of this embodiment, $Y^1$ and $Y^3$ are C—$R^1$.

Specific examples of the bicyclic fused N-heteroaryl moiety:

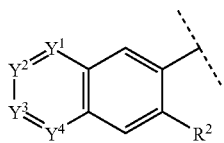

include but are not limited to the following:

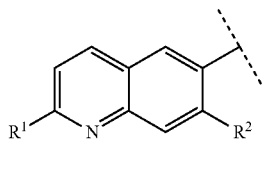 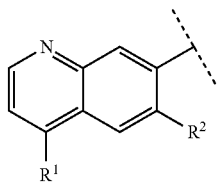

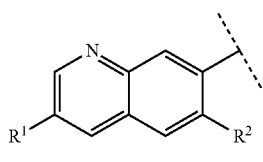 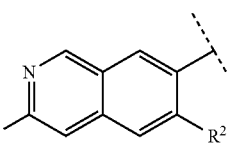

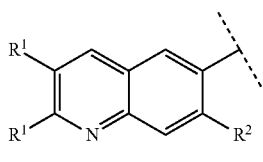 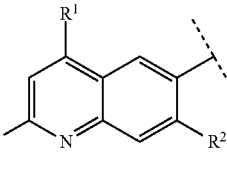

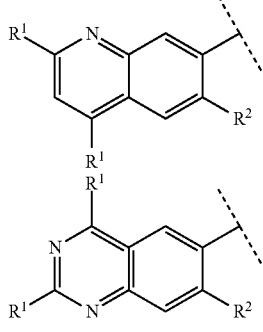 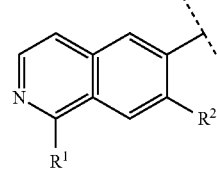

wherein each $R^1$ is the same or different and is independently selected from —$CO_2H$, —C(O)$NH_2$, —$CO_2$alkyl or acid equivalent group.

In one preferred embodiment, the bicyclic fused N-heteroaryl moiety is:

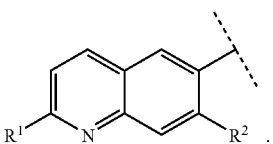

In another preferred embodiment, the bicyclic fused N-heteroaryl moiety is:

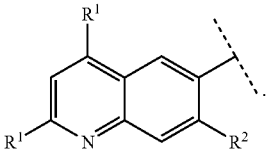

In third preferred embodiment, the bicyclic fused N-heteroaryl moiety is:

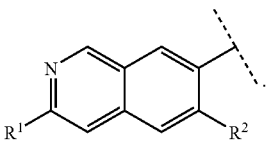

In a fourth preferred embodiment, the bicyclic fused N-heteroaryl moiety is:

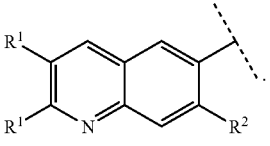

In a fifth preferred embodiment, the bicyclic fused N-heteroaryl moiety is:

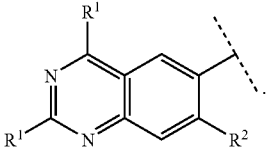

In all embodiments, at least one of $R^1$ is —$CO_2H$, —C(O)$NH_2$, —$CO_2$alkyl or acid equivalent group. In one embodiment, the compound of formula (I) is defined wherein each $R^1$ is the same or different and is independently selected from alkyl, fluoroalkyl, —$CO_2H$, —C(O)$NH_2$ and —$CO_2$alkyl. In such embodiment, at least one $R^1$ is —$CO_2H$, —C(O)$NH_2$ or —$CO_2$alkyl. In one preferred embodiment, at least one $R^1$ is —$CO_2H$ or —$CO_2$alkyl, such as —$CO_2CH_3$.

In one embodiment of the invention, $R^2$ is H.

In one embodiment, a is 0. In the embodiment, wherein a is 1, $R^3$ is preferably halo (particularly F or Cl), $CH_3$, $CF_3$, or $CH_2CH_3$.

In one embodiment, $Z^1$ is —O—, —S— or —N(H)—. In one preferred embodiment, $Z^1$ is O.

In one embodiment, b is 1 or 3. In one preferred embodiment, b is 1.

In one embodiment, $R^4$ is linear or branched alkyl or 2,2,2-trifluoroethyl or $C_{3-6}$cycloalkyl. Specific examples of groups defining $R^4$ include but are not limited to methyl, ethyl, 2,2,2-trifluoroethyl, propyl, isopropyl, n-butyl, t-butyl, isobutyl, cyclopropyl, cyclobutyl, cyclopentyl and cyclohexyl. In one embodiment, $R^4$ is isopropyl, isobutyl, cyclopropyl, cyclobutyl, cyclopentyl or trifluoroethyl. In one embodiment, $R^4$ is isopropyl, isobutyl, cyclopropyl or cyclobutyl. In one particular embodiment, $R^4$ is isopropyl or isobutyl. In one preferred embodiment, $R^4$ is isopropyl.

The invention includes compounds of formula I' wherein c and d are both 0 and thus Ring D is bound directly to the isoxazole ring as shown in formula (I'):

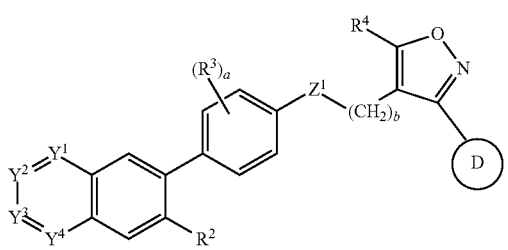

I' wherein all other variables are as defined above.

The invention includes of formula (I") wherein c is 1 and d is 0 or 1 and thus Ring D is bound to $C_{1-3}$ alkylene ($R^5$) or $Z^2$ (when d is 1) as shown in formula (I").

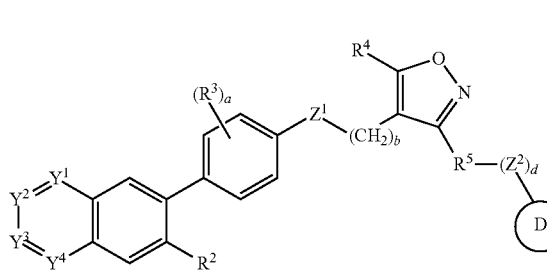

I"

wherein all other variables are as defined above.

In one embodiment, wherein c is 1, $R^5$ is preferably methylene or ethylene. In the embodiment wherein both c and d are 1, $R^5$ is preferably methylene. In one embodiment, c is 1, d is 1 and $Z^2$ is O. In one particular embodiment, c is 1, d is 1, $R^5$ is methylene and $Z^2$ is O, as in formula (I''').

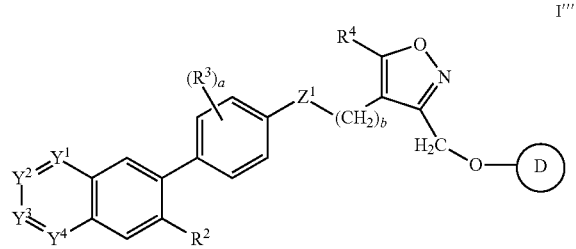

I''' wherein all other variables are as defined above. The invention includes compounds of formula I'''.

Ring D is $C_{3-6}$cycloalkyl or $C_{3-6}$cycloalkenyl, optionally substituted one, two, or three times with alkyl or fluoroalkyl, or Ring D is a moiety of formula i, ii or iii:

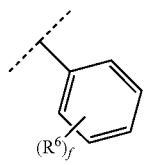

i

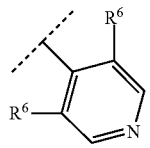

ii

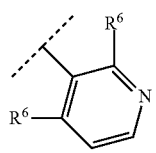

iii wherein:

f is 1, 2 or 3; and each $R^6$ is the same or different and is independently selected from halo, alkyl, fluoroalkyl, —O-alkyl, —O-fluoroalkyl, alkyl-OH, and alkenyl;

In the embodiment wherein D is $C_{3-6}$cycloalkyl or $C_{3-6}$cycloalkenyl optionally substituted one, two, or three times with alkyl or fluoroalkyl, typically at least one alkyl or fluoroalkyl substituent is adjacent to the point of attachment of the cycloalkyl or cycloakenyl ring to the isoxazole R, $R^5$ or $Z^2$ as the case may be. The following specific (but not limiting) examples a, b, and c illustrate at least one substituent adjacent to the point of attachment:

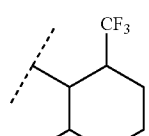

a

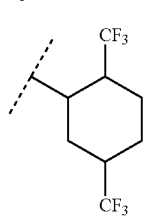

b

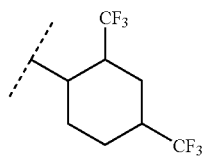

c

In one embodiment, Ring D is $C_{3-6}$cycloalkyl or $C_{3-6}$cycloalkenyl, optionally substituted symmetrically with dialkyl or di(fluoroalkyl). Example a above illustrates a $C_{3-6}$cycloalkyl substituted symmetrically. More particularly in one embodiment, Ring D is $C_{3-6}$cycloalkyl or $C_{3-6}$cycloalkenyl, optionally substituted symmetrically with di(fluoromethyl).

In one embodiment, Ring D is a moiety of formula i, ii or iii. In one particular embodiment, Ring D is a moiety of formula i or ii. In the embodiment wherein Ring D is

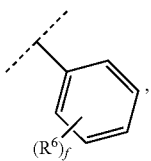

f is preferably 2. More particularly, in one embodiment f is 2 and Ring D is a moiety of formula i-b:

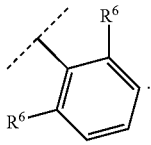

In one embodiment, the compound of formula (I) is defined wherein Ring D is a moiety of formula i, ii or iii and each $R^6$ is the same and is halo or alkyl. In one particular embodiment, Ring D is a moiety of formula i, ii or iii and each $R^6$ is the same and is F, Cl or methyl. In one preferred embodiment, Ring D is

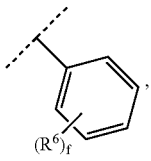

f is 2 and each $R^6$ is Cl.

In one particular preferred embodiment, Ring D is a moiety of formula i-b

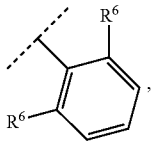

and each $R^6$ is Cl.

In one preferred embodiment, the invention provides compounds of formula (I-B):

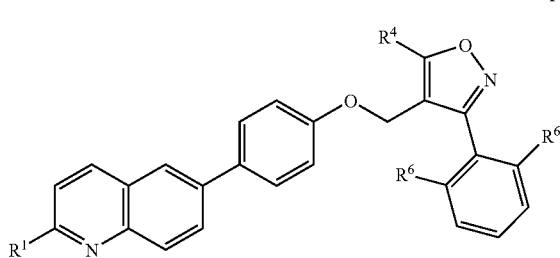

wherein
$R^1$ is —$CO_2H$, —$C(O)NH_2$, —$CO_2$alkyl, or an acid equivalent group; more particularly —$CO_2H$, —$C(O)NH_2$ or —$CO_2$alkyl;

$R^4$ is isopropyl, isobutyl, cyclopropyl or cyclobutyl; and both $R^6$ are the same and are selected from F, Cl, $CH_3$ and $CF_3$.

In another preferred embodiment, the invention provides compounds of formula (I-Z)

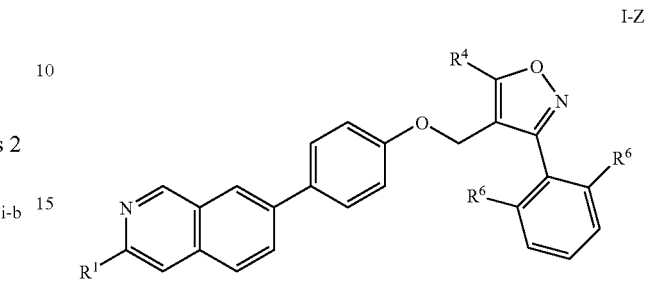

wherein
$R^1$ is —$CO_2H$, —$C(O)NH_2$, —$CO_2$alkyl, or an acid equivalent group; more particularly —$CO_2H$, —$C(O)NH_2$ or —$CO_2$alkyl;
$R^4$ is isopropyl, isobutyl, cyclopropyl or cyclobutyl; and
both $R^6$ are the same and are selected from F, Cl, $CH_3$ and $CF_3$.

The present invention contemplates and includes all combinations and subsets of the particular groups defined above.

Specific examples of particular compounds of the present invention are selected from the group consisting of:

6-[4-({[3-(2,6-Dichlorophenyl)-5-(1-methylethyl) -4-isoxazolyl]methyl}oxy)phenyl]-2-quinolinecarboxylic acid;

7-[4-({[3-(2,6-Dichlorophenyl)-5-(1-methylethyl) -4-isoxazolyl]methyl}oxy)phenyl]-3-quinolinecarboxylic acid;

7-[4-({[3-(2,6-Dichlorophenyl)-5-(1-methylethyl) -4-isoxazolyl]methyl}oxy)phenyl]-2,4-quinolinedicarboxylic acid;

7-[4-({[3-(2,6-Dichlorophenyl)-5-(1-methylethyl) -4-isoxazolyl]methyl}oxy)phenyl]-4-quinolinecarboxylic acid;

7-[4-({[3-(2,6-Dichlorophenyl)-5-(1-methylethyl) -4-isoxazolyl]methyl}oxy)phenyl]-3-isoquinolinecarboxylic acid;

6-[4-({[5-Cyclopentyl-3-(2,6-dichlorophenyl)-4-isoxazolyl] methyl}oxy)phenyl]-2-quinolinecarboxylic acid;

6-[4-({[5-Cyclobutyl-3-(2,6-dichlorophenyl)-4-isoxazolyl] methyl}oxy)phenyl]-2-quinolinecarboxylic acid 6-[4-({[5-Cyclobutyl-3-(3,5-dichloro-4-pyridinyl) -4-isoxazolyl]methyl}oxy)phenyl]-2-quinolinecarboxylic acid;

7-[4-({[5-Cyclobutyl-3-(3,5-dichloro-4-pyridinyl) -4-isoxazolyl]methyl}oxy)phenyl]-3-isoquinolinecarboxylic acid;

7-[4-({[5-Cyclopropyl-3-(2,6-dichlorophenyl)-4-isoxazolyl]methyl}oxy)phenyl]-3-isoquinolinecarboxylic acid;

6-[4-({[5-Cyclopropyl-3-(2,6-dichlorophenyl)-4-isoxazolyl]methyl}oxy)phenyl]-2-quinolinecarboxylic acid;

6-[4-({[5-Cyclopropyl-3-(3,5-dichloro-4-pyridinyl)-4-isoxazolyl]methyl}oxy)phenyl]-2-quinolinecarboxylic acid;

6-{4-[({3-(2,6-Dichlorophenyl)-5-[(1S)-1-methylpropyl]-4-isoxazolyl}methyl)oxy]phenyl}-2-quinolinecarboxylic acid;

6-{4-[({3-(2,6-Dichlorophenyl)-5-[(1R)-1-methylpropyl]-4-isoxazolyl}methyl)oxy]phenyl}-2-quinolinecarboxylic acid;

6-[4-({3-[3-(2,6-Dichlorophenyl)-5-(1-methylethyl)-4-isoxazolyl]propyl}oxy)phenyl]-2-quinolinecarboxylic acid;

7-[4-({[3-{[(2,6-Dimethylphenyl)oxy]methyl}-5-(1-methylethyl)-4-isoxazolyl]methyl}oxy)phenyl]-3-isoquinolinecarboxylic acid;

7-(4-{[(5-Cyclobutyl-3-{[(2,6-dimethylphenyl)oxy]methyl}-4-isoxazolyl)methyl]oxy}phenyl)-3-isoquinolinecarboxylic acid;

6-[4-({[3-{[(2,6-Dimethylphenyl)oxy]methyl}-5-(1-methylethyl)-4-isoxazolyl]methyl}oxy)phenyl]-2-quinolinecarboxylic acid;

6-(4-{[(5-(1-Methylethyl)-3-{[(2,4,6-trifluorophenyl)oxy]methyl}-4-isoxazolyl)methyl]oxy}phenyl)-2-quinolinecarboxylic acid;

6-[4-({[3-{[(2,6-Dichlorophenyl)oxy]methyl}-5-(1-methylethyl)-4-isoxazolyl]methyl}oxy)phenyl]-2-quinolinecarboxylic acid;

6-[4-({[3-{[(2,6-Dichlorophenyl)amino]methyl}-5-(1-methylethyl)-4-isoxazolyl]methyl}oxy)phenyl]-2-quinolinecarboxylic acid;

6-[4-({[3-{[(2,6-Dichlorophenyl)thio]methyl}-5-(1-methylethyl)-4-isoxazolyl]methyl}oxy)phenyl]-2-quinolinecarboxylic acid;

6-[4-({[3-{[(2,6-Dichlorophenyl)sulfinyl]methyl}-5-(1-methylethyl)-4-isoxazolyl]methyl}oxy)phenyl]-2-quinolinecarboxylic acid;

6-[4-({[3-{[(2,6-Dichlorophenyl)sulfonyl]methyl}-5-(1-methylethyl)-4-isoxazolyl]methyl}oxy)phenyl]-2-quinolinecarboxylic acid;

6-[4-({[3-(3,5-Dichloro-4-pyridinyl)-5-(1-methylethyl)-4-isoxazolyl]methyl}oxy)phenyl]-2-quinolinecarboxylic acid;

6-(4-{[(3,5-Dicyclopentyl-4-isoxazolyl)methyl]oxy}phenyl-2-quinolinecarboxylic acid;

6-[4-({[3-[(Cyclopentyloxy)methyl]-5-(1-methylethyl)-4-isoxazolyl]methyl}oxy)phenyl]-2-quinolinecarboxylic acid;

6-[4-({[3-(2,4-Dichloro-3-pyridinyl)-5-(1-methylethyl)-4-isoxazolyl]methyl}oxy)phenyl]-2-quinolinecarboxylic acid;

6-[4-({[3-(2,4-Dimethyl-3-pyridinyl)-5-(1-methylethyl)-4-isoxazolyl]methyl}oxy)phenyl]-2-quinolinecarboxylic acid;

6-[4-({[3-(2,6-Dichlorophenyl)-5-(1-methylethyl) -4-isoxazolyl]methyl}oxy)phenyl]-7-fluoro-2-quinolinecarboxylic acid;

6-[4-({[3-(2,6-dichlorophenyl)-5-(1-methylethyl) -4-isoxazolyl]methyl}oxy)phenyl]-3-methyl-2-quinolinecarboxylic acid;

6-[4-({[3-(2,6-Dichlorophenyl)-5-(1-methylethyl) -4-isoxazolyl]methyl}oxy)-3-methylphenyl]-2-quinolinecarboxylic acid;

6-[4-({[3-(2,6-Dichlorophenyl)-5-(1-methylethyl) -4-isoxazolyl]methyl}oxy)-2-methylphenyl]-2-quinolinecarboxylic acid;

6-[4-({[3-(2,6-Dichlorophenyl)-5-(1-methylethyl) -4-isoxazolyl]methyl}oxy)phenyl]-4-methyl-2-quinolinecarboxylic acid;

6-[4-({[3-(2,6-Dichlorophenyl)-5-(1-methylethyl) -4-isoxazolyl]methyl}oxy)phenyl]-2-methyl-3-quinolinecarboxylic acid;

6-[4-({[3-(2,6-Dichlorophenyl)-5-(1-methylethyl) -4-isoxazolyl]methyl}oxy)phenyl]-1-isoquinolinecarboxylic acid;

6-[4-({[3-(2,6-Dichlorophenyl)-5-(1-methylethyl) -4-isoxazolyl]methyl}oxy)phenyl]-4-methyl-2-quinazolinecarboxylic acid;

6-[4-({[3-(2,6-Dichlorophenyl)-5-(1-methylethyl) -4-isoxazolyl]methyl}thio)phenyl]-2-quinolinecarboxylic acid;

6-[4-({[3-(2,6-Dichlorophenyl)-5-(1-methylethyl) -4-isoxazolyl]methyl}oxy)phenyl]-2-quinoxalinecarboxylic acid;

and pharmaceutically acceptable salts or solvates thereof.

One preferred compound of the invention is 6-[4-({[3-(2,6-dichlorophenyl)-5-(1-methylethyl)-4-isoxazolyl]methyl}oxy)phenyl]-2-quinolinecarboxylic acid; or a pharmaceutically acceptable salt or solvate thereof. In one particular embodiment, 6-[4-({[3-(2,6-dichlorophenyl)-5-(1-methylethyl)-4-isoxazolyl]methyl}oxy)phenyl]-2-quinolinecarboxylic acid; or pharmaceutically acceptable salt or solvate thereof is in crystalline form. In one preferred embodiment, the compound of the invention is 6-[4-({[3-(2,6-dichlorophenyl)-5-(1-methylethyl)-4-isoxazolyl]methyl}oxy)phenyl]-2-quinolinecarboxylic acid (i.e. the form of the acid).

One preferred compound of the invention is 7-[4-({[3-(2,6-dichlorophenyl)-5-(1-methylethyl)-4-isoxazolyl]methyl}oxy)phenyl]-3-isoquinolinecarboxylic acid; or a pharmaceutically acceptable salt or solvate thereof. In one particular embodiment, 7-[4-({[3-(2,6-dichlorophenyl)-5-(1-methylethyl)-4-isoxazolyl]methyl}oxy)phenyl]-3-isoquinolinecarboxylic acid; or pharmaceutically acceptable salt or solvate thereof is in crystalline form. In one preferred embodiment, the compound of the invention is 7-[4-({[3-(2,6-dichlorophenyl)-5-(1-methylethyl)-4-isoxazolyl]methyl}oxy)phenyl]-3-isoquinolinecarboxylic acid (i.e. the form of the acid).

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted.

Suitable pharmaceutically acceptable salts according to the present invention will be readily determined by one skilled in the art and will include, for example, salts prepared from inorganic bases such as lithium hydroxide, sodium hydroxide, potassium hydroxide, lithium hydride, sodium hydride, potassium hydride, lithium carbonate, lithium hydrogen carbonate, sodium carbonate, sodium hydrogen carbonate, potassium carbonate, potassium hydrogen carbonate, as well as potassium tert-butoxide and organic bases such as diethyl amine, lysine, arginine, choline, tris(hydroxymethyl)aminomethane(tromethamine), triethanolamine, diethanolamine, and ethanolamine. In one embodiment, the compounds of formula (I) are in the form of the potassium salt.

When used in medicine, the salts of a compound of formula (I) should be pharmaceutically acceptable, but pharmaceutically unacceptable salts may conveniently be used to prepare the corresponding free base or pharmaceutically acceptable salts thereof. One specific example of a salt of a compound of the invention is 6-[4-({[3-(2,6-dichlorophenyl)-5-(1-methylethyl)-4-isoxazolyl]methyl}oxy)phenyl]-2-quinolinecarboxylic acid potassium salt.

As used herein, the term "solvate" refers to a crystal form containing the compound of formula (I) or a pharmaceutically acceptable salt thereof and either a stoichiometric or a non-stoichiometric amount of a solvent. Solvents, by way of example, include water (thus producing hydrates), methanol, ethanol, or acetic acid. Hereinafter, reference to a compound of formula (I) is to any physical form of that compound, unless a particular form, salt or solvate thereof is specified.

Processes for preparing pharmaceutically acceptable salts and solvates of the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts and/or solvates of the compound. Those terms as applied to any intermediate employed in the process of preparing compounds of formula (I) have the same meanings as noted above with respect to compounds of formula (I). Processes for preparing pharmaceutically acceptable salts and solvates of such intermediates are known in the art and are analogous to the process for preparing pharmaceutically acceptable salts and solvates of the compounds of formula (I).

In one embodiment, the compounds of formula (I) are FXR agonists. As used herein, the term "FXR agonist" refers to compounds which exhibit a $pEC_{50}$ greater than 4 in the FXR Cofactor Recruitment Assay described below. More particularly, FXR agonists are compounds which exhibit a $pEC_{50}$ greater than 5 in the FXR Cofactor Recruitment Assay described below.

Compounds of formula (I) are useful in therapy in subjects such as mammals, and particularly humans. In particular, the compounds of formula (I) are useful in the treatment of a condition mediated by decreased FXR activity in a subject such as a mammal, particularly a human. As used herein, the term "treatment" includes the prevention of occurrence of symptoms of the condition or disease in the subject, the prevention of recurrence of symptoms of the condition or disease in the subject, the delay of recurrence of symptoms of the condition or disease in the subject, the decrease in severity or frequency of outward symptoms of the condition or disease in the subject, slowing or eliminating the progression of the condition and the partial or total elimination of symptoms of the disease or condition in the subject.

Conditions which have been reported to be mediated by a decreased FXR activity include but are not limited to dyslipidemia (Sinal, C., et al. 2000 Cell 102:731-744; Zhang, Y., et al., 2006 Proc. Nat. Acad. Sci., U.S.A., 103:1006-1011); cardiovascular diseases such as atherosclerosis (Hanniman, E. A., et al., J. Lipid Res. 2005, 46:2595-2604); obesity (Chen, L., et al., 2006 Diabetes 55 suppl. 1:A200; Cariou, B., et al., 2006 J. Biol. Chem. 281:11039-11049; Rizzo, G., et al. 2006 Mol. Pharmacol. 70:1164-1173); diabetes mellitus (Duran-Sandoval, D., et al., 2004 Diabetes 53:890-898; Bilz, S., et al., 2006 Am. J. Physiol. Endocrinol. Metab. 290:E716-E722; Nozawa, H., 2005 Biochem. Biophys. Res. Commun. 336: 754-761; Duran-Sandoval, D., et al., 2005 Biochimie 87:93-98; Claudel, T., et al., 2005 Arterioscler. Thromb. Vasc. Biol. 25:2020-2030; Duran-Sandoval, D., et al., 2005 J. Biol. Chem. 280:29971-29979; Savkur, R. S., et al., 2005 Biochem. Biophys. Res. Commun., 329:391-396; Cariou, B., et al., 2006 J. Biol. Chem. 281:11039-11049; Ma, K., et al., 2006 J. Clin. Invest. 116:1102-1109; Zhang, Y., et al., 2006 Proc. Nat. Acad. Sci. U.S.A. 103:1006-1011); metabolic syndrome (Chen, L., et al., 2006 Diabetes 55 suppl. 1:A200); disorders of the liver such as cholestatic liver disease (Liu, Y. et al., 2003 J. Clin. Invest. 112:1678-1687) and cholesterol gallstone disease (Moschetta, A., et al., 2004 Nat. Med. 10: 1352-1358); organ fibrosis (Fiorucci, S., et al. 2004 Gastroenterology 127:1497-1512 and Fiorucci, S., et al., 2005 J. Pharmacol. Exp. Ther. 314:584-595) including liver fibrosis (Fiorucci, S., et al. 2004 Gastroenterology 127:1497-1512); inflammatory bowel disease (Inagaki, T., et al., 2006 Proc. Nat. Acad. Sci., U.S.A. 103:3920-3925); and liver regeneration (Huang, W., et al., 2006 Science 312:233-236).

Compounds of formula (I) are believed to be useful for the treatment of dyslipidemia in a subject, such as a mammal, particularly a human. The compounds of the present invention are currently believed to increase the flow of bile acid. Increased flow of bile acids improves the flux of bile acids from the liver to the intestine. FXR null mice demonstrate that FXR not only plays a role in bile acid homeostasis, but also plays a role in lipid homeostasis by virtue of the regulation of enzymes and transporters that are involved in lipid catabolism and excretion.

Compounds of formula (I) are also believed to be useful for lowering triglycerides in a subject, such as a mammal, particularly a human. As used herein "lowering triglycerides" means lowering triglycerides in a subject in need thereof below the initial level of triglyercides in that subject before administration of a compound of formula (I). For example, the compounds of formula (I) may lower triglycerides by decreasing fat absorption, decreasing hepatic triglyceride production or decreasing hepatic triglyceride secretion. The compounds of formula (I) may also lower serum and hepatic triglycerides.

By treating dyslipidemia, compounds of formula (I) are currently believed to be useful in the treatment of hypertriglyceridemia and hypercholesterolemia related cardiovascular disease such as atherosclerosis in a subject such as a mammal, particularly a human. Compounds of formula (I) are also believed to be useful for the treatment of non-alcoholic fatty liver disease and non-alcoholic steatohepatitis in a subject, such as a mammal, particularly a human (Chen, L., et al., 2006 Diabetes 55 suppl. 1:A200; Watanabe, M., et al., 2004 J. Clin. Invest., 113:1408-1418).

The compounds of formula (I) are useful for the treatment of obesity in a subject, such as a mammal, particularly a human.

Compounds of formula (I) are also useful for the treatment of diabetes mellitus in a subject, such as a mammal, particularly a human. For example, the compounds of formula (I) are useful for the treatment of type 2 diabetes. The effects of an FXR agonist, GW4064, on body weight, glucose tolerance, serum glucose, serum insulin, serum triglyceride, and liver triglyceride contents via oral administration have been observed in an high-fat diet induced insulin resistant, glucose intolerant, and obese mouse model (Chen, L., et al., 2006 Diabetes 55 suppl. 1:A200). Male 20 to 25 g C57BL mice (Charles River, Indianapolis, Ind.) were housed at 72° F. and 50% relative humidity with a 12 h light and dark cycle and fed with standard rodent chow (Purina 5001, Harlan Teklad, Indianapolis, Ind.) or a high-fat diet (TD93075, Harlan Teklad, Indianapolis, Ind.) for seven weeks. After two weeks, mice on high-fat diet were randomized to vehicle or treatment groups. There were no significant difference in body weight, body fat mass, serum glucose and insulin, and area under the curve (AUC) for glucose in glucose tolerance test (GTT) between the vehicle group and the treatment group. Starting from the fourth week, mice were given either vehicle or GW4064 (100 mg/kg) twice a day orally. Mice on the standard rodent chow were also given vehicle as a control. At the end of the third week of compound treatment, a GTT was performed and body composition was measured using the quantitative magnetic resonance (QMR) method. At the end of the study (fourth week of compound treatment), blood samples were taken from inferior vena cava and tissue samples were collected for further analysis. Blood glucose during GTT was measured using Bayer Glucometer Elite® XL. Serum chemistry levels were measured using the Instrumentation Laboratory Ilab600™ clinical chemistry analyzer (Instrumentation Laboratory, Boston, Mass.). Liver triglyceride contents were measured using the methanolic-KOH saponification method and a triglyceride assay kit (GPO-TRINDER, Sigma Diagnostics, St. Louis, Mo.). The results indicated that GW4064 reduced the high-fat diet induced body weight gain. It is believed that the result may have been due to a decrease in fat mass. GW4064 also appeared to improve glucose tolerance, decreased serum glucose, insulin and triglyceride, and reduced liver triglyceride content. In addition, Cariou and colleagues treated male ob/ob mice with GW4064 (30 mg/kg) intraperitoneally (2006 J. Biol. Chem. 281:11039-11049). GW4064 treatment did not alter body weight as well as food intake. Whereas GW4064 had no effect on fasting blood glucose in ob/ob mice, it decreased insulin concentration in the treated group. GW4064 treated ob/ob mice also showed an improved glucose tolerance and enhanced insulin sensitivity compared to controls. In another study, it was reported that GW4064 significantly improved hyperglycemia and hyperlipidemia in diabetic db/db mice (Zhang, Y., et al, 2006 Proc. Nat. Acad. Sci. U.S.A. 103:1006-1011). Oral GW4064 (30 mg/kg, bid) treatment decreased blood glucose, serum β-hydroxybutyrate, triglyceride, NEFA, and total cholesterol in db/db mice. It was also demonstrated that GW4064 treatment enhanced insulin signalling and glycogen storage in the liver of db/db mice. These data suggest that FXR agonists, including the compounds of the formula (I), may be used for the treatment of obesity, insulin resistance, glucose intolerance, diabetes mellitus, fatty liver disease and metabolic syndrome.

Compounds of formula (I) are also useful for the treatment of metabolic syndrome in a subject, such as a mammal, particularly a human. Metabolic syndrome is characterized by a group of metabolic risk factors in one person. They include abdominal obesity (excessive fat tissue in and around the abdomen), atherogenic dyslipidemia (high triglycerides, low high density lipoprotein (HDL) cholesterol and high low density lipoprotein (LDL) cholesterol), elevated blood pressure, insulin resistance or glucose intolerance, prothrombotic state and proinflammatory state. People with metabolic syndrome are at increased risk of coronary heart disease and atherosclerosis-related diseases (e.g., stroke and peripheral vascular disease) and type 2 diabetes mellitus. There are several clinical criteria for metabolic syndromes including ATP III, WHO, and AACE (American Association of Clinical Endocrinologists) (see tables, for review see Grundy, S. M., et al., 2004 Circulation 109:433-438). The present invention provides a method for the treatment of metabolic syndrome characterized by abdominal obesity, atherogenic dyslipidemia and insulin resistance with or without glucose interance, and may benefit other components of metabolic syndrome in a subject.

TABLE 1

ATP III Clinical Identification of the Metabolic Syndrome

| Risk Factor | Defining Level |
|---|---|
| Abdominal obesity, given as waist circumference*† | |
| Men | >102 cm (>40 in) |
| Women | >88 cm (>35 in) |
| Triglycerides | ≧150 mg/dL |
| HDL cholesterol | |
| Men | <40 mg/dL |
| Women | <50 mg/dL |

TABLE 1-continued

ATP III Clinical Identification of the Metabolic Syndrome

| Risk Factor | Defining Level |
|---|---|
| Blood pressure | ≧130/≧85 mm Hg |
| Fasting glucose | ≧110 mg/dL‡ |

*Overweight and obesity are associated with insulin resistance and the metabolic syndrome. However, the presence of abdominal obesity is more highly correlated with the metabolic risk factors than is an elevated BMI. Therefore, the simple measure of waist circumference is recommended to identify the body weight component of the metabolic syndrome.
†Some male patients can develop multiple metabolic risk factors when the waist circumference is only marginally increased, eg, 94 to 102 cm (37 to 39 in). Such patients may have a strong genetic contribution to insulin resistance. They should benefit from changes in life habits, similarly to men with categorical increases in waist circumference.
‡The American Diabetes Association has recently established a cutpoint of ≧100 mg/dL, above which persons have either prediabetes (impaired fasting glucose) or diabetes. This new cutpoint should be applicable for identifying the lower boundary to define an elevated glucose as one criterion for the metabolic syndrome.

TABLE 2

WHO Clinical Criteria for Metabolic Syndrome

Insulin resistance, identified by 1 of the following:

Type 2 diabetes
Impaired fasting glucose
Impaired glucose tolerance
or for those with normal fasting glucose levels
(<110 mg/dL), glucose uptake below the lowest quartile
for background population under investigation under
hyperinsulinemic, euglycemic conditions
Plus any 2 of the following:

Antihypertensive medication and/or high blood pressure
(≧140 mm Hg systolic or ≧90 mm Hg diastolic)
Plasma triglycerides ≧150 mg/dL (≧1.7 mmol/L)
HDL cholesterol <35 mg/dL (<0.9 mmol/L) in men or <39 mg/dL (1.0 mmol/L) in women
BMI >30 kg/m² and/or waist:hip ratio >0.9 in men, >0.85 in women
Urinary albumin excretion rate ≧20 μg/min or albumin:creatinine ratio ≧30 mg/g

TABLE 3

AACE Clinical Criteria for Diagnosis of the Insulin Resistance Syndrome*

| Risk Factor Components | Outpoints for Abnormality |
|---|---|
| Overweight/obesity | BMI ≧ 25 kg/m² |
| Elevated triglycerides | ≧150 mg/dL (1.69 mmol/L) |
| Low HDL cholesterol | |
| Men | <40 mg/dL (1.04 mmol/L) |
| Women | <50 mg/dL (1.29 mmol/L) |
| Elevated blood pressure | ≧130/85 mm Hg |
| 2-Hour postglucose challenge | >140 mg/dL |
| Fasting glucose | Between 110 and 126 mg/dL |
| Other risk factors | Family history of type 2 diabetes, hypertension, or CVD |
| | Polycystic ovary syndrome |
| | Sedentary lifestyle |
| | Advancing age |
| | Ethnic groups having high risk for type 2 diabetes or CVD |

*Diagnosis depends on clinical judgment based on risk factors.

Compounds of formula (I) are believed to be useful for the treatment of cholestatic liver disease. For example, the compounds of formula (I) are believed to be useful in the treatment of primary biliary cirrhosis or primary sclerosing cholangitis. FXR therefore is a target for the treatment of a number of cholestatic liver diseases and non-alcoholic steatohepatitis. The compounds of formula (I) are also believed to be useful for the treatment of gall stones. For example, the compounds of formula (I) are believed to be useful in the treatment of cholesterol gallstone disease. The compounds of formula (I) are also believed to be useful for decreasing liver lipid accumulation.

Compounds of formula (I) are also believed to be useful for the treatment of organ fibrosis. Fibrotic disorders can be characterized as acute or chronic, but share the common characteristic of excessive collagen accumulation and an associated loss of function as normal tissues are replaced or displaced by fibrotic tissues. Acute forms of fibrosis include response to trauma, infections, surgery, burns, radiation and chemotherapy. Chronic forms of fibrosis may be due to viral infection, diabetes mellitus, obesity, fatty liver, hypertension, scleroderma and other chronic conditions that induce fibrosis.

Organs that are most commonly affected by fibrosis include liver, kidney, and lung.

Organ fibrosis can cause the progressive loss of organ function. Retroperitoneal fibrosis (including idiopathic retroperitoneal fibrosis) may not originate from any major organ, but can involve and adversely affect the function of organs such as the kidneys.

Accordingly, as used herein, the term fibrosis refers to all recognized fibrotic disorders, including fibrosis due to pathological conditions or diseases, fibrosis due to physical trauma ('traumatic fibrosis'), fibrosis due to radiation damage, and fibrosis due to exposure to chemotherapeutics. As used herein, the term "organ fibrosis" includes but is not limited to liver fibrosis, fibrosis of the kidneys, fibrosis of lung, and fibrosis of the intestine. "Traumatic fibrosis" includes but is not limited to fibrosis secondary to surgery (surgical scarring), accidental physical trauma, burns, and hypertrophic scarring.

In one embodiment, compounds of formula (I) are useful for the treatment of liver fibrosis in a subject, particularly a mammal such as a human, in need of treatment thereof. As used herein, "liver fibrosis" includes liver fibrosis due to any cause, including but not limited to virally-induced liver fibrosis such as that due to hepatitis B or C virus; exposure to alcohol (alcoholic liver disease), certain pharmaceutical compounds including but not limited to methotrexate, some chemotherapeutic agents, and chronic ingestion of arsenicals or vitamin A in megadoses, oxidative stress, cancer radiation therapy or certain industrial chemicals including but not limited to carbon tetrachloride and dimethylnitrosamine; and diseases such as primary biliary cirrhosis, primary sclerosing colangitis, fatty liver, obesity, non-alcoholic steatohepatitis, cystic fibrosis, hemochromatosis, auto-immune hepatitis, and steatohepatitis. Current therapy in liver fibrosis is primarily directed at removing the causal agent, e.g., removing excess iron (e.g., in the case of hemochromatosis), decreasing viral load (e.g., in the case of chronic viral hepatitis), or eliminating or decreasing exposure to toxins (e.g., in the case of alcoholic liver disease). Anti-inflammatory drugs such as corticosteroids and colchicine are also known for use in treating inflammation that can lead to liver fibrosis. Other strategies for treating liver fibrosis are under development (see, e.g., Murphy, F., et al., 2002 Expert Opin. Invest. Drugs 11: 1575-1585; Bataller, R. and Brenner, D. A., 2001 Sem. Liver Dis. 21:437-451). Thus in another embodiment, the present invention provides a method for the treatment of liver fibrosis in a subject which comprises administering a therapeutically effective amount of a compound of formula (I) in combination with another therapeutic agent useful for the treatment of symptoms associated with liver fibrosis. Examples of therapeutic agents useful for the treatment of symptoms associated with liver fibrosis include corticosteroids and cholchicine.

The response of the liver to hepatocellular damage, similar to wound healing in other tissues, includes inflammation and tissue remodeling, with associated changes in the quantity and quality of the extracellular matrix. Progressive accumulation of extracellular matrix proteins, including collagen types I and III, eventually distorts the architecture of the liver by forming fibrous scars, resulting in disrupted blood flow and an eventual deterioration in hepatic function. (Bissell, D. M. and Maher, J. J., "Hepatic Fibrosis and Cirrhosis." Ed. Zakim, D. and Thomas, D. B., 4 ed. 2 vols. Philadelphia: Saunders, 2003. 395-416, Hanauske-Abel, H. M., "Fibrosis of the Liver: Representative Molecular Elements and Their Emerging Role As Anti-Fibrotic Targets." Ed. Zakim, D., and Thomas, D. B., 4 ed. 2 vols. Philadelphia: Saunders, 2003. 347-394). Hepatic stellate cells (HSC) have been identified as important mediators of the fibrotic process in the liver, and are believed to be primarily responsible for the synthesis of excess extracellular matrix seen in liver disease. Liver injury can result in quiescent HSCs converting to activated myofibroblast-like cells that proliferate, migrate, recruit inflammatory cells, and synthesize collagens and other extracellular matrix proteins. (Bissell, D. M. and Maher, J. J., "Hepatic Fibrosis and Cirrhosis." Ed. Zakim, D. and Thomas, D. B., 4 ed. 2 vols. Philadelphia: Saunders, 2003. 395-416, Hanauske-Abel, H. M., "Fibrosis of the Liver: Representative Molecular Elements and Their Emerging Role As Anti-Fibrotic Targets." Ed. Zakim, D., and Thomas, D. B., 4 ed. 2 vols. Philadelphia: Saunders, 2003. 347-394). Various cytokines are reported to activate HSCs, including transforming growth factor β (TGFβ). Following liver injury, HSCs synthesize α-smooth muscle actin (α-SMA) as part of the migration response, consequently a marked accumulation of α-SMA can be seen at areas of active liver fibrogenesis. (Bissell, D. M. and Maher, J. J., "Hepatic Fibrosis and Cirrhosis." Ed. Zakim, D. and Thomas, D. B., 4 ed. 2 vols. Philadelphia: Saunders, 2003. 395-416, Hanauske-Abel, H. M., "Fibrosis of the Liver: Representative Molecular Elements and Their Emerging Role As Anti-Fibrotic Targets." Ed. Zakim, D., and Thomas, D. B., 4 ed. 2 vols. Philadelphia: Saunders, 2003. 347-394). Derangement of the normal epithelial/mesenchymal interaction, characterised by cholangiocyte damage/proliferation, can also lead to extracellular matrix-producing and progressive fibrogenesis. [Pinzani, M., et al., 2004 Digest. Liver Dis. 36:231-242.]

As is known in the art, liver fibrosis may be clinically classified into five stages of severity (S0 to S4), usually based on histological examination of a biopsy specimen. S0 indicates no fibrosis, whereas S4 indicates cirrhosis. While various criteria for staging the severity of liver fibrosis exist, in general early stages of fibrosis are identified by discrete, localized areas of scarring in one portal (zone) of the liver, whereas later stages of fibrosis are identified by bridging fibrosis (scarring that crosses zones of the liver).

Compounds of formula (I) are also useful for the treatment of inflammatory bowel disease in a subject, such as a mammal, particularly a human. Inflammatory bowel disease (IBD) is defined as a group of idiopathic relapsing inflammatory disorders of the bowel—the large or small intestine. The pathogenesis of IBD remains obscure and may involve genetic, environmental and immunological factors. [Drossman, D. A. 1999 Aliment Pharmacol. Ther. 13(s2):3-14; Danese, S., et al. 2004 Autoimmunity Reviews 3: 394-400; Stokkers, P. C. F. and Hommes, D. W. 2004 Cytokine 28:167-173.] The most common types of inflammatory bowel disease are ulcerative colitis and Crohn disease.

Compounds of formula (I) are also believed to be useful for enhancing liver regeneration in a subject, such as a mammal, particularly a human. For example, the compounds of formula (I) are believed to be useful for enhancing liver regeneration for liver transplantation.

The present invention provides a method for the treatment of a condition mediated by decreased FXR activity, particularly a condition in which a FXR agonist may be useful, in a subject, such as a mammal, particularly a human, in need thereof. The present invention also provides the use of a compound of formula (I) for the preparation of a medicament for the treatment of a condition mediated by decreased FXR activity, particularly a condition in which a FXR agonist may be useful, in a subject, such as a mammal, particularly a human in need thereof.

The present invention also provides a method for lowering triglycerides in a subject, such as a mammal, particularly a human, in need thereof. The present invention also provides the use of a compound of formula (I) for the preparation of a medicament for lowering triglycerides in a subject. In one embodiment, the compound of formula (I) is 6-[4-({[3-(2,6-dichlorophenyl)-5-(1-methylethyl)-4-isoxazolyl]methyl}oxy)phenyl]-2-quinolinecarboxylic acid or a pharmaceutically acceptable salt thereof. In another embodiment, the compound of formula (I) is 7-[4-({[3-(2,6-dichlorophenyl)-5-(1-methylethyl)-4-isoxazolyl]methyl}oxy)phenyl]-3-isoquinolinecarboxylic acid or a pharmaceutically acceptable salt thereof.

The present invention provides a method for the treatment of obesity in a subject, such as a mammal, particularly a human, in need thereof. The present invention also provides the use of a compound of formula (I) for the preparation of a medicament for the treatment of obesity in a subject. In one embodiment, the compound of formula (I) is 6-[4-({[3-(2,6-dichlorophenyl)-5-(1-methylethyl)-4-isoxazolyl]methyl}oxy)phenyl]-2-quinolinecarboxylic acid or a pharmaceutically acceptable salt thereof. In another embodiment, the compound of formula (I) is 7-[4-({[3-(2,6-dichlorophenyl)-5-(1-methylethyl)-4-isoxazolyl]methyl}oxy)phenyl]-3-isoquinolinecarboxylic acid or a pharmaceutically acceptable salt thereof.

The present invention provides a method for the treatment of diabetes mellitus in a subject, such as a mammal, particularly a human, in need thereof. The present invention also provides the use of a compound of formula (I) for the preparation of a medicament for the treatment of diabetes mellitus in a subject. In one embodiment, the compound of formula (I) is 6-[4-({[3-(2,6-dichlorophenyl)-5-(1-methylethyl)-4-isoxazolyl]methyl}oxy)phenyl]-2-quinolinecarboxylic acid or a pharmaceutically acceptable salt thereof. In another embodiment, the compound of formula (I) is 7-[4-({[3-(2,6-dichlorophenyl)-5-(1-methylethyl)-4-isoxazolyl]methyl}oxy)phenyl]-3-isoquinolinecarboxylic acid or a pharmaceutically acceptable salt thereof.

The present invention provides a method for the treatment of metabolic syndrome in a subject, such as a mammal, particularly a human, in need thereof. The present invention also provides the use of a compound of formula (I) for the preparation of a medicament for the treatment of metabolic syndrome in a subject. In one embodiment, the compound of formula (I) is 6-[4-({[3-(2,6-dichlorophenyl)-5-(1-methylethyl)-4-isoxazolyl]methyl}oxy)phenyl]-2-quinolinecarboxylic acid or a pharmaceutically acceptable salt thereof. In another embodiment, the compound of formula (I) is 7-[4-({[3-(2,6-dichlorophenyl)-5-(1-methylethyl)-4-isoxazolyl]methyl}oxy)phenyl]-3-isoquinolinecarboxylic acid or a pharmaceutically acceptable salt thereof.

The present invention provides a method for the treatment of cholestatic liver disease in a subject, such as a mammal, particularly a human, in need thereof. The present invention also provides the use of a compound of formula (I) for the preparation of a medicament for the treatment of cholestatic liver disease in a subject. In one embodiment, the compound of formula (I) is 6-[4-({[3-(2,6-dichlorophenyl)-5-(1-methylethyl)-4-isoxazolyl]methyl}oxy)phenyl]-2-quinolinecarboxylic acid or a pharmaceutically acceptable salt thereof. In another embodiment, the compound of formula (I) is 7-[4-({[3-(2,6-dichlorophenyl)-5-(1-methylethyl)-4-isoxazolyl]methyl}oxy)phenyl]-3-isoquinolinecarboxylic acid or a pharmaceutically acceptable salt thereof.

The present invention provides a method for the treatment of organ fibrosis in a subject, such as a mammal, particularly a human, in need thereof. The present invention also provides the use of a compound of formula (I) for the preparation of a medicament for the treatment of organ fibrosis in a subject. In one embodiment, the compound of formula (I) is 6-[4-({[3-(2,6-dichlorophenyl)-5-(1-methylethyl)-4-isoxazolyl]methyl}oxy)phenyl]-2-quinolinecarboxylic acid or a pharmaceutically acceptable salt thereof. In another embodiment, the compound of formula (I) is 7-[4-({[3-(2,6-dichlorophenyl)-5-(1-methylethyl)-4-isoxazolyl]methyl}oxy)phenyl]-3-isoquinolinecarboxylic acid or a pharmaceutically acceptable salt thereof.

The present invention provides a method for the treatment of liver fibrosis in a subject, such as a mammal, particularly a human, in need thereof. The present invention also provides the use of a compound of formula (I) for the preparation of a medicament for the treatment of liver fibrosis in a subject. In one embodiment, the compound of formula (I) is 6-[4-({[3-(2,6-dichlorophenyl)-5-(1-methylethyl)-4-isoxazolyl]methyl}oxy)phenyl]-2-quinolinecarboxylic acid or a pharmaceutically acceptable salt thereof. In another embodiment, the compound of formula (I) is 7-[4-({[3-(2,6-dichlorophenyl)-5-(1-methylethyl)-4-isoxazolyl]methyl}oxy)phenyl]-3-isoquinolinecarboxylic acid or a pharmaceutically acceptable salt thereof.

All of the methods of the present invention comprise the step of administering a therapeutically effective amount of the compound of formula (I) or a pharmaceutically acceptable salt or solvate thereof. As used herein, the term "therapeutically effective amount" refers to an amount of a compound of formula (I) which is sufficient to achieve the stated effect in the subject to which it is administered. Accordingly, a therapeutically effective amount of a compound of formula (I) used in the method for the treatment of a condition mediated by decreased FXR activity in a human will be an amount sufficient for the treatment of the condition mediated by decreased FXR activity in a human. A therapeutically effective amount of a compound of formula (I) for use in the method for the treatment of diabetes mellitus in a human will be an amount sufficient for the treatment of diabetes mellitus in a human. A therapeutically effective amount of a compound of formula (I) for use in the method for the treatment of metabolic syndrome in a human will be an amount sufficient for the treatment of metabolic syndrome in a human. A therapeutically effective amount of a compound of formula (I) for use in the method for the treatment of organ (e.g., liver) fibrosis in a human will be an amount sufficient for the treatment of organ fibrosis in a human.

The amount of a compound of formula (I) which is required to achieve the desired therapeutic or biological effect will depend on a number of factors such as the use for which it is intended, the means of administration, the recipient and the type and severity of the condition or disease being treated, and will be ultimately at the discretion of the attendant physician or veterinarian. In general, a typical daily dose for the treatment of a disease or condition mediated by decreased FXR activity in a human, for instance, may be expected to lie in the range of from about 0.01 mg/kg to about 100 mg/kg for a 70 kg human. This dose may be administered as a single unit dose or as several separate unit doses or as a continuous infusion. Similar dosages would be applicable for the treatment of other diseases, conditions and therapies including diabetes mellitus and obesity in humans.

While it is possible that, for use in therapy, a therapeutically effective amount of a compound of formula (I) may be administered as the raw chemical, it is typically presented as the active ingredient of a pharmaceutical composition or formulation. Accordingly, the invention further provides a pharmaceutical composition comprising a compound of the formula (I). The pharmaceutical composition may further comprise one or more pharmaceutically acceptable carriers or diluents. The carrier(s) and/or diluent(s) must be acceptable in the sense of being compatible with the other ingredients of the formulation and not deleterious to the recipient thereof. In one particular embodiment, the compound is in crystalline form. The invention also specifically contemplates compositions comprising the potassium salt of the aforementioned compound. In accordance with another aspect of the invention there is also provided a process for the preparation of a pharmaceutical formulation including admixing a compound of the formula (I) with one or more pharmaceutically acceptable carriers and/or diluents.

Pharmaceutical formulations may be presented in unit dose form containing a predetermined amount of active ingredient per unit dose. Such a unit may contain a therapeutically effective dose of the compound of formula (I) or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethyl-cellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of active ingredient. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

A compound of formula (I) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

A compound of formula (I) may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in 1986 Pharmaceutical Research 3:318.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Pharmaceutical compositions adapted for nasal administration wherein the carrier is a solid include a coarse powder having a particle size for example in the range of about 20 microns to about 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical compositions adapted for administration by inhalation include fine particle dusts or mists, which may be generated by means of various types of metered, dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

In the above-described methods of treatment and uses, a compound of formula (I) may be employed alone, in combination with one or more other compounds of formula (I) or in combination with other therapeutic agents. Thus, the present invention also encompasses pharmaceutical compositions further comprising one or more therapeutic agents. In one embodiment, the pharmaceutical compositions further comprise one or more lipid-altering agents. Examples of lipid-altering agents include but are not limited to liver X receptor (LXR) agonists described in PCT Publication No. WO02/24632 to GlaxoSmithKline. Examples of other therapeutic agents include, but are not limited to, 3-Hydroxy-3-Methyl-Glutaryl-CoA reductase inhibitors such as statins (atorvastatin, fluvastatin, pravastatin, lovastatin, cerivastatin, and nisvastatin); squalene epoxidase inhibitors, squalene synthetase inhibitors, bile acid transport inhibitors (BATi), human peroxisome proliferator activated receptor (PPAR) gamma agonists such as rosiglitazone, troglitazone, and pioglitazone and thiazolidinediones; PPAR α agonists such as clofibrate, fenofibrate and gemfibrozil; PPAR dual α/γ agonists; cyclooxygenase-2 (COX-2) inhibitors such as rofecoxib and celecoxib; thrombin inhibitors; acyl-coenzyme A; cholesterol acyltransferase (ACAT) inhibitors including selective ACAT inhibitors; microsomal triglyceride transfer protein (MTP) inhibitors; probucol, niacin; cholesterol absorption inhibitors; bile acid sequestrants; LDL receptor inducers; platelet aggregation inhibitors such as glycoprotein IIb/IIIa fibrinogen receptor antagonists and aspirin; vitamin B6 and pharmaceutically acceptable salts thereof, vitamin B12; folic acid or a pharmaceutically acceptable salt or ester thereof, antioxidant vitamins such as C and E and beta carotene; beta blockers; angiotensin II antagonists such as losartan; angiotensin converting enzyme inhibitors such as enalapril and captopril; calcium channel blockers such as nifedipine and diltiazem; endothelian antagonists; agents other than LXR ligands that enhance ATP-Binding Cassette Transporter-A1 gene expression; and bisphosphonate compounds such as alendronate sodium.

The methods and uses employing these combinations may comprise the administration of the compound of formula (I) and another therapeutic agent either sequentially in any order or simultaneously in separate or combined pharmaceutical compositions. When combined in the same composition it will be appreciated that the compounds must be stable and compatible with each other and the other components of the composition and may be formulated for administration. When formulated separately they may be provided in any convenient formulation, in such a manner as are known for such compounds in the art.

When a compound of formula (I) is used in combination with another therapeutic agent, the dose of each compound may differ from that when the compound is used alone. Appropriate doses will be readily appreciated by those skilled in the art. The appropriate dose of the compound(s) of formula (I) and the other therapeutically active agent(s) and the relative timings of administration will be selected in order to achieve the desired combined therapeutic effect, and are within the expertise and discretion of the attendant clinician.

Compounds of the invention can be made according to any suitable method of organic chemistry. As will be apparent to those skilled in the art and as depicted in the schemes which follow, the order of the steps in each reaction is not critical to the practice of the processes of the present invention. The reaction steps depicted in each scheme may be carried out in any suitable order based upon the knowledge of those skilled in the art. Further, it will be apparent to those skilled in the art that certain reaction steps may be most efficiently performed by installing protecting groups prior to the reaction, which are removed subsequently. The choice of protecting groups as well as general techniques for their installation and removal are within the skill of those in the art.

According to one method, a compound of formula (I) may be prepared using the process depicted in Scheme 1, below.

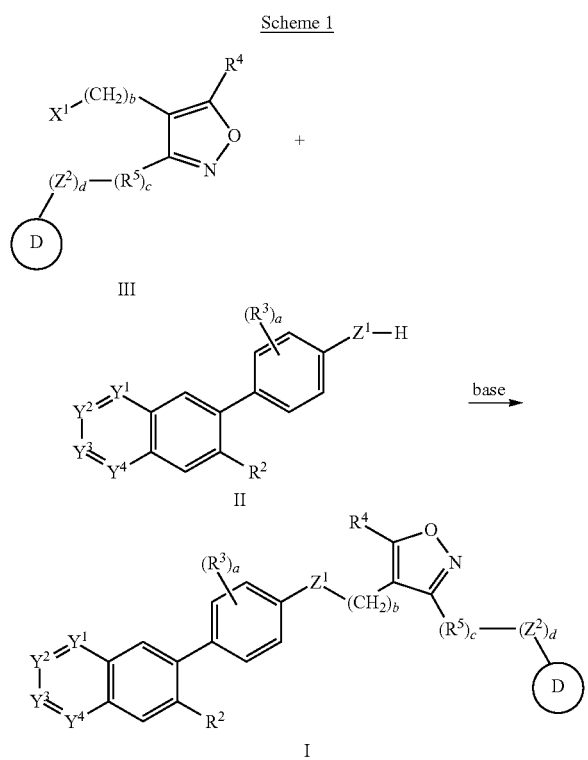

Scheme 1 wherein:
$X^1$ is chloride, iodide, bromide, triflate, tosylate, nosylate, besylate or mesylate, (preferably chloro);
each $R^1$ is the same or different and is independently selected from alkyl, fluoroalkyl or —$CO_2$alkyl; wherein at least one $R^1$ is —$CO_2$alkyl; and
all other variables are as defined above for formula (I).

In general, the process for preparing a compound of formula (I) as depicted in Scheme 1 comprises the steps of:
a) reacting a compound of formula (II) with a compound of formula (III) to prepare a compound of formula (I);
d) optionally converting the compound of formula (I) into a pharmaceutically acceptable salt or solvate thereof, and
e) optionally converting the compound of formula (I) or a pharmaceutically acceptable salt or solvate thereof into a different compound of formula (I) or a pharmaceutically acceptable salt or solvate thereof A compound of formula (I), prepared by any suitable process, may be converted into a pharmaceutically acceptable salt or solvate thereof or may be converted to a different compound of formula (I) or a pharmaceutically acceptable salt or solvate thereof using techniques described herein below and those conventional in the art.

More particularly, the compound of formula (I) may be prepared by reacting the compound of formula (II) with a compound of formula (III) in the presence of a suitable base such as cesium carbonate or potassium carbonate, in a polar aprotic solvent, such as N,N-dimethylformamide, at ambient or elevated temperature.

The compound of formula (III) may be prepared by reacting a compound of formula (IV) with the appropriate reagent to prepare a compound having the desired leaving group ($X^1$).

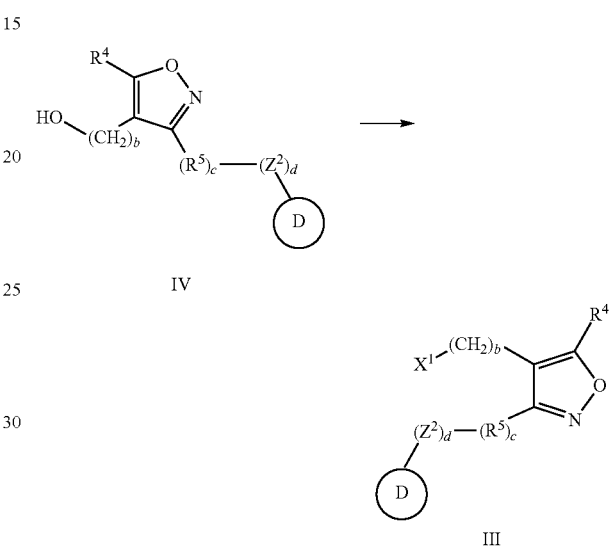

wherein all variables are as defined above.

In the embodiment wherein $X^1$ is halide, the reaction is performed by halogenating the compound of formula (IV). Any suitable halogenating reagent conventional in the art may be employed in the reaction. Examples of suitable halogenating reagents include, but are not limited to, thionyl chloride and triphenylphosphine dichloride. The reaction is typically carried out in a non-polar solvent such as dichloromethane or 1,2-dichloroethane at ambient temperature.

In the embodiment wherein $X^1$ is triflate, tosylate or mesylate, the reaction process may be carried out according to the conventional methods. See, Vedejs, E., et al., 1977 J. Org. Chem. 42:3109-3113; Handy, S. T., et al. 2004 J. Org. Chem. 69:2362-2366; and Copp, F. C., et al. 1955 J. Chem. Soc. 2021-2027.

The compound of formula (IV) may be prepared by reducing a compound of formula (V).

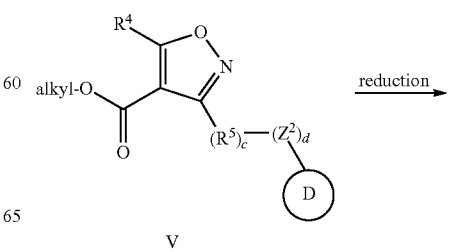

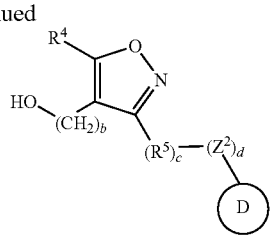

IV wherein all variables are as defined above.

A compound of formula (V) may be treated with a reducing agent, such as diisobutylaluminum hydride, in a suitable solvent such as tetrahydrofuran.

In another embodiment, the compound of formula (V) may be saponified to the corresponding carboxylic acid prior to reducing with a suitable reducing agent, such as borane, to prepare a compound of formula (IV). In addition, the carboxylic acid may also converted to a mixed anhydride before reducing with a reducing agent such as sodium borohydride to prepare a compound of formula (IV).

Compounds of formula (V) may be prepared by multiple routes. In one embodiment, the compound of formula (V) may be prepared by a process comprising the steps of:
a) chlorinating a compound of formula (VI); and
b) cyclizing with a β-ketoester of formula (VII).

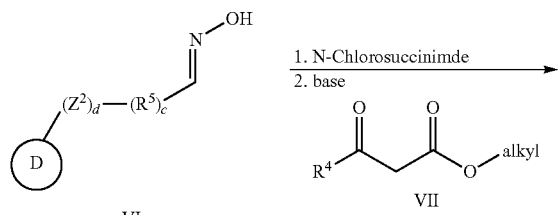

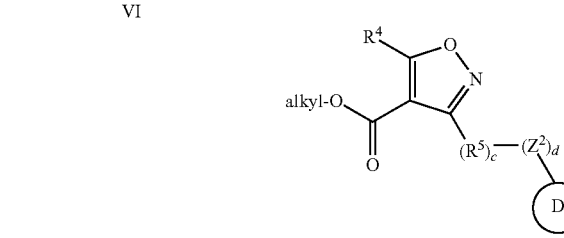

wherein all variables are as defined above.

The process is conveniently carried out according to the method described by Doyle, F. P., et. al., 1963 J. Chem. Soc. 5838-5845. Esters of formula (VII) are commercially available or can be prepared using conventional techniques.

The compound of formula (VI) may be prepared by condensing a compound of formula (VIII) with hydroxylamine.

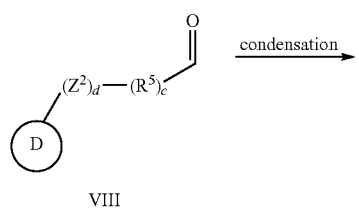

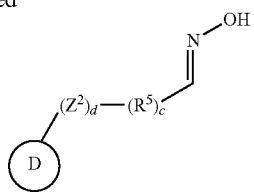

VI wherein all variables are as defined above.

Conditions suitable for this condensation reaction are conventional in the art.

In another embodiment, a compound of formula (V) is prepared by a process comprising the steps of: a) reacting a compound of formula (IX) with tin chloride in the presence of a compound of formula (VII) to prepare a compound of formula (X) and b) reacting the compound of formula (X) with hydroxylamine to yield a compound of formula (V). See, Singh, B. and Lesher, G. Y. 1978 Synthesis 829-830.

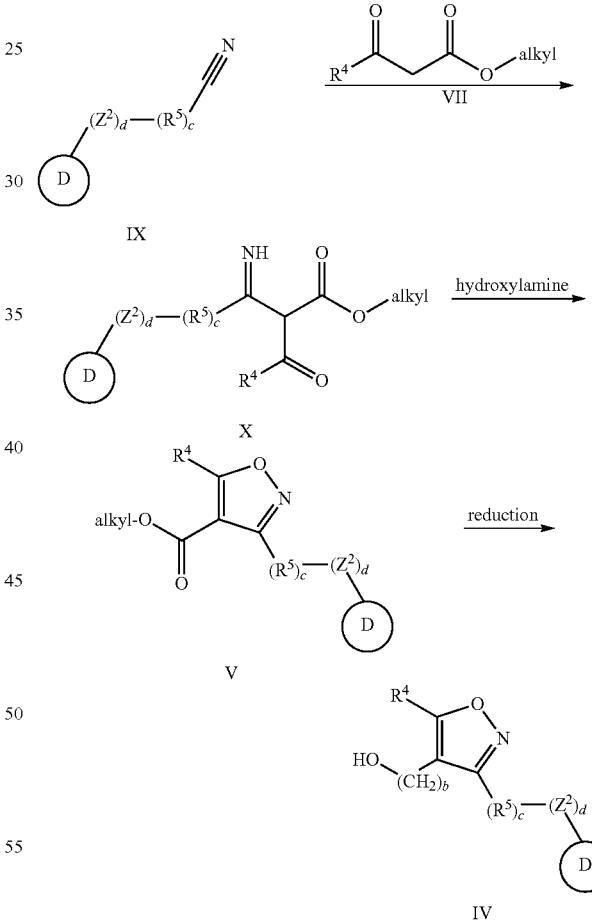

wherein all variables are as defined above.

The compound of formula (IX) may be obtained commercially or by procedures in the literature. See, Guo, H. and Zhang, Y. 2000 Syn. Commun. 30:1879-1885. The compound of formula (V) may then be reduced with a suitable reducing agent, such as diisobutylaluminum hydride, in the manner described above, to prepare a compound of formula (IV).

In another embodiment, a compound of formula (V) wherein d is 1, may be prepared by a process comprising the steps of: a) hydrolyzing a compound of formula (XI) to prepare a compound of formula (XII) and b) reacting the alcohol of formula (XII) under Mitsunobu conditions with a compound of formula (I-b), (ii-b) or (iii-b).

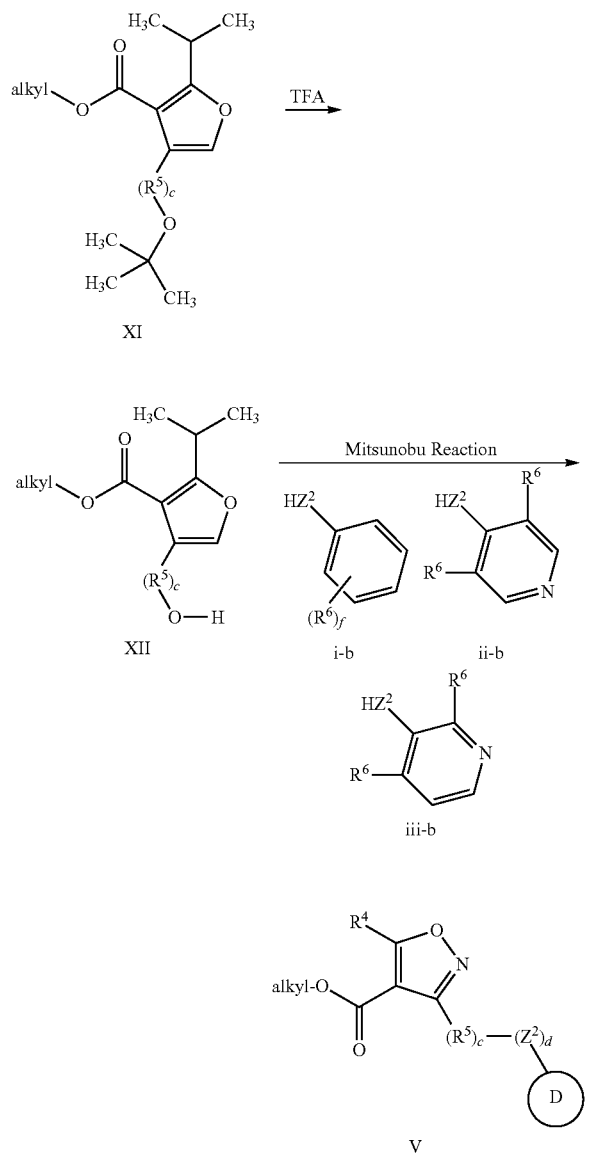

wherein:
c and d are each 1;
$Z^2$ is —O—, —S— or —NH—;
Ring D is a moiety of formula i, ii or iii;
and all other variables are defined as above.

The hydrolysis of the compound of formula (XI) may be carried out using conventional techniques, including by reaction with an acid, such as trifluoroacetic acid, in a solvent such as dichloromethane or 1,2-dichloroethane. The resulting compound of formula (XII) may be reacted under Mitsunobu reaction conditions with a compound of formula of i, ii, or iii to prepare a compound of formula (V). Suitable reaction conditions for the Mitsunobu reaction are known to those skilled in the art. For example, the reaction may be carried out in a solution of dichloromethane, 1,2-dichloroethane or toluene with triphenyl phosphine and a dialkyl azodicarboxylate, such as diisopropyl azodicarboxylate or di-tert-butyl azodicarboxylate. To prepare Compounds of formula (V) wherein d is 1 and $Z^2$ is NH it may be desirable to first prepare the trifluoroacetamide derivative of the compound of formula (I, ii, or iii, such that $Z^2$ is $NC(O)CF_3$) before performing the Mitsunobu reaction. To prepare a compound of formula (V) wherein $Z^2$ is SO or $SO_2$, a compound of formula (V) wherein $Z^2$ is S is oxidized using an oxidant, such as 3-chloroperbenzoic acid.

A compound of formula (V) may also be prepared by reacting the compound of a formula (XII) with an appropriate reagent to install a leaving group, such as chloro, iodo, bromo, triflate, tosylate, nosylate, besylate or mesylate, (preferably bromo), to prepare a compound of formula (XIII) having the desired leaving group ($X^1$).

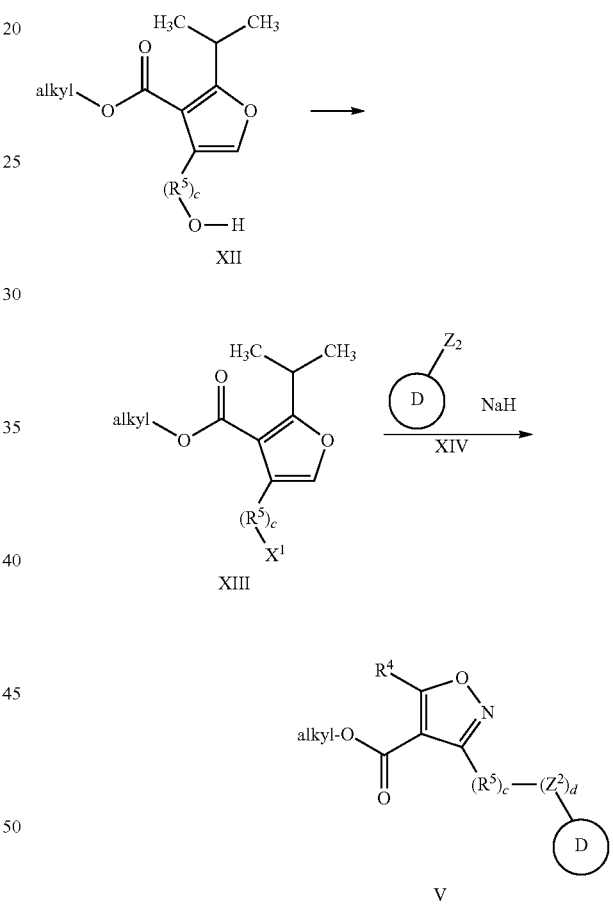

wherein:
$X^1$ is selected from Cl, I, Br, triflate, tosylate, nosylate, besylate or mesylate and
all other variables are as defined above.

For example, a bromide leaving group may be installed by reacting a solution of the compound of formula (XII) in a solvent such as dichloromethane, with carbon tetrabromide and triphenylphosphine to prepare a compound of formula (XIII) wherein $X^1$ is Br. The compound of formula (XIII) may then be reacted in solvent, such as tetrahydrofuran, with a compound of formula (XIV) that has been pretreated with a base such as sodium hydride, to prepare the compound of formula (V).

A compound of formula (V) may also be synthesized by the condensation of a tricarbonyl compound of formula (XV) with hydroxylamine according to the procedure of Doyle, F. P., et. al., 1963 J. Chem. Soc. 5838-5845.

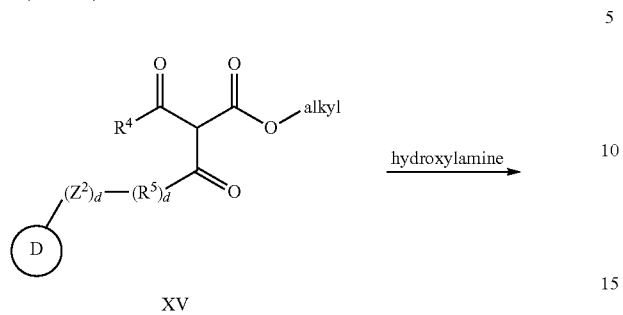

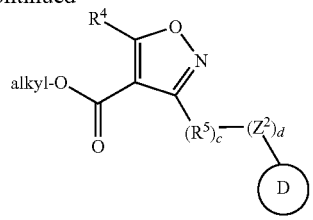

wherein all variables are as defined above.

A compound of formula (IV) wherein b is 2 or 3 may be prepared by the homologation of a compound of the formula (IV) wherein b is 1 (i.e., a compound of formula (IV-1), as depicted below.

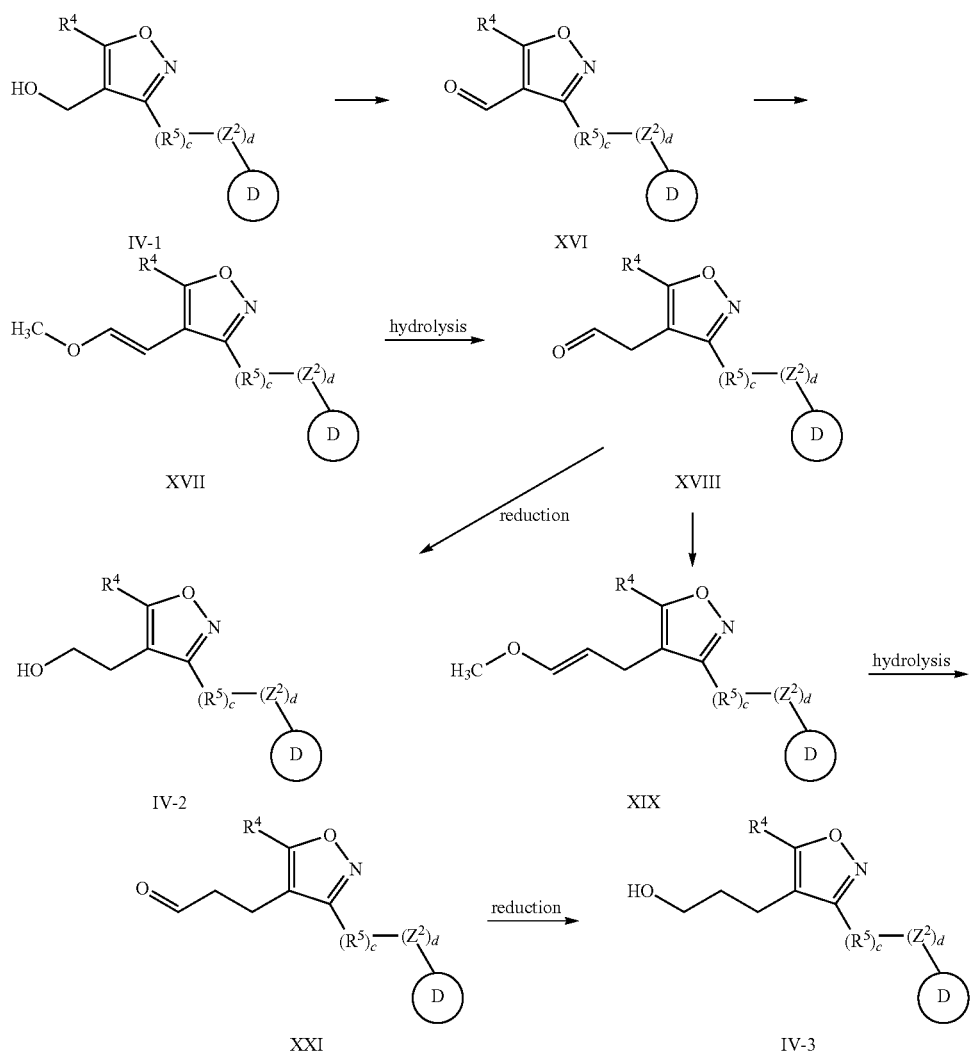

wherein all variables are as defined above.

More specifically, a compound of formula (IV) wherein b is 2 or 3 (formula IV-2 and IV-3, respectively) may be prepared by oxidizing the compound of formula (IV-1) with an oxidizing agent such as pyridium chlorochromate, to prepare the compound of formula (XVI). The compound of formula (XVI) may be reacted with the ylide formed from the reaction of (methoxymethyl)triphenyl-phosphonium chloride and potassium tert butoxide to prepare a compound of formula (XVII). The compound of formula (XVII) may be hydrolyzed with aqueous hydrochloric acid to prepare the compound of formula (XVIII). The compound of formula (XVIII) may be reduced with sodium borohydride to prepare a compound of formula (IV-2) or may be further homologated by the repeating the Wittig/hydrolysis sequence to prepare a compound of formula (IV-3).

A compound of formula (II) may be prepared by coupling the compound of formula (XXV) with a boronic acid or ester compound of formula (XXVI) using conventional Suzuki coupling techniques.

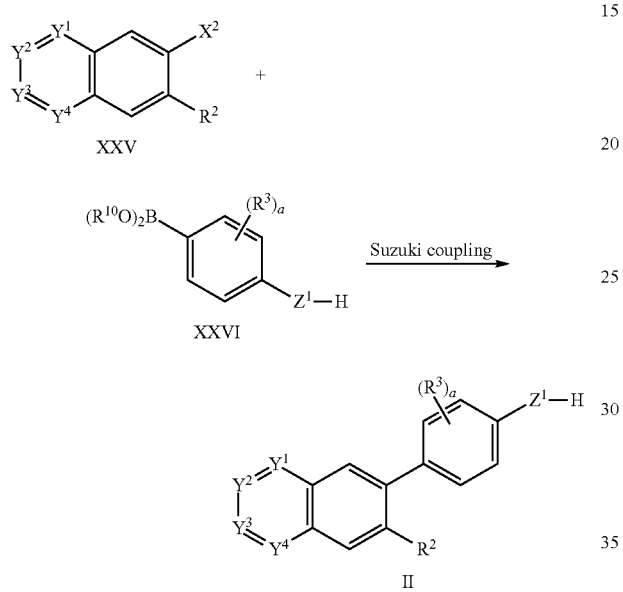

wherein: $X^2$ is chloro, bromo, iodo, or triflate;

$R^{10}$ is H or alkyl;

$Z^1$ is —O— or —NH—; and all other variables are as defined above.

For example, the compound of formula (II) may be prepared by coupling a compound of formula (XXV) with a compound of formula (XXVI) in the presence of a suitable palladium complex such as tetrakis(triphenylphosphine)palladium(0) and a base such as sodium carbonate in a mixture of water and ethereal solvent such as 1,2-dimethoxyethane, at an elevated temperature.

A compound of formula (XXVI) may be synthesized by techniques known to those skilled in the art or purchased commercially.

A compound of formula (XXV) wherein $Y^1$ is CH, $Y^2$ is C—$R^1$ where $R^1$ is H or alkyl, $Y^3$ is C—$R^1$ where $R^1$ is —$CO_2$alkyl, and $Y^4$ is N (i.e., formula XXV-1) may be prepared by the steps of:

a) reducing a compound of formula (XXVII) with zinc(II) chloride and tin(II)chloride to prepare a compound of formula (XXVIII), and b) condensing the compound of formula (XXVIII) in situ with an alpha ketoester of formula (XXIX). Suitable alpha ketoesters of formula (XXIX) are commercially available or can be prepared using conventional techniques known to those skilled in the art.

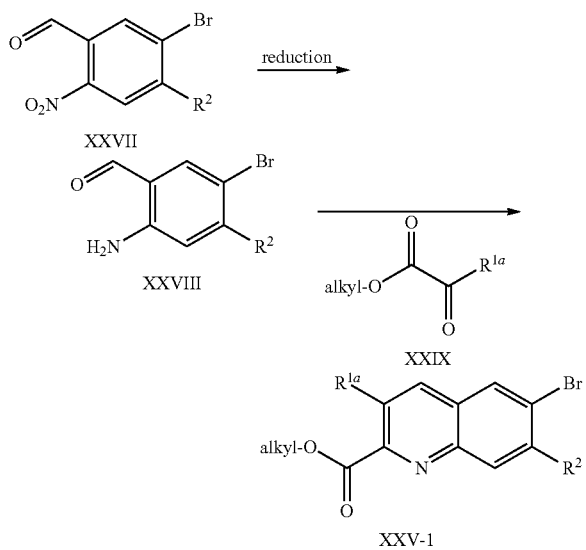

wherein: $R^{13}$ is H or alkyl, and all other variables are as defined above.

A compound of formula (XVII) may be made by nitrating a compound of formula (XXX) using nitric acid and concentrated sulfuric acid.

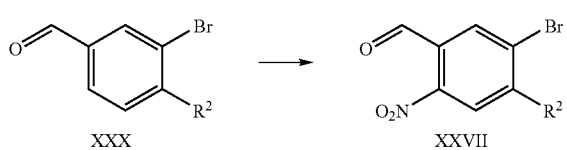

wherein: all variables are as defined above.

Suitable reaction conditions for such nitration are conventional in the art. Compounds of formula (XXX) are commercially available.

As another example, a compound of formula (XXV) wherein $Y^1$ and $Y^4$ are both CH, $Y^2$ is N and $Y^3$ is C—$R^1$ where $R^1$ is —$CO_2$alkyl (i.e., formula XXV-2) may be prepared by the steps of reacting a phenol of formula (XXXI) with a reagent suitable for installing the leaving group, $X^2$.

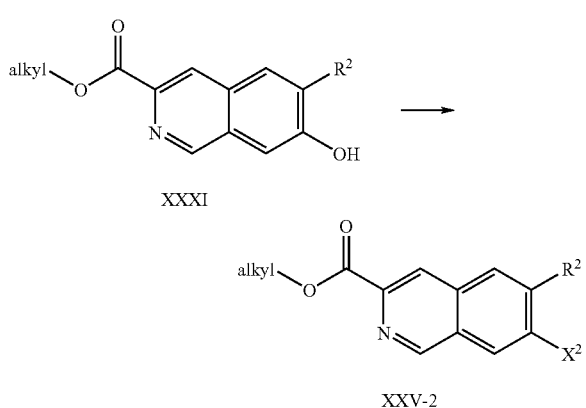

wherein: $X^2$ is triflate.

Reagents suitable for installing the leaving group include but are not limited to triflic anhydride. The reaction may be carried out in a solvent, such as dichloromethane and in the presence of a suitable base, such as pyridine. In another embodiment, a compound of formula (XXV-2) may be prepared by reacting the compound of formula (XXXI) in a suspension of toluene with an aqueous solution of tribasic potassium phosphate and then reacting with triflic anhydride.

A compound of formula (XXXI) may be prepared by heating a solution of a tetrahydroisoquinoline of formula (XXXII) in xylenes with palladium on carbon.

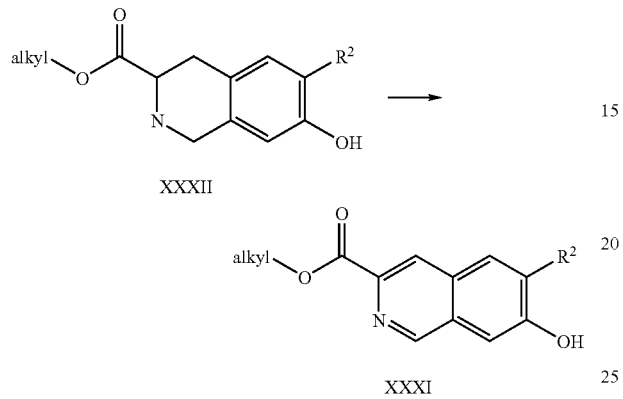

XXXII

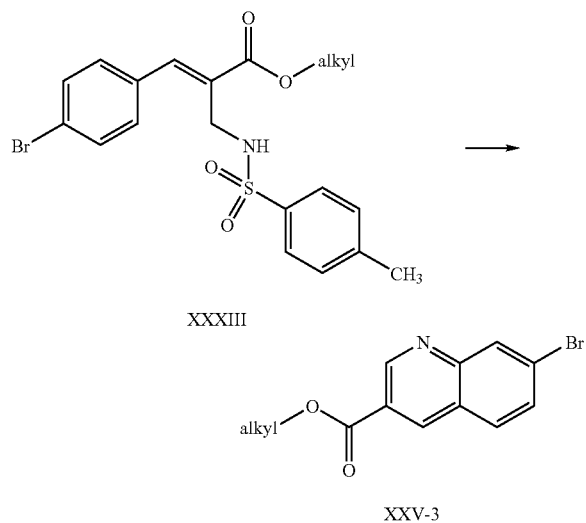

XXXI

A tetrahydroquinoline of formula (XXXII) may be made according to the procedure of K. Verschueren et al., 1992 Synthesis 458-460.

A quinoline compound of formula (XXV) wherein $Y^1$ is N, $Y^2$ is CH, $Y^3$ is C—$R^1$ where $R^1$ is —$CO_2$alkyl, $Y^4$ is CH and $R^2$ is H (i.e., formula XXV-3) may be prepared by the steps of:
a) reacting a sulfonamide compound of formula (XXXIII) with bis(acetyloxy)(phenyl)-$\lambda^3$-iodane and iodine; and
b) reacting the resulting intermediate with a base, such as potassium carbonate.

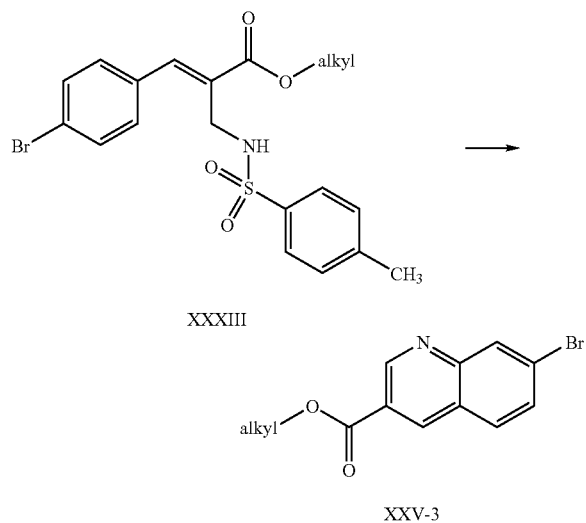

Both reaction steps may be carried out at elevated temperatures and in solvent such as dimethyl formamide.

An aminoester compound of formula (XXXIII) may be prepared by the steps of:
a) reacting a compound of formula (XXXIV) with acetylchloride and a base, to prepare a diester compound of formula (XXXV); and
b) reacting the compound of formula (XXXV) with 4-methylbenzenesulfonamide and a base.

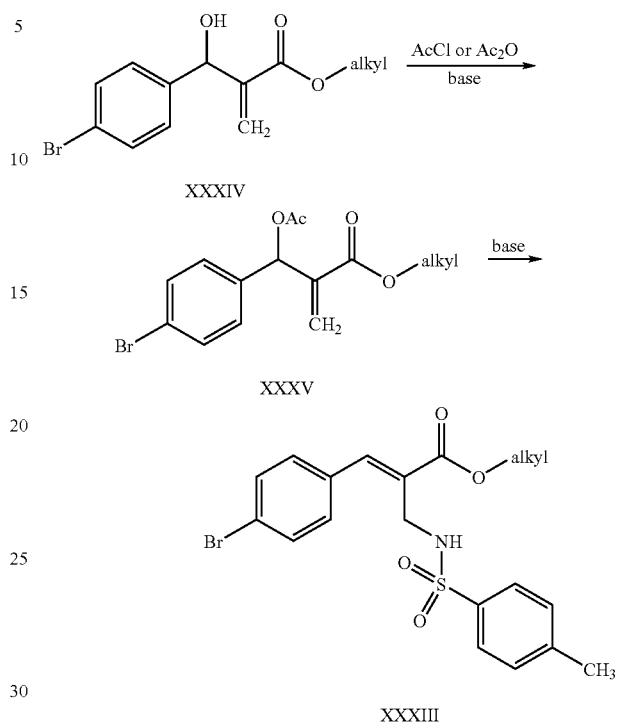

wherein Ac refers to acetyl.

Suitable bases for the step (a) of reacting the compound of formula XXXIV with acetyl chloride or acetate include but are not limited to triethylamine or pyridine.

The step of reacting the compound of formula XXXV with methylbenzenesulfonamide may be carried out in a suitable solvent, such as dimethylformamide with heating. Suitable bases for this reaction include but are not limited to potassium carbonate, sodium carbonate, or cesium carbonate.

A beta hydroxyester of formula of (XXXIV) may be prepared by reacting an aromatic aldehyde of formula (XXXVI) with methyl acrylate and a base, such as 1,4-diazobicyclo[2.2.2]octane (DABCO).

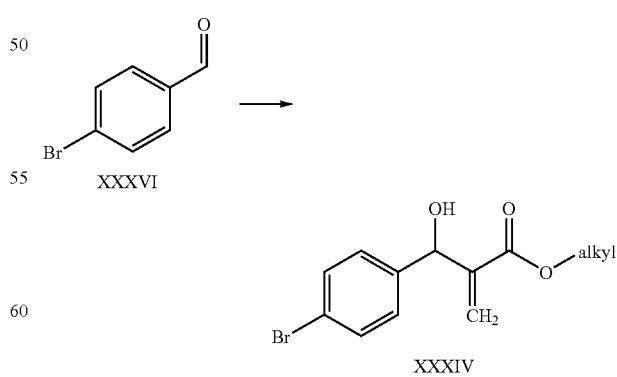

A quinoline compound of formula (XXV) wherein $Y^1$ is N, $Y^2$ and $Y^1$ are CH, $Y^1$ is C—$R^1$ where $R^1$ is —$CO_2$alkyl and $R^2$ is H (i.e., formula XXV-4) may be prepared by the steps of:

a) saponifying a diesaster of formula (XXXVII) with a suitable base to prepare a diacid compound of formula (XXXVIII);
b) heating the compound of formula (XXXVIII) and reesterifying the carboxylic acid to prepare a compound of formula (XXV-4);
c) reesterification of the carboxylic acid with an alcohol and an acid such as sulfuric acid.

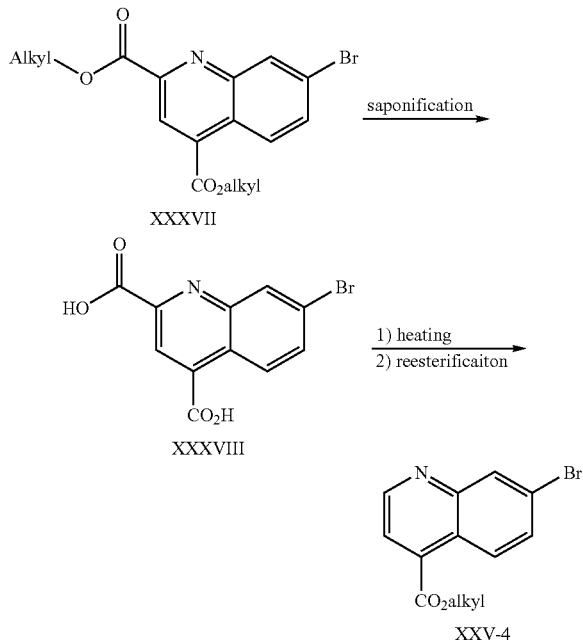

The saponification reaction may be carried out using conventional reaction conditions. Suitable bases for the saponification include but are not limited to sodium hydroxide. The reaction may be carried out at ambient or elevated temperature. The step of decarboxylating the compound of formula (XXXVIII) is typically carried out in diphenyl ether. The re-esterifying reaction is typically carried out in an appropriate alcoholic solvent, such as methanol or ethanol, and an acid such as sulfuric acid.

In another embodiment, a compound of formula (I) may be prepared as depicted in Scheme 2.

Scheme 2

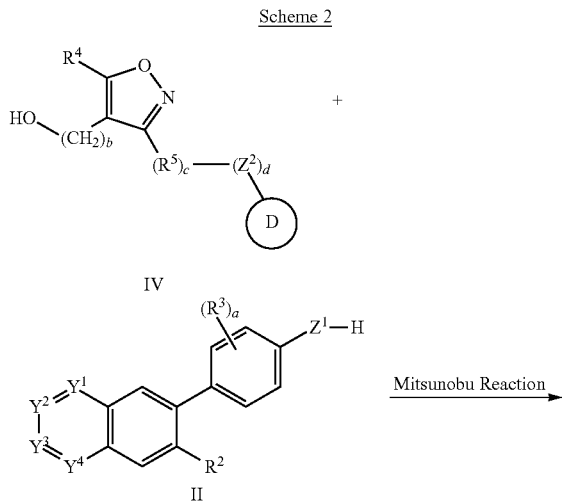

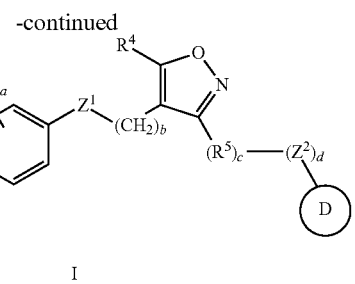

wherein at least one $R^1$ is —$CO_2$alkyl, and all other variables are as defined above.

In general, the process for preparing a compound of formula (I) as depicted in Scheme 2 comprises the steps of:
a) reacting a compound of formula (IV) with a compound of formula (II) under Mitsunobu reaction conditions to prepare a compound of formula (I);
b) optionally converting the compound of formula (I) into a pharmaceutically acceptable salt or solvate thereof, and
c) optionally converting the compound of formula (I) or a pharmaceutically acceptable salt or solvate thereof into a different compound of formula (I) or a pharmaceutically acceptable salt or solvate thereof.

More specifically, the compound of formula (I) is prepared by reacting the compound of formula (IV) with a compound of formula (II) under Mitsunobu reaction conditions. For example, a compound of formula (I) can be prepared by the reacting a compound of formula (II) with an alcohol of formula (IV) in a solution of dichloromethane or toluene with triphenyl phosphine and a dialkyl azodicarboxylate, such as diisopropyl azodicarboxylate or di-tert-butyl azodicarboxylate. The compound of formula (IV) may be prepared by processes described above.

In another embodiment, a compound of formula (I) wherein at least one $R^1$ is —$CO_2$alkyl; d is 1; $Z^2$ is —O—, —S— and —N(H)—; and Ring D is a moiety of formula i, ii or iii:

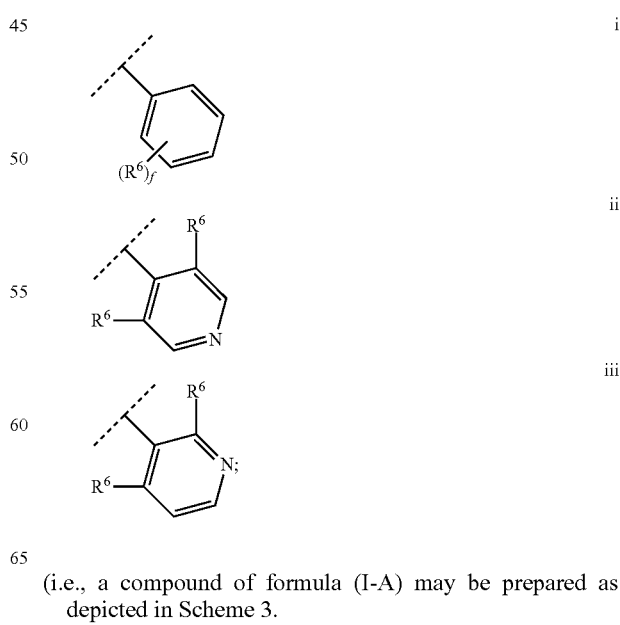

(i.e., a compound of formula (I-A) may be prepared as depicted in Scheme 3.

Scheme 3

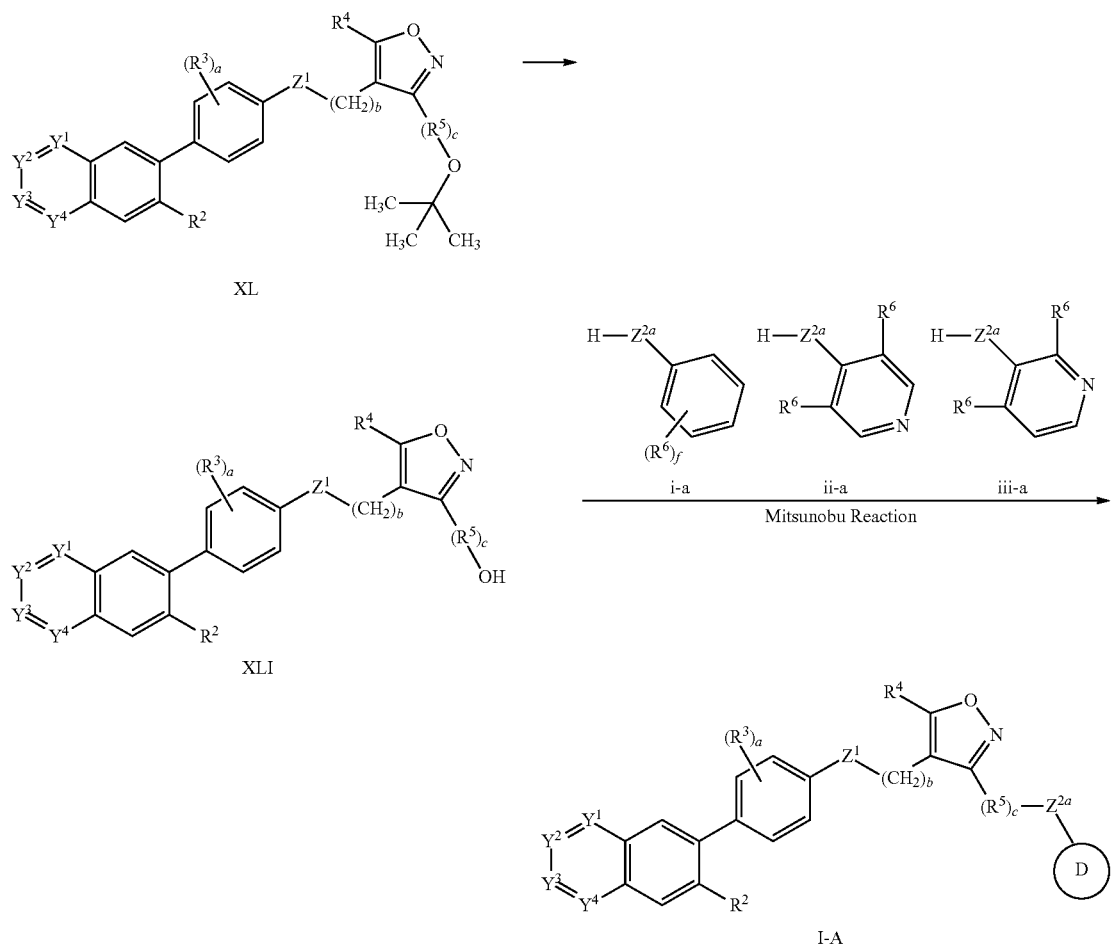

wherein: at least one $R^1$ is —$CO_2$alkyl;
$Z^{2a}$ is selected from —O—, —S—, —N(H)—, and —NC(O)$CF_3$;
Ring D is a moiety of formula i, ii or iii:

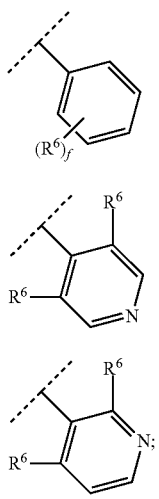

and
all other variables are as defined above.

In general, the process of preparing a compound of formula (I-A) according to Scheme 3 comprises the steps of:
a) reacting a compound of formula (XL) with acid to prepare a compound of formula (XLI);
b) reacting a compound of formula (XLI) under Mitsunobu reaction conditions with a compound of formula i-a, ii-a, or iii-a to prepare a compound of formula (I-A);
c) optionally converting the compound of formula (I-A) into a pharmaceutically acceptable salt or solvate thereof, and
d) optionally converting the compound of formula (I-A) or a pharmaceutically acceptable salt or solvate thereof into a different compound of formula (I) or a pharmaceutically acceptable salt or solvate thereof.

More specifically, a compound of formula (XL) may be prepared by reacting the compound of formula (XL) with an acid. The reaction may be carried out in a solvent, such as dichloromethane or 1,2-dichloroethane. Suitable acids for use in this reaction will be apparent to those skilled in the art and include, but are not limited to trifluoroacetic acid. The resulting alcohol compound of formula (XLI) may be reacted with a suitable Ring D moiety of formula of i-a, ii-a, or iii-a under conventional Mitsunobu reaction conditions. For example, this reaction may be carried out in a solvent, such as dichloromethane or toluene, with triphenyl phosphine and a dialkyl azodicarboxylate like diisopropyl azodicarboxylate or di-tert-butyl azodicarboxylate to prepare a compound of formula (I-A).

Upon hydrolysis of the ester to the acid the trifluoroacetamide may be hydrolysed to the corresponding amine and trifluoroacetic acid.

Compounds of formula (I) wherein d is 1 and $Z^2$ is —SO— or —$SO_2$— may be prepared by oxidizing a compound of formula (I-A) using a conventional oxidant, such as 3-chloroperbenzoic acid.

As another example, a compound of formula (I-A) may be prepared as depicted in Scheme 3a.

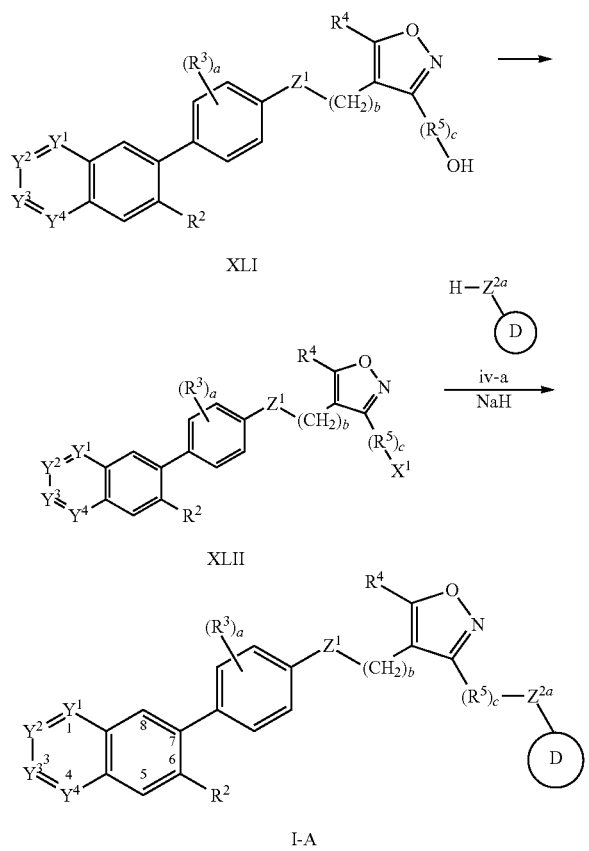

wherein:
$X^1$ is chloride, iodide, bromide, triflate, tosylate, nosylate, besylate or mesylate, (preferably chloride);
each $R^1$ is the same or different and is independently selected from alkyl, fluoroalkyl or —$CO_2$alkyl; wherein at least one $R^1$ is —$CO_2$alkyl;
c is 1; and
all other variables are as defined above.

In general, the process of preparing a compound of formula (I-A) according to Scheme 3a comprises the steps of:
a) reacting a compound of formula (XLI) with a suitable reagent to convert the alcohol to a leaving group, to prepare a compound of formula (XLII);
b) reacting a compound of formula (XLII) with a suitable Ring D moiety of formula iv-a in the presence of sodium hydride;
c) optionally converting the compound of formula (I-A) into a pharmaceutically acceptable salt or solvate thereof, and
d) optionally converting the compound of formula (I-A) or a pharmaceutically acceptable salt or solvate thereof into a different compound of formula (I) or a pharmaceutically acceptable salt or solvate thereof.

More specifically, a compound of formula (XLII) may be prepared by converting the alcohol compound of formula (XLI) into a leaving group, $X^1$ using conventional techniques. For example, a solution of the compound of formula (XLI) in a solvent, such as dichloromethane, may be reacted with a carbon tetrahalide, such as carbon tetrabromide, followed by triphenylphosphine to provide a compound of formula (XLII) wherein $X^1$ is chloride, iodide, or bromide. As another example, a solution of the compound of formula (XLI) may be reacted with sulfonylchloride and a suitable base, such as pyridine, to provide a compound of formula (XLII) wherein $X^1$ is triflate, tosylate, nosylate, besylate or mesylate. Typically, the Ring D moiety is pretreated with a base such as sodium hydride then reacted with a compound of formula (XLII) to prepare the corresponding ether. The reaction of the compound of formula (XLII) with the Ring D moiety may be carried out in a solvent such as tetrahydrofuran.

In another embodiment, a compound of formula (I) may be prepared as depicted in Scheme 4.

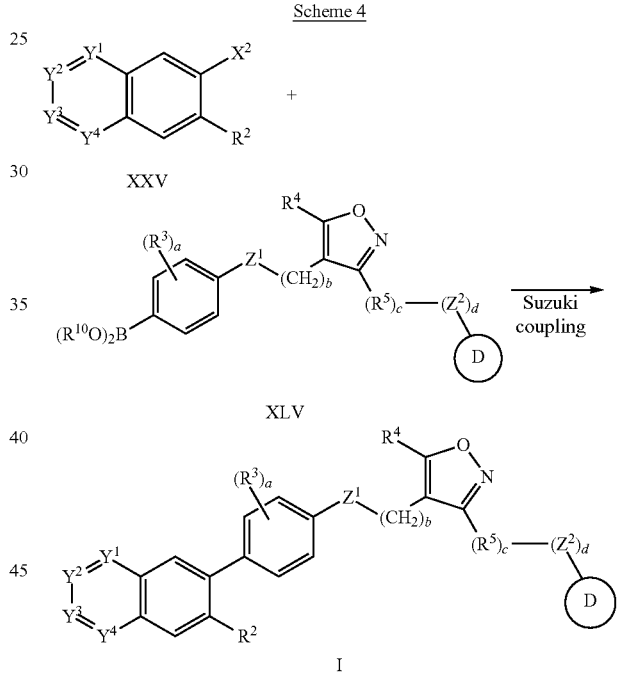

wherein:
at least one $R^1$ is —$CO_2$alkyl;
$R^{10}$ is H or alkyl; and
all other variables are as defined above.

In general, the process of Scheme 4 comprises the steps of:
a) reacting a compound of formula (XXV) with a boronic acid or ester compound of formula (XLV) under Suzuki coupling conditions to prepare a compound of formula (I);
b) optionally converting the compound of formula (I) into a pharmaceutically acceptable salt or solvate thereof, and
c) optionally converting the compound of formula (I) or a pharmaceutically acceptable salt or solvate thereof into a different compound of formula (I) or a pharmaceutically acceptable salt or solvate thereof.

More specifically, a compound of formula (I) may prepared reacting a compound of formula (XXV) with a compound of formula (XLV) under conventional Suzuki coupling reaction conditions. For example, the reaction may be carried out in the presence of a suitable palladium complex such as tetrakis (triphenylphosphine)-palladium(0) and a base such as sodium carbonate in a mixture of water and ethereal solvent such as 1,2-dimethoxyethane, at an elevated temperature. A compound of formula (XXV) may be prepared as described above.

A compound of formula (XLV) may be prepared by reacting a compound of formula (XXVI) with a compound of formula (III) in the presence of a base such as cesium carbonate or potassium carbonate. The reaction may be carried out in a polar aprotic solvent, such as N,N-dimethylformamide.

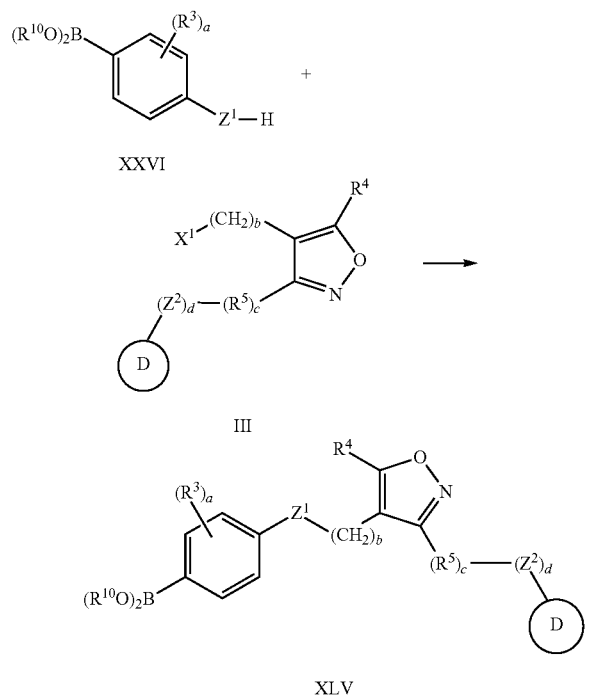

wherein:
$X^1$ is chloro, iodo, bromo, triflate, tosylate, nosylate, besylate or mesylate, (preferably chloro);
each $R^1$ is the same or different and is independently selected from alkyl, fluoroalkyl or —$CO_2$alkyl; wherein at least one $R^1$ is —$CO_2$alkyl; and
all other variables are as defined above.

The boronic ester of formula (XLV) wherein $R^{10}$ is alkyl, may optionally be hydrolyzed to the corresponding boronic acid if desired. A compound of formula (XXVI) may be synthesized by techniques known to those skilled in the art or purchased commercially. A compound of formula (III) may be prepared as described above.

According to one method, a compound of formula (I) may be prepared using the process depicted in Scheme 5, below.

Scheme 5

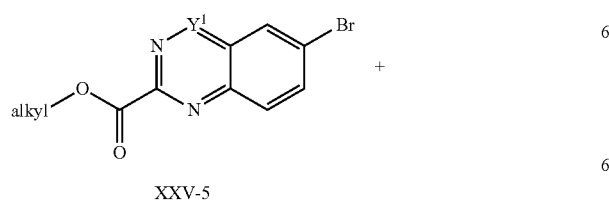

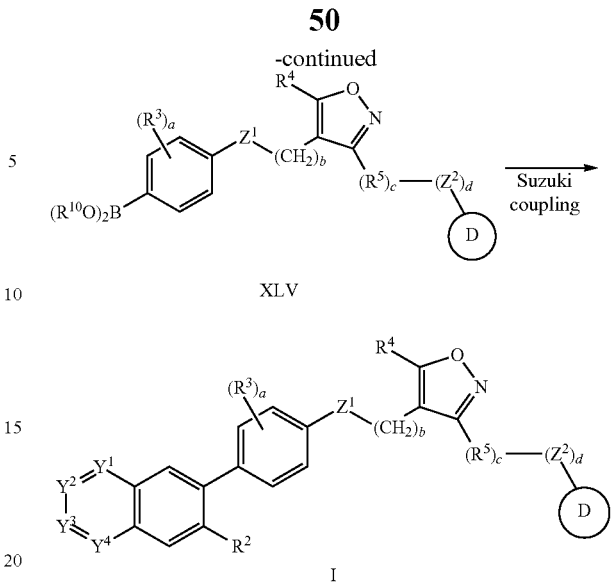

wherein:
at least one $R^1$ is $C_{1-6}$alkyl or fluoroalkyl;
$R^{10}$ is H or alkyl;
$Y^2$ is N;
$Y^4$ is N; and
all other variables are as defined above.

In general, the process of Scheme 5 comprises the steps of:
a) reacting a compound of formula (XXV-5) with a boronic acid or ester compound of formula (XLV) under Suzuki coupling conditions to prepare a compound of formula (I);
b) optionally converting the compound of formula (I) into a pharmaceutically acceptable salt or solvate thereof; and
c) optionally converting the compound of formula (I) or a pharmaceutically acceptable salt or solvate thereof into a different compound of formula (I) or a pharmaceutically acceptable salt or solvate thereof.

More specifically, a compound of formula (I) may be prepared by reacting a compound of formula (XXV-5) with a compound of formula (XLV) under conventional Suzuki coupling reaction conditions. For example, the reaction may be carried out in the presence of a suitable palladium complex such as tetrakis(triphenylphosphine)-palladium (0) and a base such as sodium carbonate in a mixture of water and ethereal solvent such as 1,2-dimethoxyethane, at an elevated temperature. A compound of formula (XLV) may be prepared as described above.

A compound of formula (XXV-5) may be prepared by cyclizing a compound of formula (LII) with a source of ammonia in acid, such as ammonium acetate in acetic acid, at elevated temperatures.

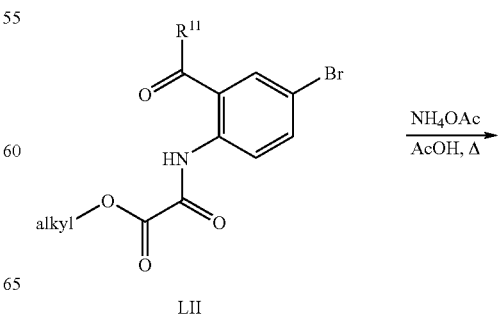

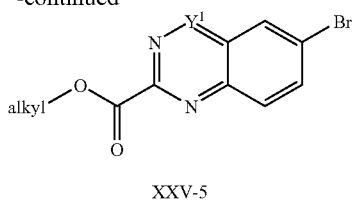

XXV-5 wherein:
$R^{11}$ is selected from $C_{1-6}$alkyl or fluoroalkyl;
all other variables are as defined above.

A compound of formula (LII) may be prepared by reacting an alkyl chlorooxoacetate of formula (L), like ethyl chlorooxoacetate, with an aniline of formula (LI) in the presence of a base like pyridine. Alkyl chlorooxoacetates of formula (L) are commercially available. Anilines of formula (LI) can be made according to techniques well known in the art.

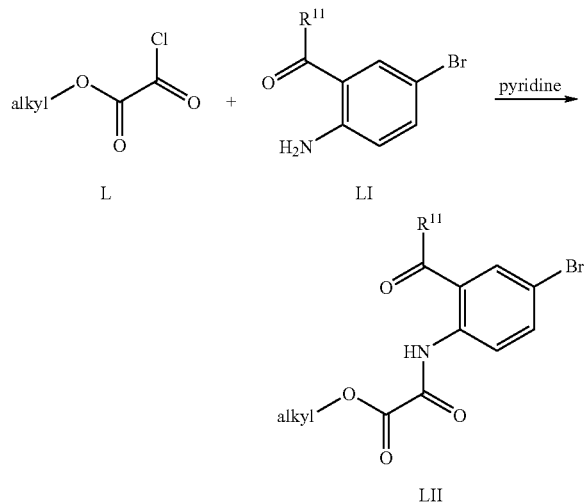

wherein:
$R^{11}$ is a selected from H, alkyl, fluoroalkyl, —$CO_2H$ and —$CO_2$alkyl;
all other variables are as defined above.

According to one method, a compound of formula (I) may be prepared using the process depicted in Scheme 6, below.

Scheme 6

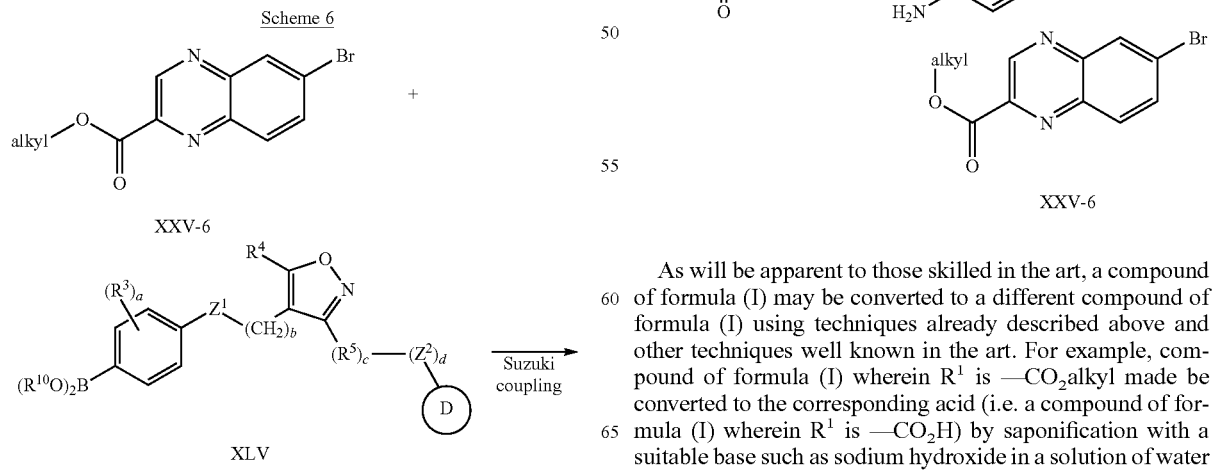

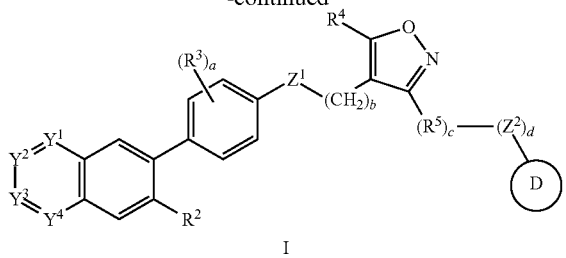

I wherein:
$R^{10}$ is H or alkyl;
$Y^1$ is N;
$Y^2$ is CH;
$Y^4$ is N; and
all other variables are as defined above.

In general, the process of Scheme 6 comprises the steps of:
a) reacting a compound of formula (XXV-6) with a boronic acid or ester compound of formula (XLV) under Suzuki coupling conditions to prepare a compound of formula (I);
b) optionally converting the compound of formula (I) into a pharmaceutically acceptable salt or solvate thereof, and
c) optionally converting the compound of formula (I) or a pharmaceutically acceptable salt or solvate thereof into a different compound of formula (I) or a pharmaceutically acceptable salt or solvate thereof.

More specifically, a compound of formula (I) may be prepared by reacting a compound of formula (XXV-6) with a compound of formula (XLV) under conventional Suzuki coupling reaction conditions. For example, the reaction may be carried out in the presence of a suitable palladium complex such as tetrakis(triphenylphosphine)-palladium(0) and a base such as sodium carbonate in a mixture of water and ethereal solvent such as 1,2-dimethoxyethane, at an elevated temperature.

A compound of formula (XLV) may be prepared as described above.

A compound of formula (XXV-6) may be prepared by reacting 4-bromo-o-phenylenediamine with an alkylbromopyruvate in a solvent like 1-methyl-2-pyrrolidinone.

As will be apparent to those skilled in the art, a compound of formula (I) may be converted to a different compound of formula (I) using techniques already described above and other techniques well known in the art. For example, compound of formula (I) wherein $R^1$ is —$CO_2$alkyl made be converted to the corresponding acid (i.e. a compound of formula (I) wherein $R^1$ is —$CO_2H$) by saponification with a suitable base such as sodium hydroxide in a solution of water and tetrahydrofuran and optionally an alcoholic co-solvent.

A compound of formula (I) wherein R¹ is CO₂H (1-B) may be reacted with an amine to prepare the corresponding amide (i.e. a compound of formula (I) wherein R¹ is —C(O)NH₂, hereinafter a compound of formula (I-C)). This reaction may be carried out using conventional techniques. For example, a compound of formula (I-B) may be reacted with di-tert-butyl dicarbonate in acetonitrile with a base such as pyridine then ammonium hydrogen carbonate to produce a compound of formula (I-C). See, C. D. Haffner, et al., US2004/0171848.

A compound of formula (I-C) may be dehydrated to prepare a corresponding nitrile. This reaction may be carried out using conventional amide dehydration techniques. For example, a compound of formula (I-C) may be dehydrated with phosphorous oxychloride in a solution of methylene chloride and a suitable base such as triethylamine to prepare the corresponding nitrile analogue of the compound of formula (I). (Uiterweerd, P. G. H., et al., 2003 Tetrahedron: Asymmetry, 14:3479-3485). The nitrile analogue of the compound of formula (I) may be condensed with sodium azide to prepare the corresponding tetrazole (i.e. a compound of formula (I) wherein R¹ is the acid-equivalent group tetrazole; hereinafter a compound of formula (I-D)). This reaction may be carried out using conventional techniques. For example, a compound of formula (I-D) may be prepared by reacting the nitrile analogue of the compound of formula (I) with sodium azide in the presence of ammonium chloride in a polar aprotic solvent such as N,N-dimethylformamide at an elevated temperature. (Meyer, E., et al., 2003 Synthesis 899-905). Other techniques for converting the nitrile analogue of the compound of formula (I) into compounds of formula (I) wherein R¹ is the acid-equivalent group are known in the art. See, Ellingboe, J. W., et al., 1993 J. Med. Chem. 36:2485-2493 and Weller, H. N., et al., 1993 Heterocycles 36:1027-1038.

Based upon these examples and the disclosure contained herein one skilled in the art can readily convert compounds of formula (I) into other compounds of formula (I), or salts or solvates thereof.

The following examples are intended for illustration only and are not intended to limit the scope of the invention in any way, the present invention being defined by the claims.

In the examples, the following terms have the designated meaning:
Å =angstrom
g=gram;
mg=milligram;
mol=mole;
mmol=millimole;
M=molar;
N=normal;
L=liter;
mL=milliliter;
μL=microliter;
hr=hour;
min=minute;
aq=aqueous;
wt %=(weight percent)
CH₂Cl₂=dichloromethane;
DMF=N,N-dimethylformamide;
DMSO=dimethylsulfoxide;
DTT=dithiothreitol
EtOAc=ethyl acetate;
EtOH=ethanol
HCl=hydrogen chloride;
H₂O=water;
K₂CO₃=potassium carbonate;
K₃PO₄=potassium phosphate
MeOH=methanol
MgSO₄=magnesium sulfate;
N₂=nitrogen;
Na₂CO₃=sodium carbonate;
NaF=sodium fluoride
NaHCO₃=sodium hydrogen carbonate;
NaOH=sodium hydroxide;
Na₂SO₄=sodium sulfate;
P₂O₅=phosphorus pentoxide;
SiO₂=silicon dioxide;
TEA=triethylamine
THF=tetrahydrofuran;
NMR=nuclear magnetic resonance;
H=Hydrogen;
Hz=hertz; MHz=megahertz
OD=optical density;
HPLC=high performance liquid chromatography;
APCI-LCMS=Atmospheric Pressure Chemical Ionization— Liquid Chromatography
Mass Spectrometry; ESI-LCMS=Electrospray Ionization— Liquid Chromatography
Mass Spectrometry; HRMS=High Resolution Mass Spectrometry.

EXAMPLE 1

6-[4-({[3-(2,6-Dichlorophenyl)-5-(1-methylethyl)-4-isoxazolyl]methyl}oxy)phenyl]-2-quinolinecarboxylic Acid

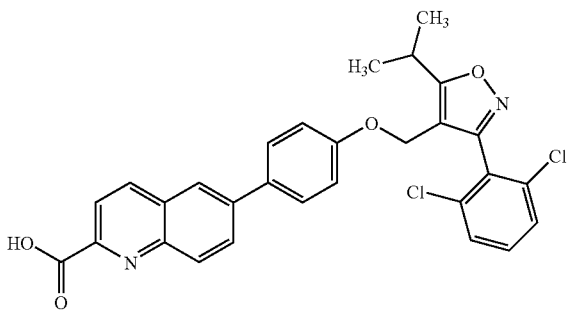

1a) 6-Bromo-2-(tribromomethyl)quinoline

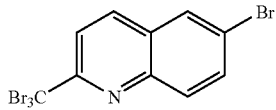

A suspension of 6-bromo-2-methylquinoline (175 g, 0.79 mol) and sodium acetate (350 g, 4.3 mol) in acetic acid (1.5 L) was stirred and heated in a 75° C. bath until a solution formed. A solution of bromine (132 mL, 2.6 mol) in acetic acid (350 mL) was added over 15 min during which time the reaction temperature rose to 86° C. The resulting suspension was heated at 120° C. for 1 hr. The suspension was cooled to 80° C. and added to ice-water (6 L) with stirring. The resulting white solid was collected by filtration, washed with water (2×1 L) and air dried to give 6-bromo-2-(tribromomethyl) quinoline (350 g, 95%). ¹H NMR (400 MHz, DMSO-d₆): δ

8.54 (d, J=9 Hz, 1H), 8.40 (d, J=2 Hz, 1H), 8.31 (d, J=9 Hz, 1H), 8.00 (m, 2H). ES-LCMS m/z 459 (M+H)⁺.

1b) 6-Bromo-2-quinolinecarboxylic Acid

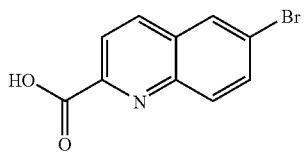

Concentrated sulfuric acid (0.75 L) was added during 15 min to a stirred suspension of 6-bromo-2-(tribromomethyl)quinoline (350 g, 0.76 mol) in water (1.75 L). The resulting suspension was heated at 150° C. (bath temperature) for 5 hr. The mixture was cooled and the precipitate was collected by filtration, washed with water and dried to give 6-bromo-2-quinolinecarboxylic acid as a solid (127.6 g). The filtrate was diluted with water (3 L) and a second crop of the product was obtained (55.7 g, combined yield 183.3 g, 96%). $^1$H NMR (400 MHz, DMSO-$d_6$): δ8.50 (d, J=9 Hz, 1H), 8.38 (d, J=2 Hz, 1H), 8.13 (d, J=9 Hz, 1H), 8.06 (d, J=9 Hz, 1H), 7.96 (m, 1H). ES-LCMS m/z 253 (M+H)⁺.

1c) Methyl 6-bromo-2-quinolinecarboxylate

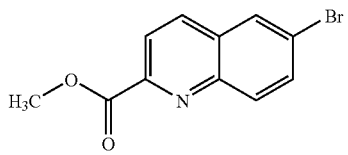

A mixture of 6-bromo-2-quinolinecarboxylic acid (331 g, from multiple batches, 1.31 mol) and methanesulfonic acid (22 mL, 33 g, 0.34 mol) in methanol (2 L) was refluxed for 6 hr. The mixture was treated with a solution of sodium bicarbonate (29 g, 0.34 mol) in water (350 mL) and the resulting suspension was slowly cooled to 20° C. and stirred overnight. The suspension was filtered and the cake was washed with water (1 L). The solid was dried in a vacuum oven at 50° C. for 3 days to yield methyl 6-bromo-2-quinolinecarboxylate (294 g, 85%). $^1$H NMR (400 MHz, DMSO-$d_6$) δ 8.52 (d, J=9 Hz, 1H), 8.40 (d, J=2 Hz, 1H), 8.14 (d, J=9 Hz, 1H), 8.08 (d, J=9 Hz, 1H), 7.97 (m, 1H), 3.93 (s, 3H). ES-LCMS m/z 267 (M+H)⁺.

1d) Methyl 6-(4-Hydroxyphenyl)-2-quinolinecarboxylate

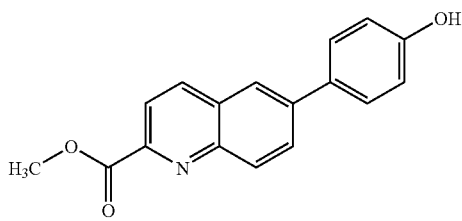

A stirred mixture of methyl 6-bromo-2-quinolinecarboxylate (297 g, from multiple batches, 1.11 mol), 4-hydroxybenzeneboronic acid (184 g, 1.33 mol), 2 M $K_3PO_4$ (1.8 L) and tetrakistriphenylphosphine palladium(0) (51.3 g, 0.04 mol) in 1,2-dimethoxyethane (1.8 L) was heated to 79° C. A solution formed and the reaction was complete. The mixture was cooled to 45° C., diluted with water (1.8 L), cooled to 15° C. and held at this temperature for 30 minutes then filtered. The filter cake was washed with methanol (4×2 L) to yield methyl 6-(4-hydroxyenyl)-2-quinolinecarboxylate (83 g). HPLC analysis showed that much of the ester was hydrolyzed. The mixture was acidified to pH 3 by adding 6 N HCl and the resulting precipitate was collected by filtering, washed with water and dried at 45° C. in a vacuum oven to yield mostly 6-(4-hydroxyphenyl)-2-quinolinecarboxylic acid (116.3 g). The methanol wash was concentrated, azetroped with toluene and dried under vacuum to yield the acid phenol (178.5 g). This material was re-esterified by refluxing with methanesulfonic acid (71 mL, 105.7 g, 1.1 mol) in methanol (1.8 L) for 22 hours. The mixture was cooled to room temperature, diluted with water (5 L) and basified to pH 8 by adding $NaHCO_3$ solution. The resulting suspension was filtered and the filter cake was dried at 50° C. in a vacuum oven to yield methyl 6-(4-hydroxyphenyl)-2-quinolinecarboxylate (222.3 g, combined yield 305 g, 98%). $^1$H NMR (400 MHz, DMSO-$d_6$): δ 9.75 (br s, 1H), 8.53 (d, J=9 Hz, 1H), 8.25 (s, 1H), 8.11 (m, 3H), 7.69 (d, J=9 Hz, 2H), 6.90 (d, J=9 Hz, 2H), 3.93 (s, 3H). ES-LCMS m/z 280 (M+H)⁺.

1e) 4-(Chloromethyl)-3-(2,6-dichlorophenyl)-5-(1-methylethyl)isoxazole

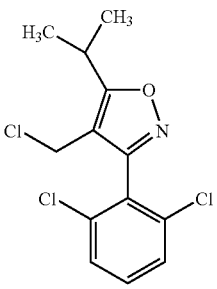

Thionyl chloride (123 mL, 202 g, 1.7 mol) was added dropwise during 30 min to a stirred suspension of benzotriazole (202 g, 1.7 mol) in dichloromethane (550 mL) at room temperature under $N_2$. The resulting yellow solution was transferred to an addition funnel and added dropwise during 1 hour to a stirred solution of [3-(2,6-dichlorophenyl)-5-(1-methylethyl)-4-isoxazolyl]methanol (372 g, 1.3 mol, Maloney, P. R., et al., 2000 J. Med. Chem. 43:2971-2974) in dichloromethane (975 mL). The reaction temperature gradually rose to a maximum of 28° C. After 1 hr the resulting suspension was filtered to remove the benzotriazole hydrochloride. The filtrate was washed with water (2×1 L), with 1 N NaOH (1 L), with water (1 L), dried over anhydrous $Na_2SO_4$, filtered and concentrated to yield 4-(chloromethyl)-3-(2,6-dichlorophenyl)-5-(1-methylethyl)isoxazole as a pale yellow oil (413 g, 80%). $^1$H NMR (400 MHz, DMSO-$d_6$): δ7.64 (m, 3H), 4.47 (s, 2H), 3.45 (m, 1H), 1.31 (d, J=7 Hz, 6H). ES-LCMS m/z 305 (M+H)⁺.

1f) Methyl 6-[4-({[3-(2,6-Dichlorophenyl)-5-(1-methylethyl)-4-isoxazolyl]methyl}oxy)phenyl]-2-quinolinecarboxylate

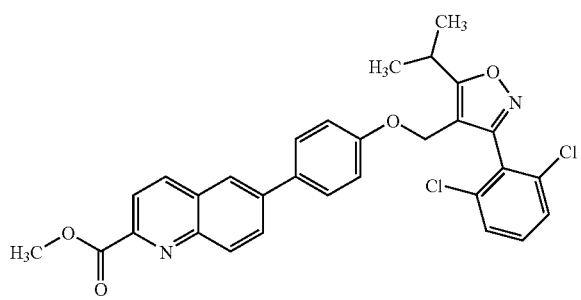

A mixture of methyl 6-(4-hydroxyphenyl)-2-quinolinecarboxylate (222 g, 0.8 mol), 4-(chloromethyl)-3-(2,6-dichlorophenyl)-5-(1-methylethyl)isoxazole (292 g, 0.96 mol) and cesium carbonate (312 g, 0.96 mol) in DMF (1.5 L) was heated at 65° C. for 28 hours. Additional 4-(chloromethyl)-3-(2,6-dichlorophenyl)-5-(1-methylethyl)isoxazole (105 g, 0.34 mol) dissolved in DMF (150 mL) was added. The mixture was cooled to room temperature and poured into water (5 L) with stirring. The resulting taffy was separated from the supernatant and stirred with ethyl acetate (2.5 L) for 3 hours at room temperature. The resulting suspension was filtered and the filter cake was dried to yield methyl 6-[4-({[3-(2,6-dichlorophenyl)-5-(1-methylethyl)-4-isoxazolyl]methyl}oxy)phenyl]-2-quinolinecarboxylate as a solid (245 g, 56%). $^1$H NMR (400 MHz, DMSO-d$_6$): δ 8.54 (d, J=9 Hz, 1H), 8.28 (d, J=1 Hz, 1H), 8.11 (m, 3H), 7.72 (d, J=9 Hz, 2H), 7.62 (d, J=8 Hz, 2H), 7.53 (m, 1H), 6.93 (d, J=9 Hz, 2H), 4.88 (s, 2H), 3.93 (s, 3H), 3.47 (m, 1H), 1.33 (d, J=7 Hz, 6H). ES-LCMS m/z 547 (M+H)$^+$.

1 g) 6-[4-({[3-(2,6-Dichlorophenyl)-5-(1-methylethyl)-4-isoxazolyl]methyl}oxy)phenyl]-2-quinolinecarboxylic acid

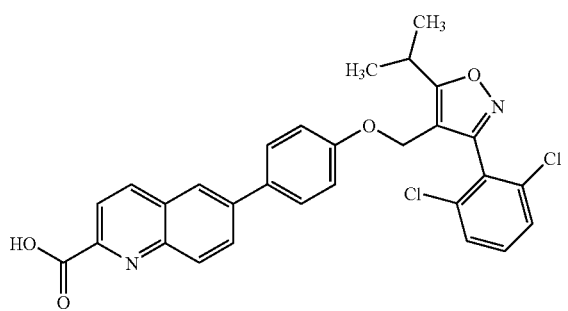

A stirred mixture of methyl 6-[4-({[3-(2,6-dichlorophenyl)-5-(1-methylethyl)-4-isoxazolyl]methyl}oxy)phenyl]-2-quinolinecarboxylate (245 g, 0.45 mol), NaOH (36 g, 0.90 mol) dissolved in water (225 mL), methanol (0.5 L) and THF (1.2 L) was heated at 65° C. for 90 min. The mixture was cooled to room temperature, treated with 6 N HCl (150 mL) and stirred at room temperature for 30 min. The resulting precipitate was collected by filtering, washed with water (2×1 L) and dried overnight at 45° C. in a vacuum oven to yield 6-[4-({[3-(2,6-dichlorophenyl)-5-(1-methylethyl)-4-isoxazolyl]methyl}oxy)phenyl]-2-quinolinecarboxylic acid (162 g, 68%). A second crop of material was similarly obtained (27.2 g, 11%). $^1$H NMR (400 MHz, DMSO-d$_6$): δ8.48 (d, J=9 Hz, 1H), 8.24 (d, J=2 Hz, 1H), 8.17 (d, J=9 Hz, 1H), 8.09 (d, J=9 Hz, 2H), 7.72 (d, J=9 Hz, 2H), 7.62 (d, J=8 Hz, 2H), 7.53 (m, 1H), 6.92 (d, J=9 Hz, 2H), 4.88 (s, 2H), 3.46 (m, 1H), 1.32 (d, J=7 Hz, 6H). ES-LCMS m/z 533 (M+H)$^+$.

1 h) Potassium 6-[4-({[3-(2,6-Dichlorophenyl)-5-(1-methylethyl)-4-isoxazolyl]methyl}oxy)phenyl]-2-quinolinecarboxylic Acid

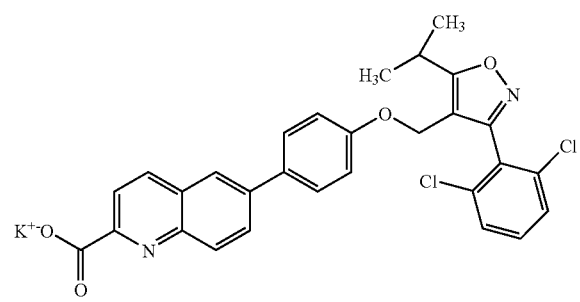

A stirred suspension of 6-[4-({[3-(2,6-dichlorophenyl)-5-(1-methylethyl)-4-isoxazolyl]methyl}oxy)phenyl]-2-quinolinecarboxylic acid (179 g, 0.335 mol) in ethanol (2.6 L) was treated with 1 N potassium tert-butoxide in tert-butyl alcohol (350 mL) and stirred at room temperature under N$_2$ for 1 hour. The mixture was then heated to a gentle reflux for 2 hours and was stirred overnight at room temperature. The suspension was filtered, then the filter cake was washed with hexane, combined with 5 g of similarly prepared material and dried at 60° C. in a vacuum oven overnight to yield 6-[4-({[3-(2,6-dichlorophenyl)-5-(1-methylethyl)-4-isoxazolyl]methyl}oxy)phenyl]-2-quinolinecarboxylic acid potassium salt as a beige solid (181 g, 84%). $^1$H NMR (400 MHz, DMSO-d$_6$): δ8.25 (d, J=9 Hz, 1H), 8.18 (d, J=9 Hz, 1H), 8.08 (d, J=2 Hz, 1H), 8.02 (d, J=8 Hz, 1H), 7.94 (dd, J=2, 9 Hz, 1H), 7.68 (d, J=9 Hz, 2H), 7.62 (d, J=8 Hz, 2H), 7.53 (dd, J=7, 9 Hz, 1H), 6.90 (d, J=9 Hz, 2H), 4.86 (s, 2H), 3.46 (m, 1H), 1.32 (d, J=7 Hz, 6H). ES-LCMS m/z 533 (M+H)$^+$.

Anal. calcd. for C$_{29}$H$_{21}$Cl$_2$KN$_2$O$_4$.0.25 KCl: C, 59.02; H, 3.59; Cl, 13.52; N, 4.75.

Found: C, 58.94; H, 3.62; Cl, 13.28; N, 4.74.

1i) Sodium 6-[4-({[3-(2,6-dichlorophenyl)-5-(1-methylethyl)-4-isoxazolyl]methyl}oxy)phenyl]-2-quinolinecarboxylate

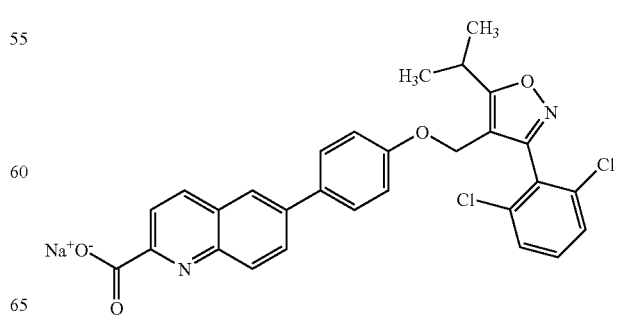

To a stirring suspension of 6-[4-({[3-(2,6-dichlorophenyl)-5-(1-methylethyl)-4-isoxazolyl]methyl}oxy)phenyl]-2-quinolinecarboxylic acid (4.12 g, 7.73 mmol) in methanol (100 mL) was added 1 N sodium hydroxide (7.73 mL, 7.73 mmol). The mixture was stirred for approximately 1 hour and then concentrated. Ether was added followed by a little water. After stirring the solid turned into a paste. The solvent was decanted and the paste triturated with ether and then dried on a rotary evaporator at 35° C. under vacuum for approximately 1.5 hours to afford sodium 6-[4-({[3-(2,6-dichlorophenyl)-5-(1-methylethyl)-4-isoxazolyl]methyl}oxy)phenyl]-2-quinolinecarboxylate (4.24 g, 98%). $^1$H-NMR (400 MHz, DMSO-$d_6$) δ 8.28-8.22 (m, 2H), 8.09-7.96 (m, 3H), 7.68 (d, J=9 Hz, 2H), 7.63-7.51 (m, 3H), 6.90 (d, J=9 Hz, 2H), 4.87 (s, 2H), 3.46 (septet, J=7 Hz, 1H), 1.33 (d, J=7 Hz, 6H). LRMS (APCI) $C_{29}H_{21}Cl_2N_2O_4Na$ calculated: 533 (M+H)$^+$, found: 533 (M+H)$^+$.

EXAMPLE 2

7-[4-({[3-(2,6-Dichlorophenyl)-5-(1-methylethyl)-4-isoxazolyl]methyl}oxy)phenyl]-3-quinolinecarboxylic acid

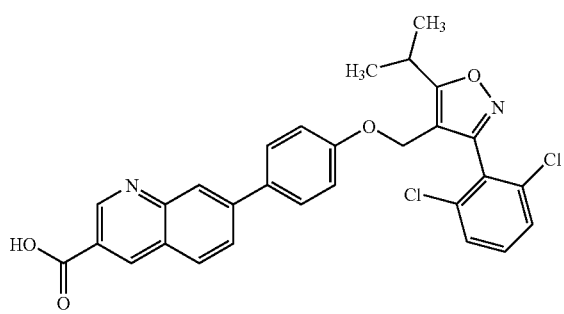

2a) Methyl 2-[(4-bromophenyl)(hydroxy)methyl]-2-propenoate

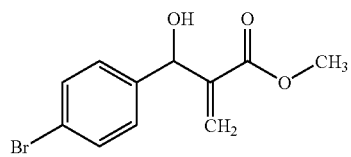

A solution of 2.46 g (13.3 mmol) of 4-bromobenzaldehyde, 1.0 mL (11.1 mmol) of methyl acrylate and 125 mg (1.11 mmol) of 1,4-diazobicyclo[2.2.2]octane in 5 mL MeOH was stirred at ambient temperature for 46 hr. The solvent was evaporated and the residue taken up in EtOAc. The organics were washed with 0.5 N HCl (aq), then with brine, and concentrated. The residue was purified by silica gel chromatography (120 g of silica gel eluting with 0-30% EtOAc in hexanes over 45 minutes) to give 1.42 g (40%) of methyl 2-[(4-bromophenyl)(hydroxy)methyl]-2-propenoate as a clear oil. $^1$H NMR (400 MHz, CDCl$_3$): δ 7.47 (d, J=2 Hz, 2H), 7.27 (d, J=2 Hz, 2H), 6.33 (s, 1H), 5.82 (s, 1H), 5.51 (d, J=5 Hz, 1H), 3.72 (s, 3H), 3.07 (d, J=5 Hz, 1H). ESI-LCMS m/z 293 (M+Na)$^+$.

2b) Methyl (2E)-3-(4-bromophenyl)-2-({[(4-methylphenyl)sulfonyl]amino}methyl)-2-propenoate

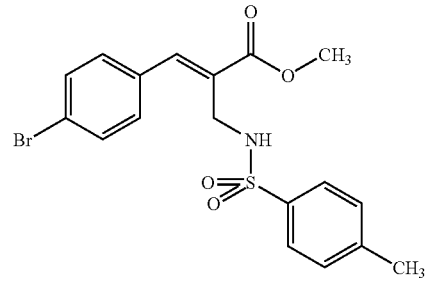

To a solution of 390 μL (5.46 mmol) of acetyl chloride in 10 mL of THF at 0° C. was added 1.41 g (5.20 mmol) of methyl 2-[(4-bromophenyl)(hydroxy)methyl]-2-propenoate and 870 μL (6.24 mmol) of TEA in 10 mL THF. After 2 hr at ambient temperature another 870 μL (6.24 mmol) of TEA and 390 μL (5.46 mmol) of acetyl chloride was added and the solution stirred at ambient temperature for an additional 1 hr. EtOAc was added and the organics washed with three 50 mL portions of H$_2$O then 50 mL of brine. The organics were dried over Na$_2$SO$_4$ then concentrated. This residue was then taken up in 25 mL of DMF and 4.35 g (25.4 mmol) of 4-methylbenzenesulfonamide and 3.51 g (25.4 mmol) of K$_2$CO$_3$ were added. The mixture was stirred at 50° C. for 3 hr. To the mixture was added 100 mL of EtOAc which was then washed with three 50 mL portions of water, then brine. The solution was concentrated and the residue purified by silica gel chromatography (120 g of silica gel eluting with 0-40% EtOAc in hexanes over 45 minutes) to give 820 mg (37%) of methyl (2E)-3-(4-bromophenyl)-2-({[(4-methylphenyl)sulfonyl]amino}methyl)-2-propenoate as a beige glass. $^1$H NMR (400 MHz, CDCl$_3$): δ 7.68-7.66 (m, 3H), 7.52 (d, J=7 Hz, 2H), 7.29-7.25 (m, 4H), 5.51 (t, J =6 Hz, 1H), 3.86 (d, J=6 Hz, 2H), 3.75 (s, 3H), 2.43 (s, 3H). ESI-LCMS m/z 425 (M+H)$^+$.

2c) Methyl 7-bromo-3-quinolinecarboxylate

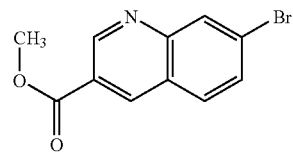

A solution of 820 mg (1.93 mmol) of methyl (2E)-3-(4-bromophenyl)-2-({[(4-methylphenyl)sulfonyl]amino}methyl)-2-propenoate, 995 mg (3.09 mmol) of bis(acetyloxy)(phenyl)-λ$^3$-iodane and 490 mg (1.93 mmol) of iodine in 35 mL of 1,2-dichloroethane were stirred at 70° C. for 30 min. The solvent was evaporated and the residue taken up in 25 mL DMF and 1.07 g (7.73 mmol) of K$_2$CO$_3$ was added. The mixture was stirred at 120° C. for 6 hr. EtOAc was added and the organics were washed with three portions of H$_2$O then brine. The solution was then concentrated and the residue purified by silica gel chromatography (40 g of silica gel eluting with 0-40% EtOAc in hexanes over 45 minutes) to give 80 mg (16%) of methyl 7-bromo-3-quinolinecarboxylate as an off-white solid. $^1$H NMR (400 MHz, CDCl$_3$): δ 9.34 (s, 1H), 8.81 (s, 1H), 8.35 (s, 1H), 7.80 (d, J=9 Hz, 1H), 7.73 (d, J=9 Hz, 1H), 4.02 (s, 3H). ESI-LCMS m/z 267 (M+H)$^+$.

2d) Methyl 7-[4-({[3-(2,6-dichlorophenyl)-5-(1-methylethyl)-4-isoxazolyl]methyl}oxy)phenyl]-3-quinolinecarboxylate

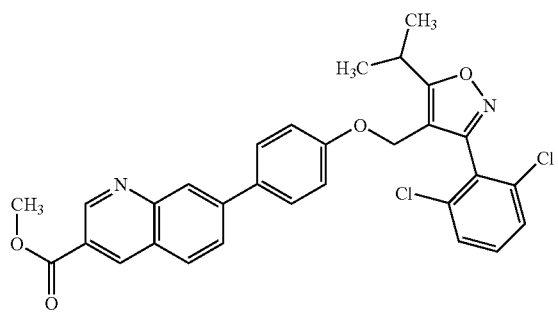

A solution of 78 mg (0.29 mmol) of methyl 7-bromo-3-quinolinecarboxylate, 97 mg (0.44 mmol) of 4-(4,4,5,5-tetramethyl-1,3,2-dioxaborolan-2-yl)phenol, 3 mg (0.01 mmol) of palladium acetate, 8 mg (0.03 mmol) of triphenylphosphine, 218 mg (1.03 mmol) of K$_3$PO$_4$ and 25 µL of H$_2$O in 1.0 mL of dioxane was stirred at 60° C. for 1 hr. EtOAc was added and the organics were washed with water and brine then concentrated. To the residue was added 65 mg (0.21 mmol) of 4-(chloromethyl)-3-(2,6-dichlorophenyl)-5-(1-methylethyl) isoxazole, 74 mg (0.54 mmol) of K$_2$CO$_3$ and 1.5 mL of DMF and the mixture was then stirred at 60° C. for 1 hr. EtOAc was added and the organics were washed with three portions of water, then brine. The solution was concentrated and the residue purified by silica gel chromatography (12 g of silica gel eluting with 0-40% EtOAc in hexanes over 45 minutes) to give 47 mg (30%) of methyl 7-[4-({[3-(2,6-dichlorophenyl)-5-(1-methylethyl)-4-isoxazolyl]methyl}oxy)phenyl]-3-quinolinecarboxylate as a clear glass. $^1$H NMR (400 MHz, CDCl$_3$): δ 9.44 (s, 1H), 8.83 (s, 1H), 8.28 (s, 1H), 7.96 (d, J=9 Hz, 1H), 7.82 (d, J=9 Hz, 1H), 7.64 (d, J=9 Hz, 2H), 7.41 (d, J=8 Hz, 2H), 7.35-7.31 (m, 1H), 6.92 (d, J=9 Hz, 2H), 4.79 (s, 2H), 4.02 (s, 3H), 3.38-3.34 (m, 1H), 1.45 (d, J=7 Hz, 6H). ESI-LCMS m/z 548 (M+H)$^+$.

2e) 7-[4-({[3-(2,6-Dichlorophenyl)-5-(1-methylethyl)-4-isoxazolyl]methyl}oxy)phenyl]-3-quinolinecarboxylic acid

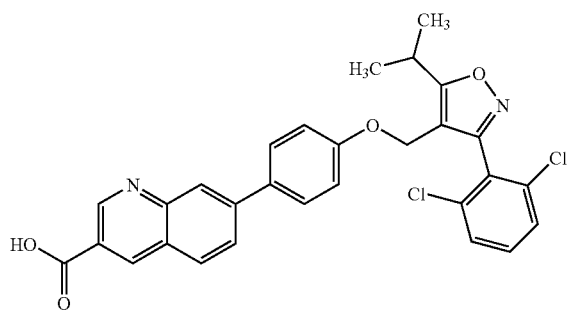

To 47 mg (0.09 mmol) of methyl 7-[4-({[3-(2,6-dichlorophenyl)-5-(1-methylethyl)-4-isoxazolyl]methyl}oxy)phenyl]-3-quinolinecarboxylate in a mixture of 3 mL of EtOH, 1 mL THF and 1 mL H$_2$O was added 35 mg (0.86 mmol) of NaOH and the mixture stirred at 50° C. for 16 hr. The mixture was concentrated to ⅓ volume then added dropwise to a a stirred solution of 10 mL of 0.5 M HCl (aq.). The resulting solids were collected by suction filtration, washed with water then dried to yield 32 mg (70%) of 7-[4-({[3-(2,6-dichlorophenyl)-5-(1-methylethyl)-4-isoxazolyl]methyl}oxy)phenyl]-3-quinolinecarboxylic acid as a yellow solid. $^1$H NMR (400 MHz, DMSO-d$_6$): δ 9.30 (s, 1H), 8.97 (s, 1H), 8.24-8.21 (m, 2H), 7.99 (d, J=8 Hz, 1H), 7.76 (d, J=8 Hz, 2H), 7.63-7.61 (m, 2H), 7.55-7.52 (m, 1H), 6.93 (d, J=9 Hz, 2H), 4.88 (s, 2H), 3.50-3.44 (septet, J =7 Hz, 1H), 1.33 (d, J=7 Hz, 6H). ESI-LCMS m/z 534 (M+H)$^+$.

EXAMPLE 3

7-[4-({[3-(2,6-Dichlorophenyl)-5-(1-methylethyl)-4-isoxazolyl]methyl}oxy)phenyl]-2,4-quinolinedicarboxylic acid

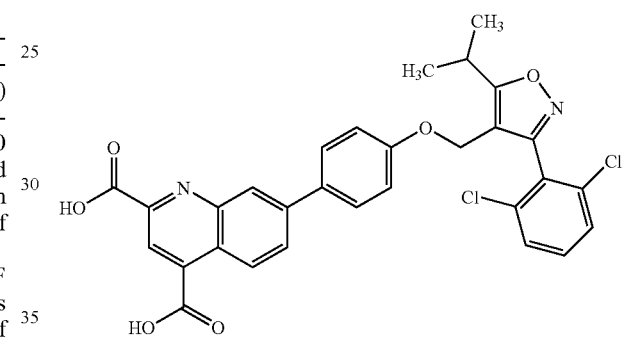

3a) Dimethyl 7-(4-hydroxyphenyl)-2,4-quinolinedicarboxylate

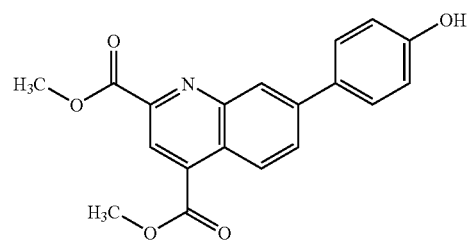

A mixture of 150 mg (0.46 mmol) of dimethyl 7-bromo-2,4-quinolinedicarboxylate synthesized according the procedure of Corey, E. J. and Tramontano, A., 1981 J. Am. Chem. Soc. 103:5599-5600 and Carrigan, C. N., et al, 1999 Bioorg. Med. Chem. Lett. 9:2607-2612, 153 mg (0.69 mmol) of 4-(4,4,5,5-tetramethyl-1,3,2-dioxaborolan-2-yl)phenol, 5 mg (0.02 mmol) of palladium acetate, 12 mg (0.05 mmol) of triphenylphosphine, 345 mg (1.62 mmol) of K$_3$PO$_4$, and 40 µL (2.31 mmol) of H$_2$O in 3 mL of dioxane were stirred at 60° C. for 1.5 hr. EtOAc was then added and the solution washed with H$_2$O. The aqueous layer was extracted with EtOAc and then the combined organics were washed with brine and concentrated. A small amount of cold EtOAc was added to the residue and the solids were collected by suction filtration, washed with cold EtOAc then dried to yield 79 mg (51%) of dimethyl 7-(4-hydroxyphenyl)-2,4-quinolinedicarboxylate as a brown solid. $^1$H NMR (400 MHz, CDCl$_3$): δ 9.79 (s, 1H), 8.72 (d, J=9 Hz, 1H), 8.41-8.38 (m, 2H), 8.17 (d, J=9 Hz, 1H), 7.77 (d, J=8 Hz, 2H), 6.91 (d, J=8 Hz, 2H), 4.00 (s, 3H), 3.97 (s, 3H). ESI-LCMS m/z 338 (M+H)$^+$.

3b) Dimethyl 7-[4-({[3-(2,6-dichlorophenyl)-5-(1-methylethyl)-4-isoxazolyl]methyl}oxy)phenyl]-2,4-quinolinedicarboxylate

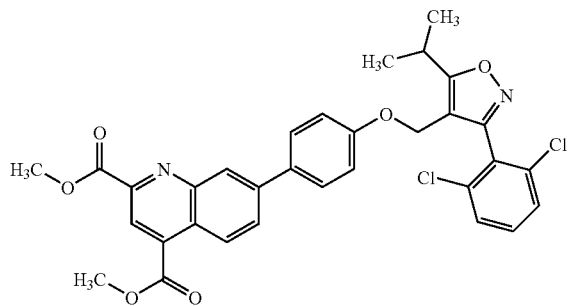

A solution of 75 mg (0.22 mmol) of dimethyl 7-(4-hydroxyphenyl)-2,4-quinolinedicarboxylate, 135 mg (0.44 mmol) of 4-(chloromethyl)-3-(2,6-dichlorophenyl)-5-(1-methylethyl)isoxazole and 125 mg (0.89 mmol) of K$_2$CO$_3$ in 2 mL DMF was stirred at ambient temperature for 60 hr. EtOAc was added and the mixture washed with three portions of H$_2$O then brine. The solution was concentrated and the residue purified by silica gel chromatography (12 g of silica gel eluting with 0-50% EtOAc in hexanes over 45 minutes) to give 62 mg (46%) of dimethyl 7-[4-({[3-(2,6-dichlorophenyl)-5-(1-methylethyl)-4-isoxazolyl]methyl}oxy)phenyl]-2,4-quinolinedicarboxylate as a clear glass. $^1$H NMR (400 MHz, CDCl$_3$): δ 8.88 (d, J=9.0 Hz, 1H), 8.65 (s, 1H), 8.50 (s, 1H), 7.98 (d, J=9 Hz, 1H), 7.65 (d, J=9 Hz, 2H), 7.41 (d, J=8 Hz, 2H), 7.35-7.31 (m, 1H), 6.91 (d, J=9 Hz, 2H), 4.79 (s, 2H), 4.11 (s, 3H), 4.07 (s, 3H), 3.36 (septet, J=7 Hz, 1H), 1.44 (d, J=7 Hz, 6H). ESI-LCMS m/z 606 (M+H)$^+$.

3c) 7-[4-({[3-(2,6-Dichlorophenyl)-5-(1-methylethyl)-4-isoxazolyl]methyl}oxy)phenyl]-2,4-quinolinedicarboxylic acid

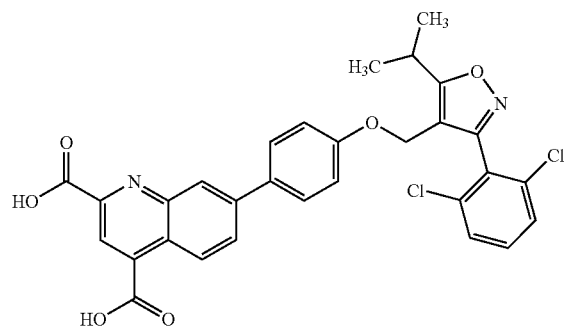

To a solution of 60 mg (0.10 mmol) of dimethyl 7-[4-({[3-(2,6-dichlorophenyl)-5-(1-methylethyl)-4-isoxazolyl]methyl}oxy)phenyl]-2,4-quinolinedicarboxylate in a mixture of 1 mL THF, 3 mL EtOH, and 1 mL H$_2$O was added 40 mg (0.99 mmol) of NaOH. The mixture was stirred at 60° C. for 16 hr. H$_2$O (1.5 mL) was added to dissolve some solids then the solution was concentrated to ⅓ volume and added dropwise to 10 mL of 0.5 N HCl (aq). After sitting for 5 min, the resulting solids were collected by suction filtration, washed with H$_2$O and dried to yield 36 mg (63%) of 7-[4-({[3-(2,6-dichlorophenyl)-5-(1-methylethyl)-4-isoxazolyl]methyl}oxy)phenyl]-2,4-quinolinedicarboxylic acid as an orange solid. $^1$H NMR (400 MHz, DMSO-d$_6$): δ 8.82 (d, J=9 Hz, 1H), 8.41 (s, 1H), 8.38 (s, 1H), 8.14 (dd, J$_A$=2 Hz, J$_B$=9 Hz, 1H), 7.79 (d, J=9 Hz, 2H), 7.61 (d, J=8 Hz, 2H), 7.55-7.51 (m, 1H), 6.94 (d, J=9 Hz, 2H), 4.88 (s, 2H), 3.45 (septet, J=7 Hz, 1H), 1.34 (d, J=7, 6H). ESI-LCMS m/z 578 (M+H)$^+$.

EXAMPLE 4

7-[4-({[3-(2,6-Dichlorophenyl)-5-(1-methylethyl)-4-isoxazolyl]methyl}oxy)phenyl]-4-quinolinecarboxylic acid

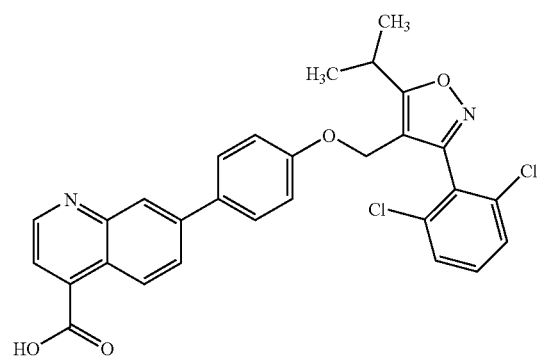

4a) Methyl 7-bromo-4-quinolinecarboxylate

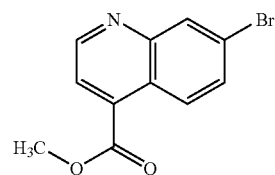

To a solution of 750 mg (2.31 mmol) of dimethyl 7-bromo-2,4-quinolinedicarboxylate in a mixture of 20 mL of EtOH, 10 mL THF and 4 mL of H$_2$O was added 925 mg (23.1 mmol) of NaOH. The mixture was stirred at 50° C. An additional 10 mL of THF and 15 mL of H$_2$O were added after 5 min. After 30 min total at 50° C., the solution was concentrated to ⅓ volume and the pH was adjusted to 4.0 with 1.0 N HCl (aq) followed by the addition of 100 mL of H$_2$O. The resulting solids were collected by suction filtration, washed with H$_2$O and dried. The solids were then added to 10 mL of diphenyl ether and the mixture stirred at 215° C. for 20 min. Upon cooling, 20 mL of hexanes was added and the resulting solids were collected by suction filtration, washed with hexanes and dried. The solids were then suspended in 20 mL of MeOH and 505 μL (6.90 mmol) of thionyl chloride was added. The mixture was refluxed for 1 hr, then an additional 505 μL (6.90 mmol) of thionyl chloride was added. After an additional 1 hr of refluxing, the solvent was evaporated. The residue was diluted with EtOAc then washed with saturated Na$_2$CO$_3$ (aq) and brine then dried over Na$_2$SO$_4$. Concentration of the solution yielded 320 mg (52%) of methyl 7-bromo-4-quinolinecarboxylate as a beige solid. $^1$H NMR (400 MHz, CDCl$_3$): δ

9.01 (d, J=4 Hz, 1H), 8.70 (d, J=9 Hz, 1H), 8.35 (s, 1H), 7.92 (d, J=4 Hz, 1H), 7.75-7.72 (m, 1H), 4.03 (s, 3H). ESI-LCMS m/z 267 (M+H)+.

4b) Methyl 7-(4-hydroxyphenyl)-4-quinolinecarboxylate

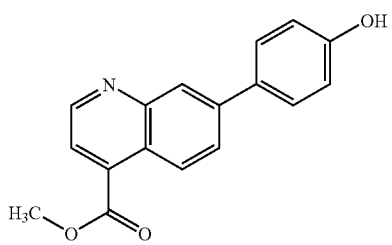

A mixture of 160 mg (0.60 mmol) of methyl 7-bromo-4-quinolinecarboxylate, 200 mg (0.90 mmol) of 4-(4,4,5,5-tetramethyl-1,3,2-dioxaborolan-2-yl)phenol, 7 mg (0.03 mmol) of palladium(II)acetate, 16 mg (0.06 mmol) of triphenylphosphine, 450 mg (2.10 mmol) of $K_3PO_4$ and 50 uL (3.01 mmol) of $H_2O$ in 3 mL of dioxane was stirred at 60° C. for 1.5 hr. EtOAc was added then the organics were washed with $H_2O$ and brine then concentrated. The residue was suspended in cold EtOAc and the solids were collected by suction filtration, washed with cold EtOAc and dried to give 92 mg (55%) of methyl 7-(4-hydroxyphenyl)-4-quinolinecarboxylate as a tan solid. $^1$H NMR (400 MHz, $CDCl_3$): δ 9.75 (s, 1H), 9.03 (s, 1H), 8.63 (d, J=9 Hz, 1H), 8.25 (d, J=2 Hz, 1H), 8.03 (dd, $J_A$=2 Hz, $J_B$=9 Hz, 1H), 7.87 (s, 1H), 7.72 (d, J=8 Hz, 2H), 6.90 (d, J=8 Hz, 2H), 3.98 (s, 3H). ESI-LCMS m/z 280 (M+H)+.

4c) Methyl 7-[4-({[3-(2,6-dichlorophenyl)-5-(1-methylethyl)-4-isoxazolyl]methyl}oxy)phenyl]-4-quinolinecarboxylate

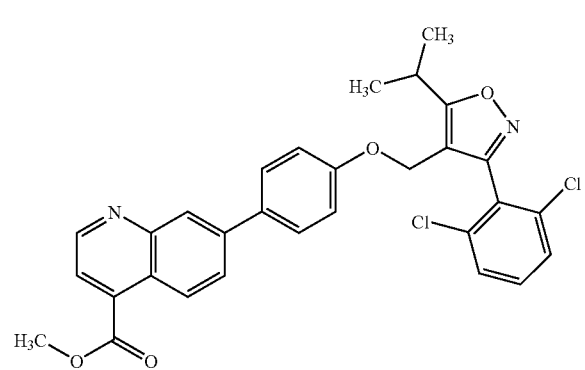

A solution of 90 mg (0.32 mmol) of methyl 7-(4-hydroxyphenyl)-4-quinolinecarboxylate, 196 mg (0.64 mmol) of 4-(chloromethyl)-3-(2,6-dichlorophenyl)-5-(1-methylethyl)isoxazole and 178 mg (1.29 mmol) of $K_2CO_3$ in 2.5 mL DMF was stirred at ambient temperature for 60 hr. EtOAc was added and the mixture washed with three portions of $H_2O$ then brine. The solution was concentrated and the residue purified by silica gel chromatography (12 g of silica gel eluting with 0-50% EtOAc in hexanes over 45 minutes) to give 98 mg (56%) of methyl 7-[4-({[3-(2,6-dichlorophenyl)-5-(1-methylethyl)-4-isoxazolyl]methyl}oxy)phenyl]-4-quinolinecarboxylate as a clear glass. $^1$H NMR (400 MHz, $CDCl_3$): δ 9.02 (d, J=4 Hz, 1H), 8.81 (d, J=9 Hz, 1H), 8.29 (s, 1H), 7.88-7.85 (m, 2H), 7.64 (d, J=8 Hz, 2H), 7.41 (d, J=8 Hz, 2H), 7.35-7.32 (m, 1H), 6.91 (d, J=8 Hz, 2H), 4.79 (s, 2H), 4.05 (s, 3H), 3.34 (septet, J=7 Hz, 1H), 1.43 (d, J=7 Hz, 6H). ESI-LCMS m/z 548 (M+H)+.

4d) 7-[4-({[3-(2,6-Dichlorophenyl)-5-(1-methylethyl)-4-isoxazolyl]methyl}oxy)phenyl]-4-quinolinecarboxylic acid

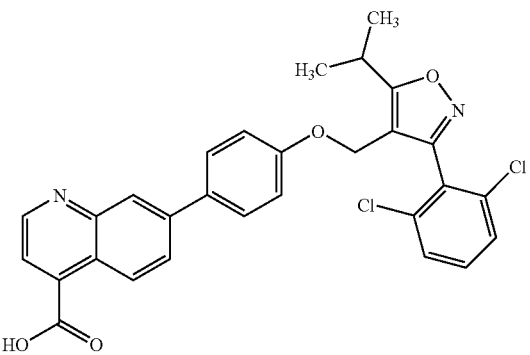

To 96 mg (0.48 mmol) of methyl 7-[4-({[3-(2,6-dichlorophenyl)-5-(1'-methylethyl)-4-isoxazolyl]methyl}oxy)phenyl]-4-quinolinecarboxylate in a mixture of 1 mL of THF, 3 mL of EtOH, and 1 mL of $H_2O$ was added 70 mg (1.75 mmol) of NaOH. After stirring at 50° C. for 16 hr, the solution was concentrated to 1/3 volume then added dropwise to a stirred solution of 10 mL of 0.5 M HCl (aq). After sitting at ambient temperature for 5 min, the resulting solids were collected by suction filtration, washed with $H_2O$ and dried to give 74 mg (79%) of 7-[4-({[3-(2,6-dichlorophenyl)-5-(1'-methylethyl)-4-isoxazolyl]methyl}oxy)phenyl]-4-quinolinecarboxylic acid as a yellow solid. $^1$H NMR (400 MHz, DMSO-$d_6$): δ 9.01 (d, J=4 Hz, 1H), 8.73 (d, J=9 Hz, 1H), 8.25 (s, 1H), 7.99 (d, J=9 Hz, 1H), 7.87 (d, J=4 Hz, 1H), 7.74 (d, J=8 Hz, 2H), 7.62 (d, J=8 Hz, 2H), 7.55-7.51 (m, 1H), 6.93 (d, J=9 Hz, 2H), 4.87 (s, 2H), 3.45 (septet, J=7 Hz, 1H), 1.33 (d, J=7, 6H). ESI-LCMS m/z 534 (M+H)+.

EXAMPLE 5

7-[4-({[3-(2,6-Dichlorophenyl)-5-(1-methylethyl)-4-isoxazolyl]methyl}oxy)phenyl]-3-isoquinolinecarboxylic acid

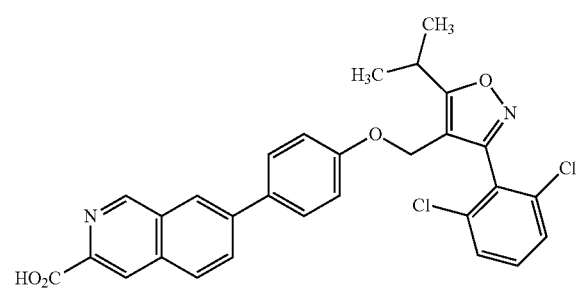

5a) Methyl 7-hydroxy-3-isoquinolinecarboxylate

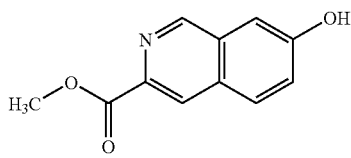

To a solution of 4.36 g (22.6 mmol) of 7-hydroxy-1,2,3,4-tetrahydro-3-isoquinolinecarboxylic acid in 100 mL of MeOH was added 4.95 mL (67.7 mmol) of thionyl chloride and the solution was refluxed for 1 hr. After evaporation of the solvent, the residue was stirred vigorously in a mixture of 200 mL of EtOAc, 500 mL of $H_2O$ and 100 mL of saturated $Na_2CO_3$ (aq) until all solids dissolved. The aqueous layer was then saturated with sodium chloride and extracted twice with EtOAc. The combined organics were then washed with brine, dried over $Na_2SO_4$ and concentrated to a solid. To this solid was added 200 mL of xylenes and 3.0 g of palladium on carbon (10%) and the suspension was refluxed for 16 hr. The suspension was filtered through a pad of Celite® and silica gel. The pad was then washed with 50 mL of xylenes. The filtrate was discarded and the filter cake washed with 500 mL of a 4:1 mixture of $CH_2Cl_2$:MeOH. This filtrate was then evaporated to give 2.09 g (46%) of methyl 7-hydroxy-3-isoquinolinecarboxylate as a light brown solid. $^1H$ NMR (400 MHz, DMSO-$d_6$): δ 10.58 (s, 1H), 9.08 (s, 1H), 8.49 (s, 1H), 8.04 (d, J=9 Hz, 1H), 7.39 (d, J=9 Hz, 1H), 7.36 (s, 1H), 3.87 (s, 3H). ESI-LCMS m/z 204 (M+H)$^+$.

5b) Methyl 7-{[(trifluoromethyl)sulfonyl]oxy}-3-isoquinolinecarboxylate

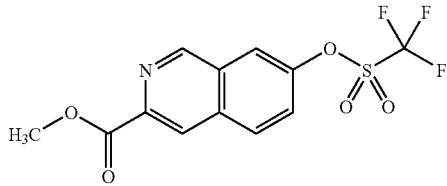

To 2.09 g (10.3 mmol) of methyl 7-hydroxy-3-isoquinolinecarboxylate in 50 mL of $CH_2Cl_2$ at 0° C. was added 3.60 mL (25.7 mmol) of TEA and 2.08 mL (12.3 mmol) of trifluoromethanesulfonic anhydride and the solution stirred at ambient temperature for 1.5 hr. The solvent was evaporated and the residue taken up in EtOAc. The organics were washed with $H_2O$, then brine and dried over $Na_2SO_4$. The solvent was evaporated and the residue purified by silica gel chromatography (120 g of silica gel eluting with 0-70% EtOAc in hexanes over 45 minutes) to give 1.48 g of methyl 7-{[(trifluoromethyl)sulfonyl]oxy}-3-isoquinolinecarboxylate as a beige solid. $^1H$ NMR (400 MHz, CDCl$_3$): δ 9.40 (s, 1H), 8.65 (s, 1H), 8.11 (d, J=9 Hz, 1H), 7.99 (d, J=2 Hz, 1H), 7.69 (dd, $J_A$=2 Hz, $J_B$=9 Hz, 1H), 4.07 (s, 3H). APCI-LCMS m/z 336 (M+H)$^+$.

Alternate 5b) Methyl 7-{[(trifluoromethyl)sulfonyl]oxy}-3-isoquinolinecarboxylate

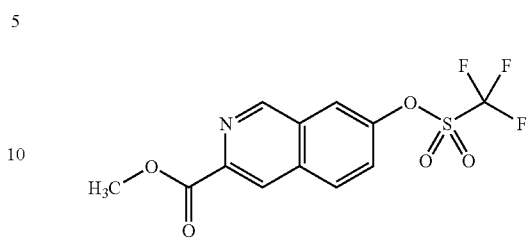

To 24.05 g (118 mmol) of methyl 7-hydroxy-3-isoquinolinecarboxylate, from multiple batches, in 500 mL of $CH_2Cl_2$ at 0° C. was added 41.2 mL (296 mmol) of TEA and 23.9 mL (142 mmol) of trifluoromethanesulfonic anhydride and the solution stirred at ambient temperature for 20 minutes. The solvent was evaporated and the residue taken up in EtOAc. The organics were washed with $H_2O$, then brine and dried over $Na_2SO_4$. The mixture was filtered and the filtrate concentrated to give methyl 7-{[(trifluoromethyl)sulfonyl]oxy}-3-isoquinolinecarboxylate (38.06 g, 96%) as a dark brown solid. $^1H$ NMR (400 MHz, CDCl$_3$): δ 9.40 (s, 1H), 8.65 (s, 1H), 8.11 (d, J=9 Hz, 1H), 7.99 (d, J=2 Hz, 1H), 7.69 (dd, $J_A$=2 Hz, $J_B$=9 Hz, 1H), 4.07 (s, 3H). APCI-LCMS m/z 336 (M+H)$^+$.

5c) Methyl 7-(4-hydroxyphenyl)-3-isoquinolinecarboxylate

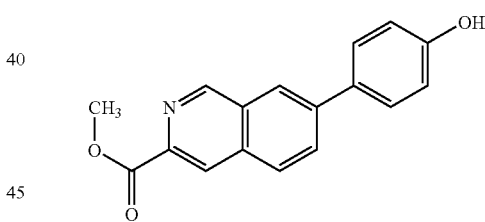

A suspension of 700 mg (2.09 mmol) of methyl 7-{[(trifluoromethyl)sulfonyl]oxy}-3-isoquinolinecarboxylate, 715 mg (3.13 mmol) of 4-(4,4,5,5-tetramethyl-1,3,2-dioxaborolan-2-yl)phenol, 240 mg (0.21 mmol) of tetrakistriphenylphosphine palladium(0) and 3.70 mL (3.31 mmol) of 2.0 M $Na_2CO_3$ (aq) in 10 mL of 1,2-dimethoxyethane was stirred at 90° C. for 20 min. The suspension was filtered through a pad of Celite® and the filter cake was washed with EtOAc. The combined organics were then evaporated and the residue purified by silica gel chromatography (40 g of silica gel eluting with 0-15% acetone in $CH_2Cl_2$ over 45 minutes) to give 360 mg (62%) of methyl 7-(4-hydroxyphenyl)-3-isoquinolinecarboxylate as a beige solid. $^1H$ NMR (400 MHz, DMSO-$d_6$): δ 9.75 (s, 1H), 9.38 (s, 1H), 8.42 (s, 1H), 8.23 (s, 1H), 8.21 (d, J=8 Hz, 1H), 8.15 (d, J=8 Hz, 1H), 7.72 (d, J=9 Hz, 2H), 6.91 (d, J=9 Hz, 2H), 3.91 (s, 3H). ESI-LCMS m/z 280 (M+H)$^+$.

Alternate 5c) Methyl 7-(4-hydroxyphenyl)-3-isoquinolinecarboxylate

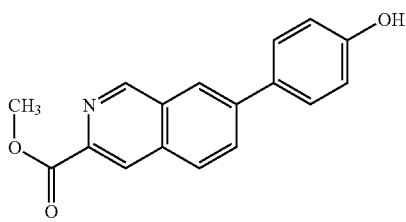

A suspension of 38 g (113 mmol) of methyl 7-{[(trifluoromethyl)sulfonyl]oxy}-3-isoquinolinecarboxylate, 23.4 g (170 mmol) of (4-hydroxyphenyl)boronic acid, 6.54 g (5.67 mmol) of tetrakistriphenylphosphine palladium(0) and 200 mL of 2.0 M $Na_2CO_3$ (aq) in 700 mL of 1,2-dimethoxyethane was stirred at 50° C. for 90 min. The suspension was filtered through a pad of Celite® and the filter cake was washed with EtOAc. The combined organics were washed with water. The aqueous layer was extracted with ethyl acetate. The combined organic layers were washed with water and brine before being dried with $Na_2SO_4$, filtered and concentrated. Ethyl acetate was added and the mixture was stirred and heated. The mixture was filtered and the concentrated filtrate was purified by silica gel chromatography (eluting with 0-20% acetone in $CH_2Cl_2$). Fractions containing the product were combined and concentrated and combined with the solid which had been collected by filtration to give 14.50 g (46%) of methyl 7-(4-hydroxyphenyl)-3-isoquinolinecarboxylate. $^1$H NMR (400 MHz, DMSO-$d_6$): δ 9.75 (s, 1H), 9.38 (s, 1H), 8.42 (s, 1H), 8.23 (s, 1H), 8.21 (d, J=8 Hz, 1H), 8.15 (d, J=8 Hz, 1H), 7.72 (d, J=9 Hz, 2H), 6.91 (d, J=9 Hz, 2H), 3.91 (s, 3H). ESI-LCMS m/z 280 (M+H)$^+$.

5d) Methyl 7-[4-({[3-(2-chlorophenyl)-5-(1-methylethyl)-4-isoxazolyl]methyl}oxy)phenyl]-3-isoquinolinecarboxylate

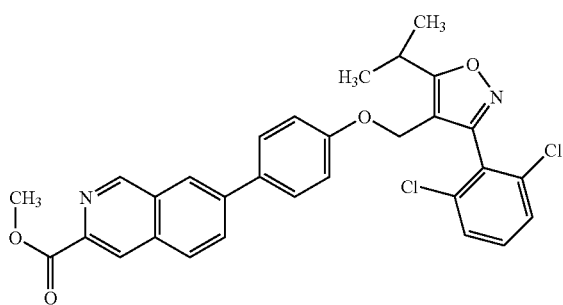

A mixture of 174 mg (0.62 mmol) of methyl 7-(4-hydroxyphenyl)-3-isoquinolinecarboxylate, 285 mg (0.92 mmol) of 4-(chloromethyl)-3-(2,6-dichlorophenyl)-5-(1-methylethyl)isoxazole and 260 mg (1.83 mmol) of $K_2CO_3$ in 2 mL of DMF was stirred at 50° C. for 20 hr. EtOAc was added then the mixture washed with three portions of $H_2O$, then brine. The organics were dried over $Na_2SO_4$ then evaporated and the residue purified by silica gel chromatography (40 g of silica gel eluting with 0-70% EtOAc in hexanes over 45 minutes) to give 196 mg (58%) of methyl 7-[4-({[3-(2-chlorophenyl)-5-(1-methylethyl)-4-isoxazolyl]methyl}oxy)phenyl]-3-isoquinolinecarboxylate as white solid. $^1$H NMR (400 MHz, CDCl$_3$): δ 9.35 (s, 1H), 8.60 (s, 1H), 8.14 (s, 1H), 7.99 (m, 2H), 7.60 (d, J=9 Hz, 2H), 7.41 (d, J=9 Hz, 2H), 7.33 (m, 1H), 6.92 (d, J=9 Hz, 2H), 4.80 (s, 2H), 4.06 (s, 3H), 3.36 (septet, 1H, J=7 Hz), 1.44 (d, J=7 Hz, 6H). ESI-LCMS m/z 548 (M+H)$^+$.

Alternate 5d) Methyl 7-[4-({[3-(2-chlorophenyl)-5-(1-methylethyl)-4-isoxazolyl]methyl}oxy)phenyl]-3-isoquinolinecarboxylate

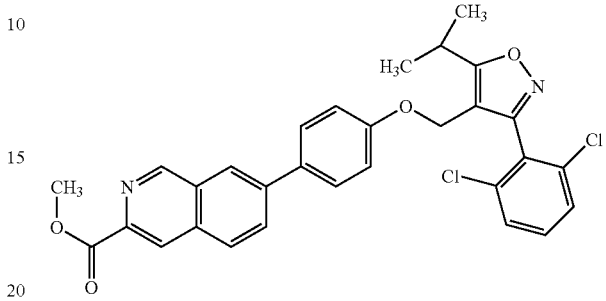

A mixture of 14.5 g (51.9 mmol) of methyl 7-(4-hydroxyphenyl)-3-isoquinolinecarboxylate, 31.6 g (104 mmol) of 4-(chloromethyl)-3-(2,6-dichlorophenyl)-5-(1-methylethyl) isoxazole and 21.5 g (156 mmol) of $K_2CO_3$ in 100 mL of DMF was stirred at 50° C. for 20 hr. Additional 4-(chloromethyl)-3-(2,6-dichlorophenyl)-5-(1-methylethyl)isoxazole (15.8 g, 52 mmol), DMF (50 mL), and $K_2CO_3$ (14.5 g, 105 mmol) was added and the reaction was heated for an additional 7 hours at 70° C. and at 60° C. for another 12 hours. The reaction was allowed to cool to room temperature and was stirred for 2 days. EtOAc was added then the mixture washed with three portions of $H_2O$, then brine. The aqueous layers were extracted with EtOAC. The combined organic layers were dried over $Na_2SO_4$, filtered, then concentrated. The crude material was dissolved in hot EtOAc and diluted with hexane. The mixture was placed in the freezer for three hours then filtered to yield the desired product (14.46 g) as a light brown solid. The filtrate was concentrated and the residue purified by silica gel chromatography (330 g of silica gel eluting with 0-80% EtOAc in hexanes over 45 minutes). Fractions containing the product were combined, concentrated, and recrystallized to give 16.82 g (59%) of methyl 7-[4-({[3-(2-chlorophenyl)-5-(1-methylethyl)-4-isoxazolyl]methyl}oxy)phenyl]-3-isoquinolinecarboxylate. $^1$H NMR (400 MHz, CDCl$_3$): δ 9.35 (s, 1H), 8.60 (s, 1H), 8.14 (s, 1H), 7.99 (m, 2H), 7.60 (d, J=9 Hz, 2H), 7.41 (d, J=9 Hz, 2H), 7.33 (m, 1H), 6.92 (d, J=9 Hz, 2H), 4.80 (s, 2H), 4.06 (s, 3H), 3.36 (septet, 1H, J=7 Hz), 1.44 (d, J=7 Hz, 6H). ESI-LCMS m/z 548 (M+H)$^+$.

5e) 7-[4-({[3-(2,6-Dichlorophenyl)-5-(1-methylethyl)-4-isoxazolyl]methyl}oxy)phenyl]-3-isoquinolinecarboxylic acid

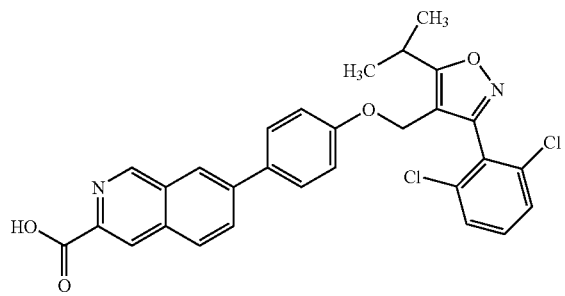

A solution of 16.4 g (30 mmol) of methyl 7-[4-({[3-(2-chlorophenyl)-5-(1-methylethyl)-4-isoxazolyl]methyl}oxy)phenyl]-3-isoquinolinecarboxylate and 11.98 g (300 mmol) of NaOH in a mixture of 250 mL of EtOH, 100 mL of THF and 75 mL of H₂O was stirred at 50° C. for 16 hr. The solution was concentrated to ⅔ volume then added dropwise to a vigorously stirred solution of 1.5 L of 1.0 N HCl (aq). After stirring for 30 min, the solids were collected by suction filtration, washed with H₂O then dried to give 15.5 g (96%) of 7-[4-({[3-(2,6-dichlorophenyl)-5-(1-methylethyl)-4-isoxazolyl]methyl}oxy)phenyl]-3-isoquinolinecarboxylic acid as a pale yellow solid. ¹H NMR (400 MHz, CDCl₃): δ 9.31 (s, 1H), 8.68 (s, 1H), 8.21 (s, 1H), 8.09-8.06 (m, 2H), 7.60 (d, J=9 Hz, 2H), 7.42 (d, J=8 Hz, 2H), 7.35-7.31 (m, 1H), 6.93 (d, J=9 Hz, 2H), 4.81 (d, 2H), 3.36 (septet, J=7 Hz, 1H), 1.44 (d, J=7 Hz, 6H). APCI-LCMS m/z 534 (M+H)⁺.

5f) Sodium 7-[4-({[3-(2,6-Dichlorophenyl)-5-(1-methylethyl)-4-isoxazolyl]methyl}oxy)phenyl]-3-isoquinolinecarboxylic acid

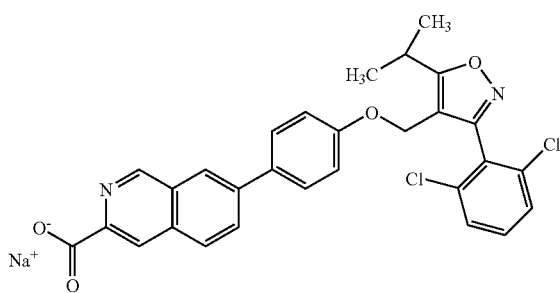

A solution of 15.5 g (29.1 mmol) of 7-[4-({[3-(2,6-dichlorophenyl)-5-(1-methylethyl)-4-isoxazolyl]methyl}oxy)phenyl]-3-isoquinolinecarboxylic acid in 350 mL of MeOH was heated to effect solution then 14.6 mL (29.1 mmol) of 2.0 M NaOH (aq) was added. The solution was then concentrated and the solids dried to yield 14.49 g (90%) of sodium 7-[4-({[3-(2,6-dichlorophenyl)-5-(1-methylethyl)-4-isoxazolyl]methyl}oxy)phenyl]-3-isoquinolinecarboxylic acid as a tan solid. ¹H NMR (400 MHz, DMSO-d₆): δ 9.35 (s, 1H), 8.56 (s, 1H), 8.42 (s, 1H), 8.17 (d, J=9 Hz, 1H), 8.12 (d, J=9 Hz, 1H), 7.74 (d, J=9 Hz, 2H), 7.62 (d, J=8 Hz, 2H), 7.55-7.51 (m, 1H), 6.93 (d, J=8 Hz, 2H), 4.88 (s, 2H), 3.45 (septet, J=7 Hz, 1H), 1.33 (d, J=7 Hz, 6H). ESI-LCMS m/z 534 (M+H)⁺.

EXAMPLE 6

6-[4-({[5-Cyclopentyl-3-(2,6-dichlorophenyl)-4-isoxazolyl]methyl}oxy)phenyl]-2-quinolinecarboxylic acid

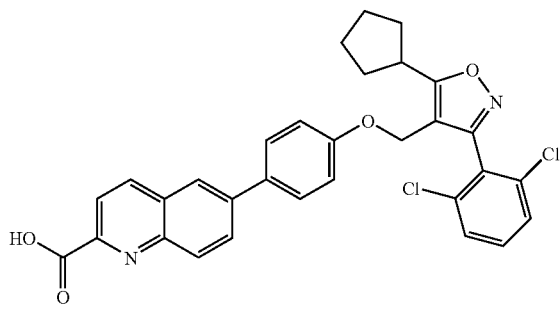

6a) Ethyl 3-cyclopentyl-3-oxopropanoate

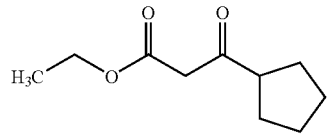

To a solution of monoethyl malonate (13.6 mL, 115 mmol) and a few milligrams of 2,2'-bipyridyl at between −55 and −65° C. was slowly added a 2.4 M solution of n-butyl lithium in hexanes (92.0 mL, 230 mmol). After the addition was complete, cyclopentanecarbonyl chloride (7.0 mL, 58 mmol) was added in portions. The solution was then allowed to stir while warming to ambient temperature and was poured into a mix of 1 N aqueous hydrochloric acid and ether. The layers were separated and the ether layer was washed three times with saturated sodium bicarbonate, dried over magnesium sulfate, concentrated and purified by chromatography (silica gel, 0-5% ethyl acetate in hexanes gradient elution) to afford ethyl 3-cyclopentyl-3-oxopropanoate (9.50 g, 89%). ¹H-NMR (400 MHz, DMSO-d₆) δ 4.06 (q, J=7 Hz, 2H), 3.60 (s, 2H), 2.99-2.91 (m, 1H), 1.78-1.47 (m, 8H), 1.15 (t, J=7 Hz, 3H).

6b) Ethyl 5-cyclopentyl-3-(2,6-dichlorophenyl)-4-isoxazolecarboxylate

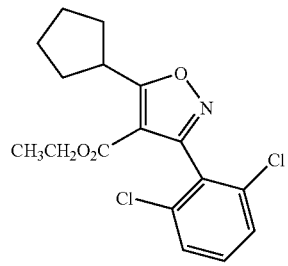

To a solution of 2,6-dichlorobenzaldehyde oxime (3.73 g, 19.6 mmol) in N,N-dimethylformamide (12 mL) was added solid N-chlorosuccinimide (2.62 g, 19.6 mmol). The solution was stirred for approximately 1 hour and the poured into water and extracted twice with ether. The combined organic layers containing the crude imidoyl chloride were dried over magnesium sulfate and concentrated. To a solution of ethyl 3-cyclopentyl-3-oxopropanoate (4.34 g, 23.6 mmol) in tetrahydrofuran (5 mL) at 0° C. was added a 25 wt % solution of sodium ethoxide in ethanol (7.4 mL, 24 mmol) quickly. The above imidoyl chloride was added. A solid was seen to precipitate. The mixture was allowed to warm to ambient temperature and stir overnight. The mixture was then poured into water and extracted three times with ethyl acetate and the combined organic layers were dried over magnesium sulfate, concentrated and the residue purified by chromatography (silica gel 5% ethyl acetate in hexanes) to afford ethyl 5-cyclopentyl-3-(2,6-dichlorophenyl)-4-isoxazolecarboxylate (3.04 g, 43%). ¹H-NMR (400 MHz, DMSO-d₆) δ 7.63-7.53 (m, 3H), 4.02 (q, J=7 Hz, 2H), 3.92-3.84 (m, 1H), 2.14-2.06 (m, 2H), 1.84-1.64 (m, 6H), 0.91 (t, J=5 Hz, 3H).

6c) [5-Cyclopentyl-3-(2,6-dichlorophenyl)-4-isoxazolyl]methanol

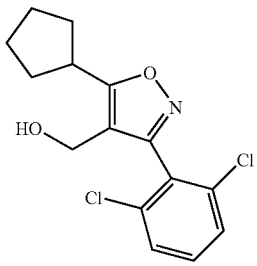

To a solution of ethyl 5-cyclopentyl-3-(2,6-dichlorophenyl)-4-isoxazolecarboxylate (3.0 g, 8.6 mmol) in tetrahydrofuran (35 mL) at 0° C. was added a 1.5 M solution of diisobutylaluminum hydride in toluene (8.6 mL, 13 mmol) dropwise. The solution was allowed to stir while warming slowly for approximately 3.5 hours and was re-cooled to 0° C. An additional portion of diisobutylaluminum hydride (4.3 mL, 6.5 mmol) was added and the solution was allowed to stir for an additional 35 minutes. Then Rochelle's salt (40 mL) was added slowly at 0° C. followed by some ethyl acetate. The mixture was allowed to warm to ambient temperature and stirred overnight. The layers were separated and the ethyl acetate was washed with brine, dried over magnesium sulfate and concentrated to afford [5-cyclopentyl-3-(2,6-dichlorophenyl)-4-isoxazolyl]methanol (2.59 g, 82%). $^1$H-NMR (400 MHz, DMSO-$d_6$) δ 7.61-7.51 (m, 3H), 4.85 (t, J=5 Hz, 1H), 4.14 (d, J=5 Hz, 2H), 3.46-3.48 (m, 1H), 2.07-1.99 (m, 2H), 1.81-1.60 (m, 6H).

6d) Methyl 6-[4-({[5-cyclopentyl-3-(2,6-dichlorophenyl)-4-isoxazolyl]methyl}oxy)phenyl]-2-quinolinecarboxylate

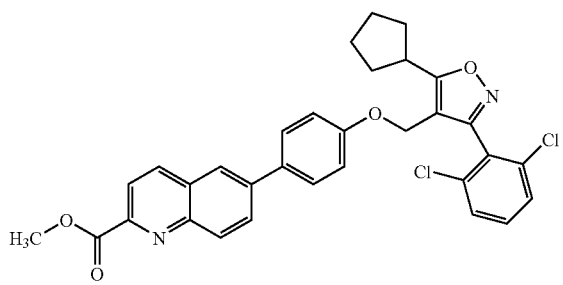

To a solution of methyl 6-(4-hydroxyphenyl)-2-quinolinecarboxylate (0.10 mg, 0.36 mmol), [5-cyclopentyl-3-(2,6-dichlorophenyl)-4-isoxazolyl]methanol (0.11 mg, 0.36 mmol) and triphenylphosphine (0.10 mg, 0.39 mmol) in dichloromethane (2.5 mL) was added diisopropyl azodicarboxylate (0.071 mL, 0.39 mmol) slowly. The solution was heated in a microwave reactor at 90° C. for 10 minutes and then was adsorbed onto silica gel and purified by chromatography (silica gel, 0-45% ethyl acetate in hexanes gradient elution) to afford methyl 6-[4-({[5-cyclopentyl-3-(2,6-dichlorophenyl)-4-isoxazolyl]methyl}oxy)phenyl]-2-quinolinecarboxylate (76 mg, 37%). $^1$H-NMR (400 MHz, DMSO $d_6$) δ 8.55 (d, J=8 Hz, 1H), 8.28 (s, 1H), 8.18-8.10 (m, 3H), 7.73 (d, J=9 Hz, 2H), 7.63-7.51 (m, 3H), 6.96 (d, J=9 Hz, 2H), 4.98 (s, 2H), 3.93 (s, 3H), 3.58-3.50 (m, 1H), 2.11-2.03 (m, 2H), 1.84-1.64 (m, 6H).

6e) 6-[4-({[5-Cyclopentyl-3-(2,6-dichlorophenyl)-4-isoxazolyl]methyl}oxy)phenyl]-2-quinolinecarboxylic acid

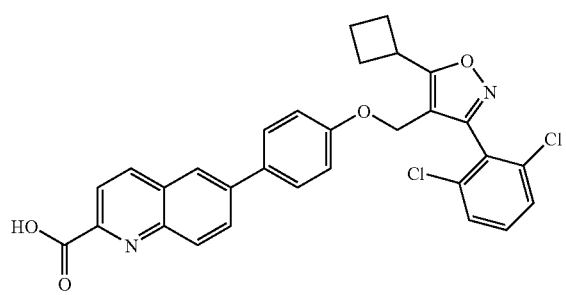

To a solution of methyl 6-[4-({[5-cyclopentyl-3-(2,6-dichlorophenyl)-4-isoxazolyl]methyl}oxy)phenyl]-2-quinolinecarboxylate (73 mg, 0.13 mmol) in 2:1 tetrahydrofuran:methanol (1.5 mL) was added 1N sodium hydroxide (0.19 mL, 0.19 mmol). A solid was seen to precipitate. The mixture was heated in a microwave reactor at 120° C. for 500 seconds and then was concentrated and the residue was taken up with water and hydrochloric acid (0.19 mL, 0.19 mmol) was added. Ethyl acetate was added and the layers were separated. The aqueous layer was extracted once more with ethyl acetate. The combined organic layers were washed with brine and concentrated to afford 6-[4-({[5-cyclopentyl-3-(2,6-dichlorophenyl)-4-isoxazolyl]methyl}oxy)phenyl]-2-quinolinecarboxylic acid (58 mg, 82%). $^1$H-NMR (400 MHz, DMSO-$d_6$) δ 13.36 (br s, 1H), 8.53 (d, J=9 Hz, 1H), 8.27 (s, 1H), 8.18-8.08 (m, 3H), 7.73 (d, J=9 Hz, 2H), 7.63-7.51 (m, 3H), 6.92 (d, J=9 Hz, 2H), 4.87 (s, 2H), 3.59-3.51 (m, 1H), 2.11-2.03 (m, 2H), 1.84-1.64 (m, 6H). HRMS (ESI) $C_{31}H_{24}Cl_2N_2O_4$ calculated: 559.1186 (M+H)$^+$, found: 559.1183 (M+H)$^+$.

EXAMPLE 7

6-[4-({[5-Cyclobutyl-3-(2,6-dichlorophenyl)-4-isoxazolyl]methyl}oxy)phenyl]-2-quinolinecarboxylic acid

7a) Ethyl 5-cyclobutyl-3-(2,6-dichlorophenyl)-4-isoxazolecarboxylate

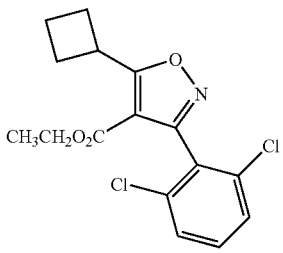

To a water bath-cooled solution of 2,6-dichlorobenzaldehyde oxime (2.20 g, 11.6 mmol) in N,N-dimethylformamide (7 mL) was added solid N-chlorosuccinimide (1.55 g, 11.6 mmol). The solution was stirred while in the water bath for approximately 20 min and outside the bath for approximately 1 hr. The solution was poured into water and extracted twice with ether. The combined organic layers containing the crude imidoyl chloride were dried over magnesium sulfate and then concentrated. To a separate solution of ethyl 3-cyclobutyl-3-oxopropanoate (2.37 g, 13.9 mmol) in THF (3 mL) at 0° C. was added sodium ethoxide (25 wt % in ethanol, 4.36 mL, 13.9 mmol). The solution was stirred for a few minutes and then the above imidoyl chloride was added. The solution was stirred at 0° C. for 10 minutes and then at ambient temperature overnight. The solution was poured into water and extracted three times with ethyl acetate. The combined organic layers were dried over magnesium sulfate, concentrated and purified by chromatography (silica gel, 0-5% ethyl acetate in hexanes gradient elution) to afford ethyl 5-cyclobutyl-3-(2,6-dichlorophenyl)-4-isoxazolecarboxylate (1.52 g, 38%). $^1$H-NMR (400 MHz, DMSO-$d_6$) δ 7.63-7.53 (m, 3H), 4.29-4.20 (m, 1H), 4.02 (q, J=7 Hz, 2H), 2.43-2.36 (m, 4H), 2.15-2.06 (m, 1H), 1.97-1.89 (m, 1H), 0.94 (t, J=7 Hz, 3H).

7b) [5-Cyclobutyl-3-(2,6-dichlorophenyl)-4-isoxazolyl]methanol

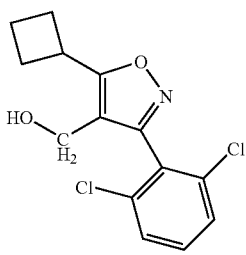

To a solution of ethyl 5-cyclobutyl-3-(2,6-dichlorophenyl)-4-isoxazolecarboxylate (1.52 g, 4.47 mmol) in THF (20 mL) at 0° C. was slowly added a 1.5 M solution of diisobutylaluminum hydride in toluene (6.26 mL, 9.39 mmol). The solution was allowed to warm slowly to ambient temperature. After approximately 4 hr of stirring, the solution was re-cooled to 0° C. and an additional 6 mL of diisobutylaluminum hydride was added. After approximately 1.5 hr of stirring the mixture was re-cooled to 0° C., quenched with aqueous Rochelle's salt and allowed to stir overnight while warming to ambient temperature. The mixture was extracted twice with ethyl acetate. The combined organic layers were washed with Rochelle's salt followed by with brine and then dried over magnesium sulfate and concentrated to afford [5-cyclobutyl-3-(2,6-dichlorophenyl)-4-isoxazolyl]methanol (1.30 g, 98%). $^1$H-NMR (400 MHz, DMSO-$d_6$) δ 7.61-7.51 (m, 3H), 4.87 (t, J=5 Hz, 1H), 4.10 (d, J=5 Hz, 2H), 3.91-3.83 (m, 1H), 2.42-2.28 (m, 4H), 2.08-1.98 (m, 1H), 1.94-1.84 (m, 1H).

7c) Methyl 6-[4-({[5-cyclobutyl-3-(2,6-dichlorophenyl)-4-isoxazolyl]methyl}oxy)phenyl]-2-quinolinecarboxylate

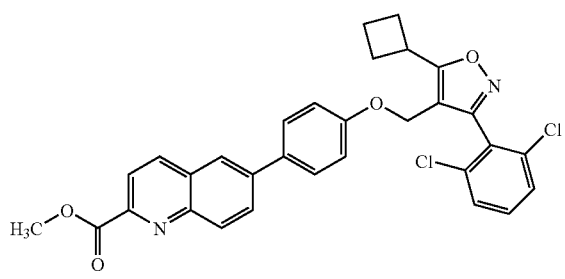

To a solution of [5-cyclobutyl-3-(2,6-dichlorophenyl)-4-isoxazolyl]methanol (0.12 g, 0.36 mmol), methyl 6-(4-hydroxyphenyl)-2-quinolinecarboxylate (0.10 g, 0.36 mmol) and triphenylphosphine (0.10 mg, 0.39 mmol) in dichloromethane (2.5 mL) was added diisopropyl azodicarboxylate (0.071 mL, 0.39 mmol) dropwise. The solution was heated in a microwave reactor to 90° C. for 10 minutes and the allowed to sit overnight. The solution was adsorbed onto silica gel and purified by chromatography (silica gel, 0-45% ethyl acetate in hexanes gradient elution) to afford methyl 6-[4-({[5-cyclobutyl-3-(2,6-dichlorophenyl)-4-isoxazolyl]methyl}oxy)phenyl]-2-quinolinecarboxylate (71 mg, 35%). $^1$H-NMR (400 MHz, DMSO-$d_6$) δ 8.55 (d, J=9 Hz, 1H), 8.28 (s, 1H), 8.16-8.10 (m, 3H), 7.73 (d, J=9 Hz, 2H), 7.62-7.51 (m, 3H), 6.92 (d, J=9 Hz, 2H), 4.84 (s, 2H), 4.05-3.97 (m, 1H), 3.93 (s, 3H), 2.43-2.31 (m, 4H), 2.14-2.02 (m, 1H), 1.97-1.89 (m, 1H). LRMS (APCI) m/z 559 (M+H)$^+$.

7d) 6-[4-({[5-Cyclobutyl-3-(2,6-dichlorophenyl)-4-isoxazolyl]methyl}oxy)phenyl]-2-quinolinecarboxylic acid

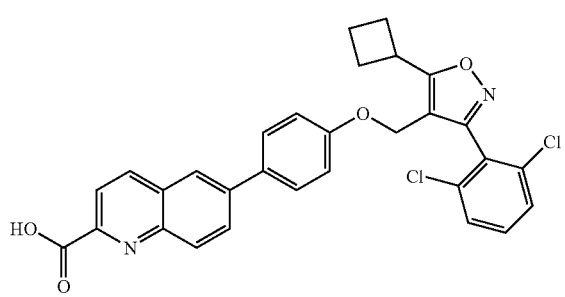

To a solution of methyl 6-[4-({[5-cyclobutyl-3-(2,6-dichlorophenyl)-4-isoxazolyl]methyl}oxy)phenyl]-2-quinolinecarboxylate (67 mg, 0.12 mmol) in 2:1 tetrahydrofuran:methanol (1.5 mL) was added 1 N sodium hydroxide (0.18 mL, 0.18 mmol). The solution was heated in a microwave reactor at 120° C. for 500 seconds. The solution was concentrated and water was added followed by 1 N hydrochloric acid (0.18 mL, 0.18 mmol). Ethyl acetate was added. The layers were separated and the aqueous layer was extracted with ethyl acetate and the combined organic layers were washed with brine and concentrated to afford of 6-[4-({[5-cyclobutyl-3-(2,6-dichlorophenyl)-4-isoxazolyl]methyl}oxy)phenyl]-2-quinolinecarboxylic acid as a solid (51 mg, 78%). $^1$H-NMR (400 MHz, DMSO-$d_6$) δ 13.38 (br s, 1H), 8.52 (d, J=8 Hz, 1H), 8.27 (s, 1H), 8.15-8.08 (m, 3H), 7.73 (d, J=9 Hz, 2H), 7.62-7.51 (m, 3H), 6.92 (d, J=9 Hz, 2H), 4.84 (s, 2H), 4.07-3.94 (m, 1H), 2.43-2.33 (m, 4H), 2.11-2.03 (m, 1H), 1.94-1.90 (m, 1H). HRMS (ESI) $C_{30}H_{22}Cl_2N_2O_4$ calculated: 545.1029 (M+H)$^+$, found: 545.1026 (M+H)$^+$.

EXAMPLE 8

6-[4-({[5-Cyclobutyl-3-(3,5-dichloro-4-pyridinyl)-4-isoxazolyl]methyl}oxy)phenyl]-2-quinolinecarboxylic acid

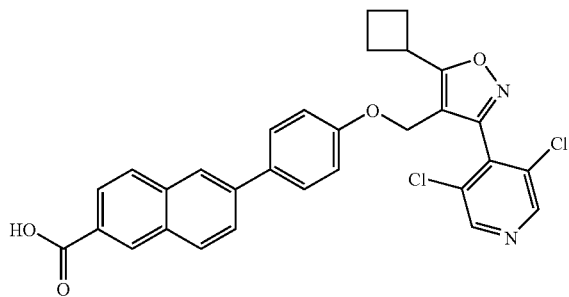

8a) Methyl 6-[4-({[5-cyclobutyl-3-(3,5-dichloro-4-pyridinyl)-4-isoxazolyl]methyl}oxy)phenyl]-2-quinolinecarboxylate

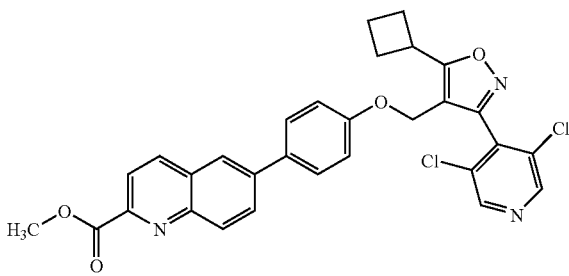

To a solution of methyl 6-(4-hydroxyphenyl)-2-quinolinecarboxylate (0.10 mg, 0.36 mmol), triphenylphosphine (94 mg, 0.36 mmol) and [5-cyclobutyl-3-(3,5-dichloro-4-pyridinyl)-4-isoxazolyl]methanol (Example 9e) (0.11 mg, 0.36 mmol) in dichloromethane (2.5 mL) was added diisopropyl azodicarboxylate (0.064 mL, 0.36 mmol). The mixture was heated to 90° C. for 10 minutes and then allowed to stand overnight. The mixture was adsorbed onto silica gel and purified by chromatography (silica gel, 0-40% ethyl acetate in hexanes gradient elution followed by further purification (silica gel, 0-30% ethyl acetate in hexanes gradient elution) to afford methyl 6-[4-({[5-cyclobutyl-3-(3,5-dichloro-4-pyridinyl)-4-isoxazolyl]methyl}oxy)phenyl]-2-quinolinecarboxylate (53 mg, 26%). $^1$H-NMR (400 MHz, DMSO-d6) δ 8.81 (s, 2H), 8.55 (d, J=9 Hz, 1H), 8.28 (s, 1H), 8.18-8.10 (m, 3H), 7.73 (d, J=9 Hz, 2H), 6.88 (d, J=9 Hz, 2H), 4.93 (s, 2H), 4.08-3.99 (m, 1H), 3.94 (s, 3H), 2.45-2.34 (m, 4H), 2.15-2.02 (m, 1H), 1.99-1.89 (m, 1H).

8b) 6-[4-({[5-Cyclobutyl-3-(3,5-dichloro-4-pyridinyl)-4-isoxazolyl]methyl}oxy)phenyl]-2-quinolinecarboxylic acid

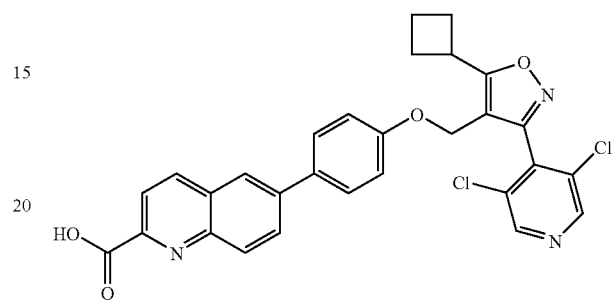

To a solution of methyl 6-[4-({[5-cyclobutyl-3-(3,5-dichloro-4-pyridinyl)-4-isoxazolyl]methyl}oxy)phenyl]-2-quinolinecarboxylate (53 mg, 0.095 mmol) in 2:1 tetrahydrofuran:methanol (1.5 mL) was added 1 N sodium hydroxide (0.14 mL, 0.14 mmol). The mixture was heated in a microwave reactor at 120° C. for 500 seconds and 1 N hydrochloric acid (0.14 mL, 0.14 mmol) was added. The mixture was concentrated, water was added and the mixture was extracted with ethyl acetate. The aqueous layer was extracted one more time with ethyl acetate. The combined organic layers were washed with brine and concentrated. The solid was washed with ether and dried overnight under a nitrogen stream at 45° C. to afford 6-[4-({[5-cyclobutyl-3-(3,5-dichloro-4-pyridinyl)-4-isoxazolyl]methyl}oxy)phenyl]-2-quinolinecarboxylic acid as a yellow solid (27 mg, 52%). $^1$H-NMR (400 MHz, DMSO-d6) δ 8.81 (s, 2H), 8.53 (d, J=9 Hz, 1H), 8.27 (s, 1H), 8.17-8.08 (m, 3H), 7.73 (d, J=9 Hz, 2H), 6.88 (d, J=9 Hz, 2H), 4.93 (s, 2H), 4.08-3.97 (m, 1H), 2.44-2.33 (m, 4H), 2.14-2.04 (m, 1H), 1.99-1.90 (m, 1H). HRMS (ESI) $C_{29}H_{21}Cl_2N_3O_4$: 546.0982 (M+H)$^+$, found: 546.0982 (M+H)$^+$.

EXAMPLE 9

7-[4-({[5-Cyclobutyl-3-(3,5-dichloro-4-pyridinyl)-4-isoxazolyl]methyl}oxy)phenyl]-3-isoquinolinecarboxylic acid

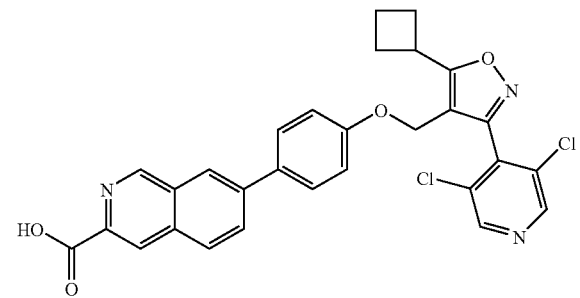

9a) Ethyl 3-cyclobutyl-3-oxopropanoate

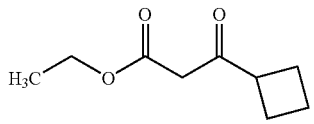

To a solution of monoethyl malonate (12.0 mL, 101 mmol) and a few milligrams of 2,2'-bipyridyl in tetrahydrofuran (250 mL) at approximately −55° C. was added in a dropwise fashion butyl lithium (2.5 M in hexanes, 81.0 mL, 202 mmol). Then cyclobutanecarbonyl chloride (6.00 mL, 50.6 mmol) was added dropwise. The flask was removed from the cold bath and the mixture was allowed to stir while warming to ambient temperature. The mixture was poured into 1 N aqueous hydrochloric acid and extracted twice with ether. The combined organic layers were dried over magnesium sulfate, washed twice with saturated sodium bicarbonate, dried again over magnesium sulfate, concentrated and purified by chromatography (silica gel, 7.5% ethyl acetate in hexanes) to afford ethyl 3-cyclobutyl-3-oxopropanoate (6.69 g, 78%). $^1$H-NMR (400 MHz, DMSO-$d_6$) δ 4.06 (q, J=7 Hz, 2H), 3.49 (s, 2H), 3.38-3.32 (m, 1H), 2.11-2.05 (m, 4H), 1.90-1.85 (m, 1H), 1.87-1.66 (m, 1H) 1.15 (t, J=7 Hz, 3H).

9b) 3,5-Dichloro-4-pyridinecarbaldehyde oxime

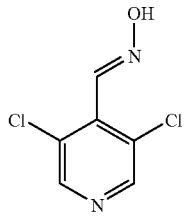

To a suspension of 3,5-dichloro-4-pyridinecarbaldehyde (6.50 g, 36.9 mmol) in ethanol (55 mL) was added a solution of sodium hydroxide (1.77 g, 44.3 mmol) and hydroxylamine hydrochloride (3.08 g, 44.3 mmol) in water (30 mL). The suspension was heated to 90° C. The mixture was stirred at 90° C. for approximately 6.5 hours and then concentrated. Water was added and the resulting solid was isolated by filtration and dried under a nitrogen stream at 45° C. over phosphorus pentoxide to afford 3,5-dichloro-4-pyridinecarbaldehyde oxime (6.38 g, 33.4 mmol, 91%). $^1$H-NMR (400 MHz, DMSO-$d_6$) δ 13.31 (s, 1H), 8.68 (s, 2H), 8.24 (s, 1H).

9c) Ethyl 5-cyclobutyl-3-(3,5-dichloro-4-pyridinyl)-4-isoxazolecarboxylate

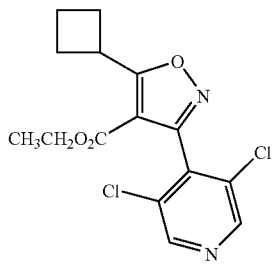

To a solution of 3,5-dichloro-4-pyridinecarbaldehyde oxime (3.15 g, 16.5 mmol) in N,N-dimethylformamide (13 mL) was added N-chlorosuccinimide (2.20 g, 16.5 mmol). The mixture was heated to 65° C. and all solids dissolved. The solution was stirred at 65° C. for approximately 1.5 hours, poured into water and extracted with ether. The ether layer containing the crude imidoyl chloride was washed with brine, dried over magnesium sulfate and concentrated. To a separate solution of ethyl 3-cyclobutyl-3-oxopropanoate (3.37 g, 19.8 mmol) in tetrahydrofuran (4 mL) at 0° C. was added sodium ethoxide (25 wt % in ethanol, 6.21 mL, 19.8 mmol) and the mixture was stirred for approximately 7 minutes. Then the above imidoyl chloride was added in tetrahydrofuran (13 mL) at a slow rate. A solid precipitated and the mixture was allowed to warm to ambient temperature and stir overnight. The mixture was concentrated and taken up with ethyl acetate and washed with water. The aqueous layer was back-extracted with ethyl acetate and the combined organic layers were washed with brine, dried over magnesium sulfate and purified by chromatography (silica gel, 0-10% ethyl acetate in hexanes gradient elution) to afford ethyl 5-cyclobutyl-3-(3,5-dichloro-4-pyridinyl)-4-isoxazolecarboxylate (2.98 g, 53%). $^1$H-NMR (400 MHz, DMSO-$d_6$) δ 8.64 (s, 2H), 4.35-4.20 (m, 1H), 4.05 (q, J=7 Hz, 2H), 2.45-2.30 (m, 4H), 2.14-2.04 (m, 1H), 2.00-1.89 (m, 1H), 0.96 (t, J=7 Hz, 3H). LRMS (APCI) m/z 341 (M+H)$^+$.

9d) 5-Cyclobutyl-3-(3,5-dichloro-4-pyridinyl)-4-isoxazolecarboxylic acid

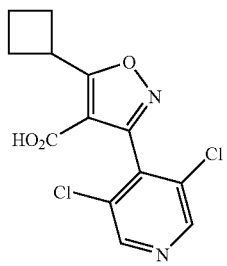

To a solution of ethyl 5-cyclobutyl-3-(3,5-dichloro-4-pyridinyl)-4-isoxazolecarboxylate (1.00 g, 2.93 mmol), in 2:1 tetrahydrofuran:methanol (15 mL) was added 1 N aqueous sodium hydroxide (4.40 mL, 4.40 mmol). The solution was heated in a microwave reactor to 120° C. for 500 seconds. Then 1 N aqueous hydrochloric acid (4.40 mL, 4.40 mmol) was added and the solution was concentrated. Water was added and the mixture was extracted twice with ethyl acetate. The combined organic layers were washed with brine, dried over magnesium sulfate, concentrated and dried under a nitrogen stream at 45° C. overnight to afford 5-cyclobutyl-3-(3,5-dichloro-4-pyridinyl)-4-isoxazolecarboxylic acid (808 mg, 88%). $^1$H-NMR (400 MHz, DMSO-$d_6$) δ 13.34 (br s, 1H), 8.81 (s, 2H), 4.33-4.25 (m, 1H), 2.42-2.32 (m, 4H), 2.15-2.05 (m, 1H), 1.96-1.88 (m, 1H).

9e) [5-Cyclobutyl-3-(3,5-dichloro-4-pyridinyl)-4-isoxazolyl]methanol

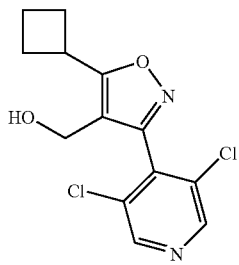

To a solution of 5-cyclobutyl-3-(3,5-dichloro-4-pyridinyl)-4-isoxazolecarboxylic acid (808 mg, 2.59 mmol) in THF (13 mL) at 0° C. was added triethylamine (0.361 mL, 2.59 mmol) followed by isopropyl chloroformate (1 M in toluene, 2.59 mL, 2.59 mmol). The solution was stirred at 0° C. for approximately 1 hour and then was filtered into a solution of sodium borohydride (127 mg, 3.37 mmol) in water (1 mL) at 0° C. The solution was allowed to warm to ambient temperature and was then concentrated. Water was added and the mixture was extracted three times with ethyl acetate. The combined organic layers were washed with brine, dried over magnesium sulfate, concentrated and purified by chromatography (silica gel, 0-40% ethyl acetate in hexanes gradient elution) to afford [5-cyclobutyl-3-(3,5-dichloro-4-pyridinyl)-4-isoxazolyl]methanol (478 mg, 62%). $^1$H-NMR (400 MHz, DMSO-$d_6$) δ 8.79 (s, 2H), 4.97-4.94 (m, 1H), 4.16-4.15 (m, 2H), 3.92-3.83 (m, 1H), 2.40-2.30 (m, 4H), 2.10-2.01 (m, 1H), 1.99-1.89 (m, 1H).

9f) Methyl 7-[4-({[5-cyclobutyl-3-(3,5-dichloro-4-pyridinyl)-4-isoxazolyl]methyl}oxy)phenyl]-3-isoquinolinecarboxylate

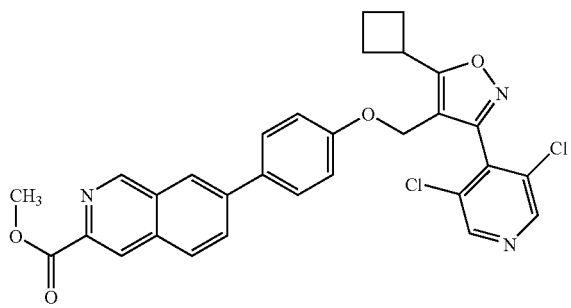

To a solution of methyl 7-(4-hydroxyphenyl)-3-isoquinolinecarboxylate (50 mg, 0.18 mmol), [5-cyclobutyl-3-(3,5-dichloro-4-pyridinyl)-4-isoxazolyl]methanol (54 mg, 0.18 mmol) and triphenylphosphine (52 mg, 0.20 mmol) in dichloromethane (1.5 mL) was added diisopropyl azodicarboxylate (0.035 mL, 0.20 mmol). The solution was heated in a microwave reactor at 90° C. for 10 minutes and allowed to stand at ambient temperature overnight. The next day the solution was adsorbed onto silica gel and purified by chromatography (first in 0-1.75% methanol in chloroform gradient elution then in 0-2% methanol in chloroform) to afford methyl 7-[4-({[5-cyclobutyl-3-(3,5-dichloro-4-pyridinyl)-4-isoxazolyl]methyl}oxy)phenyl]-3-isoquinolinecarboxylate as a white solid (39 mg, 39%). $^1$H-NMR (400 MHz, DMSO-$d_6$) δ 9.33 (s, 1H), 8.59 (s, 3H), 8.12 (s, 1H), 8.00-7.94 (m, 2H), 7.58 (d, J=9 Hz, 2H), 6.84 (d, J=9 Hz, 2H), 4.79 (s, 2H), 4.04 (s, 3H), 3.87-3.79 (m, 1H), 2.64-2.54 (m, 2H), 2.50-2.35 (m, 2H), 2.19-2.00 (m, 2H).

9 g) 7-[4-({[5-Cyclobutyl-3-(3,5-dichloro-4-pyridinyl)-4-isoxazolyl]methyl}oxy)phenyl]-3-isoquinolinecarboxylic acid

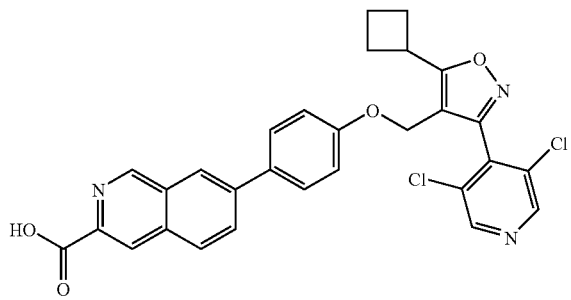

To a solution of methyl 7-[4-({[5-cyclobutyl-3-(3,5-dichloro-4-pyridinyl)-4-isoxazolyl]methyl}oxy)phenyl]-3-isoquinolinecarboxylate (39 mg, 0.070 mmol) in 2:1 tetrahydrofuran:methanol (1.5 mL) was added 1 N sodium hydroxide (0.10 mL, 0.10 mmol). The solution was heated in a microwave reactor at 120° C. for 500 seconds. The solution was concentrated under a nitrogen stream and 1 N aqueous hydrochloric acid (0.10 mL, 0.10 mmol) was added. The solution was concentrated further under an nitrogen stream and water was added followed by ethyl acetate. A solid precipitated. The water layer was removed and ether was added and the solid was isolated by filtration. The solid was dried under a nitrogen stream at 45° C. to afford 7-[4-({[5-cyclobutyl-3-(3,5-dichloro-4-pyridinyl)-4-isoxazolyl]methyl}oxy)phenyl]-3-isoquinolinecarboxylic acid (23 mg, 60%). $^1$H-NMR (400 MHz, DMSO-$d_6$) δ 9.39 (s, 1H), 8.81 (s, 2H), 8.60 (s, 1H), 8.43 (s, 1H), 8.25-8.10 (m, 2H), 7.75 (d, J=9 Hz, 2H), 6.89 (d, J=9 Hz, 2H), 4.93 (s, 2H), 4.08-3.99 (m, 1H), 2.50-2.40 (m, 4H), 2.15-2.05 (m, 1H), 2.00-1.90 (m, 1H). HRMS (ESI) $C_{29}H_{21}Cl_2N_3O_4$ calculated: 546.0982 [M+H]$^+$, found: 546.0981 [M+H]$^+$.

EXAMPLE 10

7-[4-({[5-Cyclopropyl-3-(2,6-dichlorophenyl)-4-isoxazolyl]methyl}oxy)phenyl]-3-isoquinolinecarboxylic acid

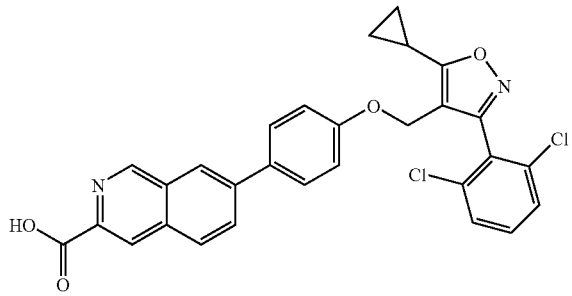

10a) Ethyl 3-cyclopropyl-3-oxopropanoate

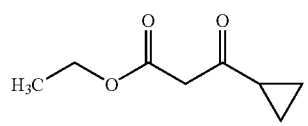

Ethyl 3-cyclopropyl-3-oxopropanoate was made by the same procedure as the one employed to synthesize methyl 3-cyclobutyl-3-oxopropanoate in example 9a, except cyclopropylcarbonyl chloride was used instead of cyclobutylcarbonyl chloride, affording ethyl 3-cyclopropyl-3-oxopropanoate (3.35 g, 56%). $^1$H-NMR (400 MHz, DMSO-$d_6$) δ 4.07 (q, J=7 Hz, 2H), 3.65 (s, 2H), 2.09-2.02 (m, 1H), 1.16 (t, J=7 Hz, 3H), 0.93-0.86 (m, 4H).

10b) Ethyl 5-cyclopropyl-3-(2,6-dichlorophenyl)-4-isoxazolecarboxylate

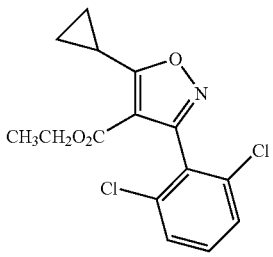

To a water bath-cooled solution of 2,6-dichlorobenzaldehyde oxime (2.20 g, 11.6 mmol) in N,N-dimethylformamide (7 mL) was added solid N-chlorosuccinimide (1.55 g, 11.6 mmol). The solutions were stirred while in the water bath for approximately 20 min and the outside the bath for approximately 1 hour. The solution was poured into water and extracted twice with ether. The combined organic layers containing the crude imidoyl chloride were dried over magnesium sulfate and then concentrated. To a separate solution of ethyl 3-cyclopropyl-3-oxopropanoate (2.17 g, 13.9 mmol) in THF (3 mL) at 0° C. was added sodium ethoxide (25 wt % in ethanol, 4.36 mL, 13.9 mmol). The solution was stirred for a few minutes and then the above imidoyl chloride was added. The solution was stirred at 0° C. for 10 minutes and then at ambient temperature overnight. The solution was poured into water and extracted three times with ethyl acetate. The combined organic layers were dried over magnesium sulfate, concentrated and purified by chromatography (silica gel, 0-5% ethyl acetate in hexanes gradient elution) to afford ethyl 5-cyclopropyl-3-(2,6-dichlorophenyl)-4-isoxazolecarboxylate (289 mg, 8%). $^1$H-NMR (400 MHz, DMSO-$d_6$) δ 7.62-7.53 (m, 3H), 4.04 (q, J=7 Hz, 2H), 2.84-2.82 (m, 1H), 1.35-1.25 (m, 4H), 0.93 (t, J=7 Hz, 3H).

10c) [5-Cyclopropyl-3-(2,6-dichlorophenyl)-4-isoxazolyl]methanol

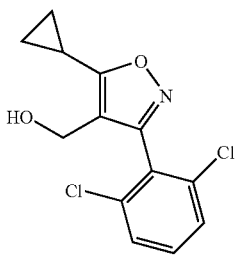

To a solution of ethyl 5-cyclopropyl-3-(2,6-dichlorophenyl)-4-isoxazolecarboxylate (289 mg, 0.886 mmol) in THF (4 mL) at 0° C. was slowly added diisobutylaluminum hydride (1.5M in toluene, 1.24 mL, 1.86 mmol). The solution was allowed to warm slowly to ambient temperature. After approximately 4 hours of stirring, the solution was re-cooled to 0° C. and an additional 1 mL of diisobutylaluminum hydride was added. After approximately 1.5 hours of stirring the mixture was re-cooled to 0° C., quenched with some aqueous Rochelle's salt and allowed to stir overnight while warming to ambient temperature. The mixture was extracted twice with ethyl acetate. The combined organic layers were washed once with Rochelle's Salt, dried over magnesium sulfate and concentrated to afford [5-cyclopropyl-3-(2,6-dichlorophenyl)-4-isoxazolyl]methanol (242 mg, 96%). $^1$H-NMR (400 MHz, DMSO-$d_6$) δ 7.61-7.51 (m, 3H), 4.93 (t, J=5 Hz, 1H), 4.19 (d, J=5 Hz, 2H), 2.31-2.27 (m, 1H), 1.11-1.04 (m, 4H).

10d) Methyl 7-[4-({[5-cyclopropyl-3-(2,6-dichlorophenyl)-4-isoxazolyl]methyl}oxy)phenyl]-3-isoquinolinecarboxylate

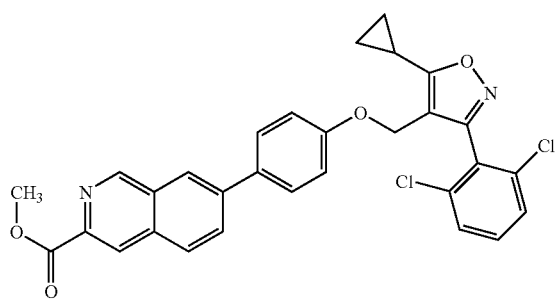

To a solution of [5-cyclopropyl-3-(2,6-dichlorophenyl)-4-isoxazolyl]methanol (51 mg, 0.18 mmol), methyl 7-(4-hydroxyphenyl)-3-isoquinolinecarboxylate (50 mg, 0.18 mmol) and triphenylphosphine (52 mg, 0.20 mmol) in dichloromethane (1.5 mL) was added diisopropyl azodicarboxylate (0.035 mL, 0.20 mmol). The solution was heated in a microwave reactor at 90° C. for 10 minutes and then allowed to stand overnight. The mixture was adsorbed onto silica gel and purified by chromatography (silica gel, 0-1.25% methanol in dichloromethane) to afford methyl 7-[4-({[5-cyclopropyl-3-(2,6-dichlorophenyl)-4-isoxazolyl]methyl}oxy)phenyl]-3-isoquinolinecarboxylate (54 mg, 55%). $^1$H-NMR (400 MHz, DMSO-$d_6$) δ 9.39 (s, 1H), 8.63 (s, 1H), 8.44 (s, 1H), 8.29-8.14 (m, 2H), 7.75 (d, J=9 Hz, 2H), 7.61-7.50 (m, 3H), 6.96 (d, J=9 Hz, 2H), 4.94 (s, 2H), 3.91 (s, 3H), 2.50-2.46 (m, 1H), 1.21-1.14 (m, 4H).

10e) 7-[4-({[5-Cyclopropyl-3-(2,6-dichlorophenyl)-4-isoxazolyl]methyl}oxy)phenyl]-3-isoquinolinecarboxylic acid

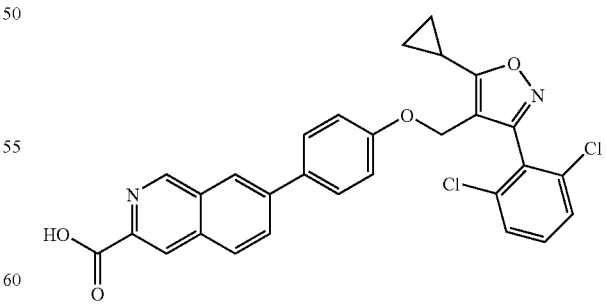

To a solution of methyl 7-[4-({[5-cyclopropyl-3-(2,6-dichlorophenyl)-4-isoxazolyl]methyl}oxy)phenyl]-3-isoquinolinecarboxylate (54 mg, 0.099 mmol) in 2:1 tetrahydrofuran:methanol (1.5 ml) was added 1 N sodium hydroxide (0.15 mL, 0.15 mmol). The solution was heated in a microwave reactor to 120° C. for 500 seconds. The solution was concentrated under a nitrogen stream and 1 N hydrochloric acid (0.15 mL, 0.15 mmol) was added. The solution was further concentrated under a nitrogen stream. Water and ethyl acetate were added and a solid precipitated that would not dissolve. The water layer was removed and the resulting mixture was washed twice with water. The organic solvents were removed under vacuum and the resulting solid was dried at 45° C. under a nitrogen stream to afford 7-[4-({[5-cyclopropyl-3-(2,6-dichlorophenyl)-4-isoxazolyl]methyl}oxy)phenyl]-3-isoquinolinecarboxylic acid (36 mg, 68%). $^1$H-NMR (400 MHz, DMSO-$d_6$) δ 13.1 (br s, 1H), 9.39 (s, 1H), 8.60 (s, 1H), 8.43 (s, 1H), 8.22-8.13 (m, 2H), 7.75 (d, J=9 Hz, 2H), 7.61-7.51 (m, 3H), 6.96 (d, J=9 Hz, 2H), 4.94 (s, 2H), 2.51-2.45 (m, 1H), 1.12-1.13 (m, 4H). HRMS (ESI) $C_{29}H_{20}Cl_2N_2O_4$ calculated: 531.0880 (M+H)$^+$, found: 531.0872 (M+H)$^+$.

Example 11

6-[4-({[5-Cyclopropyl-3-(2,6-dichlorophenyl)-4-isoxazolyl]methyl}oxy)phenyl]-2-quinolinecarboxylic acid

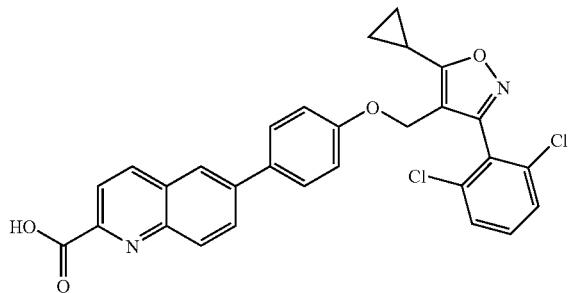

11a) Methyl 6-[4-({[5-cyclopropyl-3-(2,6-dichlorophenyl)-4-isoxazolyl]methyl}oxy)phenyl]-2-quinolinecarboxylate

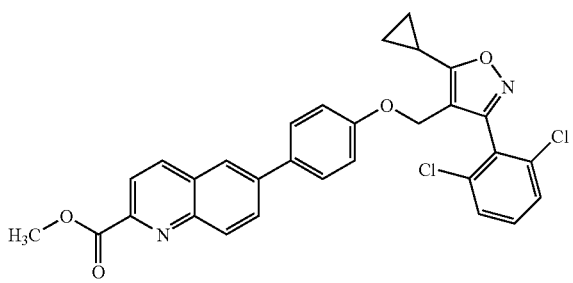

To a solution of [5-cyclopropyl-3-(2,6-dichlorophenyl)-4-isoxazolyl]methanol (0.10 g, 0.36 mmol), methyl 6-(4-hydroxyphenyl)-2-quinolinecarboxylate (0.10 g, 0.36 mmol) and triphenylphosphine (0.10 g, 0.39 mmol) in dichloromethane (2.5 mL) was added diisopropyl azodicarboxylate (0.071 mL, 0.39 mmol) dropwise. The solution was heated in a microwave reactor to 90° C. for 10 minutes and then allowed to sit overnight. The solution was adsorbed onto silica gel and purified by chromatography (silica gel, 0-45% ethyl acetate in hexanes gradient elution) to afford methyl 6-[4-({[5-cyclopropyl-3-(2,6-dichlorophenyl)-4-isoxazolyl]methyl}oxy)phenyl]-2-quinolinecarboxylate (62 mg, 32%). $^1$H-NMR (400 MHz, DMSO-$d_6$) δ 8.55 (d, J=9 Hz, 1H), 8.28 (s, 1H), 8.18-8.10 (m, 3H), 7.73 (d, J=9 Hz, 2H), 7.62-7.50 (m, 3H), 6.95 (d, J=9 Hz, 2H), 4.93 (s, 2H), 3.93 (s, 3H), 2.50-2.42 (m, overlapping DMSO ~1H), 1.20-1.12 (m, 4H). LRMS (APCI) m/z 545 (M+H)$^+$.

11b) 6-[4-({[5-Cyclopropyl-3-(2,6-dichlorophenyl)-4-isoxazolyl]methyl}oxy)phenyl]-2-quinolinecarboxylic acid

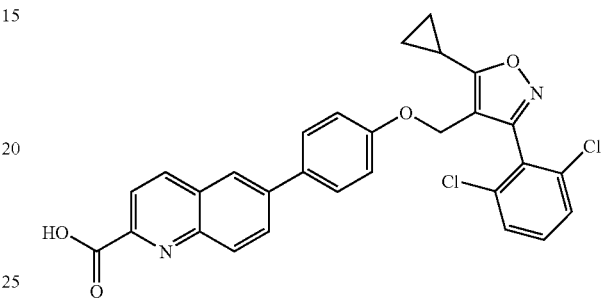

To a solution of methyl 6-[4-({[5-cyclopropyl-3-(2,6-dichlorophenyl)-4-isoxazolyl]methyl}oxy)phenyl]-2-quinolinecarboxylate (58 mg, 0.11 mmol) in 2:1 tetrahydrofuran:methanol (1.5 mL) was added 1 N sodium hydroxide (0.18 mL, 0.18 mmol). The solution was heated in a microwave reactor at 120° C. for 500 seconds. The solution was concentrated and water was added followed by 1 N hydrochloric acid (0.18 mL, 0.18 mmol). The solution was extracted twice with ethyl acetate and the combined organic layers were washed with brine and concentrated to afford 6-[4-({[5-cyclopropyl-3-(2,6-dichlorophenyl)-4-isoxazolyl]methyl}oxy)phenyl]-2-quinolinecarboxylic acid (52 mg, 92%). $^1$H-NMR (400 MHz, DMSO-$d_6$) δ 13.36 (br s, 1H), 8.53 (d, J=9 Hz, 1H), 8.27 (s, 1H), 8.17-8.08 (m, 3H), 7.73 (d, J=9 Hz, 2H), 7.62-7.51 (m, 3H), 6.95 (d, J=9 Hz, 2H), 4.93 (s, 2H), 2.49-2.43 (m, 1H), 1.20-1.10 (m, 4H). HRMS (ESI) $C_{29}H_{20}Cl_2N_2O_4$ calculated: 531.0873 [M+H]$^+$, found: 531.0873 [M+H]$^+$.

Example 12

6-[4-({[5-Cyclopropyl-3-(3,5-dichloro-4-pyridinyl)-4-isoxazolyl]methyl}oxy)phenyl]-2-quinolinecarboxylic acid

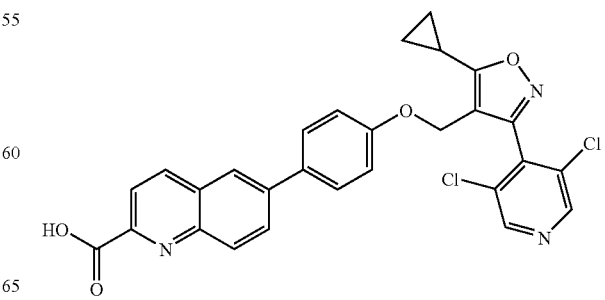

12a) Ethyl 5-cyclopropyl-3-(3,5-dichloro-4-pyridinyl)-4-isoxazolecarboxylate

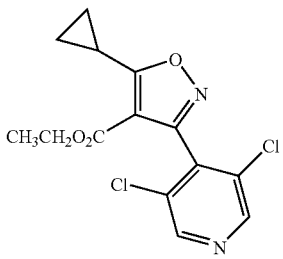

To a solution of 3,5-dichloro-4-pyridinecarbaldehyde oxime (1.44 g, 7.53 mmol) in N,N-dimethylformamide (6 mL) was added N-chlorosuccinimide (1.00 g, 7.53 mmol). The mixture was heated to 65° C. and all solids dissolved. The solution was stirred at 65° C. for approximately 1.5 hr, poured into water and extracted with ether. The ether layer containing the crude imidoyl chloride was washed with brine, dried over magnesium sulfate and concentrated. To a separate solution of ethyl 3-cyclopropyl-3-oxopropanoate (1.41 g, 9.03 mmol) in tetrahydrofuran (2 mL) at 0° C. was added a 25 wt % solution of sodium ethoxide in ethanol (2.83 mL, 9.03 mmol) and the mixture was stirred for approximately 7 min. Then the above imidoyl chloride in tetrahydrofuran (6.5 mL) was added at a slow rate. A solid precipitated and the mixture was allowed to warm to ambient temperature and stir overnight. The mixture was concentrated and taken up with ethyl acetate and washed with water. The aqueous layer was back-extracted with ethyl acetate and the combined organic layers were washed with brine, dried over magnesium sulfate and purified by chromatography (silica gel, 0-10% ethyl acetate in hexanes gradient elution). The isolated solid was washed with hexanes to afford ethyl 5-cyclopropyl-3-(3,5-dichloro-4-pyridinyl)-4-isoxazolecarboxylate (214 mg, 9%). $^1$H-NMR (400 MHz, DMSO-$d_6$) δ 8.84 (s, 2H), 4.07 (q, J=7 Hz, 2H), 2.88-2.81 (m, 1H), 1.37-1.27 (m, 4H), 0.95 (t, J=7 Hz, 3H). LRMS (APCI) m/z 327 (M+H)$^+$.

12b) 5-Cyclopropyl-3-(3,5-dichloro-4-pyridinyl)-4-isoxazolecarboxylic acid

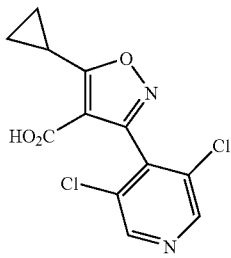

To a solution of ethyl 5-cyclopropyl-3-(3,5-dichloro-4-pyridinyl)-4-isoxazolecarboxylate (210 mg, 0.642 mmol) in 2:1 tetrahydrofuran:methanol (3 mL) was added 1 N sodium hydroxide (0.963 mL, 0.963 mmol). The solution was heated in a microwave reactor to 120° C. for 500 seconds. Then 1 N hydrochloric acid (0.963 mL, 0.963 mmol) was added and the solution was concentrated. The residue was taken up with water and extracted twice with ethyl acetate. The combined organic layers were washed with brine, dried over magnesium sulfate and concentrated to afford 5-cyclopropyl-3-(3,5-dichloro-4-pyridinyl)-4-isoxazolecarboxylic acid (158 mg, 82%). $^1$H-NMR (400 MHz, DMSO-$d_6$) δ 13.35 (s, 1H), 8.81 (s, 2H), 2.91-2.84 (m, 1H), 1.34-1.24 (m, 4H).

12c) [5-Cyclopropyl-3-(3,5-dichloro-4-pyridinyl)-4-isoxazolyl]methanol

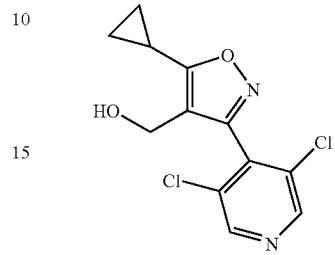

To a solution of 5-cyclopropyl-3-(3,5-dichloro-4-pyridinyl)-4-isoxazolecarboxylic acid (155 mg, 0.52 mmol) and triethylamine (0.072 mL, 0.52 mmol) in tetrahydrofuran (3 mL) at 0° C. was added isopropyl chloroformate (0.52 mL, 0.52 mmol). A white solid was seen to precipitate. The mixture was stirred at 0° C. for approximately 1 hour and then filtered into a stirring solution of sodium borohydride (25 mg, 0.67 mmol) in water at 0° C. The solution was stirred at 0° C. for approximately 30 minutes and the allowed to warm to ambient temperature. The solution was concentrated and water was added. The solution was extracted twice with ethyl acetate. The combined organic layers were washed with brine, dried over magnesium sulfate, concentrated and purified by chromatography (silica gel, 0-40% ethyl acetate in hexanes gradient elution) to afford [5-cyclopropyl-3-(3,5-dichloro-4-pyridinyl)-4-isoxazolyl]methanol (83 mg, 56%). $^1$H-NMR (400 MHz, CDCl$_3$) δ 8.62 (s, 2H), 4.44 (s, 2H), 2.20-2.14 (m, 1H), 1.30-1.44 (m, 4H).

12d) Methyl 6-[4-({[5-cyclopropyl-3-(3,5-dichloro-4-pyridinyl)-4-isoxazolyl]methyl}oxy)phenyl]-2-quinolinecarboxylate

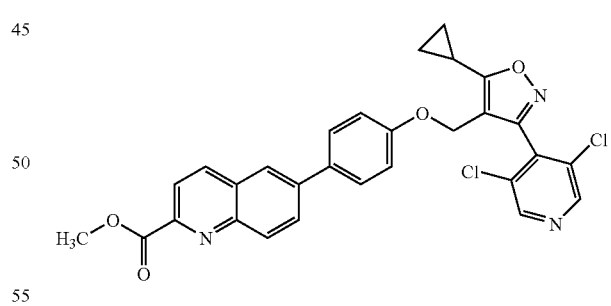

To a solution of methyl 6-(4-hydroxyphenyl)-2-quinolinecarboxylate (81 mg, 0.29 mmol), triphenylphosphine (84 mg, 0.32 mmol) and [5-cyclopropyl-3-(3,5-dichloro-4-pyridinyl)-4-isoxazolyl]methanol (83 mg, 0.29 mmol) in dichloromethane (2.5 mL) was added diisopropyl azodicarboxylate (0.058 mL, 0.32 mmol) dropwise. The solution was heated in a microwave reactor at 90° C. for 10 minutes and then allowed to stand overnight. The solution was adsorbed onto silica gel and purified by chromatography (silica gel, 0-1.25% methanol in chloroform gradient elution) to afford methyl 6-[4-({[5-cyclopropyl-3-(3,5-dichloro-4-pyridinyl)-4-isoxazolyl]methyl}oxy)phenyl]-2-quinolinecarboxylate (70 mg, 44%). $^1$H-NMR (400 MHz, CDCl$_3$) δ 8.60 (s, 2H), 8.39-8.33 (m, 2H), 8.22 (d, J=9 Hz, 1H), 8.01-7.96 (m, 2H), 7.60 (d, J=9 Hz, 2H), 6.88 (d, J=9 Hz, 2H), 4.90 (s, 2H), 4.09 (s, 3H), 2.22-2.15 (m, 1H), 1.33-1.13 (m, 4H).

12e) 6-[4-({[5-Cyclopropyl-3-(3,5-dichloro-4-pyridinyl)-4-isoxazolyl]methyl}oxy)phenyl]-2-quinolinecarboxylic acid

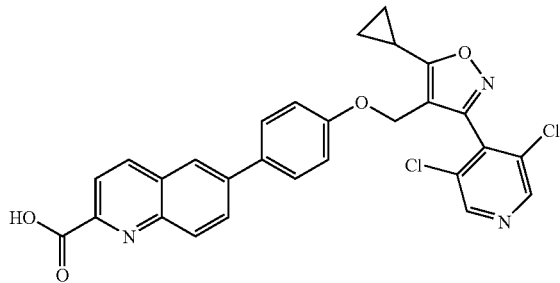

To a solution of methyl 6-[4-({[5-cyclopropyl-3-(3,5-dichloro-4-pyridinyl)-4-isoxazolyl]methyl}oxy)phenyl]-2-quinolinecarboxylate (70 mg, 0.13 mmol) in 2:1 tetrahydrofuran:methanol (1.5 mL) was added 1 N sodium hydroxide (0.19 mL, 0.19 mmol). The solution was heated in a microwave reactor at 120° C. for 500 seconds. Then (0.19 mL, 0.19 mmol) 1 N hydrochloric acid was added and the solution was concentrated. The residue was taken up with water and extracted twice with ethyl acetate. The combined organic layers were washed with brine and concentrated. The resulting solid was dried under a nitrogen stream at 45° C. over 48 hours to afford 6-[4-({[5-cyclopropyl-3-(3,5-dichloro-4-pyridinyl)-4-isoxazolyl]methyl}oxy)phenyl]-2-quinolinecarboxylic acid as a yellow solid (53 mg, 78%). $^1$H-NMR (400 MHz, DMSO-d$_6$) δ 13.37 (br s, 1H), 8.81 (s, 2H), 8.53 (d, J=9 Hz, 1H), 8.28 (s, 1H), 8.18-8.08 (m, 3H), 7.74 (d, J=9 Hz, 2H), 6.92 (d, J=9 Hz, 2H), 5.02 (s, 2H), 2.52-2.46 (m, 1H), 1.23-1.10 (m, 4H). HRMS (ESI) C$_{28}$H$_{19}$Cl$_2$N$_3$O$_4$ calculated: 532.0825 [M+H]$^+$, found: 532.0823 [M+H]$^+$.

Example 13

6-{4-[({3-(2,6-Dichlorophenyl)-5-[(1S)-1-methylpropyl]-4-isoxazolyl}methyl)oxy]phenyl}-2-quinolinecarboxylic acid

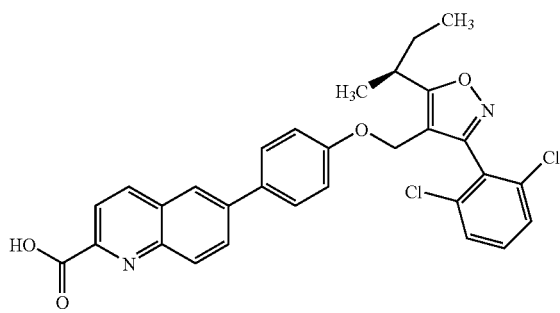

13a) Ethyl 4-methyl-3-oxohexanoate

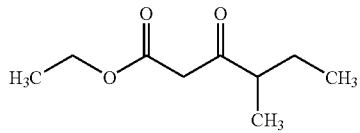

To a solution of monoethyl malonate (49.5 mL, 0.42 mol) and a few milligrams of 2,2'-bipyridyl in tetrahydrofuran at −70° C. was added 2.5 M n-butyl lithium in hexanes (0.34 L, 0.84 mol) dropwise over approximately 1.5 hours. Then 2-methylbutyryl chloride (26 mL, 0.21 mol) was added dropwise. The mixture was allowed to warm to ambient temperature and was then poured into 1 N hydrochloric acid. The mixture was extracted three times with ether and the combined organic layers were dried over magnesium sulfate and concentrated. The resulting oil was purified by vacuum distillation (boiling range 75-85° C.) to afford ethyl 4-methyl-3-oxohexanoate (36.4 g, 100%). $^1$H-NMR (400 MHz, DMSO-d$_6$) δ 4.06 (q, J=7 Hz, 2H), 3.60 (s, 2H), 2.57-2.49 (m, 1H), 1.64-1.53 (m, 1H), 1.36-1.26 (m, 1H), 1.15 (t, J=7 Hz, 3H), 0.97 (d, J=7 Hz, 3H), 0.78 (t, J=7 Hz, 3H).

13b) {3-(2,6-Dichlorophenyl)-5-[(1S)-1-methylpropyl]-4-isoxazolyl}methanol

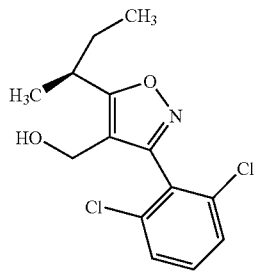

To a solution of 2,6-dichlorobenzaldehyde oxime (26.4 g, 139 mmol) in N,N-dimethylformamide (70 mL) at 5° C. was added solid N-chlorosuccinimide (18.6 g, 139 mmol) in portions. The mixture was allowed to stir and warm to ambient temperature (with occasional cooling when warming was noted) over approximately 1.5 hour and then poured into ether. The ether layer containing the crude imidoyl chloride was washed twice with water followed by brine, dried over magnesium sulfate and concentrated. To a separate solution of ethyl 4-methyl-3-oxohexanoate (28.8 g, 167 mmol) in tetrahydrofuran (50 mL) at 0° C. was added sodium ethoxide (21 wt % in ethanol, 62.3 mL, 167 mmol) quickly. Then the above imidoyl chloride was added dropwise in tetrahydrofuran (100 mL). The solution was allowed to stir while warming to ambient temperature overnight. The mixture was then poured into ether, washed twice with water followed by brine, dried over magnesium sulfate, concentrated and purified by chromatography (silica gel, 1.25% acetone in hexanes) to afford an oil which was dissolved in tetrahydrofuran (75 mL) at 0° C. Then a 1.5 M solution of diisobutylaluminum hydride in toluene (100 mL, 150 mmol) was added slowly. The solution was allowed to warm slightly while stirring for approximately 2.5 hours and then was re-cooled to 0° C. and stirred for 1.5 hours. Then aqueous Rochelle's salt (20 mL) was added carefully followed by ethyl acetate and the mixture was stirred overnight. Then the layers were separated and the aqueous layer was extracted two more times with ethyl acetate. The combined organic layers were washed with brine, dried over magnesium sulfate, concentrated and purified by chromatography (silica gel, 20% ethyl acetate in hexanes) to afford a white solid. The enantiomers were resolved by supercritical fluid chromatography (Chiralpak AD, 10% methanol in supercritical carbon dioxide) and the resulting solid was taken up with dichloromethane, dried over magnesium sulfate and concentrated to afford {3-(2,6-dichlorophenyl)-5-[(1S)-1-methylpropyl]-4-isoxazolyl}methanol (1.53 g, 7%) $^1$H-NMR (400 MHz, DMSO-$d_6$) δ 7.61-7.51 (m, 3H), 4.85 (t, J=5 Hz, 1H), 4.20-4.06 (m, 2H), 3.15-3.10 (m, 1H), 1.69-1.62 (m, 2H), 1.29 (d, J=7 Hz, 3H), 0.79 (t, J=7 Hz, 3H).

13c) Methyl 6-{4-[({3-(2,6-dichlorophenyl)-5-[(1S)-1-methylpropyl]-4-isoxazolyl}methyl)oxy]phenyl}-2-quinolinecarboxylate

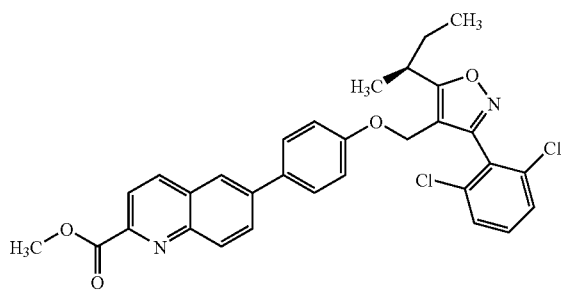

To a solution of methyl 6-(4-hydroxyphenyl)-2-quinolinecarboxylate (154 mg, 0.550 mmol), triphenylphosphine (144 mg, 0.550 mmol) and {3-(2,6-dichlorophenyl)-5-[(1S)-1-methylpropyl]-4-isoxazolyl}methanol (150 mg, 0.500 mmol) in dichloromethane (1.5 mL) was added diisopropyl azodicarboxylate (0.099 mL, 0.550 mmol) dropwise. The solution was heated in a microwave reactor at 90° C. for 10 minutes. The solution was adsorbed onto silica gel and purified by chromatography (silica gel, 0-60% ethyl acetate in hexanes gradient elution). A second purification was done by chromatography (silica gel, 2% methanol in dichloromethane) to afford methyl 6-{4-[({3-(2,6-dichlorophenyl)-5-[(1S)-1-methylpropyl]-4-isoxazolyl}methyl)oxy]phenyl}-2-quinolinecarboxylate as a white solid (118 mg, 42%). $^1$H-NMR (400 MHz, DMSO-$d_6$) δ 8.55 (d, J=9 Hz, 1H), 8.28 (s, 1H), 8.18-8.10 (m, 3H), 7.73 (d, J=8 Hz, 2H), 7.63-7.51 (m, 3H), 6.92 (d, J=8 Hz, 2H), 4.88 (app q, J=12 Hz, 2H), 3.94 (s, 3H), 3.27-3.22 (m, 1H), 1.73-1.66 (m, 2H), 1.32 (d, J=7 Hz, 3H), 0.83 (t, J=7 Hz, 3H).

13d) 6-{4-[({3-(2,6-Dichlorophenyl)-5-[(1S)-1-methylpropyl]-4-isoxazolyl}methyl)oxy]phenyl}-2-quinolinecarboxylic acid

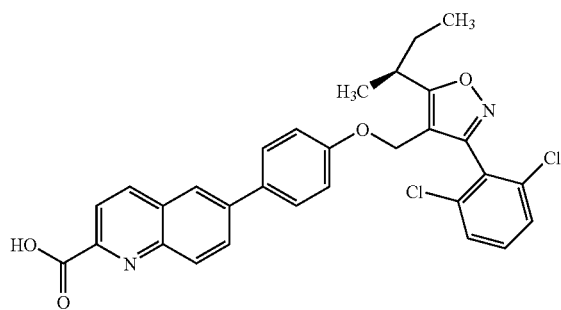

To a solution of methyl 6-{4-[({3-(2,6-dichlorophenyl)-5-[(1S)-1-methylpropyl]-4-isoxazolyl}methyl)oxy]phenyl}-2-quinolinecarboxylate (50 mg, 0.089 mmol) in 2:1 tetrahydrofuran:methanol (1.5 mL) was added 1 N sodium hydroxide (0.13 mL, 0.13 mmol). The solution was heated in a microwave reactor at 80° C. for 10 minutes and then 1 N hydrochloric acid (0.13 mL, 0.13 mmol) was added. The solution was concentrated and the residue was taken up with ethyl acetate and water. The layers were separated and the organic layer was dried over magnesium sulfate and concentrated to afford 50 mg of 6-{4-[({3-(2,6-dichlorophenyl)-5-[(1S)-1-methylpropyl]-4-isoxazolyl}methyl)oxy]phenyl}-2-quinolinecarboxylic acid as a yellow solid (0.089 mmol, 100%). $^1$H-NMR (400 MHz, DMSO-$d_6$) δ 13.37 (br s, 1H), 8.53 (d, J=9 Hz, 1H), 8.27 (s, 1H), 8.18-8.08 (m, 3H), 7.73 (d, J=9 Hz, 2H), 7.63-7.51 (m, 3H), 6.99 (d, J=9 Hz, 2H), 4.88 (app q, J=12 Hz, 2H), 3.31-3.22 (m, 1H), 1.73-1.66 (m, 2H), 3.32 (d, J=7 Hz, 3H), 0.83 (t, J=7 Hz, 3H). HRMS (ESI) $C_{30}H_{24}Cl_2N_2O_4$ calculated: 547.1186 (M+H)$^+$, found: 547.1182 (M+H)$^+$.

Example 14

6-{4-[({3-(2,6-Dichlorophenyl)-5-[(1R)-1-methylpropyl]-4-isoxazolyl}methyl)oxy]phenyl}-2-quinolinecarboxylic acid

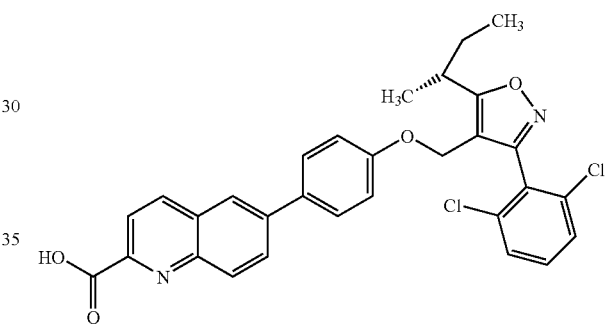

14a) {3-(2,6-Dichlorophenyl)-5-[(1R)-1-methylpropyl]-4-isoxazolyl}methanol

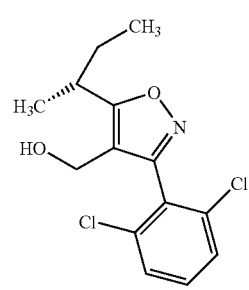

To a solution of 2,6-dichlorobenzaldehyde oxime (26.4 g, 139 mmol) in DMF (70 mL) at 5° C. was added solid N-chlorosuccinimide (18.6 g, 139 mmol) in portions. The mixture was allowed to stir and warm to ambient temperature (with occasional cooling when warming was noted) over approximately 1.5 hour and then poured into ether. The organic layer containing the crude imidoyl chloride was washed twice with water followed by brine, dried over magnesium sulfate and concentrated. To a separate solution of ethyl 4-methyl-3-oxohexanoate (28.8 g, 167 mmol) in tetrahydrofuran (50 mL)

at 0° C. was added a 21 wt % solution of sodium ethoxide in ethanol (62.3 mL, 167 mmol) quickly. The above imidoyl chloride was added dropwise in tetrahydrofuran (100 mL). The solution was allowed to stir while warming to ambient temperature overnight. The mixture was then poured into ether, washed twice with water followed by brine, dried over magnesium sulfate, concentrated and purified by chromatography (silica gel, 1.25% acetone in hexanes) to afford an oil which was dissolved in tetrahydrofuran (75 mL) at 0° C. Then a 1.5 M solution of diisobutylaluminum hydride in toluene (100 mL, 150 mmol) was added slowly. The solution was allowed to warm slightly while stirring for approximately 2.5 hours and then was re-cooled to 0° C. and stirred for 1.5 hours. Then approximately 20 mL of Rochelle's salt was added carefully followed by ethyl acetate and the mixture was stirred overnight. Then the layers were separated and the aqueous layer was extracted two more times with ethyl acetate. The combined organic layers were washed with brine, dried over magnesium sulfate, concentrated and purified by chromatography (silica gel, 20% ethyl acetate in hexanes) to afford a white solid. The enantiomers were resolved by supercritical fluid chromatography (Chiralpak AD, 10% methanol in supercritical carbon dioxide) and the resulting solid was taken up with dichloromethane, dried over magnesium sulfate and concentrated to afford {3-(2,6-dichlorophenyl)-5-[(1R)-1-methylpropyl]-4-isoxazolyl}methanol (1.35 g, 6%) $^1$H-NMR (400 MHz, DMSO-$d_6$) δ 7.61-7.51 (m, 3H), 4.85 (t, J=5 Hz, 1H), 4.20-4.06 (m, 2H), 3.15-3.10 (m, 1H), 1.69-1.62 (m, 2H), 1.29 (d, J=7 Hz, 3H), 0.79 (t, J=7 Hz, 3H).

14b) Methyl 6-{4-[({3-(2,6-dichlorophenyl)-5-[(1R)-1-methylpropyl]-4-isoxazolyl}methyl)oxy]phenyl}-2-quinolinecarboxylate

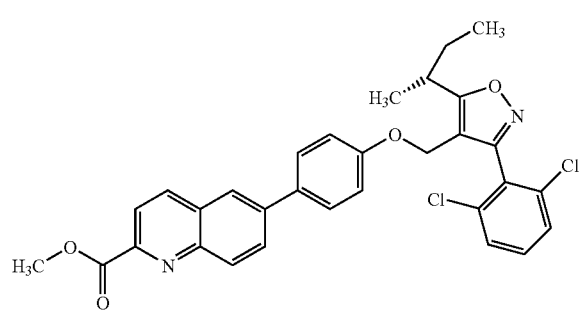

To a solution of methyl 6-(4-hydroxyphenyl)-2-quinolinecarboxylate (154 mg, 0.550 mmol), triphenylphosphine (144 mg, 0.550 mmol) and {3-(2,6-dichlorophenyl)-5-[(1R)-1-methylpropyl]-4-isoxazolyl}methanol (150 mg, 0.500 mmol) in dichloromethane (1.5 mL) was added diisopropyl azodicarboxylate (0.099 mL, 0.550 mmol) dropwise. The solution was heated in a microwave reactor at 90° C. for 10 minutes. The solution was adsorbed onto silica gel and purified by chromatography (silica gel, 0-60% ethyl acetate in hexanes gradient elution). A second purification was done by chromatography (silica gel, 1% methanol in dichloromethane) to afford methyl 6-{4-[({3-(2,6-dichlorophenyl)-5-[(1R)-1-methylpropyl]-4-isoxazolyl}methyl)oxy]phenyl}-2-quinolinecarboxylate (144 mg 0.256 mmol, 51%). $^1$H-NMR (400 MHz, DMSO-$d_6$) δ 8.55 (d, J=9 Hz, 1H), 8.28 (s, 1H), 8.18-8.10 (m, 3H), 7.73 (d, J=8 Hz, 2H), 7.63-7.51 (m, 3H), 6.92 (d, J=8 Hz, 2H), 4.88 (app q, J=12 Hz, 2H), 3.94 (s, 3H), 3.27-3.22 (m, 1H), 1.73-1.66 (m, 2H), 1.32 (d, J=7 Hz, 3H), 0.83 (t, J=7 Hz, 3H).

14c) 6-{4-[({3-(2,6-Dichlorophenyl)-5-[(1R)-1-methylpropyl]-4-isoxazolyl}methyl)oxy]phenyl}-2-quinolinecarboxylic acid

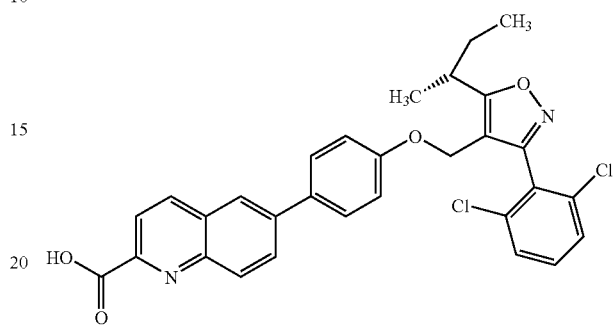

To a solution of methyl 6-{4-[({3-(2,6-dichlorophenyl)-5-[(1R)-1-methylpropyl]-4-isoxazolyl}methyl)oxy]phenyl}-2-quinolinecarboxylate (50 mg, 0.089 mmol) in 2:1 tetrahydrofuran:methanol (1.5 mL) was added 1 N sodium hydroxide (0.13 mL, 0.13 mmol). The solution was heated in a microwave reactor at 80° C. for 10 minutes and then 1 N hydrochloric acid (0.13 mL, 0.13 mmol) was added. The solution was concentrated and the residue was taken up with ethyl acetate and water. The layers were separated and the organic layer was dried over magnesium sulfate and concentrated to afford 6-{4-[({3-(2,6-dichlorophenyl)-5-[(1R)-1-methylpropyl]-4-isoxazolyl}methyl)oxy]phenyl}-2-quinolinecarboxylic acid (45 mg, 92%). $^1$H-NMR (400 MHz, DMSO-$d_6$) δ 13.37 (br s, 1H), 8.53 (d, J=9 Hz, 1H), 8.27 (s, 1H), 8.18-8.08 (m, 3H), 7.73 (d, J=9 Hz, 2H), 7.63-7.51 (m, 3H), 6.99 (d, J=9 Hz, 2H), 4.88 (app q, J=12 Hz, 2H), 3.31-3.22 (m, 1H), 1.73-1.66 (m, 2H), 3.32 (d, J=7 Hz, 3H), 0.83 (t, J=7 Hz, 3H). HRMS (ESI) $C_{30}H_{24}Cl_2N_2O_4$ calculated: 547.1186 (M+H)$^+$, found: 547.1186 (M+H)$^+$.

Example 15

6-[4-({3-[3-(2,6-Dichlorophenyl)-5-(1-methylethyl)-4-isoxazolyl]propyl}oxy)phenyl]-2-quinolinecarboxylic acid

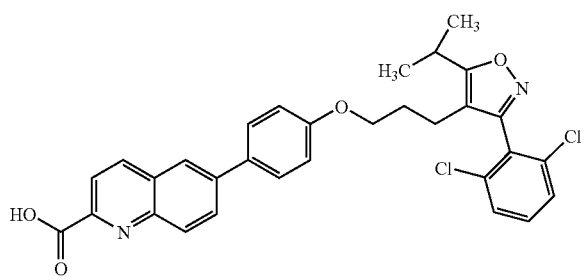

15a) 3-(2,6-Dichlorophenyl)-5-(1-methylethyl)-4-isoxazolecarbaldehyde

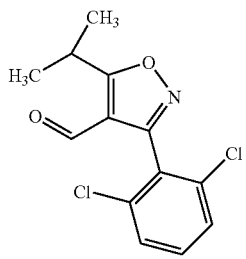

To a solution of [3-(2,6-dichlorophenyl)-5-(1-methylethyl)-4-isoxazolyl]methanol (2.40 g, 8.39 mmol) in dichloromethane (160 mL) was added pyridinium chlorochromate-silica gel (20.2 wt %, 44.7 g, 41.9 mmol). The mixture was stirred for approximately 1.5 hours and then run through a silica gel pad and concentrated to afford 3-(2,6-dichlorophenyl)-5-(1-methylethyl)-4-isoxazolecarbaldehyde (2.24 g, 7.88 mmol, 94%). $^1$H-NMR (400 MHz, DMSO-$d_6$) δ 9.89 (s, 1H), 7.64-7.55 (m, 3H), 3.83 (septet, J=7 Hz, 1H), 1.39 (d, J=7 Hz, 6H).

15b) 3-(2,6-Dichlorophenyl)-5-(1-methylethyl)-4-[(E/Z)-2-(methyloxy)ethenyl]isoxazole

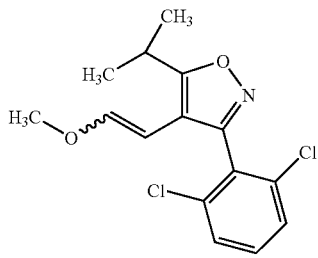

To a solution of (methoxymethyl)triphenylphosphonium chloride (8.09 g, 23.6 mmol) in tetrahydrofuran (10 mL) at 0° C. was added potassium tert-butoxide (2.65 g, 23.6 mmol) in tetrahydrofuran (40 mL) dropwise. The solution was stirred at 0° C. for approximately 10 minutes and was transferred dropwise to a stirring solution of 3-(2,6-dichlorophenyl)-5-(1-methylethyl)-4-isoxazolecarbaldehyde (2.24 g, 7.88 mmol) in tetrahydrofuran (50 mL) at 0° C. The mixture was stirred at 0° C. for approximately 45 minutes and brine was added. The mixture was poured into ether and the layers were separated. The organic layer was washed again with brine, dried over magnesium sulfate, concentrated and purified by chromatography (silica gel, 0-20% isopropanol in hexanes gradient elution) to afford 3-(2,6-dichlorophenyl)-5-(1-methylethyl)-4-[(E/Z)-2-(methyloxy)ethenyl]isoxazole (2.24 g, 7.16 mmol, 91%). $^1$H-NMR (400 MHz, DMSO-$d_6$) δ 7.66-7.47 (m, 3H), 6.15 (d, J=13 Hz, approximately 1H, major isomer), 6.12 (d, J=7 Hz, approximately 1H, minor isomer), 5.39 (d, J=13 Hz, approximately 1H, major isomer), 4.27 (d, J=7 Hz, approximately 1H, minor isomer), 3.45 (s, 3H), 3.31 (septet, J=7 Hz, 1H), 1.28 (d, J=7 Hz, 6H).

15c) 3-(2,6-Dichlorophenyl)-5-(1-methylethyl)-4-[(2E/Z)-3-(methyloxy)-2-propen-1-yl]isoxazole

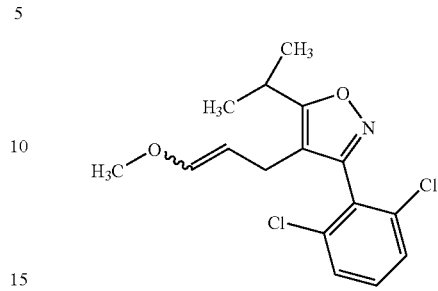

To a solution of 3-(2,6-dichlorophenyl)-5-(1-methylethyl)-4-[(E/Z)-2-(methyloxy)ethenyl]isoxazole (1.05 g, 3.35 mmol) in tetrahydrofuran (10 mL) was added 1 N hydrochloric acid (2.35 mL, 2.35 mmol). The mixture was heated in a microwave reactor at 140° C. for 10 minutes and was poured into ether, washed twice with saturated sodium bicarbonate, then with brine, and then was dried over magnesium sulfate, concentrated and stored in a freezer overnight. To a separate solution of (methoxymethyl)triphenylphosphonium chloride (4.05 g, 11.8 mmol) in tetrahydrofuran (15 mL) at 0° C. was added dropwise a solution potassium tert-butoxide (1.32 g, 11.8 mmol) in tetrahydrofuran cooled to 0° C. The mixture was stirred at 0° C. and then transferred to a solution of the above aldehyde in tetrahydrofuran (15 mL). The solution was stirred for approximately 15 minutes and brine was added. The mixture was poured into ether and the layers were separated. The aqueous layer was extracted with ether and the combined organic layers were dried over magnesium sulfate, concentrated and purified by chromatography (silica gel, 0-30% ethyl acetate in hexanes gradient elution) to afford 3-(2,6-dichlorophenyl)-5-(1-methylethyl)-4-[(2E/Z)-3-(methyloxy)-2-propen-1-yl]isoxazole (456 mg, 35%). $^1$H-NMR (400 MHz, DMSO-$d_6$) δ 7.62-7.51 (m, 3H), 5.99 (d, J=12 Hz, approximately 1H, major isomer), 5.81 (d, J=7 Hz, approximately 1H, minor isomer), 4.47-4.41 (m, approximately 1H, major isomer), 4.09-4.03 (m, approximately 1H, minor isomer), 3.30 (s, 3H), 3.28 (septet, J=7 Hz, 1H), 2.91-2.85 (m, 2H), 1.27 (d, J=7 Hz, 6H). LRMS (APCI) m/z 326 (M+H)$^+$.

15d) 3-[3-(2,6-Dichlorophenyl)-5-(1-methylethyl)-4-isoxazolyl]propanal

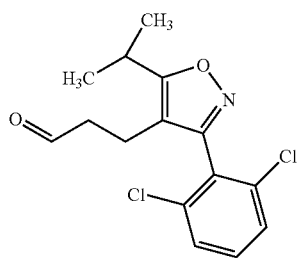

To a solution of 3-(2,6-dichlorophenyl)-5-(1-methylethyl)-4-[(2E/Z)-3-(methyloxy)-2-propen-1-yl]isoxazole (241 mg, 0.739 mmol) in tetrahydrofuran (2.5 mL) was added 1 N hydrochloric acid (0.517 mL, 0.517 mmol). The solution was heated in a microwave reactor to 80° C. for 10 minutes and was poured into ether, washed twice with saturated sodium bicarbonate then with brine, and then was dried over magnesium sulfate and concentrated to afford 3-[3-(2,6-dichlorophenyl)-5-(1-methylethyl)-4-isoxazolyl]propanal (227 mg, 98%). $^1$H-NMR (400 MHz, CDCl$_3$) δ 9.66 (s, 1H), 7.43-7.32 (m, 3H), 3.24 (septet, J=7 Hz, 1H), 2.59-2.44 (m, 4H), 1.38 (d, J=7 Hz, 6H).

15e) 3-[3-(2,6-Dichlorophenyl)-5-(1-methylethyl)-4-isoxazolyl]-1-propanol

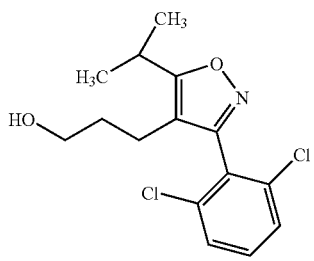

To a solution of 3-[3-(2,6-dichlorophenyl)-5-(1-methylethyl)-4-isoxazolyl]propanal (220 mg, 0.705 mmol) in methanol (7 mL) at 0° C. was added sodium borohydride (67 mg, 1.8 mmol). The solution was stirred at 0° C. for approximately 20 minutes and was then poured into aqueous ammonium chloride. The mixture was extracted twice with ether. The combined organic layers were dried over magnesium sulfate and concentrated to afford 3-[3-(2,6-dichlorophenyl)-5-(1-methylethyl)-4-isoxazolyl]-1-propanol (204 mg, 92%). $^1$H-NMR (400 MHz, CDCl$_3$) δ 7.42-7.28 (m, 3H), 3.53 (t, J=6 Hz, 2H), 3.21 (septet, J=7 Hz, 1H), 3.35 (t, J=8 Hz, 2H), 1.57-1.50 (m, 2H), 1.38 (d, J=7 Hz, 6H).

15f) Methyl 6-[4-({3-[3-(2,6-dichlorophenyl)-5-(1-methylethyl)-4-isoxazolyl]propyl}oxy)phenyl]-2-quinolinecarboxylate

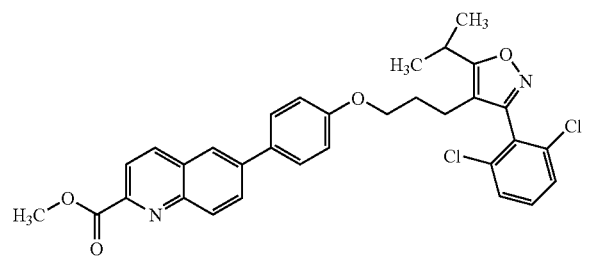

To a solution of methyl 6-(4-hydroxyphenyl)-2-quinolinecarboxylate (31 mg, 0.11 mmol), 3-[3-(2,6-dichlorophenyl)-5-(1-methylethyl)-4-isoxazolyl]-1-propanol (35 mg, 0.11 mmol) and triphenylphosphine (29 mg, 0.11 mmol) in dichloromethane (1 mL) was added diisopropyl azodicarboxylate (0.020 mL, 0.11 mmol). The solution was heated in a microwave reactor at 90° C. for 10 minutes and was then adsorbed onto silica gel and purified by chromatography (silica gel, 0-35% ethyl acetate in hexanes gradient elution) to afford methyl 6-[4-({3-[3-(2,6-dichlorophenyl)-5-(1-methylethyl)-4-isoxazolyl]propyl}oxy)phenyl]-2-quinolinecarboxylate (14 mg, 22%). $^1$H-NMR (400 MHz, CDCl$_3$) δ 8.33 (m, 2H), 8.21 (d, J=8 Hz, 1H), 8.03-7.99 (m, 2H), 7.63 (d, J=9 Hz, 2H), 7.40-7.28 (m, 3H), 6.91 (d, J=9 Hz, 2H), 4.09 (s, 3H), 3.89 (t, J=6 Hz, 2H), 3.19 (septet, J=7 Hz, 1H), 2.51 (t, J=6 Hz, 2H), 1.82-1.76 (m, 2H), 1.33 (d, J=7 Hz, 6H).

15 g) 6-[4-({3-[3-(2,6-Dichlorophenyl)-5-(1-methylethyl)-4-isoxazolyl]propyl}oxy)phenyl]-2-quinolinecarboxylic acid

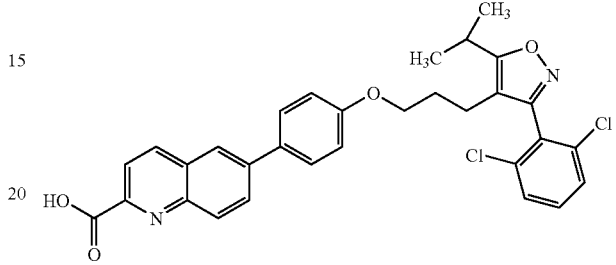

To a solution of methyl 6-[4-({3-[3-(2,6-dichlorophenyl)-5-(1-methylethyl)-4-isoxazolyl]propyl}oxy)phenyl]-2-quinolinecarboxylate (14 mg, 0.024 mmol) in 1:1 tetrahydrofuran:methanol (1 mL) was added 1 N sodium hydroxide (0.089 mL, 0.089 mmol). The solution was heated in a microwave reactor at 90° C. for 10 minutes. Then 1 N hydrochloric acid (0.089 mL, 0.089 mmol) was added and the mixture was concentrated. Water and ethyl acetate were added to the residue and the layers were separated. The ethyl acetate layer was dried over magnesium sulfate and concentrated to afford 12 mg of 6-[4-({3-[3-(2,6-dichlorophenyl)-5-(1-methylethyl)-4-isoxazolyl]propyl}oxy)phenyl]-2-quinolinecarboxylic acid as a yellow solid (0.021 mmol, 89%). $^1$H-NMR (400 MHz, DMSO-d$_6$) δ 8.42 (d, J=9 Hz, 1H), 8.28 (d, J=9 Hz, 1H), 8.19 (d, J=9 Hz, 1H), 8.06-8.04 (m, 2H), 7.64 (d, J=9 Hz, 2H), 7.41-7.29 (m, 3H), 6.93 (d, J=9 Hz, 2H), 3.90 (t, J=6 Hz, 2H), 3.20 (septet, J=7 Hz, 1H), 2.52 (t, J=6 Hz, 2H), 1.83-1.77 (m, 2H), 1.34 (d, J=7 Hz, 6H). HRMS (ESI) C$_{31}$H$_{26}$Cl$_2$N$_2$O$_4$ calculated: 561.1342 (M+H)$^+$, found: 561.1344 (M+H)$^+$.

Example 16

7-[4-({[3-{[(2,6-Dimethylphenyl)oxy]methyl}-5-(1-methylethyl)-4-isoxazolyl]methyl}oxy)phenyl]-3-isoquinolinecarboxylic acid

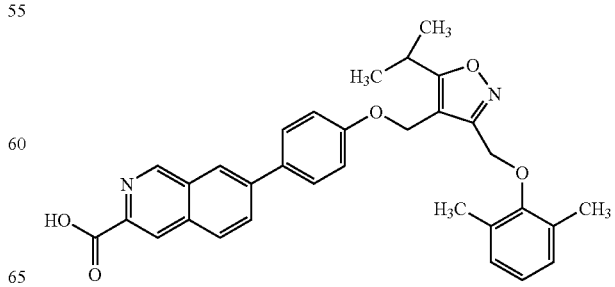

16a) (1,1-Dimethylethyl)oxyethanal oxime

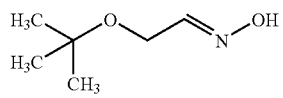

To a stirring solution of ethylene glycol tert-butyl ether (27.5 mL, 209 mmol) and triethylamine (87.5 mL, 628 mmol) in dichloromethane (600 mL) at 0° C. was added, over a period of approximately 45 minutes, a solution of sulfur trioxide-pyridine complex (100 g, 628 mmol) in dimethylsulfoxide (600 mL) that had been stirring for approximately 25 minutes. The mixture was allowed to warm to ambient temperature and stir over 6 hours and was then poured into ether, washed three times with 10% aqueous citric acid, then brine and was concentrated. The residue was taken up with ethanol (2.65 L) and filtered into a stirring solution of hydroxylamine hydrochloride (16.0 g, 230 mmol) and sodium hydroxide (9.20 g, 230 mmol) in water (125 mL). The solution was heated to approximately 90° C. and stirred for approximately 17 hours. The mixture was then concentrated and the residue was taken up with ethyl acetate and washed twice with water containing sodium chloride. The combined aqueous layers were back-extracted with ethyl acetate and the combined organic layers were dried over magnesium sulfate, concentrated and purified by chromatography (silica gel, 15% ethyl acetate in hexanes) to afford 1,1-dimethylethyl)oxyethanal oxime (8.59 g, 31%). $^1$H-NMR (400 MHz, DMSO-$d_6$) δ 11.02 (s, 0.5H), 10.73 (s, 0.5H), 7.25 (t, J=6 Hz, 0.5H), 6.67 (t, J=4 Hz, 0.5H), 4.11 (d, J=4 Hz, 1H), 3.89 (d, J=6 Hz, 1H), 1.12 (s, 9H).

16b) Methyl 3-{[(1,1-dimethylethyl)oxy]methyl}-5-(1-methylethyl)-4-isoxazolecarboxylate

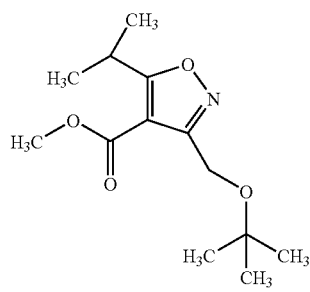

To a solution of (1,1-dimethylethyl)oxyethanal oxime (8.59 g, 65.5 mmol) in N,N-dimethylformamide (50 mL) was added N-chlorosuccinimide (8.45 g, 65.5 mmol). The solution was stirred for approximately 1 hour. The solution was poured into ether and washed twice with water. The organic layer containing the crude imidoyl chloride was then washed with brine, was dried over magnesium sulfate and concentrated. Then to a solution of methyl isobutyrylacetate (8.86 mL, 78.6 mmol) in tetrahydrofuran (40 mL) at 0° C. was added a 0.5 M solution of sodium methoxide in methanol (157 mL, 78.6 mmol). After stirring for approximately 5 minutes the above imidoyl chloride was added in tetrahydrofuran (30 mL). A solid was observed to precipitate. After the addition was complete the mixture was allowed to stir and warm to ambient temperature overnight. Then the solution was poured into ether and washed with water containing sodium chloride, dried over magnesium sulfate and concentrated to afford methyl 3-{[(1,1-dimethylethyl)oxy]methyl}-5-(1-methylethyl)-4-isoxazolecarboxylate (10.6 g, 63%). $^1$H-NMR (400 MHz, DMSO-$d_6$) δ 4.52 (s, 2H), 3.77 (s, 3H), 3.67 (septet, J=7 Hz, 1H), 1.25 (d, J=7 Hz, 6H), 1.18 (s, 9H).

16c) Methyl 3-(hydroxymethyl)-5-(1-methylethyl)-4-isoxazolecarboxylate

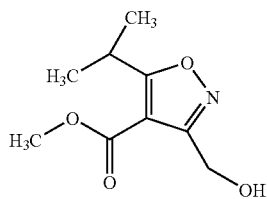

To a solution of methyl 3-{[(1,1-dimethylethyl)oxy]methyl}-5-(1-methylethyl)-4-isoxazolecarboxylate (500 mg, 1.96 mmol) in dichloromethane (97 mL) was added trifluoroacetic acid (97 mL, 1.25 mol). The solution was stirred at ambient temperature for approximately 45 minutes and then concentrated. The residue was taken up with ethyl acetate and poured into saturated sodium bicarbonate. Solid sodium bicarbonate followed by solid sodium carbonate were added until the pH was basic. The aqueous layer was extracted with ethyl acetate and the combined organic layers were dried over magnesium sulfate, concentrated and purified by chromatography (silica gel, 25% ethyl acetate in hexanes) to afford the methyl 3-(hydroxymethyl)-5-(1-methylethyl)-4-isoxazolecarboxylate (304 mg, 78%). $^1$H-NMR (400 MHz, DMSO-$d_6$) δ 5.29 (t, J=6 Hz, 1H), 4.62 (d, J=6 Hz, 2H), 3.77 (s, 3H), 3.68 (septet, J=7 Hz, 1H), 1.25 (d, J=7 Hz, 6H).

16d) Methyl 3-{[(2,6-dimethylphenyl)oxy]methyl}-5-(1-methylethyl)-4-isoxazolecarboxylate

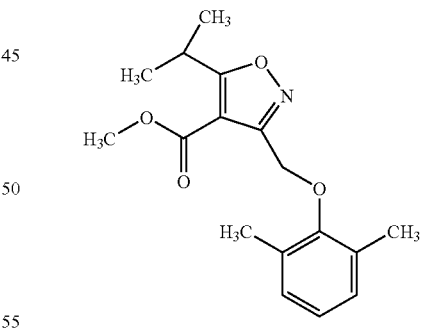

To a solution of 2,6-dimethylphenol (184 mg, 1.51 mmol), triphenylphosphine (396 mg, 1.51 mmol), and methyl 3-(hydroxymethyl)-5-(1-methylethyl)-4-isoxazolecarboxylate (300 mg, 1.51 mmol) in toluene (4 mL) was slowly added diisopropyl azodicarboxylate (0.272 mL, 1.51 mmol). The solution was heated in a microwave reactor at 90° C. for 10 minutes and then allowed to stand at ambient temperature overnight. The solution was concentrated and purified by chromatography (silica gel, 2.5% acetone in hexanes) to afford methyl 3-{[(2,6-dimethylphenyl)oxy]methyl}-5-(1-methylethyl)-4-isoxazolecarboxylate (329 mg, 72%).

¹H-NMR (400 MHz, DMSO-d₆) δ 7.02-6.90 (m, 3H), 5.00 (s, 2H), 3.74 (s, 3H), 3.72 (septet, J=7 Hz, 1H), 2.17 (s, 6H), 1.28 (d, J=7 Hz, 6H).

16e) [3-{[(2,6-Dimethylphenyl)oxy]methyl}-5-(1-methylethyl)-4-isoxazolyl]methanol

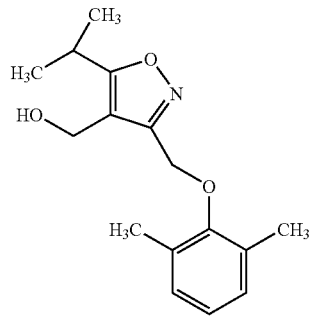

To a solution of methyl 3-{[(2,6-dimethylphenyl)oxy]methyl}-5-(1-methylethyl)-4-isoxazolecarboxylate (183 mg, 0.603 mmol) in tetrahydrofuran (2 mL) at 0° C. was added a 1.5 M solution of diisobutylaluminum hydride in toluene (1.33 mL, 1.99 mmol) dropwise. The solution was allowed to warm slowly to ambient temperature and after approximately 5 hours was re-cooled to 0° C. Then 10 mL of Rochelle's salt was slowly added followed by ethyl acetate. The mixture was allowed to stir overnight. The layers were separated and the aqueous layer was extracted with ethyl acetate. The combined organic layers were washed with brine, dried over magnesium sulfate and concentrated to afford [3-{[(2,6-dimethylphenyl)oxy]methyl}-5-(1-methylethyl)-4-isoxazolyl]methanol (158 mg, 95%). ¹H-NMR (400 MHz, DMSO-d₆) δ 7.03-6.91 (m, 3H), 4.98 (t, J=5 Hz, 1H), 4.83 (s, 2H), 4.39 (d, J=5 Hz, 2H), 3.29 (septet, J=7 Hz, 1H), 2.19 (s, 6H), 1.24 (d, J=7 Hz, 6H).

16f) Methyl 7-[4-({[3-{[(2,6-dimethylphenyl)oxy]methyl}-5-(1-methylethyl)-4-isoxazolyl]methyl}oxy)phenyl]-3-isoquinolinecarboxylate

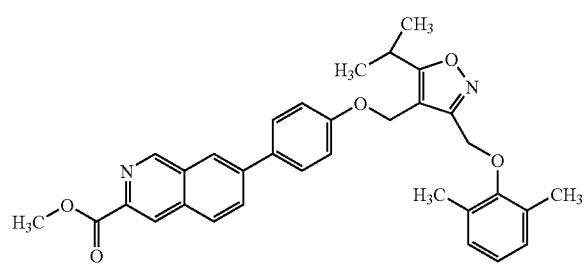

To a solution of triphenylphosphine (160 mg, 0.611 mmol), [3-{[(2,6-dimethylphenyl)oxy]methyl}-5-(1-methylethyl)-4-isoxazolyl]methanol (153 mg, 0.556 mmol) and methyl 7-(4-hydroxyphenyl)-3-isoquinolinecarboxylate (155 mg, 0.556 mmol) in dichloromethane (1.5 mL) was added diisopropyl azodicarboxylate (0.110 mL, 0.611 mmol) dropwise. The solution was heated in a microwave reactor at 90° C. for 10 minutes and then purified by chromatography (silica gel, 0-25% acetone in hexanes gradient elution) to afford methyl 7-[4-({[3-{[(2,6-dimethylphenyl)oxy]methyl}-5-(1-methylethyl)-4-isoxazolyl]methyl}oxy)phenyl]-3-isoquinolinecarboxylate (109 mg, 37%). ¹H-NMR (400 MHz, DMSO-d₆) δ 9.11 (s, 1H), 8.64 (s, 1H), 8.50 (s, 1H), 8.29-8.20 (m, 2H), 7.86 (d, J=9 Hz, 2H), 7.19 (d, J=9 Hz, 2H), 7.00-6.90 (m, 3H), 5.09 (s, 2H), 4.90 (s, 2H), 3.91 (s, 3H), 3.41 (septet, J=7 Hz, 1H), 2.14 (s, 6H), 1.28 (d, J=7 Hz, 6H).

16 g) 7-[4-({[3-{[(2,6-Dimethylphenyl)oxy]methyl}-5-(1-methylethyl)-4-isoxazolyl]methyl}oxy)phenyl]-3-isoquinolinecarboxylic acid

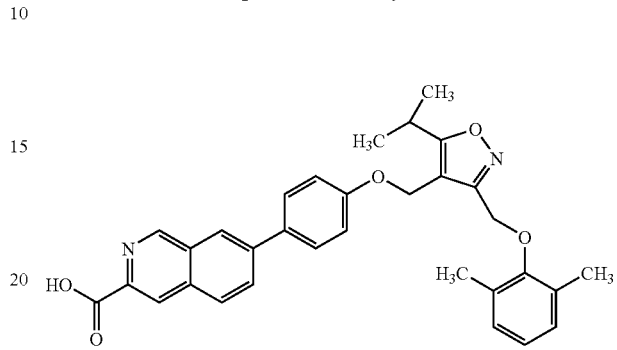

To a solution of methyl 7-[4-({[3-{[(2,6-dimethylphenyl)oxy]methyl}-5-(1-methylethyl)-4-isoxazolyl]methyl}oxy)phenyl]-3-isoquinolinecarboxylate (44 mg, 0.082 mmol) in 2:1 tetrahydrofuran:methanol (3 mL) was added 0.123 mL of 1 N sodium hydroxide. The solution was heated in a microwave reactor at 100° C. for 500 seconds. Then 1N hydrochloric acid (0.123 mL, 0.123 mmol) was added and the solution was concentrated. The residue was taken up with ethyl acetate and water. The aqueous layer was extracted with ethyl acetate and the combine organic layers were washed with brine, dried over magnesium sulfate and concentrated. The resulting solid was dried under vacuum overnight and then suspended in ethyl acetate and washed three times with water. The solvent was evaporated to afford 7-[4-({[3-{[(2,6-dimethylphenyl)oxy]methyl}-5-(1-methylethyl)-4-isoxazolyl]methyl}oxy)phenyl]-3-isoquinolinecarboxylic acid (32 mg, 75%). ¹H-NMR (400 MHz, DMSO-d₆) δ 9.41 (s, 1H), 8.61 (s, 1H), 8.50 (s, 1H), 8.24-8.19 (m, 2H), 7.86 (d, J=9 Hz, 2H), 7.19 (d, J=9 Hz, 2H), 7.00-6.91 (m, 3H), 5.09 (s, 2H), 4.90 (s, 2H), 3.41 (septet, J=7 Hz, 1H), 2.14 (s, 6H), 1.27 (d, J=7 Hz, 6H). HRMS (ESI) $C_{32}H_{30}N_2O_5$ calculated: 523.2228 (M+H)⁺, found: 523.2230 (M+H)⁺.

Example 17

7-(4-{[(5-Cyclobutyl-3-{[(2,6-dimethylphenyl)oxy]methyl}-4-isoxazolyl)methyl]oxy}phenyl)-3-isoquinolinecarboxylic acid

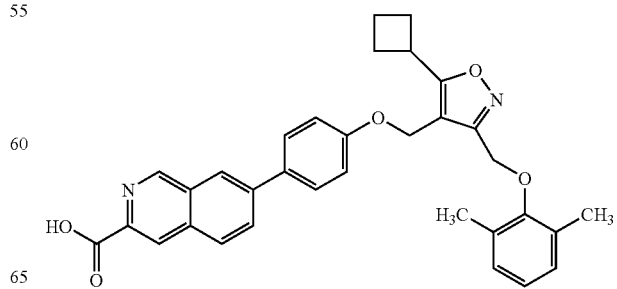

17a) Ethyl 5-cyclobutyl-3-{[(1,1-dimethylethyl)oxy]methyl}-4-isoxazolecarboxylate

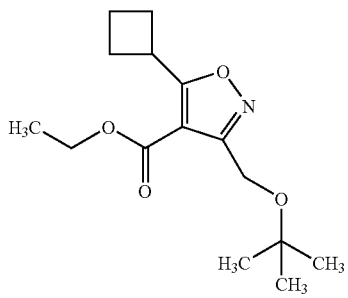

To a solution of (1,1-dimethylethyl)oxyethanal oxime (1.71 g, 13.0 mmol) in N,N-dimethylformamide (10 mL) was added N-chlorosuccinimide (1.74 g, 13.0 mmol) while the flask was in a water bath. After approximately 10 minutes the flask was removed from the water bath and the solution was stirred for approximately 1 hour. The solution, containing the crude imidoyl chloride, was then poured into ether and washed twice with water followed by brine, and then was dried over magnesium sulfate and concentrated. Then to a separate solution of ethyl 3-cyclobutyl-3-oxopropanoate (2.66 g, 15.6 mmol) in tetrahydrofuran (8 mL) at 0° C. was added sodium ethoxide (21 wt % solution in ethanol, 5.82 mL, 15.6 mmol). The above imidoyl chloride was diluted with tetrahydrofuran (6 mL) then added to the solution containing the ketoester. A solid was seen to precipitate. After the addition the solution was allowed to warm to ambient temperature and stirred overnight. The mixture was then poured into ether and washed twice with water followed by brine, dried over magnesium sulfate and concentrated to afford ethyl 5-cyclobutyl-3-{[(1,1-dimethylethyl)oxy]methyl}-4-isoxazolecarboxylate (3.13 g, 87%). $^1$H-NMR (400 MHz, DMSO-$d_6$) δ 4.53 (s, 2H), 4.22 (q, J=7 Hz, 2H), 4.17-4.05 (m, 1H), 2.33-2.27 (m, 4H), 2.09-2.03 (m, 1H), 1.95-1.86 (m, 1H), 1.26 (t, J=7 Hz, 3H), 1.17 (s, 9H).

17b) Ethyl 5-cyclobutyl-3-(hydroxymethyl)-4-isoxazolecarboxylate

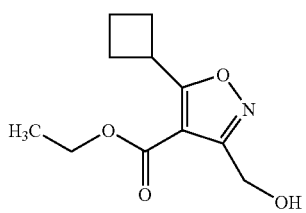

To a solution of ethyl 5-cyclobutyl-3-{[(1,1-dimethylethyl)oxy]methyl}-4-isoxazole carboxylate (1.40 g, 5.48 mmol) in dichloromethane (250 mL) was added trifluoroacetic acid (250 mL, 3.25 mol). The solution was stirred for approximately 30 minutes and then concentrated. The residue was taken up with ethyl acetate and poured into water. The mixture was stirred as solid sodium carbonate was added until the pH was basic. The layers were separated and the aqueous layer was extracted with ethyl acetate. The combined organic layers were washed with brine, dried over magnesium sulfate and concentrated. The residue was purified by chromatography (silica gel, 20% ethyl acetate in hexanes) to afford ethyl 5-cyclobutyl-3-(hydroxymethyl)-4-isoxazolecarboxylate (848 mg, 69%). $^1$H-NMR (400 MHz, DMSO-$d_6$) δ 5.27 (t, J=6 Hz, 1H), 4.63 (d, J=6 Hz, 2H), 4.21 (q, J=7 Hz, 2H), 4.18-4.08 (m, 1H), 2.33-2.27 (m, 4H), 2.10-2.00 (m, 1H), 1.90-1.83 (m, 1H), 1.26 (t, J=7 Hz, 3H).

17c) Ethyl 5-cyclobutyl-3-{[(2,6-dimethylphenyl)oxy]methyl}-4-isoxazolecarboxylate

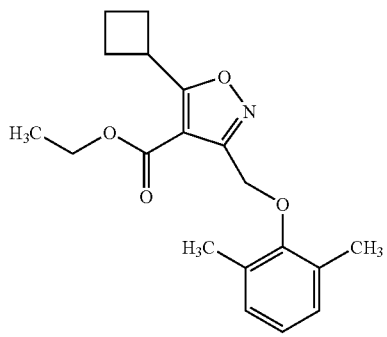

To a solution of 2,6-dimethylphenol (503 mg, 4.12 mmol), triphenylphosphine (1.08 g, 4.12 mmol) and ethyl 5-cyclobutyl-3-(hydroxymethyl)-4-isoxazolecarboxylate (929 mg, 4.12 mmol, from multiple batches) in toluene (10 mL) was added diisopropyl azodicarboxylate (0.741 mL, 4.12 mmol) dropwise. The solution was heated in a microwave reactor to 90° C. for 10 minutes. The solution was then concentrated and the residue was purified by chromatography (silica gel, 2.5% acetone in hexanes) to afford ethyl 5-cyclobutyl-3-{[(2,6-dimethylphenyl)oxy]methyl}-4-isoxazolecarboxylate (1.11 g, 81%). $^1$H-NMR (400 MHz, DMSO-$d_6$) δ 7.01-6.90 (m, 3H), 5.02 (s, 2H), 4.20 (q, J=7 Hz, 2H), 4.20-4.10 (m, 1H), 2.37-2.30 (m, 4H), 2.14 (s, 6H), 2.11-2.01 (m, 1H), 1.95-1.85 (m, 1H), 1.22 (t, J=7 Hz, 3H).

17d) (5-Cyclobutyl-3-{[(2,6-dimethylphenyl)oxy]methyl}-4-isoxazolyl)methanol

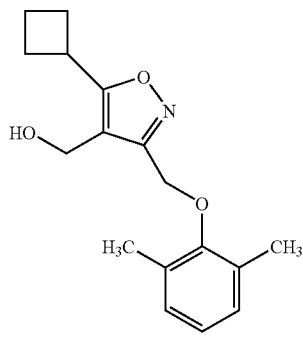

To a solution of ethyl 5-cyclobutyl-3-{[(2,6-dimethylphenyl)oxy]methyl}-4-isoxazolecarboxylate (1.08 g, 3.26 mmol) at 0° C. was added a 1.5 M solution of diisobutylaluminum hydride in toluene (7.18 mL, 10.8 mmol) at a slow pace. The solution was allowed to stir while warming slightly for approximately 1.5 hours and then was re-cooled to 0° C.

Then approximately 40 mL of Rochelle's salt was slowly added followed by ethyl acetate. The mixture was allowed to warm to ambient temperature and stirred overnight. Then the layers were separated and the aqueous layer was extracted with ethyl acetate. The combined organic layers were washed with brine, dried over magnesium sulfate and concentrated to afford (5-cyclobutyl-3-{[(2,6-dimethylphenyl)oxy]methyl}-4-isoxazolyl)methanol (937 mg, 100%). $^1$H-NMR (400 MHz, DMSO-$d_6$) δ 7.03-6.91 (m, 3H), 4.97 (t, J=5 Hz, 1H), 4.83 (s, 2H), 4.35 (d, J=5 Hz, 2H), 3.85-3.77 (m, 1H), 2.36-2.26 (m, 4H), 2.14 (s, 6H), 2.10-1.98 (m, 1H), 1.94-1.84 (m, 1H).

17e) Methyl 7-(4-{[(5-cyclobutyl-3-{[(2,6-dimethylphenyl)oxy]methyl}-4-isoxazolyl)methyl]oxy}phenyl)-3-isoquinolinecarboxylate

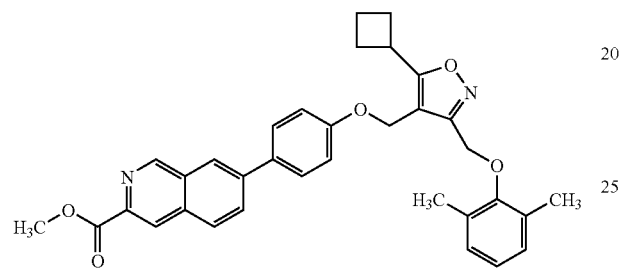

To a solution of methyl 7-(4-hydroxyphenyl)-3-isoquinolinecarboxylate (90 mg, 0.32 mmol), triphenylphosphine (93 mg, 0.35 mmol), and (5-cyclobutyl-3-{[(2,6-dimethyl phenyl)oxy]methyl}-4-isoxazolyl)methanol (93 mg, 0.32 mmol) in dichloromethane (1.5 mL) was added diisopropyl azodicarboxylate (0.064 mL, 0.35 mmol) dropwise. The solution was heated in a microwave reactor at 90° C. for 10 minutes. The solution was concentrated, adsorbed onto silica gel and purified by chromatography (silica gel, 0-25% acetone in hexanes gradient elution) to afford methyl 7-(4-{[(5-cyclobutyl-3-{[(2,6-dimethylphenyl)oxy]methyl}-4-isoxazolyl)methyl]oxy}phenyl)-3-isoquinolinecarboxylate (103 mg, 58%). $^1$H-NMR (400 MHz, DMSO-$d_6$) δ 9.41 (s, 1H), 8.64 (s, 1H), 8.50 (s, 1H), 8.26-8.19 (m, 2H), 7.85 (d, J=9 Hz, 2H), 7.16 (d, J=9 Hz, 2H), 7.00-6.90 (m, 3H), 5.06 (s, 2H), 4.90 (s, 2H), 3.99-3.90 (m, 1H), 3.91 (s, 3H), 2.37-2.30 (m, 4H), 2.14 (s, 6H), 2.09-2.01 (m, 1H), 1.98-1.89 (m, 1H).

17f) 7-(4-{[(5-Cyclobutyl-3-{[(2,6-dimethylphenyl)oxy]methyl}-4-isoxazolyl)methyl]oxy}phenyl)-3-isoquinolinecarboxylic acid

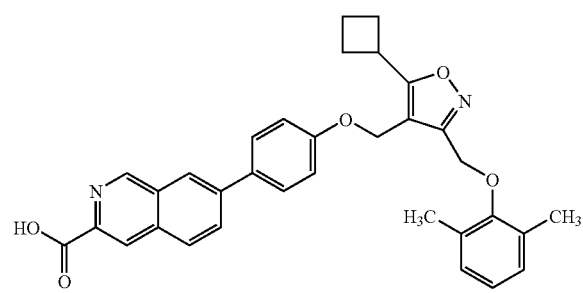

To a solution of methyl 7-(4-{[(5-cyclobutyl-3-{[(2,6-dimethylphenyl)oxy]methyl}-4-isoxazolyl)methyl]oxy}phenyl)-3-isoquinolinecarboxylate (50 mg, 0.091 mmol) in 2:1 tetrahydrofuran:methanol (3 mL) was added 1 N sodium hydroxide (0.14 mL, 0.14 mmol). The solution was heated in a microwave reactor at 100° C. for 500 seconds. Then 1 N hydrochloric acid (0.14 mL, 0.14 mmol) was added and the mixture was concentrated. The residue was taken up with ethyl acetate and water. The layers were separated and the organic layer was washed with water, dried over magnesium sulfate and concentrated to afford 7-(4-{[(5-cyclobutyl-3-{[(2,6-dimethylphenyl)oxy]methyl}-4-isoxazolyl)methyl]oxy}phenyl)-3-isoquinolinecarboxylic acid (41 mg, 84%). $^1$H-NMR (400 MHz, DMSO-$d_6$) δ 9.41 (s, 1H), 8.61 (s, 1H), 8.49 (s, 1H), 8.24-8.18 (m, 2H), 7.85 (d, J=9 Hz, 2H), 7.16 (d, J=9 Hz, 2H), 7.00-6.90 (m, 3H), 5.06 (s, 2H), 4.90 (s, 2H), 4.01-3.90 (m, 1H), 2.39-2.30 (m, 4H), 2.14 (s, 6H), 2.10-2.00 (m, 1H), 1.90-1.89 (m, 1H). HRMS (ESI) $C_{33}H_{30}N_2O_5$ calculated: 535.2228 (M+H)$^+$, found: 535.2228 (M+H)$^+$.

Example 18

6-[4-({[3-{[(2,6-Dimethylphenyl)oxy]methyl}-5-(1-methylethyl)-4-isoxazolyl]methyl}oxy)phenyl]-2-quinolinecarboxylic acid

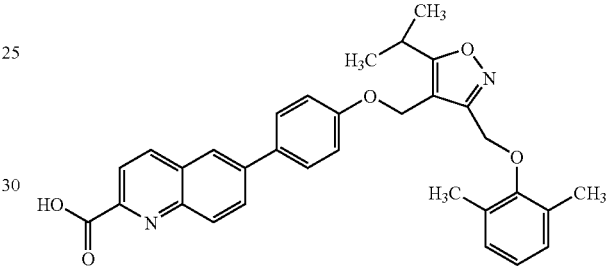

18a) [3-{[(1,1-Dimethylethyl)oxy]methyl}-5-(1-methylethyl)-4-isoxazolyl]methanol

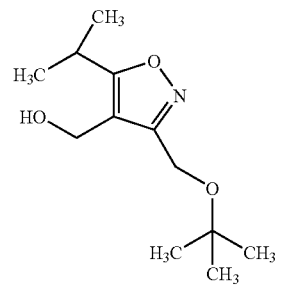

To a solution of methyl 3-{[(1,1-dimethylethyl)oxy]methyl}-5-(1-methylethyl)-4-isoxazolecarboxylate (21.5 g, 84.2 mmol) in tetrahydrofuran (250 mL) at 0° C. was added a 1.5 M solution of diisobutylaluminum hydride in toluene (185 mL, 278 mmol) slowly. The solution was allowed to warm slowly to ambient temperature overnight then was re-cooled to 0° C. and approximately 250 mL of Rochelle's salt was added dropwise followed by approximately 300 mL of ethyl acetate. An additional 250 mL of Rochelle's salt and 500 mL of ethyl acetate were added and the mixture was stirred at 0° C. for approximately 20 minutes and then at ambient temperature for approximately 4 hours. The mixture was filtered. The layers were separated and the aqueous layer was extracted with ethyl acetate. The combined organic layers were dried over magnesium sulfate, concentrated, and purified by chromatography (silica gel, 20% ethyl acetate in hexanes) to afford [3-{[(1,1-dimethylethyl)oxy]methyl}-5-(1-methylethyl)-4-isoxazolyl]methanol (15.2 g, 91%).

$^1$H-NMR (400 MHz, DMSO-d$_6$) δ 4.76 (t, J=5 Hz, 1H), 4.39 (s, 2H), 4.32 (d, J=5 Hz, 2H), 3.24 (septet, J=7 Hz, 1H), 1.21 (d, J=7 Hz, 6H), 1.18 (s, 9H).

18b) Methyl 6-[4-({[3-(hydroxymethyl)-5-(1-methylethyl)-4-isoxazolyl]methyl}oxy)phenyl]-2-quinolinecarboxylate

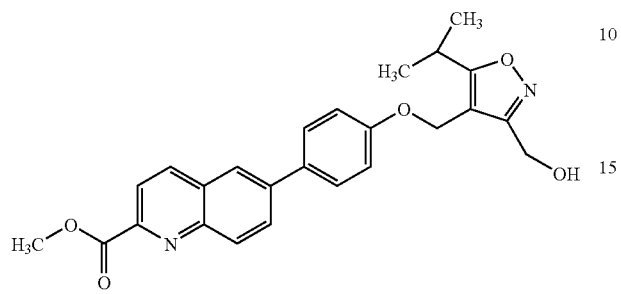

To a solution of [3-{[(1,1-dimethylethyl)oxy]methyl}-5-(1-methylethyl)-4-isoxazolyl]methanol (407 mg, 1.79 mmol), methyl 6-(4-hydroxyphenyl)-2-quinolinecarboxylate (500 mg, 1.79 mmol) and triphenylphosphine (517 mg, 1.97 mmol) in dichloromethane (4 mL) was added diisopropyl azodicarboxylate (0.354 mL, 1.97 mmol) dropwise. The solution was heated in a microwave reactor at 100° C. for 10 minutes and then adsorbed onto silica gel and purified by chromatography (silica gel, 0-40% ethyl acetate in hexanes gradient elution) to afford a solid which was dissolved in dichloromethane (114 mL). Trifluoroacetic acid (114 mL, 1.48 mol) was added at a rapid pace. The mixture was stirred for approximately 1.5 hours and then concentrated. The residue was taken up with ethyl acetate and poured into water. Then solid sodium carbonate was added until the pH was between 9 and 10. The layers were separated and the ethyl acetate layer was dried over magnesium sulfate and concentrated. The resulting solid was washed with ether to afford methyl 6-[4-({[3-(hydroxymethyl)-5-(1-methylethyl)-4-isoxazolyl]methyl}oxy)phenyl]-2-quinolinecarboxylate (545 mg, 54%). $^1$H-NMR (400 MHz, DMSO-d$_6$) δ 8.57 (d, J=9 Hz, 1H), 8.33 (s, 1H), 8.18 (s, 2H), 8.12 (d, J=9 Hz, 1H), 7.83 (d, J=9 Hz, 2H), 7.17 (d, J=9 Hz, 2H), 5.46 (br s, 1H), 5.06 (s, 2H), 4.54 (s, 2H), 3.94 (s, 3H), 3.33 (septet, J=7 Hz, 1H), 1.24 (d, J=7 Hz, 6H). LRMS (ESI) m/z 433 (M+H)$^+$.

18c) Methyl 6-[4-({[3-{[(2,6-dimethylphenyl)oxy]methyl}-5-(1-methylethyl)-4-isoxazolyl]methyl}oxy)phenyl]-2-quinolinecarboxylate

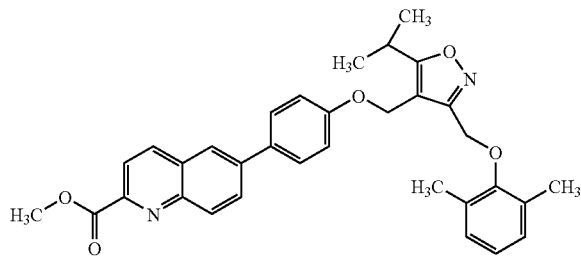

To a solution of methyl 6-[4-({[3-(hydroxymethyl)-5-(1-methylethyl)-4-isoxazolyl]methyl}oxy)phenyl]-2-quinolinecarboxylate (60 mg, 0.14 mmol), 2,6-dimethylphenol (17 mg, 0.14 mmol) and triphenylphosphine (40 mg, 0.15 mmol) in dichloromethane (1.5 mL) was added diisopropyl azodicarboxylate (0.028 mL, 0.15 mmol) dropwise. The solution was stirred at ambient temperature for approximately 1.5 hours and then in a microwave reactor at 100° C. for 10 minutes. The solution was adsorbed onto silica gel and purified by chromatography (silica gel, 0-40% ethyl acetate gradient elution). The resulting residue was taken up with ether and sonicated until a solid precipitated. The solid was isolated by filtration to afford methyl 6-[4-({[3-{[(2,6-dimethylphenyl)oxy]methyl}-5-(1-methylethyl)-4-isoxazolyl]methyl}oxy)phenyl]-2-quinolinecarboxylate (23 mg, 31%). $^1$H-NMR (400 MHz, CDCl$_3$) δ 8.37-8.32 (m, 2H), 8.23-8.21 (m, 1H), 8.05-8.01 (m, 2H), 7.69 (d, J=9 Hz, 2H), 7.08 (d, J=9 Hz, 2H), 7.01-6.01 (m, 3H), 5.04 (s, 2H), 4.96 (s, 2H), 4.09 (s, 3H), 3.29 (septet, J=7 Hz, 1H), 2.23 (s, 6H), 1.38 (d, J=7 Hz, 6H).

18d) 6-[4-({[3-{[(2,6-Dimethylphenyl)oxy]methyl}-5-(1-methylethyl)-4-isoxazolyl]methyl}oxy)phenyl]-2-quinolinecarboxylic acid

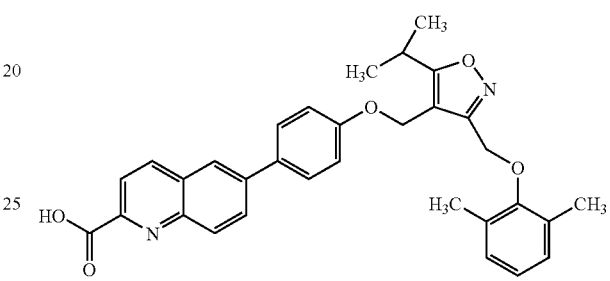

To a solution of methyl 6-[4-({[3-{[(2,6-dimethylphenyl)oxy]methyl}-5-(1-methylethyl)-4-isoxazolyl]methyl}oxy)phenyl]-2-quinolinecarboxylate (23 mg, 0.043 mmol) in 2:1 tetrahydrofuran:methanol (0.75 mL) was added 1 N sodium hydroxide (0.064 mL, 0.064 mmol). The solution was heated in a microwave reactor at 120° C. for 500 seconds. The mixture was concentrated and water was added followed by 1 N hydrochloric acid (0.064 mL, 0.064 mmol). The mixture was extracted with ethyl acetate and the combined organic layers were washed with brine and concentrated to afford 6-[4-({[3-{[(2,6-dimethylphenyl)oxy]methyl}-5-(1-methylethyl)-4-isoxazolyl]methyl}oxy)phenyl]-2-quinolinecarboxylic acid as a yellow solid (14 mg, 62%). $^1$H-NMR (400 MHz, CDCl$_3$) δ 8.43 (d, J=9 Hz, 1H), 8.29 (d, J=8 Hz, 1H), 8.21 (d, J=9 Hz, 1H), 8.07 (m, 2H), 7.70 (d, J=9 Hz, 2H), 7.10 (d, J=9 Hz, 2H), 7.01-6.62 (m, 3H), 5.06 (s, 2H), 4.97 (s, 2H), 3.30 (septet, J=7 Hz, 1H), 2.23 (s, 6H), 1.39 (d, J=7 Hz, 6H). HRMS (ESI) C$_{32}$H$_{30}$N$_2$O$_5$ calculated: 437.2263 (M+H)$^+$, found: 437.2263 (M+H)$^+$.

Example 19

6-(4-{[(5-(1-Methylethyl)-3-{[(2,4,6-trifluorophenyl)oxy]methyl}-4-isoxazolyl)methyl]oxy}phenyl)-2-quinolinecarboxylic acid

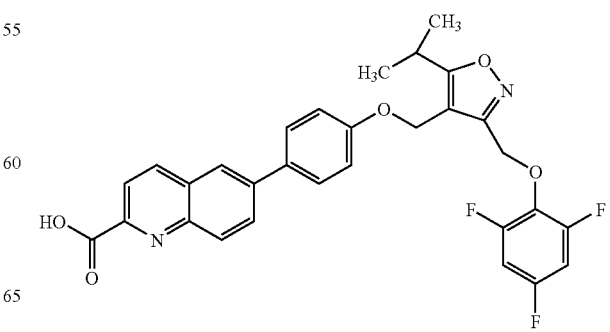

19a) 6-(4-{[(5-(1-Methylethyl)-3-{[(2,4,6-trifluorophenyl)oxy]methyl}-4-isoxazolyl)methyl]oxy}phenyl)-2-quinolinecarboxylic acid To a solution of 2,4,6-trifluorophenol (18 mg, 0.12 mmol), methyl 6-[4-({[3-(hydroxymethyl)-5-(1-methylethyl)-4-isoxazolyl]methyl}oxy)phenyl]-2-quinoline carboxylate (52 mg, 0.12 mmol) and triphenylphosphine (35 mg, 0.13 mmol) in dichloromethane (2 mL) was added diisopropyl azodicarboxylate (0.024 mL, 0.13 mmol) slowly. The solution was heated in a microwave reactor at 100° C. for 10 minutes. The solution was adsorbed onto silica gel and purification was done by chromatography (0-70% ethyl acetate in hexanes) to afford a solid which was dissolved in 2:1 tetrahydrofuran:methanol (1.5 mL). Then 1 N sodium hydroxide (0.19 mmol, 0.19 mmol) was added. The solution was subjected to microwave radiation at 120° C. for 500 seconds. The solution was concentrated then diluted with water before the addition of 1 N hydrochloric acid (0.19 mmol, 0.19 mmol). The resulting solid was extracted with ethyl acetate twice and the combined organic layers were dried over magnesium sulfate and concentrated. The resulting solid was washed with methanol and dried to afford 6-(4-{[(5-(1-methylethyl)-3-{[(2,4,6-trifluorophenyl)oxy]methyl}-4-isoxazolyl)methyl]oxy}phenyl)-2-quinolinecarboxylic acid (24 mg, 35%). $^1$H-NMR (400 MHz, DMSO-d$_6$) δ 8.44-8.06 (m, 5H), 7.69 (d, J=9 Hz, 2H), 7.11 (d, J=9 Hz, 2H), 6.65 (t, J=9 Hz, 2H), 5.23 (s, 2H), 5.12 (s, 2H), 3.29 (septet, J=7 Hz, 1H), 1.37 (d, J=7 Hz, 6H). HRMS (ESI) $C_{30}H_{23}F_3N_2O_5$ calculated: 549.1632 (M+H)$^+$, found: 549.1631 (M+H)$^+$.

Example 20

6-[4-({[3-{[(2,6-Dichlorophenyl)oxy]methyl}-5-(1-methylethyl)-4-isoxazolyl]methyl}oxy)phenyl]-2-quinolinecarboxylic acid

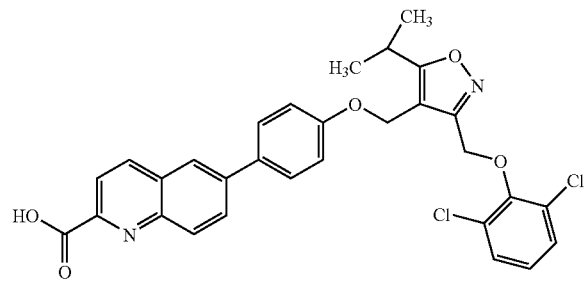

20a) 6-[4-({[3-{[(2,6-Dichlorophenyl)oxy]methyl}-5-(1-methylethyl)-4-isoxazolyl]methyl}oxy)phenyl]-2-quinolinecarboxylic acid To a solution of triphenylphosphine (34 mg, 0.13 mmol), 2,6-dichlorophenol (21 mg, 0.13 mmol) and methyl 6-[4-({[3-(hydroxymethyl)-5-(1-methylethyl)-4-isoxazolyl]methyl}oxy)phenyl]-2-quinolinecarboxylate (56 mg, 0.13 mmol) was added diisopropyl azodicarboxylate (0.023 mL, 0.13 mmol). The solution was heated in a microwave reactor at 100° C. for 10 minutes. This heating was repeated again for 10 minutes. The mixture was adsorbed onto silica gel and purified by chromatography (silica gel, 0-60% ethyl acetate in hexanes gradient elution) to afford a solid that was dissolved in 2:1 tetrahydrofuran/methanol (1.5 mL). Then 1 N sodium hydroxide (0.13 mL, 0.13 mmol) was added. The solution was heated in a microwave reactor at 120° C. for 500 seconds. The mixture was concentrated and the residue was taken up with methanol. Then 10% aqueous citric acid was added and the mixture was extracted with ethyl acetate. The aqueous layer was acidified with additional citric acid until the pH was approximately 2-3 and was extracted one more time with ethyl acetate. The combined organic layers were concentrated and the residue was taken up with ether which was removed under vacuum. The resulting solid was dissolved in ethyl acetate and the solution was washed with water and brine and then concentrated to afford 6-[4-({[3-{[(2,6-dichlorophenyl)oxy]methyl}-5-(1-methylethyl)-4-isoxazolyl]methyl}oxy)phenyl]-2-quinolinecarboxylic acid (12 mg, 24%). $^1$H-NMR (400 MHz, CDCl$_3$) δ 8.36 (d, J=9 Hz, 1H), 8.24-8.19 (m, 2H), 8.02 (d, J=10 Hz, 2H), 7.66 (d, J=9 Hz, 2H), 7.24 (d, J=9 Hz, 2H), 7.08 (d, J=9 Hz, 2H), 6.99-6.97 (m, 1H) 5.15 (s, 4H), 3.27 (3.27 (septet, J=7 Hz, 1H), 1.34 (d, J=7 Hz, 6H). HRMS (ESI) $C_{30}H_{24}Cl_2N_2O_5$ calculated: 563.1135 (M+H)$^+$, found: 563.1130 (M+H)$^+$.

Example 21

6-[4-({[3-{[(2,6-Dichlorophenyl)amino]methyl}-5-(1-methylethyl)-4-isoxazolyl]methyl}oxy)phenyl]-2-quinolinecarboxylic acid

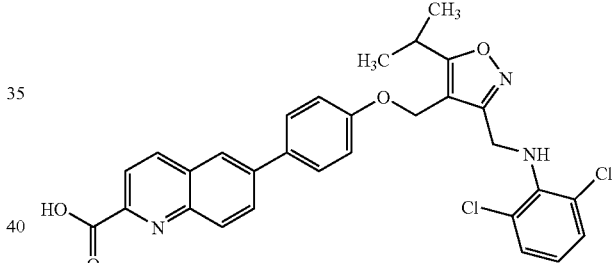

21a) N-(2,6-Dichlorophenyl)-2,2,2-trifluoroacetamide

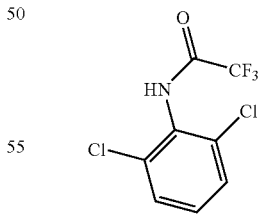

To a solution of 2,6-dichloroaniline (243 mg, 1.50 mmol) in dichloromethane (50 mL) at 0° C. was added trifluoroacetic anhydride (0.254 mL, 1.80 mmol) dropwise. The solution was stirred while the flask was in the cold bath for approximately 3 hours and then at ambient temperature for approximately 1 hour. The solution was concentrated and the residue was diluted with ethyl acetate, washed with aqueous sodium bicarbonate, dried over magnesium sulfate and concentrated to afford N-(2,6-dichlorophenyl)-2,2,2-trifluoroacetamide (350 mg, 90%). $^1$H-NMR (400 MHz, DMSO-$d_6$) δ 11.58 (s, 1H), 7.63-7.43 (m, 3H).

21b) Methyl 6-[4-({[3-{[(2,6-dichlorophenyl)(trifluoroacetyl)amino]methyl}-5-(1-methylethyl)-4-isoxazolyl]methyl}oxy)phenyl]-2-quinolinecarboxylate

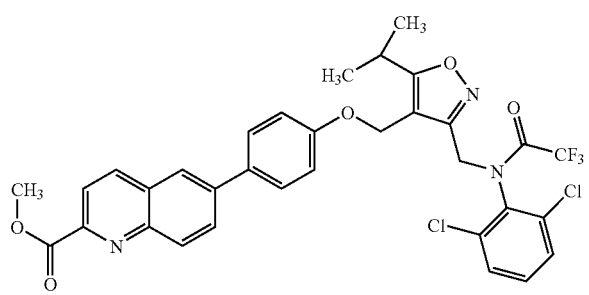

To a solution of methyl 6-[4-({[3-(hydroxymethyl)-5-(1-methylethyl)-4-isoxazolyl]methyl}oxy)phenyl]-2-quinolinecarboxylate (25 mg, 0.058 mmol), N-(2,6-dichlorophenyl)-2,2,2-trifluoroacetamide (15 mg, 0.058 mmol) and triphenylphosphine (30 mg, 0.12 mmol) in dichloromethane was added di-tert-butyl azodicarboxylate (27 mg, 0.12 mmol). The solution was stirred at ambient temperature for approximately 1.5 hours and then was adsorbed onto silica gel and purified by chromatography (silica gel, 0-100% ethyl acetate in hexanes gradient elution). The resulting mixture was further purified by chromatography (silica gel, 2% methanol in dichloromethane) to afford methyl 6-[4-({[3-{[(2,6-dichlorophenyl)(trifluoroacetyl)amino]methyl}-5-(1-methylethyl)-4-isoxazolyl]methyl}oxy)phenyl]-2-quinolinecarboxylate (10 mg, 26%). $^1$H-NMR (400 MHz, CDCl$_3$) δ 8.36-8.33 (m, 2H), 8.22 (d, J=9 Hz, 1H), 8.06-8.01 (m, 2H), 7.71 (d, J=9 Hz, 2H), 7.42-7.29 (m, 3H), 7.11 (d, J=9 Hz, 2H), 5.05 (s, 2H), 5.04 (s, 2H), 4.05 (s, 3H), 3.27 (septet, J=7 Hz, 1H), 1.34 (d, J=7 Hz, 6H). LRMS (APCI) m/z 672 (M+H)$^+$.

21c) 6-[4-({[3-{[(2,6-Dichlorophenyl)amino]methyl}-5-(1-methylethyl)-4-isoxazolyl]methyl}oxy)phenyl]-2-quinolinecarboxylic acid

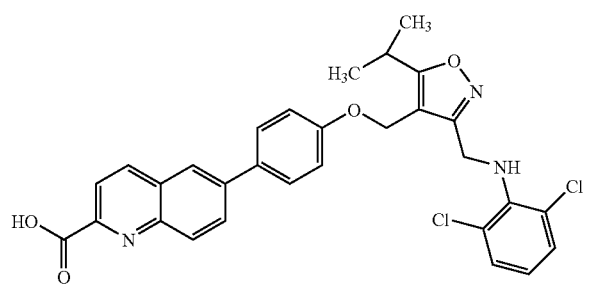

To a solution of methyl 6-[4-({[3-{[(2,6-dichlorophenyl)(trifluoroacetyl)amino]methyl}-5-(1-methylethyl)-4-isoxazolyl]methyl}oxy)phenyl]-2-quinolinecarboxylate (10 mg, 0.015 mmol) in 1:1 tetrahydrofuran:methanol (0.75 mL) was added 1 N sodium hydroxide (0.37 mL, 0.37 mmol). The solution was heated in a microwave reactor at 90° C. for 10 minutes. The solution was concentrated and the residue was taken up with ethyl acetate. Then 1 N hydrochloric acid (0.37 mL, 0.37 mmol) was added followed by water. The layers were separated and the aqueous layer was extracted one more time with ethyl acetate. The combined organic layers were dried over magnesium sulfate and concentrated to afford 6-[4-({[3-{[(2,6-dichlorophenyl)amino]methyl}-5-(1-methylethyl)-4-isoxazolyl]methyl}oxy)phenyl]-2-quinolinecarboxylic acid (8 mg, 100%). $^1$H-NMR (400 MHz, CDCl$_3$) δ 8.46 (d, J=9 Hz, 1H), 8.31-8.24 (m, 2H), 8.11-8.07 (m, 2H), 7.69 (d, J=9 Hz, 2H), 7.25-7.20 (m, 2H), 7.07 (d, J=9 Hz, 2H), 6.84-6.80 (m, 1H), 4.96 (s, 2H), 4.60 (s, 2H), 3.24 (septet, J=7 Hz, 1H), 1.36 (d, J=7 Hz, 6H). HRMS (ESI) $C_{30}H_{25}Cl_2N_3O_4$ calculated: 562.1300 (M+H)$^+$, found: 562.1292 (M+H)$^+$.

Example 22

6-[4-({[3-{[(2,6-Dichlorophenyl)thio]methyl}-5-(1-methylethyl)-4-isoxazolyl]methyl}oxy)phenyl]-2-quinolinecarboxylic acid

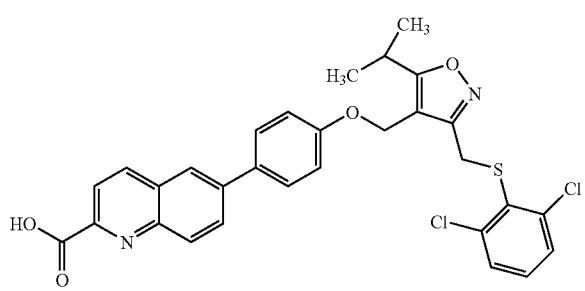

22a) Methyl 3-{[(2,6-dichlorophenyl)thio]methyl}-5-(1-methylethyl)-4-isoxazolecarboxylate

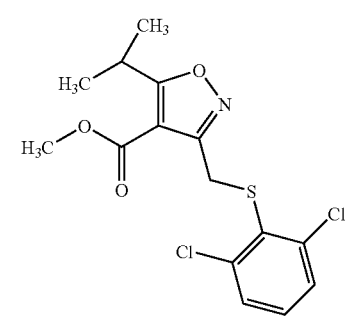

To a solution of 2,6-dichlorobenzenethiol (530 mg, 2.96 mmol), methyl 3-(hydroxymethyl)-5-(1-methylethyl)-4-isoxazolecarboxylate (629 mg, 2.46 mmol) and triphenylphosphine (1.29 g, 4.93 mmol) in dichloromethane (20 mL) was added di-tert-butyl azodicarboxylate (1.14 g, 4.93 mmol). The solution was stirred at ambient temperature overnight. The solution was then adsorbed onto silica gel and purified by chromatography (silica gel, 0-100% ethyl acetate in hexanes gradient elution) to afford methyl 3-{[(2,6-dichlorophenyl)thio]methyl}-5-(1-methylethyl)-4-isoxazolecarboxylate (886 mg, 100%). $^1$H-NMR (400 MHz, CDCl$_3$) δ

7.52-7.35 (m, 3H), 4.18 (s, 3H), 3.72 (s, 2H), 3.64 (septet, J=7 Hz, 1H), 1.20 (d, J=7 Hz, 6H). LRMS (APCI) m/z 360 (M+H)⁺.

22b) [3-{[(2,6-Dichlorophenyl)thio]methyl}-5-(1-methylethyl)-4-isoxazolyl]methanol

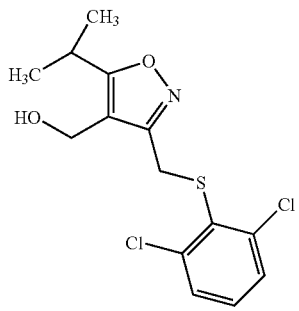

To a solution of methyl 3-{[(2,6-dichlorophenyl)thio]methyl}-5-(1-methylethyl)-4-isoxazolecarboxylate (50 mg, 0.14 mmol) in tetrahydrofuran (0.5 mL) at 0° C. was slowly added a 1.5 M solution of diisobutylaluminum hydride in toluene (0.46 mL, 0.69 mmol). The solution was allowed to warm slowly to ambient temperature and stir overnight. The next day the solution was cooled to 0° C. and methanol (approximately 0.25 mL) was added followed by aqueous Rochelle's salt (approximately 3 mL). The mixture was diluted with ethyl acetate and allowed to warm to ambient temperature while stirring. The layers were separated and the organic layer was dried over magnesium sulfate and concentrated to afford [3-{[(2,6-dichlorophenyl)thio]methyl}-5-(1-methylethyl)-4-isoxazolyl]methanol (43 mg, 93%). ¹H-NMR (400 MHz, CDCl₃) δ 7.35-7.16 (m, 3H), 4.60 (s, 2H), 4.10 (s, 2H), 3.17 (septet, J=8 Hz, 1H), 1.28 (d, J=6 Hz, 6H).

22c) Ethyl 6-(4-hydroxyphenyl)-2-quinolinecarboxylate

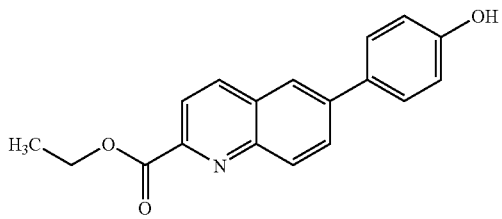

Palladium(II)acetate (17.1 mg, 76.0 μmol) was added to ethyl 6-bromo-2-quinolinecarboxylate (426.0 mg, 1.52 mmol, from Example 32c), 4-hydroxy-phenyl-boronic acid (314.6 mg, 2.28 mmol), triphenylphosphine (39.9 mg, 152.1 μmol), and potassium phosphate (1.13 g, 5.32 mmol). Then, dioxane (7.6 mL) was added to the mixture, followed by water (152 μL), and the reaction mixture was heated open to the atmosphere at 60° C. in an oil bath for 16 hours, then allowed to cool to room temperature. Water was added followed by ethyl acetate and the mixture was filtered through Celite®. The filtrate was extracted with ethyl acetate and the organic layer was dried over anhydrous magnesium sulfate, then filtered and concentrated. The residue was purified by silica gel chromatography eluting with 2:3 ethyl acetate:hexanes to give 260.5 mg (58%) of ethyl 6-(4-hydroxyphenyl)-2-quinolinecarboxylate as a solid. ¹H NMR (400 MHz, d₆-DMSO): δ 9.74 (s, 1H), 8.55 (d, J=9 Hz, 1H), 8.28 (s, 1H), 8.19-8.10 (m, 3H), 7.72 (d, J=9 Hz, 2H), 6.92 (d, J=9 Hz, 2H), 4.42 (q, J=7 Hz, 2H), 1.38 (t, J=7 Hz, 3H). ESI-LCMS m/z 294 (M+H)⁺.

22d) Ethyl 6-[4-({[3-{[(2,6-Dichlorophenyl)thio]methyl}-5-(1-methylethyl)-4-isoxazolyl]methyl}oxy)phenyl]-2-quinolinecarboxylate

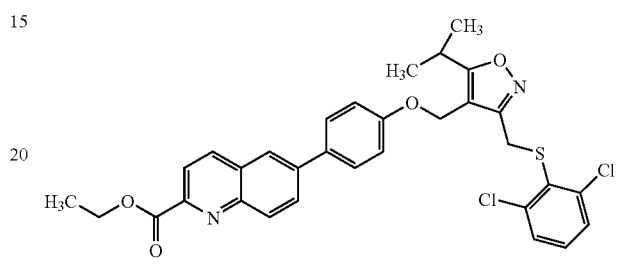

To a solution of [3-{[(2,6-dichlorophenyl)thio]methyl}-5-(1-methylethyl)-4-isoxazolyl]methanol (22 mg, 0.066 mmol), ethyl 6-(4-hydroxyphenyl)-2-quinolinecarboxylate (19 mg, 0.066 mmol) and triphenylphosphine (35 mg, 0.13 mmol) in dichloromethane (1 mL) was added di-tert-butyl azodicarboxylate (30 mg, 0.13 mmol). The solution was stirred at ambient temperature approximately 4.5 hours and then was adsorbed onto silica gel. Purification was done by chromatography (silica gel, 0-75% ethyl acetate in hexanes gradient elution) to afford ethyl 6-[4-({[3-{[(2,6-dichlorophenyl)thio]methyl}-5-(1-methylethyl)-4-isoxazolyl]methyl}oxy)phenyl]-2-quinolinecarboxylate (26 mg, 65%). ¹H-NMR (400 MHz, CDCl₃) δ 8.36-8.31 (m, 2H), 8.20 (d, J=9 Hz, 1H), 8.03-8.00 (m, 2H), 7.69 (d, J=9 Hz, 2H), 7.32-7.13 (m, 3H), 7.08 (d, J=9 Hz, 2H), 5.08 (s, 2H), 4.56 (q, J=7 Hz, 2H), 4.16 (s, 2H), 3.20 (septet, J=7 Hz, 1H), 1.49 (t, J=7 Hz, 3H), 1.31 (d, J=7 Hz, 6H). LRMS (APCI) m/z 607 (M+H)⁺.

22e) 6-[4-({[3-{[(2,6-Dichlorophenyl)thio]methyl}-5-(1-methylethyl)-4-isoxazolyl]methyl}oxy)phenyl]-2-quinolinecarboxylic acid

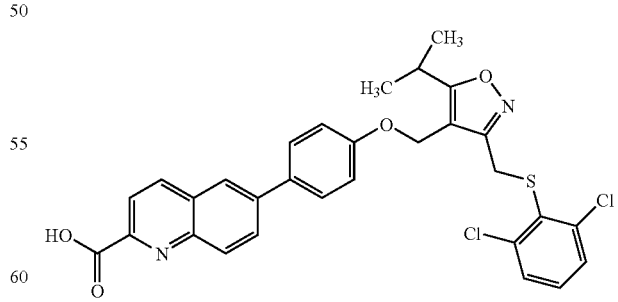

To a solution of ethyl 6-[4-({[3-{[(2,6-dichlorophenyl)thio]methyl}-5-(1-methylethyl)-4-isoxazolyl]methyl}oxy)phenyl]-2-quinolinecarboxylate (5 mg, 0.008 mmol) in 1:1 tetrahydrofuran:methanol (0.5 mL) was added 1 N sodium hydroxide (0.04 mL, 0.04 mmol). The solution was heated in a microwave reactor at 90° C. for 10 minutes and 1 N hydrochloric acid (0.04 mL, 0.04 mmol) was added. The mixture was concentrated and the residue was taken up with ethyl acetate and washed with water. The organic layer was dried over magnesium sulfate and concentrated to afford 6-[4-({[3-{[(2,6-dichlorophenyl)thio]methyl}-5-(1-methylethyl)-4-isoxazolyl]methyl}oxy)phenyl]-2-quinolinecarboxylic acid (5 mg, 100%). $^1$H-NMR (400 MHz, CDCl$_3$) δ 8.44 (d, J=9 Hz, 1H), 8.29 (d, J=9 Hz, 1H), 8.21 (d, J=9 Hz, 1H), 8.10-8.07 (m, 2H), 7.70 (d, J=9 Hz, 2H), 7.34-7.14 (m, 3H), 7.10 (d, J=9 Hz, 2H), 5.08 (s, 2H), 4.16 (s, 2H), 3.20 (septet, J=7 Hz, 1H), 1.32 (d, J=7 Hz, 6H). HRMS (ESI) C$_{30}$H$_{24}$Cl$_2$N$_2$O$_4$S calculated: 579.0912 (M+H)$^+$, found: 579.0925 (M+H)$^+$.

Example 23

6-[4-({[3-{[(2,6-Dichlorophenyl)sulfinyl]methyl}-5-(1-methylethyl)-4-isoxazolyl]methyl}oxy)phenyl]-2-quinolinecarboxylic acid

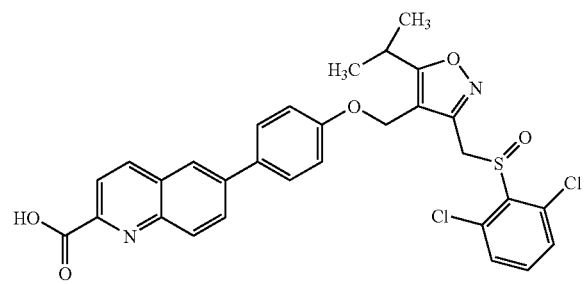

23a) Ethyl 6-[4-({[3-{[(2,6-dichlorophenyl)sulfinyl]methyl}-5-(1-methylethyl)-4-isoxazolyl]methyl}oxy)phenyl]-2-quinolinecarboxylate

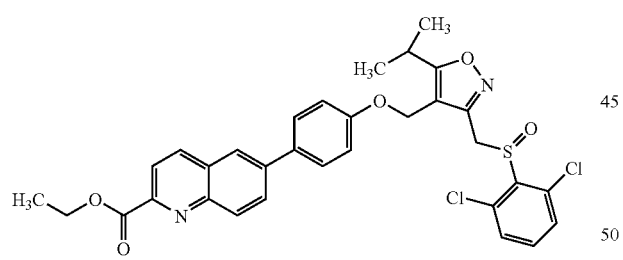

To a solution of ethyl 6-[4-({[3-{[(2,6-dichlorophenyl)thio]methyl}-5-(1-methylethyl)-4-isoxazolyl]methyl}oxy)phenyl]-2-quinolinecarboxylate (20 mg, 0.033 mmol) in dichloromethane (1 mL) at 0° C. was added meta-chloroperoxybenzoic acid (15 mg, 0.066 mmol). The mixture was stirred at 0° C. for approximately 30 minutes. Aqueous sodium bicarbonate was added and the mixture was extracted twice with dichloromethane. The combined organic layers were dried over magnesium sulfate, adsorbed onto silica gel and purified by chromatography (silica gel, 0-100% ethyl acetate in hexanes gradient elution) to afford ethyl 6-[4-({[3-{[(2,6-dichlorophenyl)sulfinyl]methyl}-5-(1-methylethyl)-4-isoxazolyl]methyl}oxy)phenyl]-2-quinolinecarboxylate (12 mg, 0.019 mmol, 57%). $^1$H-NMR (400 MHz, CDCl$_3$) δ 8.39 (d, J=9 Hz, 1H), 8.23 (d, J=9 Hz, 2H), 8.05-8.03 (m, 2H), 7.68 (d, J=9 Hz, 2H), 7.31 (s, 3H), 7.07 (d, J=9 Hz, 2H), 5.10-4.90 (m, 2H), 4.80-4.58 (m, 2H), 3.22 (septet, J=7 Hz, 1H), 1.32 (d, J=7 Hz, 6H). LRMS m/z 623 (M+H)$^+$.

23b) 6-[4-({[3-{[(2,6-Dichlorophenyl)sulfinyl]methyl}-5-(1-methylethyl)-4-isoxazolyl]methyl}oxy)phenyl]-2-quinolinecarboxylic acid

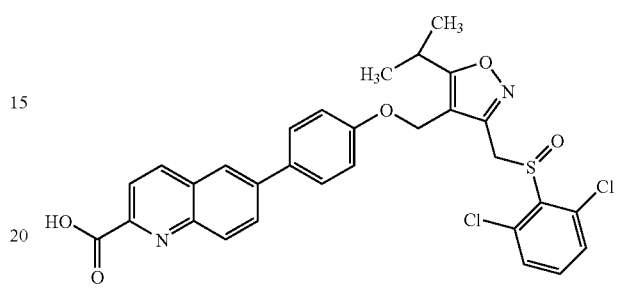

To a solution of ethyl 6-[4-({[3-{[(2,6-dichlorophenyl)sulfinyl]methyl}-5-(1-methylethyl)-4-isoxazolyl]methyl}oxy)phenyl]-2-quinolinecarboxylate (6 mg, 0.01 mmol) in 1:1 tetrahydrofuran:methanol (0.5 mL) was added 1 N sodium hydroxide (0.020 mL, 0.020 mmol). The solution was heated in a microwave reactor at 90° C. for approximately 10 minutes and then 1 N hydrochloric acid (0.020 mL, 0.020 mmol) was added. The solution was concentrated and then dichloromethane and water were added. The layers were separated and the organic layer was dried over magnesium sulfate and concentrated to afford 6-[4-({[3-{[(2,6-dichlorophenyl)sulfinyl]methyl}-5-(1-methylethyl)-4-isoxazolyl]methyl}oxy)phenyl]-2-quinolinecarboxylic acid (6 mg, 100%). $^1$H-NMR (400 MHz, CDCl$_3$) δ 8.38 (d, J=8 Hz, 1H), 8.23 (d, J=8 Hz, 2H), 8.04-8.01 (m, 2H), 7.68 (d, J=9 Hz, 2H), 7.31 (s, 3H), 7.07 (d, J=9 Hz, 2H), 5.14-4.99 (m, 2H), 4.84-4.59 (m, 2H), 3.24 (septet, J=7 Hz, 1H), 1.35 (d, J=7 Hz, 6H). LRMS (APCI) m/z 595 (M+H)$^+$.

Example 24

6-[4-({[3-{[(2,6-Dichlorophenyl)sulfonyl]methyl}-5-(1-methylethyl)-4-isoxazolyl]methyl}oxy)phenyl]-2-quinolinecarboxylic acid

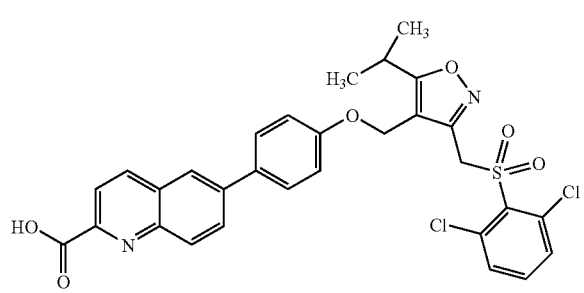

24a) Ethyl 6-[4-({[3-{[(2,6-dichlorophenyl)sulfonyl]methyl}-5-(1-methylethyl)-4-isoxazolyl]methyl}oxy)phenyl]-2-quinolinecarboxylate

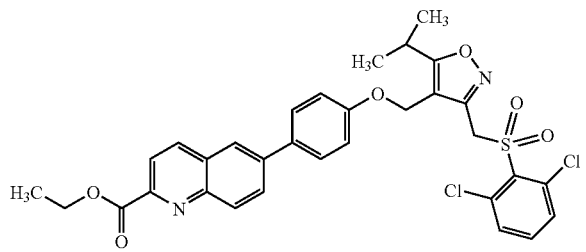

To a solution of ethyl 6-[4-({[3-{[(2,6-dichlorophenyl)thio]methyl}-5-(1-methylethyl)-4-isoxazolyl]methyl}oxy)phenyl]-2-quinolinecarboxylate (43 mg, 0.071 mmol) in dichloromethane at 0° C. was added meta-chloroperoxybenzoic acid (39 mg, 0.16 mmol) and the mixture was allowed to stir at 0° C. for 30 minutes. Then an additional 20 mg of meta-chloroperoxybenzoic acid was added and the mixture was allowed to stir overnight while warming slowly to ambient temperature. The next day aqueous sodium bicarbonate was added and the solution was extracted twice with dichloromethane. The combined organic layers were dried over magnesium sulfate, adsorbed onto silica gel and purified by chromatography (silica gel, 0-100% ethyl acetate in hexanes gradient elution). The resulting solid was diluted with dichloromethane and washed with aqueous sodium bicarbonate, dried over magnesium sulfate and concentrated to afford ethyl 6-[4-({[3-{[(2,6-dichlorophenyl)sulfonyl]methyl}-5-(1-methylethyl)-4-isoxazolyl]methyl}oxy)phenyl]-2-quinolinecarboxylate (4 mg, 0.006 mmol). $^1$H-NMR (400 MHz, CDCl$_3$) δ 8.39-8.33 (m, 2H), 8.21 (d, J=9 Hz, 1H), 8.05-8.01 (m, 2H), 7.71 (d, J=9 Hz, 2H), 7.45-7.37 (m, 3H), 7.10 (d, J=9 Hz, 2H), 5.15 (s, 2H), 4.86 (s, 2H), 4.57 (q, J=7 Hz, 2H), 3.25 (septet, J=7 Hz, 1H), 1.50 (t, J=7 Hz, 3H), 1.33 (d, J=7 Hz, 6H). LRMS (ESI) m/z 639 (M+H)$^+$.

24b) 6-[4-({[3-{[(2,6-Dichlorophenyl)sulfonyl]methyl}-5-(1-methylethyl)-4-isoxazolyl]methyl}oxy)phenyl]-2-quinolinecarboxylic acid

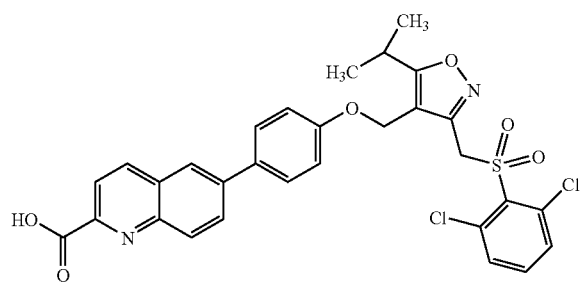

To a solution of ethyl 6-[4-({[3-{[(2,6-dichlorophenyl)sulfonyl]methyl}-5-(1-methylethyl)-4-isoxazolyl]methyl}oxy)phenyl]-2-quinolinecarboxylate (4 mg, 0.006 mmol) in 1:1 tetrahydrofuran:methanol (0.5 mL) was added 1 N sodium hydroxide (0.020 mL, 0.020 mmol). The solution was heated in a microwave reactor at 75° C. for approximately 10 minutes. Then the mixture was diluted with dichloromethane and 1 N hydrochloric (0.020 mL, 0.020 mmol) was added. The solution was washed with water, dried over magnesium sulfate and concentrated to afford 6-[4-({[3-{[(2,6-dichlorophenyl)sulfonyl]methyl}-5-(1-methylethyl)-4-isoxazolyl]methyl}oxy)phenyl]-2-quinolinecarboxylic acid (1 mg, 25%). $^1$H-NMR (400 MHz, CDCl$_3$) δ 8.44 (d, J=8 Hz, 1H), 8.29 (d, J=8 Hz, 1H), 8.21 (d, J=8 Hz, 1H), 8.10-8.07 (m, 2H), 7.71 (d, J=8 Hz, 2H), 7.47-7.38 (m, 3H), 7.12 (d, J=8 Hz, 2H), 5.16 (s, 2H), 4.86 (s, 2H), 3.25 (septet, J=7 Hz, 1H), 1.34 (d, J=7 Hz, 6H). LRMS m/z 609 [M–H]$^-$.

Example 25

6-[4-({[3-(3,5-Dichloro-4-pyridinyl)-5-(1-methylethyl)-4-isoxazolyl]methyl}oxy)phenyl]-2-quinolinecarboxylic acid

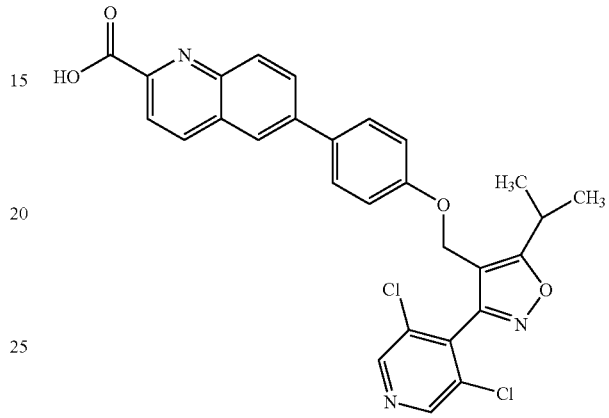

25a) 3-(3,5-Dichloro-4-pyridinyl)-5-(1-methylethyl)-4-isoxazolecarboxylic acid

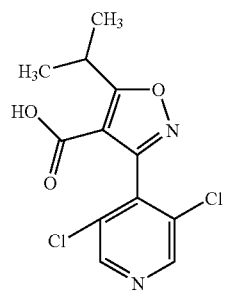

N-chlorosuccinimide (1.36 g, 10.2 mmol) was added to a stirred solution of 3,5-dichloro-4-pyridinecarbaldehyde oxime (1.94 g, 10.2 mmol) in dimethylformamide (8 mL) and the solution was heated in a 65° C. oil bath for 1.5 hours. The solution was poured into water and extracted with ether. The organic layer was dried with MgSO$_4$, filtered and concentrated to yield a crude carboximidoyl chloride. A solution of methylisobutyrylacetate (1.7 mL, 12.3 mmol) in THF (2.5 mL) was stirred at 0° C. as 0.5 N solution of sodium methoxide in methanol (24.6 mL, 12.3 mmol) was added. The solution was allowed to stir for ten minutes before the addition of the crude 3,5-dichloro-N-hydroxy-4-pyridinecarboximidoyl chloride in THF (8.1 mL). The solution was allowed to stir at room temperature overnight. The solution was then concentrated and the residue was partitioned between water and ethyl acetate. The organic layer was dried with MgSO$_4$, filtered and concentrated. The residue was purified by chromatography (silica gel, hexane to 1:9 ethyl acetate:hexanes). Fractions containing the intermediate were combined and concentrated. The residue was azetroped with methanol then was diluted with THF (11 mL) and methanol (5.5 mL). A 1 N solution of sodium hydroxide (3.3 mL) was added and the solution of heated to 100° C. for 500 seconds in a microwave reactor. The solution was neutralized with 1 N HCl and concentrated to yield a white solid. The residue was slurried in water and filtered to yield 3-(3,5-dichloro-4-pyridinyl)-5-(1-methylethyl)-4-isoxazolecarboxylic acid (0.57 g, 18%). $^1$H NMR (400 MHz, DMSO-d6): δ 13.39 (s, 1H), 8.81 (s, 2H), 3.82 (septet, J=7 Hz, 1H), 1.34 (d, J=7 Hz, 6H).

25b) [3-(3,5-Dichloro-4-pyridinyl)-5-(1-methylethyl)-4-isoxazolyl]methanol

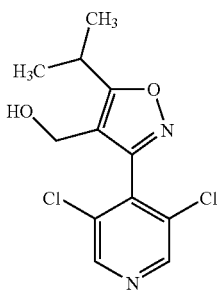

A solution of 3-(3,5-dichloro-4-pyridinyl)-5-(1-methylethyl)-4-isoxazolecarboxylic acid (0.54 g, 1.8 mmol) in THF (9 mL), was stirred as triethylamine (0.25 mL, 1.8 mmol) was added. The solution was cooled in ice bath before the addition of a 1 N solution of isopropylchloroformate in toluene (1.8 mL, 1.8 mmol). The solution was allowed to stir for 30 minutes before being filtered into a solution of sodium borohydride (91 mg, 2.4 mmol) in water (0.62 mL). The mixture was allowed to warm to room temperature and stir for 3 days. The mixture was filtered and the filtrate was partitioned between brine and ethyl acetate. The organic layer was dried with MgSO$_4$, filtered and concentrated. The residue was purified by chromatography (silica gel, hexane to 2:3 ethyl acetate:hexanes) to provide [3-(3,5-dichloro-4-pyridinyl)-5-(1-methylethyl)-4-isoxazolyl]methanol (0.32 g, 57% as 0.3 ethyl acetate). $^1$H NMR (400 MHz, DMSO-d$_6$): δ 8.79 (s, 2H), 4.96 (t, J=5 Hz, 1H), 4.20 (d, J=5 Hz, 2H), 3.35 (septet, J=7 Hz, 1H), 1.29 (d, J=7 Hz, 6H).

25c) Methyl 6-[4-({[3-(3,5-dichloro-4-pyridinyl)-5-(1-methylethyl)-4-isoxazolyl]methyl}oxy)phenyl]-2-quinolinecarboxylate

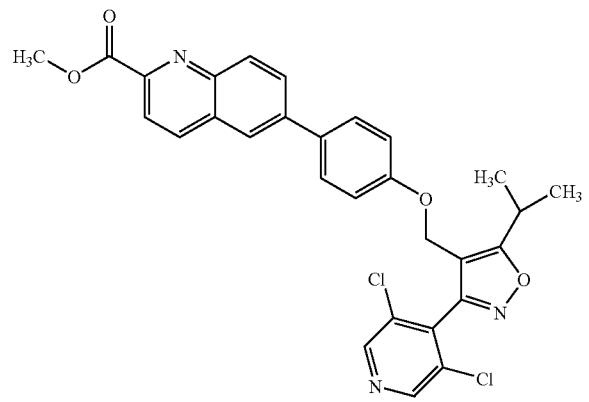

Methyl 6-(4-hydroxyphenyl)-2-quinolinecarboxylate (100 mg, 0.36 mmol), [3-(3,5-dichloro-4-pyridinyl)-5-(1-methylethyl)-4-isoxazolyl]methanol (103 mg, 0.36 mmol), triphenyl phosphine (94 mg, 0.36 mmol), diisopropyl azodicarboxylate (0.07 mL, 0.36 mmol) and dichloromethane (3.6 mL) were placed in a microwave reaction tube, sealed and heated in a microwave reactor to 100° C. for 10 minutes. The solution was concentrated then slurried in a 3:7 mixture of acetone: hexane. The resulting off-white solid was purified by chromatography (silica gel, 3:7 acetone:hexanes) to provide methyl 6-[4-({[3-(3,5-dichloro-4-pyridinyl)-5-(1-methylethyl)-4-isoxazolyl]methyl}oxy)phenyl]-2-quinolinecarboxylate (0.10 g, 52%). $^1$H NMR (400 MHz, DMSO-d$_6$): δ 8.81 (s, 2H), 8.55 (d, J=9 Hz, 1H), 8.29 (d, J=2 Hz, 1H), 8.18-8.10 (m, 3H), 7.74 (d, J=9 Hz, 2H), 6.89 (d, J=9 Hz, 2H), 4.97 (s, 2H), 3.94 (s, 3H), 3.49 (septet, 7 Hz, 1H), 1.34 (d, J=7 Hz, 6H). ESI-LCMS m/z 548 (M+H)$^+$.

25d) 6-[4-({[3-(3,5-Dichloro-4-pyridinyl)-5-(1-methylethyl)-4-isoxazolyl]methyl}oxy)phenyl]-2-quinolinecarboxylic acid

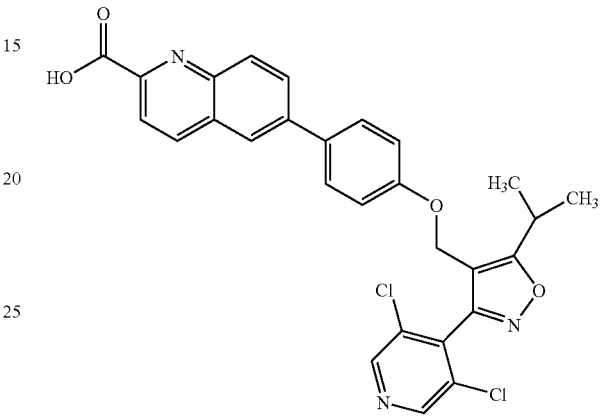

A solution of methyl 6-[4-({[3-(3,5-dichloro-4-pyridinyl)-5-(1-methylethyl)-4-isoxazolyl]methyl}oxy)phenyl]-2-quinolinecarboxylate (98 mg, 0.18 mmol) in THF (1.8 mL) was placed in a microwave reaction tube. Methanol (0.9 mL) was added followed by 1.0 N sodium hydroxide (0.27 mL, 0.27 mmol) before the tube was sealed and heated at 100° C. for 600 seconds. The solution was neutralized with 1 N HCl. The resulting mixture was partitioned between brine and ethyl acetate. The organic layer was separated and concentrated to yield 6-[4-({[3-(3,5-dichloro-4-pyridinyl)-5-(1-methylethyl)-4-isoxazolyl]methyl}oxy)phenyl]-2-quinolinecarboxylic acid as a yellow powder (0.08 g, 80% as 0.25 ethyl acetate). $^1$H NMR (400 MHz, DMSO-d$_6$): δ 13.37 (br s, approximately 1H), 8.81 (s, approximately 2H), 8.53 (d, J=9 Hz, 1H), 8.27 (s, 1H), 8.17-8.08 (m, 3H), 7.73 (d, J=9 Hz, 2H), 6.89 (d, J=9 Hz, 2H), 4.97 (s, 2H), 3.49 (septet, J=7 Hz, 1H), 1.34 (d, J=7 Hz, 6H). HRMS C$_{28}$H$_{21}$N$_3$O$_4$Cl$_2$ m/z 534.0982 (M+H)$^+{}_{Cal}$; 534.0981 (M+H)$^+{}_{Obs}$.

Example 26

6-(4-{[(3,5-Dicyclopentyl-4-isoxazolyl)methyl]oxy}phenyl)-2-quinolinecarboxylic acid

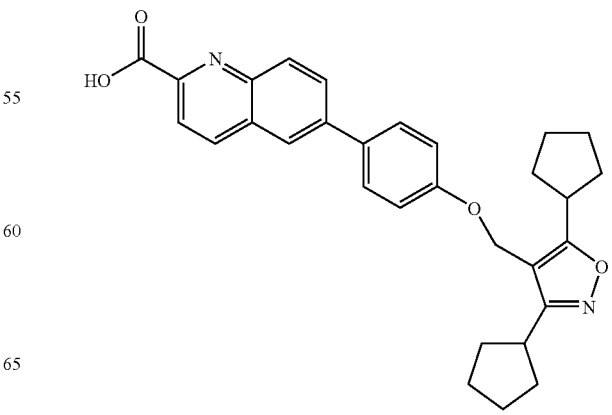

26a) Ethyl 3-cyclopentyl-2-(cyclopentylcarbonyl)-3-oxopropanoate

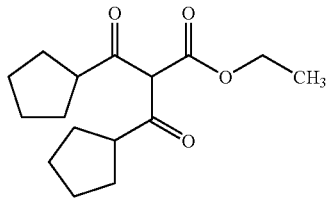

A solution of ethyl 3-cyclopentyl-3-oxopropanoate (2.00 g, 10.9 mmol) in THF (20.4 mL) was stirred as sodium hydride 60% oil dispersion (501 mg, 12.5 mmol) was added. The resulting solution was allowed to stir for 30 minutes before the addition of cyclopentanecarbonyl chloride (1.32 mL, 10.9 mmol). The mixture was then allowed to stir at room temperature overnight. The solution was then partitioned between ether and brine. The organic layer was dried with MgSO$_4$, filtered and concentrated. The residue was purified by chromatography (silica gel, hexane to 1:19 ethyl acetate:hexanes). Fractions containing the product were combined and concentrated to yield 3-cyclopentyl-2-(cyclopentylcarbonyl)-3-oxopropanoate (2.21 g, 72%). ESI-LCMS m/z 279 (M−H)$^-$.

26b) Ethyl 3,5-dicyclopentyl-4-isoxazolecarboxylate

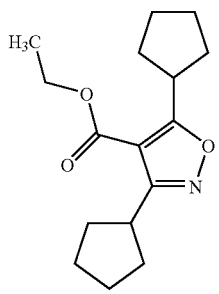

A solution of ethyl 3-cyclopentyl-2-(cyclopentylcarbonyl)-3-oxopropanoate (2.20 g, 7.84 mmol) in EtOH (6.4 mL) was stirred as water (1.2 mL) followed by hydroxylamine hydrochloride (1.02 g, 14.7 mmol) was added. The solution was then heated to reflux for 3 hours. The solution was concentrated and the residue was partitioned between ether and saturated aqueous NaHCO$_3$ solution. The organic layer was washed with brine, dried with MgSO$_4$, filtered and concentrated to yield ethyl 3,5-dicyclopentyl-4-isoxazolecarboxylate as a yellow oil (1.58 g, crude yield 73%). $^1$H NMR (400 MHz, DMSO-d$_6$): δ 4.23 (q, J=7 Hz, 2H), 3.78-3.72 (m, 1H), 3.45-3.37 (m, 1H), 2.00-1.92 (m, 4H), 1.83-1.49 (m, 12H), 1.26 (t, J=7 Hz, 3H). ESI-LCMS m/z 278 (M+H)$^+$.

26c) (3,5-Dicyclopentyl-4-isoxazolyl)methanol

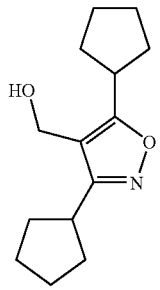

A solution of ethyl 3,5-dicyclopentyl-4-isoxazolecarboxylate (1.57 g, 5.67 mmol) in THF (15.7 mL) was stirred in an ice bath as a 1.5 M solution of diisobutylaluminum hydride in toluene (8.1 mL, 12.1 mmol) was added dropwise. The solution was allowed to stir at 0° C. for 30 minutes then at room temperature for 5.5 hours. An additional portion of diisobutylaluminum hydride (1.6 mL, 2.4 mmol) was added and the solution was allowed to stir for 45 minutes. The solution was cooled in ice bath before the addition of a 10% aqueous solution of Rochelle's salt. The resulting solution was allowed to stir overnight. The solution was extracted with ethyl acetate and the organic layer was dried with MgSO$_4$, filtered and concentrated. The residue was purified by chromatography (silica gel, 3:7 ethyl acetate:hexanes) to provide (3,5-dicyclopentyl-4-isoxazolyl)methanol (0.80 g, 57% as 0.15 ethyl acetate). $^1$H NMR (400 MHz, DMSO-d$_6$): δ 4.84 (s, 1H), 4.26 (d, J=4 Hz, 2H), 3.30-3.22 (m, overlapping H$_2$O), 3.13-3.06 (m, 1H), 1.98-1.87 (m, 4H), 1.74-1.56 (m, 12H).

26d) Methyl 6-(4-{[(3,5-dicyclopentyl-4-isoxazolyl)methyl]oxy}phenyl)-2-quinolinecarboxylate

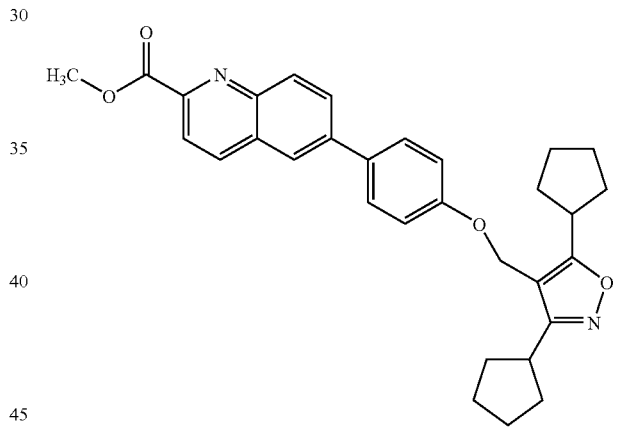

Methyl 6-(4-hydroxyphenyl)-2-quinolinecarboxylate (109 mg, 0.39 mmol), (3,5-dicyclopentyl-4-isoxazolyl)methanol (92 mg, 0.39 mmol), triphenyl phosphine (102 mg, 0.39 mmol), diisopropyl azodicarboxylate (0.075 mL, 0.39 mmol) and dichloromethane (3.9 mL) were placed in a microwave reaction tube, sealed and heated in a microwave reactor to 100° C. for 10 minutes. The solution was concentrated and the residue was purified by chromatography (silica gel, hexane to 1:1 ethyl acetate:hexanes). Fractions containing the product were combined and concentrated. The residue was recrystallized from ethyl acetate and filtered to yield methyl 6-(4-{[(3,5-dicyclopentyl-4-isoxazolyl)methyl]oxy}phenyl)-2-quinolinecarboxylate (67 mg, 35%). $^1$H NMR (400 MHz, DMSO-d$_6$): δ 8.57 (d, J=9 Hz, 1H), 8.33 (s, 1H), 8.19 (s, 2H), 8.12 (d, J=8 Hz, 1H), 7.84 (d, J=9 Hz, 2H), 7.17 (d, J=9 Hz, 2H), 4.98 (s, 2H), 3.94 (s, 3H), 3.41-3.37 (m, 1H), 3.16 (m, 1H), 1.98-1.94 (m, 4H), 1.76-1.56 (m, 12H).

26e) 6-(4-{[(3,5-Dicyclopentyl-4-isoxazolyl)methyl]oxy}phenyl)-2-quinolinecarboxylic acid

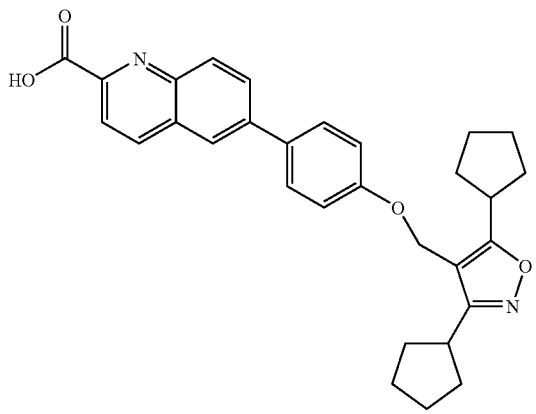

A solution of methyl 6-(4-{[(3,5-dicyclopentyl-4-isoxazolyl)methyl]oxy}phenyl)-2-quinolinecarboxylate (65 mg, 0.13 mmol) in THF (1.3 mL) was placed in a microwave reaction tube. Methanol (0.7 mL) was added followed by 1.0 N sodium hydroxide (0.2 mL, 0.2 mmol) before the tube was sealed and stirred at room temperature for 30 minutes. The mixture was heated at 100° C. for 10 minutes. The solution was concentrated and the residue was suspended in water before neutralization with 1 N HCl. The resulting mixture was filtered and the sample was dried in a drying oven at 45° C. under reduced pressure with $P_2O_5$ to yield 6-(4-{[(3,5-dicyclopentyl-4-isoxazolyl)methyl]oxy}phenyl)-2-quinolinecarboxylic acid (0.53 g, 84%). $^1$H NMR (400 MHz, DMSO-$d_6$): δ 8.47 (d, J=9 Hz, 1H), 8.27 (s, 1H), 8.18-8.11 (m, 2H), 8.07 (d, J=9 Hz, 1H), 7.82 (d, J=9 Hz, 2H), 7.16 (d, J=9 Hz, 2H), 4.98 (s, 2H), 3.40-3.20 (m, overlapping $H_2O$), 3.16-3.12 (m, 1H), 1.99 (m, 4H), 1.76-1.56 (m, 12H). HRMS $C_{30}H_{30}N_2O_4$ m/z 483.2278, (M+H)$^+_{Cal}$; 483.2277 (M+H)$^+_{Obs}$.

Example 27

6-[4-({[3-[(Cyclopentyloxy)methyl]-5-(1-methylethyl)-4-isoxazolyl]methyl}oxy)phenyl]-2-quinolinecarboxylic acid

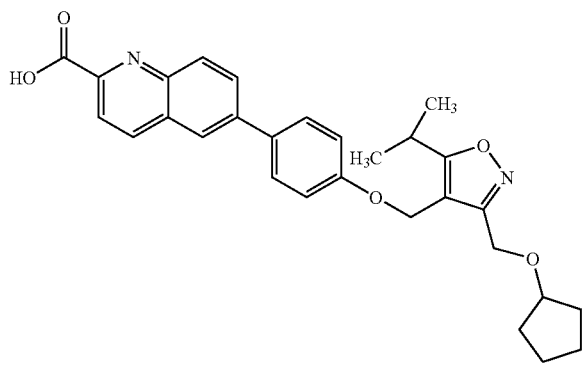

27a) Methyl 3-(bromomethyl)-5-(1-methylethyl)-4-isoxazolecarboxylate

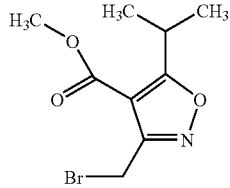

A solution of methyl 3-{[(1,1-dimethylethyl)oxy]methyl}-5-(1-methylethyl)-4-isoxazolecarboxylate (2.00 g, 7.83 mmol) in dichloromethane (32.5 mL) was stirred at 0° C. as trifluoroacetic acid (32.5 mL, 0.42 mol) was added dropwise. The resulting solution was allowed to stir at 0° C. for 5 minutes then at room temperature for 30 minutes. The solution was concentrated and the residue was partitioned between ethyl acetate and saturated aqueous $NaHCO_3$. The organic layer was dried with $MgSO_4$, filtered and concentrated. The residue was purified by chromatography (silica gel, hexane to 2:3 ethyl acetate:hexanes). Fractions containing methyl 3-(hydroxymethyl)-5-(1-methylethyl)-4-isoxazolecarboxylate were combined and concentrated. A solution of methyl 3-(hydroxymethyl)-5-(1-methylethyl)-4-isoxazolecarboxylate (1.042 g, 5.23 mmol) in dichloromethane (24.3 mL) was stirred as carbon tetrabromide (1.85 g, 5.5 mmol) was added. The solution was cooled in ice bath before the addition of triphenyl phosphine (1.44 g, 5.5 mmol) in three portions. The solution was allowed to stir at 0° C. for 30 minutes then at room temperature for 1.5 hours. Hexane (67 mL) was added before the mixture was filtered through Celite® and concentrated. The residue was purified by chromatography (silica gel, hexane to 1:4 ethyl acetate:hexanes). Fractions containing the product were combined and concentrated to yield methyl 3-(bromomethyl)-5-(1-methylethyl)-4-isoxazolecarboxylate (0.809 g, 57% as 0.10 ethyl acetate). $^1$H NMR (400 MHz, DMSO-$d_6$): δ 4.70 (s, 2H), 3.82 (s, 3H), 3.69 (septet, J=7 Hz, 1H), 1.26 (d, J=7 Hz, 6H). ESI-LCMS m/z 262 (M+H)$^+$.

27b) Cyclopentyl 3-[(cyclopentyloxy)methyl]-5-(1-methylethyl)-4-isoxazolecarboxylate

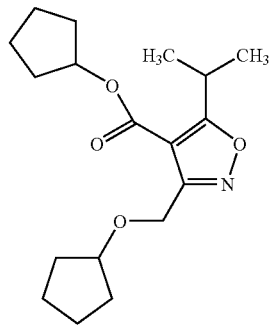

A solution of cyclopentanol (0.44 mL, 4.8 mmol), in THF (10 mL), was stirred at 0° C. as sodium hydride 60% oil dispersion (192 mg, 4.8 mmol) was added. The solution was allowed to stir for 30 minutes. A solution of methyl 3-(bromomethyl)-5-(1-methylethyl)-4-isoxazolecarboxylate (500 mg, 1.91 mmol), in THF (5 mL) was then added and the resulting solution was allowed to warm to room temperature and stir for 3 hours. The solution was then partitioned between brine and ethyl acetate. The organic layer was dried with MgSO$_4$, filtered and concentrated. The residue purified by chromatography (silica gel, hexane to 1:4 ethyl acetate: hexanes). Fractions containing the product were combined and concentrated to yield cyclopentyl 3-[(cyclopentyloxy) methyl]-5-(1-methylethyl)-4-isoxazolecarboxylate (94 mg, 15%). $^1$H NMR (400 MHz, DMSO-d$_6$): δ 5.29-5.26 (m, 1H), 4.54 (s, 2H), 3.98 (m, 1H), 3.64 (septet, 7 Hz, 1H), 1.85 (m, 2H), 1.72-1.56 (m, 12H), 1.47-1.40 (m, 2H), 1.25 (d, J=7 Hz, 6H). ESI-LCMS m/z 322 (M+H)$^+$.

27c) [3-[(Cyclopentyloxy)methyl]-5-(1-methylethyl)-4-isoxazolyl]methanol

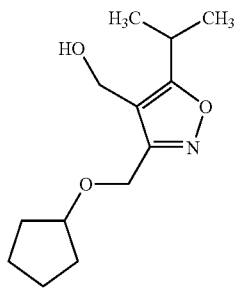

A solution of cyclopentyl 3-[(cyclopentyloxy)methyl]-5-(1-methylethyl) -4-isoxazolecarboxylate (0.093 g, 0.29 mmol) in THF (2.8 mL) was stirred in an ice bath as a 1.5M solution of diisobutylaluminum hydride in toluene (0.42 mL, 0.63 mmol) was added dropwise. The solution was allowed to stir at room temperature for 2 hours. The solution was cooled to 0° C. before an additional portion of diisobutylaluminum hydride (0.42 mL, 0.63 mmol) was added and the solution was allowed to stir at room temperature for one hour. A 10% aqueous solution of Rochelle's salt (30 mL) was added and the solution was allowed to stir for 20 hours. The solution was extracted with ethyl acetate and the organic layer was dried with MgSO$_4$, filtered and concentrated. The residue was purified by chromatography (silica gel, hexane to 1:1 ethyl acetate:hexanes) to provide [3-[(cyclopentyloxy)methyl]-5-(1-methylethyl)-4-isoxazolyl]methanol (0.051 g, 74%). $^1$H NMR (400 MHz, DMSO-d$_6$): δ 4.82 (t, J=5 Hz, 1H), 4.42 (s, 2H), 4.30 (d, J=5 Hz, 2H), 3.95 (m, 1H) 3.24 (septet, J=7 Hz, overlapping H$_2$O), 1.64-1.55 (m, 6H), 1.46 (m, 2H), 1.21 (d, J=7 Hz, 6H).

27d) Methyl 6-[4-({[3-[(cyclopentyloxy)methyl]-5-(1-methylethyl)-4-isoxazolyl]methyl}oxy)phenyl]-2-quinolinecarboxylate

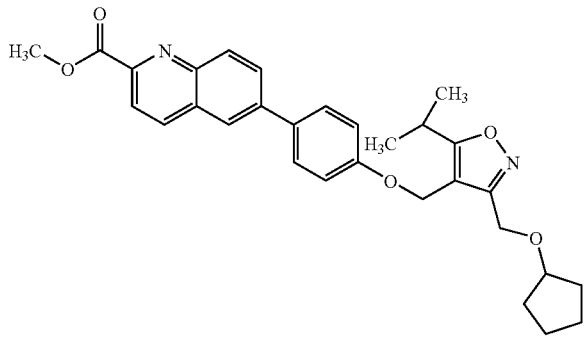

A solution of [3-[(cyclopentyloxy)methyl]-5-(1-methylethyl)-4-isoxazolyl]methanol (50 mg, 0.21 mmol) in dichloromethane (2.1 mL) was added to a mixture of methyl 6-(4-hydroxyphenyl)-2-quinolinecarboxylate (57 mg, 0.21 mmol) and triphenyl phosphine (82 mg, 0.31 mmol) in a microwave reaction tube. Diisopropyl azodicarboxylate (60 μL, 0.31 mmol) was added before the tube was sealed and heated for 20 minutes at 100° C. The mixture was concentrated and the residue was purified by chromatography (silica gel, hexane to 2:3 ethyl acetate:hexanes). Fractions containing the product were combined and concentrated. The residue was purified by chromatography (silica gel, 10:9:1 hexanes:dichloromethane:ethyl acetate) to provide methyl 6-[4-({[3-[(cyclopentyloxy)methyl]-5-(1-methylethyl)-4-isoxazolyl] methyl}oxy)phenyl]-2-quinolinecarboxylate (11 mg, 11% as 0.10 ethyl acetate). $^1$H NMR (400 MHz, CDCl$_3$): δ 8.37-8.32 (m, 2H), 8.22 (d, J=9 Hz, 1H), 8.05-8.00 (m, 2H), 7.69 (d, J=9 Hz, 2H), 7.08 (d, J=9 Hz, 2H), 4.99 (s, 2H), 4.58 (s, 2H), 4.09 (s, 3H), 3.99-3.97 (m, 1H), 3.27 (septet, J=7 Hz, 1H), 1.70-1.59 (m, 6H), 1.49-1.46 (m, 2H), 1.33 (d, J=7 Hz, 6H).

27e) 6-[4-({[3-[(Cyclopentyloxy)methyl]-5-(1-methylethyl)-4-isoxazolyl]methyl}oxy)phenyl]-2-quinolinecarboxylic acid

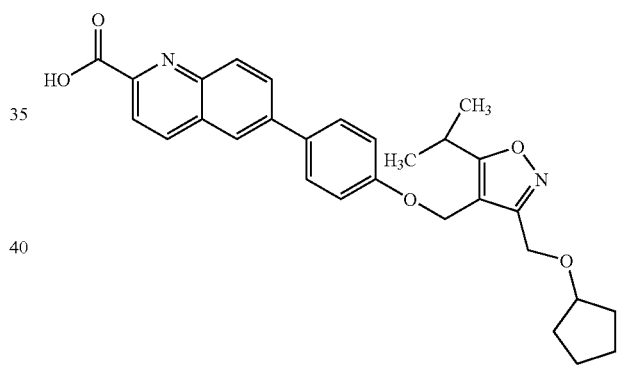

A solution of methyl 6-[4-({[3-[(cyclopentyloxy)methyl]-5-(1-methylethyl)-4-isoxazolyl]methyl}oxy)phenyl]-2-quinolinecarboxylate (11 mg, 0.02 mmol) in THF (0.22 mL) was placed in a microwave reaction tube. Methanol (0.11 mL) was added followed by 1 N sodium hydroxide (0.05 mL, 0.05 mmol). The tube was sealed and heated to 100° C. for 800 seconds. The solution was concentrated then neutralized with 1 N HCl. Water was added and the mixture was filtered to yield a bright yellow solid. The sample was dried in a vacuum oven under reduced pressure at 45° C. with P$_2$O$_5$. The sample was removed from the oven to yield 6-[4-({[3-[(cyclopentyloxy)methyl]-5-(1-methylethyl)-4-isoxazolyl]methyl}oxy) phenyl]-2-quinolinecarboxylic acid (10 mg, 95%). $^1$H NMR (400 MHz, DMSO-d$_6$): δ 8.37 (d, J=9 Hz, 1H), 8.20-8.17 (m, 2H), 8.08-8.03 (m, 2H), 7.80 (d, J=9 Hz, 2H), 7.14 (d, J=9 Hz, 2H), 5.01 (s, 2H), 4.49 (s, 2H), 3.95-3.93 (m, 1H), 3.40-3.20 (br s, 1H overlapped by water), 1.60-1.37 (m, 8H), 1.24 (d, J=7 Hz, 6H). HRMS C$_{29}$H$_{30}$N$_2$O$_5$ m/z 487.2228, (M+H)$^+_{Cal}$; 487.2227 (M+H)$^+_{Obs}$.

Example 28

6-[4-({[3-(2,4-Dichloro-3-pyridinyl)-5-(1-methyl-ethyl)-4-isoxazolyl]methyl}oxy)phenyl]-2-quinolinecarboxylic acid

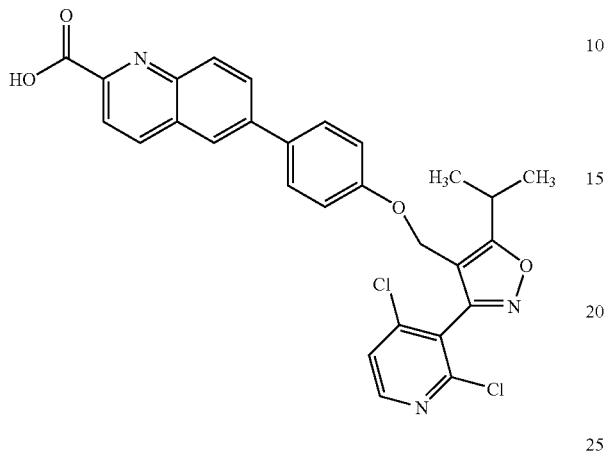

28a) 2,4-Dichloro-3-pyridinecarbaldehyde

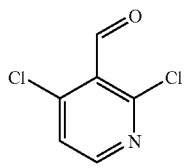

A solution of diisopropylamine (2.6 mL, 18.5 mmol) in THF (18.5 mL) was stirred at −78° C. as a 2.5 N solution of n-butyl lithium (7.4 mL, 18.5 mmol) was added. The solution was stirred at 0° C. for 30 minutes, then cooled to −78° C. for 30 minutes before the addition of 2,4-dichloropyridine (2 mL, 18.5 mmol). The solution was stirred at −78° C. for another 30 minutes before the addition of methyl formate (1.14 mL, 18.5 mmol). The solution was stirred for 30 minutes then was partitioned between ethyl acetate and saturated aqueous NaHCO$_3$. The organic layer was dried with MgSO$_4$, filtered and concentrated. The residue was purified by chromatography (silica gel, hexane to 3:7 ethyl acetate:hexanes) to provide 2,4-dichloro-3-pyridinecarbaldehyde (2.18 g, 67%). $^1$H NMR (400 MHz, DMSO-d$_6$): δ 10.29 (s, 1H), 8.54 (d, J=5 Hz, 1H), 7.75 (d, J=5 Hz, 1H).

28b) 2,4-Dichloro-3-pyridinecarbaldehyde oxime

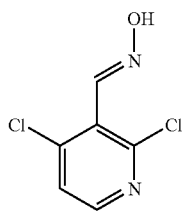

A solution of 2,4-dichloro-3-pyridinecarbaldehyde (2.15 g, 12.4 mmol) in ethanol (18 mL) was added to a solution of hydroxylamine hydrochloride (1.01 g, 14.5 mmol) and sodium hydroxide (0.58 g, 14.5 mL) in water (9 mL). The resulting solution was heated in a 65° C. oil bath for 3 hours. The mixture was filtered to yield a white solid which was dried in a vacuum oven at 45° C. with P$_2$O$_5$ to yield 2,4-dichloro-3-pyridinecarbaldehyde oxime (1.89 g, 80%). $^1$H NMR (400 MHz, DMSO-d$_6$): δ 12.00 (s, 1H), 8.35 (d, J=5 Hz, 1H), 8.19 (s, 1H), 7.68 (d, J=5 Hz, 1H).

28c) 2,4-Dichloro-N-hydroxy-3-pyridinecarboximidoyl chloride

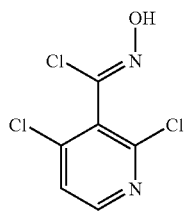

A solution of 2,4-dichloro-3-pyridinecarbaldehyde oxime (1.88 g, 9.9 mmol) in DMF (7.9 mL) was stirred as N-chlorosuccinimide (1.32 g, 9.9 mmol) was added. The solution was stirred in a 64° C. oil bath for 1 hour then allowed to cool to room temperature. The solution was poured onto ice. The solution was extracted with ether and the organic layer was washed with brine, dried with MgSO$_4$, filtered and concentrated to yield 2,4-dichloro-N-hydroxy-3-pyridinecarboximidoyl chloride (1.94 g, 87%). $^1$H NMR (400 MHz, DMSO-d$_6$): δ 12.89 (s, 1H), 8.52 (d, J=5 Hz, 1H), 7.81 (d, J=5 Hz, 1H).

28d) Methyl 3-(2,4-dichloro-3-pyridinyl)-5-(1-methylethyl)-4-isoxazolecarboxylate

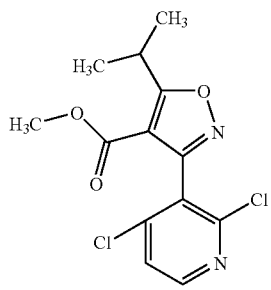

A solution of methyl isobutyrylacetate (1.37 mL, 10.2 mmol) in THF (2.1 mL) was stirred at 0° C. as a 0.5 N solution of sodium methoxide in methanol (20.3 mL, 10.2 mmol) was added. A solution of 2,4-dichloro-N-hydroxy-3-pyridinecarboximidoyl chloride (1.94 g, 8.64 mmol) in THF (19 mL) was added and the resulting solution was allowed to warm to room temperature and stir overnight. The mixture was concentrated and the residue partitioned between ethyl acetate and brine. The organic layer was dried with MgSO$_4$, filtered and concentrated. The residue was purified by chromatography (silica gel, hexanes to 3:7 ethyl acetate:hexanes gradient elution) and fractions containing the product concentrated. The residue was azetroped with methanol then dichloromethane to provide methyl 3-(2,4-dichloro-3-pyridinyl)-5-(1-methylethyl)-4-isoxazolecarboxylate (1.64 g, 66% as 0.15 dichloromethane). $^1$H NMR (400 MHz, DMSO-d$_6$): δ 8.65 (d, J=5 Hz, 1H), 7.82 (d, J=5 Hz, 1H), 3.79 (septet, J=7 Hz, 1H), 3.63 (s, 3H), 1.34 (m, 6H).

28e) [3-(2,4-Dichloro-3-pyridinyl)-5-(1-methylethyl)-4-isoxazolyl]methanol

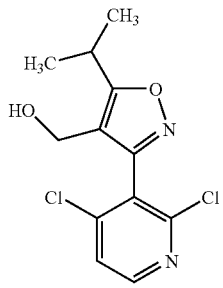

A solution of methyl 3-(2,4-dichloro-3-pyridinyl)-5-(1-methylethyl)-4-isoxazolecarboxylate (1.32 g, 4.2 mmol) in THF (11.7 mL) was stirred at a 0° C. as a 1.5 M solution of diisopropylaluminum hydride in toluene (9 mL, 13.4 mmol) was added; the solution was allowed to warm to room temperature and stirred overnight. A 10% aqueous solution of Rochelle's salt was added and the solution was then allowed to stir for three hours. The layers were separated and the organic layer was washed with brine. The organic layer was dried with MgSO$_4$, filtered and concentrated. The residue was purified by chromatography (silica gel, hexane to ethyl acetate gradient elution) to yield [3-(2,4-dichloro-3-pyridinyl)-5-(1-methylethyl)-4-isoxazolyl]methanol (1.20 g, 94% 0.2 ethyl acetate). $^1$H NMR (400 MHz, DMSO-d$_6$): δ 8.52 (d, J=5 Hz, 1H), 7.78 (d, J=5 Hz, 1H), 4.94 (t, J=5 Hz, 1H), 4.20 (d, J=5 Hz, 2H), 3.34 (septet, J=7 Hz, overlapping water), 1.29 (d, J=7 Hz, 6H).

28f) Methyl 6-[4-({[3-(2,4-dichloro-3-pyridinyl)-5-(1-methylethyl)-4-isoxazolyl]methyl}oxy)phenyl]-2-quinolinecarboxylate

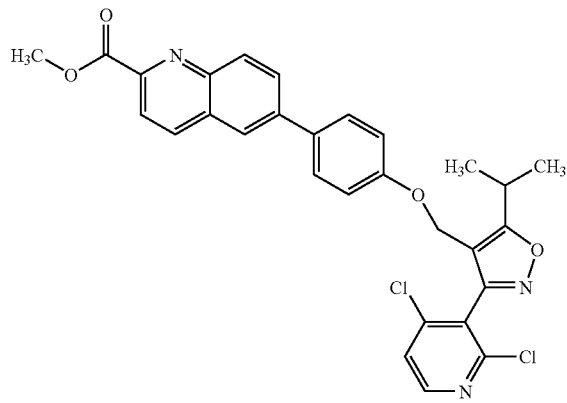

A solution of [3-(2,4-dichloro-3-pyridinyl)-5-(1-methylethyl)-4-isoxazolyl]methanol (55 mg, 0.19 mmol) in dichloromethane (1.9 mL) was added to a mixture of methyl 6-(4-hydroxyphenyl)-2-quinolinecarboxylate (54 mg, 0.19 mmol) and triphenyl phosphine (50 mg, 0.19 mmol) in a microwave reaction tube. Diisopropyl azodicarboxylate (37 μL, 0.19 mmol) was added before the tube was sealed and heated for 10 minutes at 100° C. The mixture was concentrated and the residue was purified by chromatography (silica gel, hexane to 7:3 ethyl acetate:hexanes). Fractions containing the product were combined and concentrated to yield the product (14 mg). Fractions containing the product and other impurities were combined and the residue was chromatographed (silica gel, dichloromethane to 1:19 methanol:dichloromethane) to provide the still impure product (20 mg). A second reaction was run according to the above procedure with the following modifications: the scale of the reaction was doubled for all reagents except 102 μL of diisopropyl azodicarboxylate was used; the reaction was then heated to 100° C. for 20 minutes. The mixture was concentrated and combined with the impure product from the first reaction (20 mg). The sample was purified by chromatography (silica gel, hexane to 7:3 ethyl acetate:hexanes). Fractions containing the product were combined and concentrated. The residue was slurried in methanol to yield methyl 6-[4-({[3-(2,4-dichloro-3-pyridinyl)-5-(1-methylethyl)-4-isoxazolyl]methyl}oxy)phenyl]-2-quinolinecarboxylate (87 mg, 32% combined yield) $^1$H NMR (400 MHz, DMSO-d$_6$): δ 8.56-8.51 (m, 2H), 8.29 (s, 1H), 8.18-8.10 (m, 3H), 7.80 (d, J=5 Hz, 1H), 7.74 (d, J=9 Hz, 2H), 6.92 (d, J=9 Hz, 2H), 4.96 (s, 2H), 3.94 (s, 3H), 3.49 (septet, J=7 Hz, 1H), 1.34 (d, J=7 Hz, 6H).

28 g) 6-[4-({[3-(2,4-Dichloro-3-pyridinyl)-5-(1-methylethyl)-4-isoxazolyl]methyl}oxy)phenyl]-2-quinolinecarboxylic acid

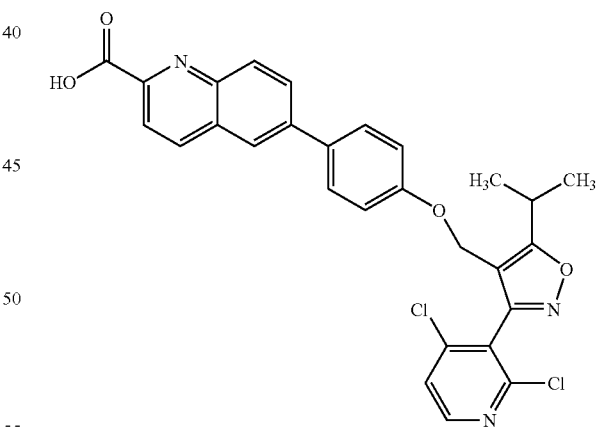

A solution of methyl 6-[4-({[3-(2,4-dichloro-3-pyridinyl)-5-(1-methylethyl)-4-isoxazolyl]methyl}oxy)phenyl]-2-quinolinecarboxylate (85 mg, 0.16 mmol) (from multiple batches) in THF (1.6 mL) was stirred as a 1 N aqueous sodium hydroxide solution (0.24 mL, 0.24 mmol) was added. The solution was allowed to stir at room temperature overnight. The solution was neutralized with 1 N HCl and concentrated. The residue was partitioned between ethyl acetate and brine. The organic layer was dried with MgSO$_4$. The MgSO$_4$ was slurried in dichloromethane, filtered and the combined filtrates were concentrated to yield 6-[4-({[3-(2,4-dichloro-3- pyridinyl)-5-(1-methylethyl)-4-isoxazolyl]methyl}oxy)phenyl]-2-quinolinecarboxylic acid as a bright yellow foam (66 mg, 76% 0.12 ethyl acetate). $^1$H NMR (400 MHz, DMSO-d$_6$): δ 13.37 (s, 1H), 8.54-8.51 (m, 2H), 8.28 (d, J=1 Hz, 1H), 8.17-8.08 (m, 3H), 7.80 (d, J=5 Hz, 1H), 7.74 (d, J=9 Hz, 2H), 6.92 (d, J=9 Hz, 2H), 4.96 (s, 2H), 3.49 (septet, J=7 Hz, 1H), 1.34 (d, J=7 Hz, 6H). HRMS C$_{28}$H$_{21}$N$_3$O$_4$Cl$_2$ m/z 534.0982, (M+H)$^+_{Cal}$; 534.0980 (M+H)$^+_{Obs}$.

Example 29

6-[4-({[3-(2,4-Dimethyl-3-pyridinyl)-5-(1-methylethyl)-4-isoxazolyl]methyl}oxy)phenyl]-2-quinolinecarboxylic acid

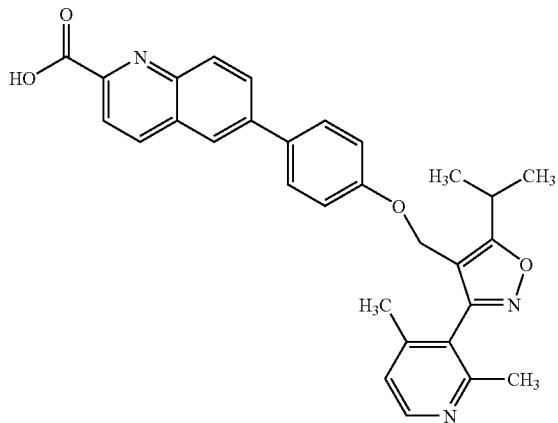

29a) 2,4-Dimethyl-3-pyridinecarbaldehyde oxime

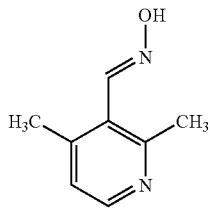

A solution of hydroxylamine hydrochloride (0.21 g, 3.0 mmol) and sodium hydroxide (0.12 g, 3.0 mmol) in water (1.9 mL) was added to a solution of 2,4-dimethyl-3-pyridinecarbaldehyde (0.35 g, 2.6 mmol) in ethanol (3.8 mL). The solution was heated in a 65° C. oil bath for 2 hours. The mixture was concentrated and the residue diluted with water and filtered. The resulting white solid was dried in a 45° C. vacuum oven with P$_2$O$_5$ to yield 2,4-dimethyl-3-pyridinecarbaldehyde oxime (345 mg, 88%). $^1$H NMR (400 MHz, DMSO-d$_6$): δ 11.44 (s, 1H), 8.33 (s, 1H), 8.23 (d, J=5 Hz, 1H), 7.08 (d, J=5 Hz, 1H), 2.48 (s, overlapping DMSO), 2.33 (s, 3H).

29b) Methyl 3-(2,4-dimethyl-3-pyridinyl)-5-(1-methylethyl)-4-isoxazolecarboxylate

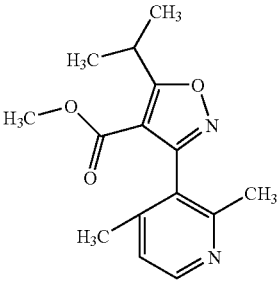

A solution of 2,4-dimethyl-3-pyridinecarbaldehyde oxime (341 mg, 2.27 mmol) in DMF (1.8 mL) was stirred as N-chlorosuccinimide (303 mg, 2.27 mmol) was added. The solution was stirred in a 65° C. oil bath for 3 hours. The solution was allowed to cool before being poured on ice. The solution was extracted with ether. The organic layer containing the crude N-hydroxy-2,4-dimethyl-3-pyridinecarboximidoyl chloride was dried with MgSO$_4$, filtered and concentrated.

A 0.5 N solution of sodium methoxide in methanol (2.8 mL, 1.4 mmol) was added to a solution of methyl isobutyrylacetate (0.19 mL, 1.34 mmol) in THF (0.24 mL) at 0° C. A solution of the crude N-hydroxy-2,4-dimethyl-3-pyridinecarboximidoyl chloride (0.22 g, 1.2 mmol) in THF (2.2 mL) was added and the resulting mixture was allowed to warm to room temperature and stir overnight. The solution was concentrated and the residue was partitioned between ethyl acetate and brine. The organic layer was dried with MgSO$_4$, filtered and concentrated. The residue was chromatographed (silica gel, hexane to 3:2 ethyl acetate:hexane) to provide methyl 3-(2,4-dimethyl-3-pyridinyl)-5-(1-methylethyl)-4-isoxazolecarboxylate (0.17 g, 52%). ESI-LCMS m/z 275 (M+H)$^+$.

29c) [5-(2,4-Dimethyl-3-pyridinyl)-2-(1-methylethyl)-1,4-cyclopentadien-1-yl]methanol

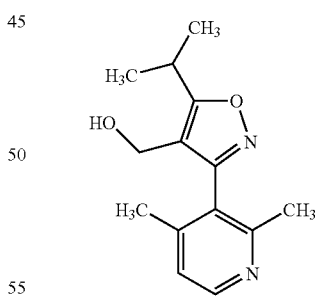

A solution of methyl 5-(2,4-dimethyl-3-pyridinyl)-2-(1-methylethyl)-1,4-cyclopentadiene-1-carboxylate (0.17 g, 0.62 mmol) in THF (1.7 mL) was stirred at 0° C. as a 1.5 M solution of diisopropylaluminum hydride in toluene (0.88 mL, 1.32 mmol) was added. The solution was allowed to warm to room temperature and stir overnight. The solution was then cooled to 0° C. before adding additional portion of diisopropylaluminum hydride in toluene (0.88 mL, 1.32 mmol). The solution was allowed to stir overnight before the addition a 10% aqueous solution of Rochelle's salt. The solution was then allowed to stir overnight. The solution was extracted with ethyl acetate and the organic layer was dried with MgSO$_4$, filtered and concentrated. The residue was purified by chromatography (silica gel, dichloromethane to 19:1 dichloromethane:methanol) to yield [5-(2,4-dimethyl-3-pyridinyl)-2-(1-methylethyl)-1,4-cyclopentadien-1-yl]methanol (98 mg, 64%). $^1$H NMR (400 MHz, DMSO-d$_6$): δ 8.37 (d, J=5 Hz, 1H), 7.18 (d, J=5 Hz, 1H), 4.87 (t, J=5 Hz, 1H), 4.04 (d, J=5 Hz, 2H), 3.34 (septet, J=7 Hz, overlapping water), 2.18 (s, 3H), 2.02 (s, 3H), 1.30 (d, J=7 Hz, 6H).

29d) Methyl 6-[4-({[3-(2,4-dimethyl-3-pyridinyl)-5-(1-methylethyl)-4-isoxazolyl]methyl}oxy)phenyl]-2-quinolinecarboxylate

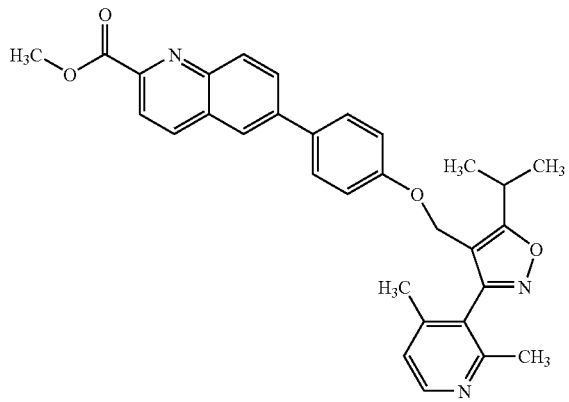

A mixture of [5-(2,4-dimethyl-3-pyridinyl)-2-(1-methylethyl)-1,4-cyclopentadien-1-yl]methanol (96 mg, 0.39 mmol), methyl 6-(4-hydroxyphenyl)-2-quinolinecarboxylate (0.14 g, 0.39 mmol), triphenyl phosphine (0.10 g, 0.39 mmol), and diisopropyl azodicarboxylate (0.10 mL, 0.39 mmol) in dichloromethane (3.9 mL) was heated in a microwave reactor at 100° C. for 20 minutes. The solution was concentrated and the residue was purified by chromatography (silica gel, hexane to ethyl acetate). Fractions containing the product were combined and concentrated. The residue was recrystallized from ethyl acetate and hexane to yield methyl 6-[4-({[3-(2,4-dimethyl-3-pyridinyl)-5-(1-methylethyl)-4-isoxazolyl]methyl}oxy)phenyl]-2-quinolinecarboxylate (22 mg, 11%). $^1$H NMR(400 MHz, DMSO-d$_6$): δ 8.55 (d, J=9 Hz, 1H), 8.36 (d, J=5 Hz, 1H), 8.28 (s, 1H), 8.18-8.10 (m, 3H), 7.74 (d, J=9 Hz, 2H), 7.19 (d, J=5 Hz, 1H), 6.96 (d, J=9 Hz, 2H), 4.79 (s, 2H), 3.94 (s, 3H), 3.47 (septet, J=7 Hz, 1H), 2.23 (s, 3H), 2.07 (s, 3H), 1.33 (d, J=7 Hz, 6H). ESI-LCMS m/z 508 (M+H)$^+$.

29e) 6-[4-({[3-(2,4-Dimethyl-3-pyridinyl)-5-(1-methylethyl)-4-isoxazolyl]methyl}oxy)phenyl]-2-quinolinecarboxylic acid

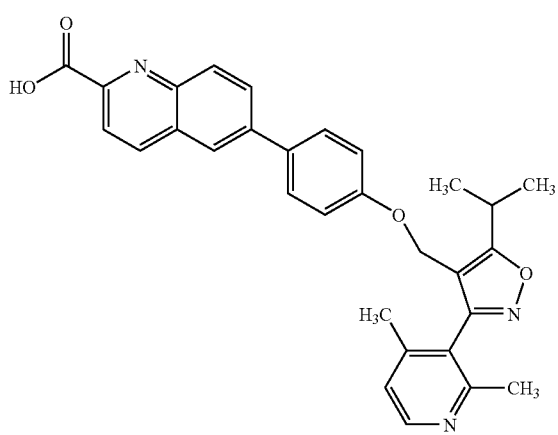

A solution of methyl 6-[4-({[3-(2,4-dimethyl-3-pyridinyl)-5-(1-methylethyl)-4-isoxazolyl]methyl}oxy)phenyl]-2-quinolinecarboxylate (20 mg, 0.04 mmol) in THF (0.4 mL) was placed in a microwave reaction tube followed by methanol (0.20 mL) followed by a 1 N solution of sodium hydroxide (0.08 mL, 0.08 mmol). The tube was sealed and heated to 100° C. for 10 minutes. The solution was neutralized with 1 N HCl and concentrated. The residue was diluted with water and filtered. The resulting solid was dried with P$_2$O$_5$ in a 45° C. vacuum oven under reduced pressure to yield 6-[4-({[3-(2,4-dimethyl-3-pyridinyl)-5-(1-methylethyl)-4-isoxazolyl]methyl}oxy)phenyl]-2-quinolinecarboxylic acid (17 mg, 86%). $^1$H NMR (400 MHz, DMSO-d$_6$): δ 13.5-13.2 (br s, 1H), 8.53 (d, J=9 Hz, 1H), 8.38 (d, J=5 Hz, 1H), 8.27 (s, 1H), 8.17-8.08 (m, 3H), 7.74 (d, J=9 Hz, 2H), 7.22 (d, J=5 Hz, 1H), 7.22 (d, J=9 Hz, 2H), 4.79 (s, 2H), 3.47 (septet, J=7 Hz, 1H), 2.24 (s, 3H), 2.08 (s, 3H), 1.33 (d, J=7 Hz, 6H). ESI-LCMS m/z 494 (M+H)$^+$.

Example 30

6-[4-({[3-(2,6-Dichlorophenyl)-5-(1-methylethyl)-4-isoxazolyl]methyl}oxy)phenyl]-7-fluoro-2-quinolinecarboxylic acid

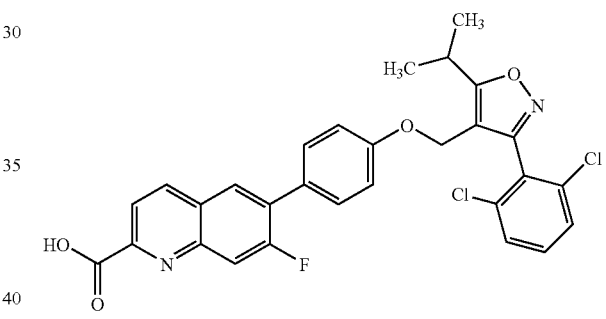

30a) 5-Bromo-4-fluoro-2-nitro-benzaldehyde

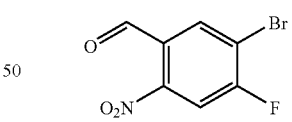

4-Fluoro-3-bromo-benzaldehyde (3.00 g, 14.78 mmol) was added to a stirred solution of concentrated nitric acid (67%, 2.02 mL, 29.55 mmol) in concentrated sulfuric acid (18 mL) at 0° C. After the addition was complete, the ice bath was removed and the reaction was allowed to stir for 3 hours at room temperature. Then, the mixture was poured into ice and extracted with diethyl ether. The organic layer was dried over anhydrous magnesium sulfate, then filtered and concentrated. The residue was purified by silica gel chromatography eluting with 1:9 ethyl acetate:hexanes to give 2.66 g (73%) of 5-bromo-4-fluoro-2-nitro-benzaldehyde as a solid. $^1$H NMR (400 MHz, d$_6$-DMSO): δ 10.14 (s, 1H), 8.31 (d, J=8 Hz, 1H), 8.25 (d, J=7 Hz, 1H).

30b) Ethyl 6-bromo-7-fluoro-2-quinolinecarboxylate

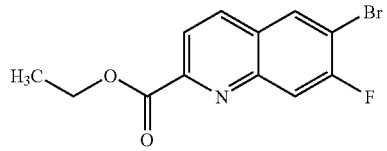

5-Bromo-4-fluoro-2-nitro-benzaldehyde (1.50 g, 6.05 mmol) and ethyl pyruvate (737.4 mg, 6.35 mmol) in ethanol (15 mL) was added via canula to zinc(II)chloride (4.12 g, 30.24 mmol), tin(II)chloride (5.73 g, 30.24 mmol), and activated 4 Å molecular sieve pellets (1.50 g) in ethanol (15 mL) under argon. The mixture was heated at 70° C. in an oil bath for four hours, then allowed to cool to room temperature, and carefully quenched with saturated sodium bicarbonate. Ethyl acetate was added and the mixture was filtered through Celite®. The filtrate was extracted with ethyl acetate and the organic layer was dried over anhydrous magnesium sulfate, then filtered and concentrated. The residue was purified by silica gel chromatography eluting with 1:6 ethyl acetate:hexanes to give 368.5 mg (20%) of ethyl 6-bromo-7-fluoro-2-quinolinecarboxylate as a solid. $^1$H NMR (400 MHz, $d_6$-DMSO): δ 8.63 (d, J=8 Hz, 1H), 8.58 (d, J=9 Hz, 1H), 8.15 (s, 1H), 8.13 (s, 1H), 4.42 (q, J=7 Hz, 2H), 1.37 (t, J=7 Hz, 3H). ESI-LCMS m/z 297 (M+H)$^+$.

30c) Ethyl 7-fluoro-6-(4-hydroxyphenyl)-2-quinolinecarboxylate

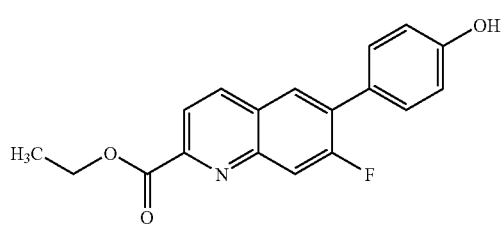

Palladium(II)acetate (8.2 mg, 36.5 μmol) was added to ethyl 6-bromo-7-fluoro-2-quinolinecarboxylate (217.8 mg, 730.6 μmol), 4-hydroxy-phenyl-boronic acid (246.0 mg, 1.10 mmol), triphenylphosphine (19.2 mg, 73.1 μmol), and potassium phosphate (542.8 mg, 2.56 mmol). Then, dioxane (3.6 mL) was added to the mixture, followed by water (73 μL), and the reaction mixture was heated open to the atmosphere at 60° C. in an oil bath for 14 hours, then allowed to cool to room temperature. Water was added followed by ethyl acetate and the mixture was filtered through Celite®. The filtrate was extracted with ethyl acetate and the organic layer was dried over anhydrous magnesium sulfate, then filtered and concentrated. The residue was purified by silica gel chromatography eluting with 2:3 ethyl acetate:hexanes to give 138.9 mg (61%) of ethyl 7-fluoro-6-(4-hydroxyphenyl)-2-quinolinecarboxylate as a solid. $^1$H NMR (400 MHz, $d_6$-DMSO): δ 9.82 (s, 1H), 8.61 (d, J=9 Hz, 1H), 8.23 (d, J=9 Hz, 1H), 8.11 (d, J=8 Hz, 1H), 8.01 (d, J=12 Hz, 1H), 7.53 (d, J=8 Hz, 2H), 6.92 (d, J=8 Hz, 2H), 4.42 (q, J=7 Hz, 2H), 1.38 (t, J=7 Hz, 3H). ESI-LCMS m/z 312 (M+H)$^+$.

30d) Ethyl 6-[4-({[3-(2,6-dichlorophenyl)-5-(1-methylethyl)-4-isoxazolyl]methyl}oxy)phenyl]-7-fluoro-2-quinolinecarboxylate

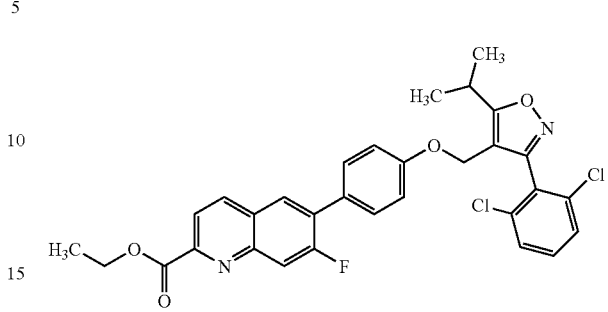

Cesium carbonate (62.6 mg, 192.2 μmol) was added to ethyl 7-fluoro-6-(4-hydroxyphenyl)-2-quinolinecarboxylate (54.4 mg, 174.7 μmol) and 4-(chloromethyl)-3-(2,6-dichlorophenyl)-5-(1-methylethyl)isoxazole (58.6 mg, 192.2 μmol) in N,N-dimethylformamide (1.7 mL) at room temperature. The resulting suspension was stirred for 68 hours, then water was added and the reaction mixture was extracted with ethyl acetate. The organic layer was dried over anhydrous magnesium sulfate, then filtered and concentrated. The residue was purified by silica gel chromatography eluting with 3:7 ethyl acetate:hexanes to give 49.4 mg (49%) of ethyl 6-[4-({[3-(2,6-dichlorophenyl)-5-(1-methylethyl)-4-isoxazolyl]methyl}oxy)phenyl]-7-fluoro-2-quinolinecarboxylate as an oil. $^1$H NMR (400 MHz, $d_6$-DMSO): δ 8.61 (d, J=9 Hz, 1H), 8.23 (d, J=9 Hz, 1H), 8.11 (d, J=9 Hz, 1H), 8.02 (d, J=12 Hz, 1H), 7.65-7.62 (m, 2H), 7.56 (d, J=7 Hz, 2H), 7.56-7.52 (m, 1H), 6.96 (d, J=9 Hz, 2H), 4.90 (s, 2H), 4.42 (q, J=7 Hz, 2H), 3.48 (septet, J=7 Hz, 1H), 1.38 (t, J=7 Hz, 3H), 1.34 (d, J=7 Hz, 6H). ESI-LCMS m/z 579 (M+H)$^+$.

30e) 6-[4-({[3-(2,6-Dichlorophenyl)-5-(1-methylethyl)-4-isoxazolyl]methyl}oxy)phenyl]-7-fluoro-2-quinolinecarboxylic acid

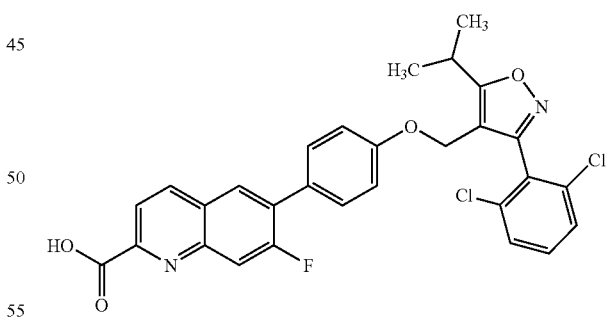

A 1 N solution of sodium hydroxide (154.6 μL, 154.6 μmol) was added to ethyl 6-[4-({[3-(2,6-dichlorophenyl)-5-(1-methylethyl)-4-isoxazolyl]methyl}oxy)phenyl]-7-fluoro-2-quinolinecarboxylate (44.8 mg, 77.3 μmol) in tetrahydrofuran and methanol (1:1, 1.6 mL) and the mixture was heated in the microwave at 90° C. for 10 minutes. After cooling, the mixture was neutralized with 1 N hydrochloric acid (154.6 μL), water added, and the reaction mixture was extracted with ethyl acetate. The organic layer was washed with brine, then dried over anhydrous magnesium sulfate, filtered and concentrated to give 40.6 mg (95%) of 6-[4-({[3-(2,6-Dichlorophenyl)-5-(1-methylethyl)-4-isoxazolyl]methyl}oxy)phenyl]-7-fluoro-2-quinolinecarboxylic acid as a solid. $^1$H NMR (400 MHz, d$_6$-DMSO): δ 13.52 (br s, 1H), 8.56 (d, J=9 Hz, 1H), 8.21 (d, J=9 Hz, 1H), 8.09 (d, J=9 Hz, 1H), 7.98 (d, J=12 Hz, 1H), 7.65-7.61 (m, 2H), 7.56 (d, J=9 Hz, 2H), 7.56-7.52 (m, 1H), 6.96 (d, J=9 Hz, 2H), 4.90 (s, 2H), 3.48 (septet, J=7 Hz, 1H), 1.34 (d, J=7 Hz, 6H). HRMS C$_{29}$H$_{21}$Cl$_2$FN$_2$O$_4$ m/z 551.0941 (M+H)$^+_{Cal}$; 551.0952 (M+H)$^+_{Obs}$.

Example 31

6-[4-({[3-(2,6-dichlorophenyl)-5-(1-methylethyl)-4-isoxazolyl]methyl}oxy)phenyl]-3-methyl-2-quinolinecarboxylic acid

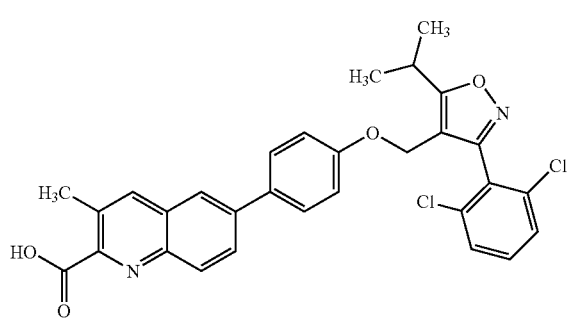

31a) 5-Bromo-2-nitro-benzaldehyde

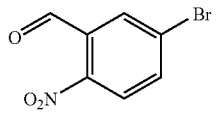

3-Bromo-benzaldehyde (18.50 g, 99.99 mmol) was added to a stirred solution of concentrated nitric acid (70%, 13.09 mL, 199.98 mmol) in concentrated sulfuric acid (125 mL) at 0° C. After the addition was complete, the ice bath was removed and the reaction was allowed to stir for 5 hours at room temperature. Then, the mixture was poured into ice and the solid was collected by filtration. The filtrate was extracted with diethyl ether. The organic layer was dried over anhydrous magnesium sulfate, then filtered and concentrated. The residue was combined with the solid previously obtained via the first filtration and dissolved in diethyl ether. Hexanes were added and after crystallization 14.66 g (64%) of 5-bromo-2-nitro-benzaldehyde was collected by filtration and drying. $^1$H NMR (400 MHz, d$_6$-DMSO): δ 10.19 (s, 1H), 8.10 (s, 2H), 8.02 (s, 1H).

31b) Ethyl 2-oxobutanoate

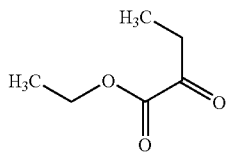

Jones Reagent (2.67 M, 7.51 mL, 20.05 mmol) was added dropwise to ethyl 2-hydroxybutanoate (2.65 g, 20.05 mmol) in acetone (67 mL) at 0° C., then the reaction mixture was stirred for 10 minutes. Any excess Jones reagent was quenched by the addition of iso-propanol, then the reaction mixture was neutralized with saturated sodium bicarbonate, and the acetone was removed by evaporation. Water was added and the solution was extracted with diethyl ether. The organic layer was dried over anhydrous magnesium sulfate, then filtered and concentrated. The residue was purified by silica gel chromatography eluting with 1:4 diethyl ether:hexanes to give 346.7 mg (13%) of ethyl 2-oxobutanoate as an oil. $^1$H NMR (400 MHz, d$_6$-DMSO): δ 4.19 (q, J=7 Hz, 2H), 2.80 (q, J=7 Hz, 2H), 1.24 (t, J=7 Hz, 3H), 0.94 (t, J=7 Hz, 3H).

31c) Ethyl 6-bromo-3-methyl-2-quinolinecarboxylate

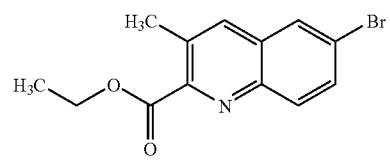

A 2.2 M solution of zinc(II)chloride (6.05 mL, 13.32 mmol) in diethyl ether was added to tin(II)chloride (2.53 g, 13.32 mmol) and activated 4 Å molecular sieve pellets (612.8 mg) under argon. Then, 5-bromo-2-nitro-benzaldehyde (612.8 mg, 2.66 mmol) and ethyl 2-oxobutanoate (346.7 mg, 2.66 mmol) in ethanol (13 mL) were added to the reaction mixture via canula. The mixture was heated at 70° C. in an oil bath for three hours, then allowed to cool to room temperature, and carefully quenched with saturated sodium bicarbonate. Ethyl acetate was added and the mixture was filtered through Celite®. The filtrate was extracted with ethyl acetate and the organic layer was dried over anhydrous magnesium sulfate, then filtered and concentrated. The residue was purified by silica gel chromatography eluting with 1:6 ethyl acetate:hexanes to give 137.9 mg (18%) of ethyl 6-bromo-3-methyl-2-quinolinecarboxylate as a solid. $^1$H NMR (400 MHz, d$_6$-DMSO): δ 8.30 (s, 1H), 8.27 (d, J=2 Hz, 1H), 7.99 (d, J=9 Hz, 1H), 7.88 (dd, J=9, 2 Hz, 1H), 4.41 (q, J=7 Hz, 2H), 2.54 (s, 3H), 1.35 (t, J=7 Hz, 3H). ESI-LCMS m/z 294 (M+H)$^+$.

31d) Ethyl 6-(4-hydroxyphenyl)-3-methyl-2-quinolinecarboxylate

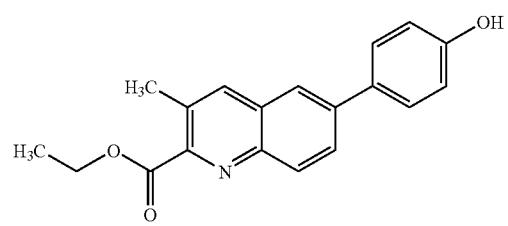

Palladium(II)acetate (4.9 mg, 22.0 µmol) was added to ethyl 6-bromo-3-methyl-2-quinolinecarboxylate (129.6 mg, 440.6 µmol), 4-hydroxy-phenyl-boronic acid (91.2 mg, 660.9 µmol), triphenylphosphine (11.6 mg, 44.0 µmol), and potassium phosphate (327.3 mg, 1.54 mmol). Then, dioxane (4.4 mL) was added to the mixture, followed by water (44.1 µL), and the reaction mixture was heated open to the atmosphere at 60° C. in an oil bath for 17 hours, then allowed to cool to room temperature. Water was added followed by ethyl acetate and the mixture was filtered through Celite®. The filtrate was extracted with ethyl acetate and the organic layer was dried over anhydrous magnesium sulfate, then filtered and concentrated. The residue was purified by silica gel chromatography eluting with 2:3 ethyl acetate:hexanes to give 66.4 mg (49%) of ethyl 6-(4-hydroxyphenyl)-3-methyl-2-quinolinecarboxylate as a solid. $^1$H NMR (400 MHz, $d_6$-DMSO): δ 9.71 (s, 1H), 8.31 (s, 1H), 8.13 (s, 1H), 8.07-8.02 (m, 2H), 7.68 (d, J=9 Hz, 2H), 6.90 (d, J=9 Hz, 2H), 4.41 (q, J=7 Hz, 2H), 2.55 (s, 3H), 1.36 (t, J=7 Hz, 3H). ESI-LCMS m/z 308 (M+H)$^+$.

31e) Ethyl 6-[4-({[3-(2,6-dichlorophenyl)-5-(1-methylethyl)-4-isoxazolyl]methyl}oxy)phenyl]-3-methyl-2-quinolinecarboxylate

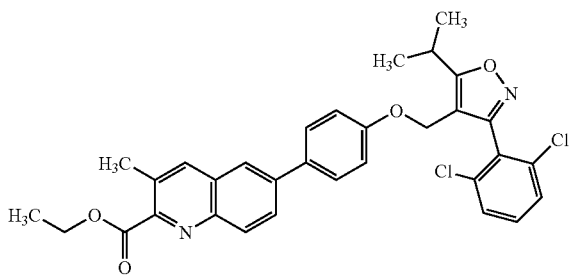

Cesium carbonate (71.7 mg, 220.1 μmol) was added to ethyl 6-(4-hydroxyphenyl)-3-methyl-2-quinolinecarboxylate (61.5 mg, 200.1 μmol) and 4-(chloromethyl)-3-(2,6-dichlorophenyl)-5-(1-methylethyl)isoxazole (67.0 mg, 220.1 μmol) in N,N-dimethylformamide (4 mL) at room temperature. The resulting suspension was stirred for 18 hours, then water was added and the reaction mixture was extracted with ethyl acetate. The organic layer was dried over anhydrous magnesium sulfate, then filtered and concentrated. The residue was purified by silica gel chromatography eluting with 3:7 ethyl acetate:hexanes to give 50.7 mg (44%) of ethyl 6-[4-({[3-(2,6-dichlorophenyl)-5-(1-methylethyl)-4-isoxazolyl]methyl}oxy)phenyl]-3-methyl-2-quinolinecarboxylate as an oil. $^1$H NMR (400 MHz, $d_6$-DMSO): δ 8.32 (s, 1H), 8.14 (s, 1H), 8.08-8.01 (m, 2H), 7.72 (s, 1H), 7.70 (s, 1H), 7.63 (d, J=8 Hz, 2H), 7.55 (dd, J=9, 7 Hz, 1H), 6.93 (d, J=9 Hz, 2H), 4.89 (s, 2H), 4.41 (q, J=7 Hz, 2H), 3.48 (septet, J=7 Hz, 1H), 2.55 (s, 3H), 1.36 (t, J=7 Hz, 3H), 1.34 (d, J=7 Hz, 6H). ESI-LCMS m/z 575 (M+H)$^+$.

31f) 6-[4-({[3-(2,6-Dichlorophenyl)-5-(1-methylethyl)-4-isoxazolyl]methyl}oxy)phenyl]-3-methyl-2-quinolinecarboxylic acid

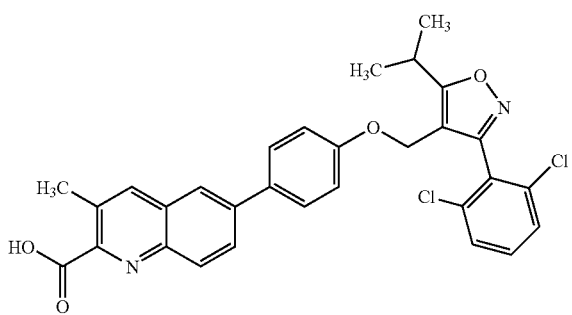

A 1 N solution of sodium hydroxide (150.5 μL, 150.5 μmol) was added to ethyl 6-[4-({[3-(2,6-dichlorophenyl)-5-(1-methylethyl)-4-isoxazolyl]methyl}oxy)phenyl]-3-methyl-2-quinolinecarboxylate (43.3 mg, 75.2 μmol) in tetrahydrofuran and methanol (1:1, 1.5 mL) and the mixture was heated in the microwave at 90° C. for 10 minutes. After cooling, the mixture was neutralized with 1 N hydrochloric acid (150.5 μL), water was added, and the reaction mixture was extracted with ethyl acetate. The organic layer was washed with brine, then dried over anhydrous magnesium sulfate, filtered and concentrated to give 40.0 mg (97%) of 6-[4-({[3-(2,6-dichlorophenyl)-5-(1-methylethyl)-4-isoxazolyl]methyl}oxy)phenyl]-3-methyl-2-quinolinecarboxylic acid as a solid. $^1$H NMR (400 MHz, $d_6$-DMSO): δ 13.44 (br s, 1H), 8.29 (s, 1H), 8.14 (s, 1H), 8.08-8.00 (m, 2H), 7.72 (s, 1H), 7.70 (s, 1H), 7.64 (d, J=8 Hz, 2H), 7.55 (dd, J=9, 7 Hz, 1H), 6.93 (d, J=9 Hz, 2H), 4.89 (s, 2H), 3.48 (septet, J=7 Hz, 1H), 2.57 (s, 3H), 1.34 (d, J=7 Hz, 6H). HRMS $C_{30}H_{24}Cl_2N_2O_4$ m/z 547.1191 (M+H)$^+_{Cal}$; 547.1196 (M+H)$^+_{Obs}$.

Example 32

6-[4-({[3-(2,6-Dichlorophenyl)-5-(1-methylethyl)-4-isoxazolyl]methyl}oxy)-3-methylphenyl]-2-quinolinecarboxylic acid

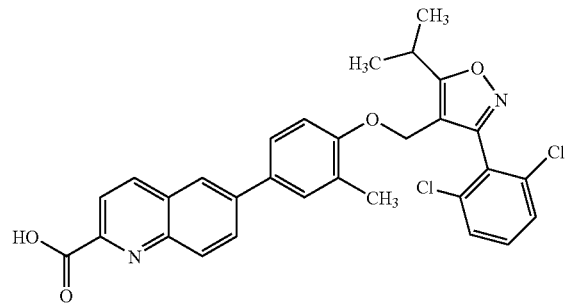

32a) 2-Methyl-4-(4,4,5,5-tetramethyl-1,3,2-dioxaborolan-2-yl)phenol

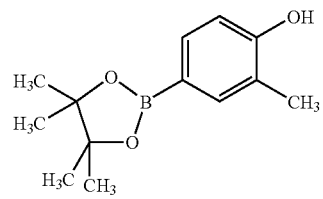

Potassium acetate (7.08 g, 72.18 mmol) was added to 4-bromo-2-methyl-phenol (3.00 g, 16.04 mmol) in N,N-dimethylformamide (40 mL) at room temperature under argon. Then, 4,4,4',4',5,5,5',5'-octamethyl-2,2'-bi-1,3,2-dioxaborolane (6.11 g, 24.06 mmol) was added to the reaction mixture, followed by the addition of dichloro[1,1'-bis(diphenylphosphino)ferrocene]palladium(II)dichloromethane adduct (654.9 mg, 802.0 μmol), and the reaction vessel was evacuated and purged with argon. The mixture was heated at 80° C. in an oil bath for sixty-eight hours, then allowed to cool to room temperature, and concentrated. Water was added, followed by diethyl ether, and the mixture was filtered through Celite®. The filtrate was extracted with diethyl ether and the organic layer was dried over anhydrous magnesium sulfate, then filtered and concentrated. The residue was purified by silica gel chromatography eluting with 1:6 ethyl acetate:hexanes to give 1.63 g (43%) of 2-methyl-4-(4,4,5,5-tetramethyl-1,3,2-dioxaborolan-2-yl)phenol as a oil. $^1$H NMR (400 MHz, d$_6$-DMSO): δ 9.66 (s, 1H), 7.36 (s, 1H), 7.31 (d, J=8 Hz, 1H), 6.74 (d, J=8 Hz, 1H), 2.09 (s, 3H), 1.24 (s, 12H). ESI-LCMS m/z 233 (M−H)$^−$.

32b) (4-hydroxy-3-methylphenyl)boronic acid

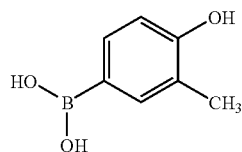

Sodium periodate (4.22 g, 19.74 mmol) was added to 2-methyl-4-(4,4,5,5-tetramethyl-1,3,2-dioxaborolan-2-yl)phenol (1.54 g, 6.58 mmol) and ammonium acetate (1.52 g, 19.74 mmol) in acetone and water (2:1, 66 mL) at room temperature. The mixture was stirred for nineteen hours, then filtered, and concentrated. Sodium chloride was added to the filtrate, and it was extracted with ethyl acetate. The organic layer was dried over anhydrous magnesium sulfate, then filtered and concentrated. The residue was purified by silica gel chromatography eluting with 1:1 ethyl acetate:hexanes to ethyl acetate to give 364.4 mg (36%) of (4-hydroxy-3-methylphenyl)boronic acid as a solid. $^1$H NMR (400 MHz, d$_6$-DMSO): δ 9.31 (s, 1H), 7.55 (s, 1H), 7.52 (d, J=8 Hz, 1H), 6.76 (d, J=8 Hz, 1H), 2.14 (s, 3H). ESI-LCMS m/z 151 (M−H)$^−$.

32c) Ethyl 6-bromo-2-quinolinecarboxylate

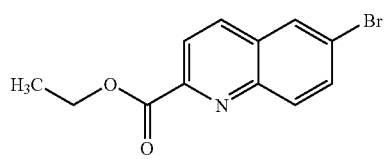

Ethyl pyruvate (535.4 mg, 4.61 mmol) was added to 5-Bromo-2-nitro-benzaldehyde (1.01 g, 4.39 mmol) in ethanol (22 mL) at room temperature under argon. Then, tin(II) chloride (4.16 g, 21.95 mmol) was added to the reaction mixture, followed by the addition of zinc(II)chloride (2.99 g, 21.95 mmol), and finally activated 4 Å molecular sieve pellets (1.01 g). The mixture was heated at 70° C. in an oil bath for twenty hours, then allowed to cool to room temperature, and carefully quenched with saturated sodium bicarbonate. Ethyl acetate was added, and the mixture was filtered through Celite®. The filtrate was extracted with ethyl acetate, and the organic layer was dried over anhydrous magnesium sulfate, then filtered and concentrated. The residue was purified by silica gel chromatography eluting with dichloromethane and subsequently a second silica gel chromatography purification eluting with 1:4 ethyl acetate:hexanes to give 173.6 mg (14%) of ethyl 6-bromo-2-quinolinecarboxylate as a solid. $^1$H NMR (400 MHz, d$_6$-DMSO): δ 8.55 (d, J=9 Hz, 1H), 8.42 (d, J=2 Hz, 1H), 8.16 (d, J=9 Hz, 1H), 8.11 (d, J=9 Hz, 1H), 7.98 (dd, J=9, 2 Hz, 1H), 4.42 (q, J=7 Hz, 2H), 1.37 (t, J=7 Hz, 3H). ESI-LCMS m/z 280 (M+H)$^+$.

32d) Ethyl 6-(4-hydroxy-3-methylphenyl)-2-quinolinecarboxylate

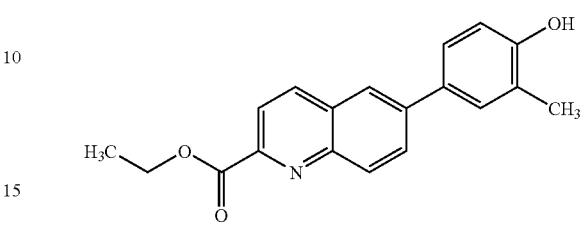

Palladium(II)acetate (4.7 mg, 21.0 µmol) was added to ethyl 6-bromo-2-quinolinecarboxylate (117.8 mg, 420.5 µmol), (4-hydroxy-3-methylphenyl)boronic acid (95.9 mg, 630.8 µmol), triphenylphosphine (11.0 mg, 42.1 µmol), and potassium phosphate (312.4 mg, 1.47 mmol). Then, dioxane (4.2 mL) was added to the mixture, followed by water (42 µL), and the reaction mixture was heated open to the atmosphere at 60° C. in an oil bath for 16 hours, then allowed to cool to room temperature. Water was added, followed by ethyl acetate, and the mixture was filtered through Celite®. The filtrate was extracted with ethyl acetate, and the organic layer was dried over anhydrous magnesium sulfate, then filtered and concentrated. The residue was purified by silica gel chromatography eluting with 2:3 ethyl acetate:hexanes to give 51.4 mg (40%) of ethyl 6-(4-hydroxy-3-methylphenyl)-2-quinolinecarboxylate as a solid. $^1$H NMR (400 MHz, d$_6$-DMSO): δ 9.64 (s, 1H), 8.55 (d, J=9 Hz, 1H), 8.27 (s, 1H), 8.18-8.13 (m, 2H), 8.11 (d, J=8 Hz, 1H), 7.62 (s, 1H), 7.53 (dd, J=8, 2 Hz, 1H), 6.91 (d, J=8 Hz, 1H), 4.42 (q, J=7 Hz, 2H), 2.22 (s, 3H), 1.38 (t, J=7 Hz, 3H). ESI-LCMS m/z 308 (M+H)$^+$.

32e) Ethyl 6-[4-({[3-(2,6-dichlorophenyl)-5-(1-methylethyl)-4-isoxazolyl]methyl}oxy)-3-methylphenyl]-2-quinolinecarboxylate

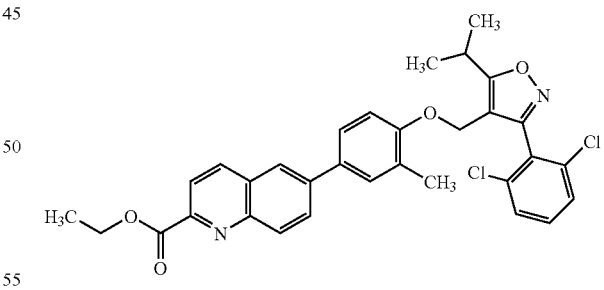

Cesium carbonate (54.9 mg, 168.6 µmol) was added to ethyl 6-(4-hydroxy-3-methylphenyl)-2-quinolinecarboxylate (47.1 mg, 153.3 µmol) and 4-(chloromethyl)-3-(2,6-dichlorophenyl)-5-(1-methylethyl)isoxazole (51.3 mg, 168.6 µmol) in N,N-dimethylformamide (3.1 mL) at room temperature. The resulting suspension was stirred for twenty hours, then water was added and the reaction mixture was extracted with ethyl acetate. The organic layer was dried over anhydrous magnesium sulfate, then filtered and concentrated. The residue was purified by silica gel chromatography eluting with 3:7 ethyl acetate:hexanes to give 19.1 mg (22%) of ethyl 6-[4-({[3-(2,6-dichlorophenyl)-5-(1-methylethyl)-4-isoxazolyl]methyl}oxy)-3-methylphenyl]-2-quinolinecarboxylate as an oil. $^1$H NMR (400 MHz, $d_6$-DMSO): δ 8.56 (d, J=9 Hz, 1H), 8.28 (s, 1H), 8.19-8.09 (m, 3H), 7.66-7.59 (m, 4H), 7.55 (dd, J=9, 7 Hz, 1H), 7.09 (d, J=9 Hz, 1H), 4.91 (s, 2H), 4.42 (q, J=7 Hz, 2H), 3.52 (septet, J=7 Hz, 1H), 1.97 (s, 3H), 1.38 (t, J=7 Hz, 3H), 1.36 (d, J=7 Hz, 6H). ESI-LCMS m/z 575 (M+H)$^+$.

32f) 6-[4-({[3-(2,6-Dichlorophenyl)-5-(1-methylethyl)-4-isoxazolyl]methyl}oxy)-3-methylphenyl]-2-quinolinecarboxylic acid

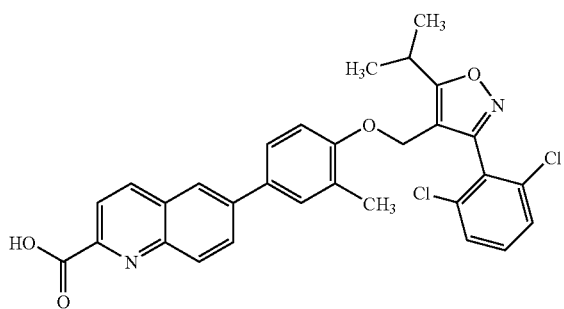

A 1 N solution of sodium hydroxide (59.4 µL, 59.4 µmol) was added to ethyl 6-[4-({[3-(2,6-dichlorophenyl)-5-(1-methylethyl)-4-isoxazolyl]methyl}oxy)-3-methylphenyl]-2-quinolinecarboxylate (17.1 mg, 29.7 µmol) in tetrahydrofuran and methanol (1:1, 594.3 µL) and the mixture was heated in the microwave at 90° C. for 10 minutes. After cooling, the mixture was neutralized with 1 N hydrochloric acid (59.4 µL), water was added, and the reaction mixture was extracted with ethyl acetate. The organic layer was washed with brine, then dried over anhydrous magnesium sulfate, filtered and concentrated to give 16.1 mg (99%) of 6-[4-({[3-(2,6-Dichlorophenyl)-5-(1-methylethyl)-4-isoxazolyl]methyl}oxy)-3-methylphenyl]-2-quinolinecarboxylic acid as a solid. $^1$H NMR (400 MHz, $d_6$-DMSO): δ 13.37 (br s, 1H), 8.53 (d, J=8 Hz, 1H), 8.28 (s, 1H), 8.18-8.12 (m, 2H), 8.10 (d, J=8 Hz, 1H), 7.66-7.58 (m, 4H), 7.55 (dd, J=9, 7 Hz, 1H), 7.09 (d, J=9 Hz, 1H), 4.91 (s, 2H), 3.52 (septet, J=7 Hz, 1H), 1.98 (s, 3H), 1.36 (d, J=7 Hz, 6H). HRMS $C_{30}H_{24}Cl_2N_2O_4$ m/z 547.1191 (M+H)$^+_{Cal}$; 547.1198 (M+H)$^+_{Obs}$.

Example 33

6-[4-({[3-(2,6-Dichlorophenyl)-5-(1-methylethyl)-4-isoxazolyl]methyl}oxy)-2-methylphenyl]-2-quinolinecarboxylic acid

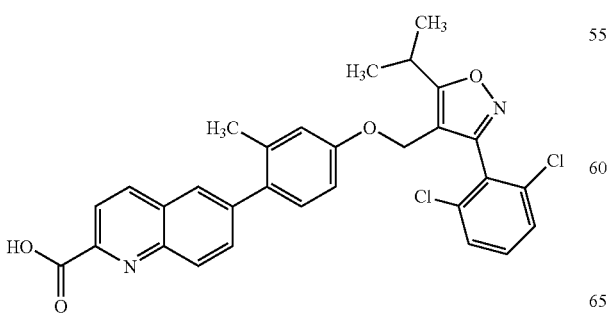

33a) 3-Methyl-4-(4,4,5,5-tetramethyl-1,3,2-dioxaborolan-2-yl)phenol

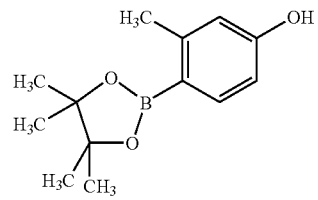

Potassium acetate (2.46 g, 25.02 mmol) was added to 4-bromo-3-methyl-phenol (1.04 g, 5.56 mmol) in N,N-dimethylformamide (14 mL) at room temperature under argon. Then, 4,4,4',4',5,5,5',5'-octamethyl-2,2'-bi-1,3,2-dioxaborolane (2.12 g, 8.34 mmol) was added to the reaction mixture, followed by the addition of dichloro[1,1'-bis(diphenylphosphino)ferrocene]palladium(II)dichloromethane adduct (227.0 mg, 278.0 µmol), and the reaction vessel was evacuated and purged with argon. The mixture was heated at 80° C. in an oil bath for nineteen hours, then allowed to cool to room temperature, and concentrated. Water was added, followed by diethyl ether, and the mixture was filtered through Celite®. The filtrate was extracted with diethyl ether and the organic layer was dried over anhydrous magnesium sulfate, then filtered and concentrated. The residue was purified by silica gel chromatography eluting with 1:6 ethyl acetate:hexanes to give 912.4 mg (70%) of 3-methyl-4-(4,4,5,5-tetramethyl-1,3,2-dioxaborolan-2-yl)phenol as a solid. $^1$H NMR (400 MHz, $d_6$-DMSO): δ 9.60 (s, 1H), 7.45 (d, J=8 Hz, 1H), 6.56-6.51 (m, 2H), 2.36 (s, 3H), 1.25 (s, 12H). ESI-LCMS m/z 233 (M–H)$^-$.

33b) (4-hydroxy-2-methylphenyl)boronic acid

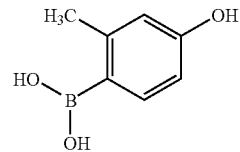

Sodium periodate (2.39 g, 11.15 mmol) was added to 3-methyl-4-(4,4,5,5-tetramethyl-1,3,2-dioxaborolan-2-yl)phenol (870.4 mg, 3.72 mmol) and ammonium acetate (859.8 mg, 11.15 mmol) in acetone and water (2:1, 36 mL) at room temperature. The mixture was stirred for sixty-eight hours, then filtered, and concentrated. Sodium chloride was added to the filtrate, and it was extracted with ethyl acetate. The organic layer was dried over anhydrous magnesium sulfate, then filtered and concentrated. The residue was purified by silica gel chromatography eluting with 1:4 ethyl acetate:hexanes to give 275.7 mg (49%) of (4-hydroxy-2-methylphenyl)boronic acid as a solid. $^1$H NMR (400 MHz, $d_6$-DMSO): δ 9.28 (s, 1H), 7.70 (d, J=9 Hz, 1H), 6.56-6.52 (m, 2H), 2.55 (s, 3H). ESI-LCMS m/z 151 (M–H)$^-$.

33c) Ethyl 6-(4-hydroxy-2-methylphenyl)-2-quinolinecarboxylate

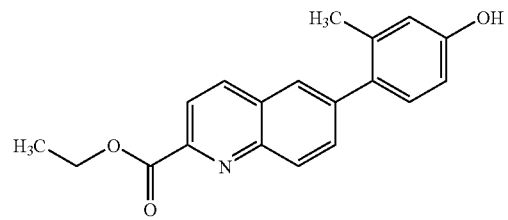

Palladium(II)acetate (3.2 mg, 14.5 µmol) was added to ethyl 6-bromo-2-quinolinecarboxylate (81.1 mg, 289.5 µmol), (4-hydroxy-2-methylphenyl)boronic acid (66.0 mg, 434.2 µmol), triphenylphosphine (7.6 mg, 29.0 µmol), and potassium phosphate (215.1 mg, 1.01 mmol). Then, dioxane (2.8 mL) was added to the mixture, followed by water (289.5 µL), and the reaction mixture was heated open to the atmosphere at 60° C. in an oil bath for 18 hours, then allowed to cool to room temperature. Water was added, followed by ethyl acetate, and the mixture was filtered through Celite®. The filtrate was extracted with ethyl acetate, and the organic layer was dried over anhydrous magnesium sulfate, then filtered and concentrated. The residue was purified by silica gel chromatography eluting with 2:3 ethyl acetate:hexanes to give 53.2 mg (60%) of ethyl 6-(4-hydroxy-2-methylphenyl)-2-quinolinecarboxylate as a solid. $^1$H NMR (400 MHz, d$_6$-DMSO): δ 9.51 (s, 1H), 8.56 (d, J=9 Hz, 1H), 8.16 (d, J=9 Hz, 1H), 8.13 (d, J=9 Hz, 1H), 7.98 (s, 1H), 7.82 (d, J=9 Hz, 1H), 7.16 (d, J=8 Hz, 1H), 6.74 (s, 1H), 6.71 (dd, J=8, 2 Hz, 1H), 4.43 (q, J=7 Hz, 2H), 2.23 (s, 3H), 1.39 (t, J=7 Hz, 3H). ESI-LCMS m/z 308 (M+H)$^+$.

33d) Ethyl 6-[4-({[3-(2,6-dichlorophenyl)-5-(1-methylethyl)-4-isoxazolyl]methyl}oxy)-2-methylphenyl]-2-quinolinecarboxylate

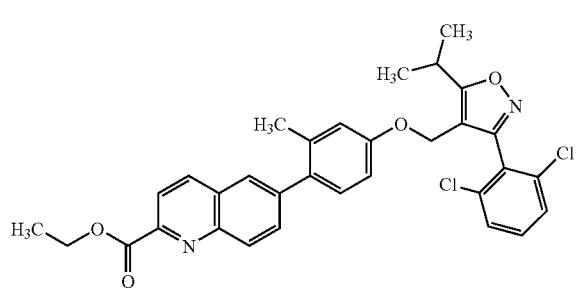

Cesium carbonate (55.4 mg, 170.0 µmol) was added to ethyl 6-(4-hydroxy-2-methylphenyl)-2-quinolinecarboxylate (47.5 mg, 154.5 µmol) and 4-(chloromethyl)-3-(2,6-dichlorophenyl)-5-(1-methylethyl)isoxazole (51.8 mg, 170.0 µmol) in N,N-dimethylformamide (3.1 mL) at room temperature. The resulting suspension was stirred for eighteen hours, then water added and the reaction mixture was extracted with ethyl acetate. The organic layer was dried over anhydrous magnesium sulfate, then filtered and concentrated. The residue was purified by silica gel chromatography eluting with 3:7 ethyl acetate:hexanes to give 60.2 mg (68%) of ethyl 6-[4-({[3-(2,6-dichlorophenyl)-5-(1-methylethyl)-4-isoxazolyl]methyl}oxy)-2-methylphenyl]-2-quinolinecarboxylate as an oil. $^1$H NMR (400 MHz, d$_6$-DMSO): δ 8.56 (d, J=9 Hz, 1H), 8.16 (d, J=9 Hz, 1H), 8.13 (d, J=9 Hz, 1H), 7.97 (d, J=2 Hz, 1H), 7.80 (dd, J=9, 2 Hz, 1H), 7.66-7.60 (m, 2H), 7.56 (dd, J=9, 7 Hz, 1H), 7.19 (d, J=8 Hz, 1H), 6.78 (d, J=2 Hz, 1H), 6.73 (dd, J=9, 2 Hz, 1H), 4.86 (s, 2H), 4.43 (q, J=7 Hz, 2H), 3.47 (septet, J=7 Hz, 1H), 2.21 (s, 3H), 1.38 (t, J=7 Hz, 3H), 1.35 (d, J=7 Hz, 6H). ESI-LCMS m/z 575 (M+H)$^+$.

33e) 6-[4-({[3-(2,6-Dichlorophenyl)-5-(1-methylethyl)-4-isoxazolyl]methyl}oxy)-2-methylphenyl]-2-quinolinecarboxylic acid

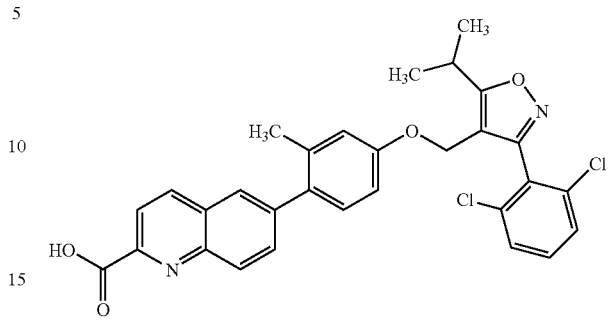

A 1 N solution of sodium hydroxide (187.7 µL, 187.7 µmol) was added to ethyl 6-[4-({[3-(2,6-dichlorophenyl)-5-(1-methylethyl)-4-isoxazolyl]methyl}oxy)-2-methylphenyl]-2-quinolinecarboxylate (54.0 mg, 93.8 µmol) in tetrahydrofuran and methanol (1:1, 1.9 mL) and the mixture was heated in the microwave at 90° C. for 10 minutes. After cooling, the mixture was neutralized with 1 N hydrochloric acid (187.7 µL), water was added, and the reaction mixture was extracted with ethyl acetate. The organic layer was washed with brine, then dried over anhydrous magnesium sulfate, filtered and concentrated to give 50.4 mg (98%) of 6-[4-({[3-(2,6-dichlorophenyl)-5-(1-methylethyl)-4-isoxazolyl]methyl}oxy)-2-methylphenyl]-2-quinolinecarboxylic acid as a solid. $^1$H NMR (400 MHz, d$_6$-DMSO): δ 13.41 (br s, 1H), 8.54 (d, J=9 Hz, 1H), 8.14 (d, J=9 Hz, 1H), 8.12 (d, J=9 Hz, 1H), 7.96 (s, 1H), 7.79 (dd, J=9.2 Hz, 1H), 7.66-7.60 (m, 2H), 7.56 (dd, J=9, 7 Hz, 1H), 7.19 (d, J=9 Hz, 1H), 6.78 (d, J=2 Hz, 1H), 6.73 (dd, J=8, 2 Hz, 1H), 4.86 (s, 2H), 3.47 (septet, J=7 Hz, 1H), 2.21 (s, 3H), 1.35 (d, J=7 Hz, 6H). HRMS C$_{30}$H$_{24}$Cl$_2$N$_2$O$_4$ m/z 547.1191 (M+H)$^+_{Cal}$; 547.1188 (M+H)$^+_{Obs}$.

Example 34

6-[4-({[3-(2,6-Dichlorophenyl)-5-(1-methylethyl)-4-isoxazolyl]methyl}oxy)phenyl]-4-methyl-2-quinolinecarboxylic acid

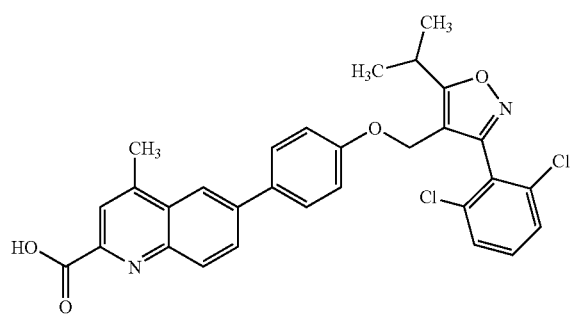

34a) 1-(5-bromo-2-nitrophenyl)-ethanol

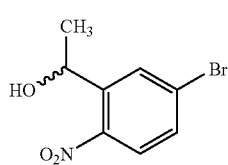

Methyl magnesium bromide (7.97 mL of 3.0 M in tetrahydrofuran, 23.91 mmol) was added dropwise to 5-bromo-2-nitro-benzaldehyde (5.00 g, 21.73 mmol) in tetrahydrofuran (72 mL) at −78° C. After the addition was complete, the reaction was stirred for 15 min at −78° C. Then, the mixture was quenched with water and diethyl ether was added. The reaction was allowed to warm to room temperature and 10% citric acid solution was added. The layers were separated and the organic layer was dried over anhydrous magnesium sulfate, then filtered and concentrated. The residue was purified by silica gel chromatography eluting with 1:7 ethyl acetate:hexanes to give 1.68 g (31%) of 1-(5-bromo-2-nitrophenyl)-ethanol as a solid. $^1$H NMR (400 MHz, d$_6$-DMSO): δ 7.95 (d, J=2 Hz, 1H), 7.87 (d, J=9 Hz, 1H), 7.71 (dd, J=9, 2 Hz, 1H), 5.64 (d, J=4 Hz, 1H), 5.16-5.09 (m, 1H), 1.36 (d, J=6 Hz, 3H).

34b) 1-(5-Bromo-2-nitrophenyl)-ethanone

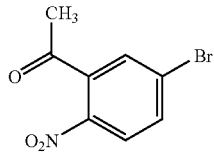

Jones Reagent (2.67 M, 2.54 mL, 6.79 mmol) was added dropwise to 1-(5-bromo-2-nitrophenyl)-ethanol (1.67 g, 6.79 mmol) in acetone (34 mL) at 0° C., then the reaction mixture was stirred for 10 minutes. Any excess Jones reagent was quenched by the addition of iso-propanol, then the reaction mixture was neutralized with saturated sodium bicarbonate, and the acetone was removed by evaporation. Water was added and the solution was extracted with diethyl ether. The organic layer was dried over anhydrous magnesium sulfate, then filtered and concentrated. The residue was purified by silica gel chromatography eluting with 1:9 ethyl acetate:hexanes to give 1.27 g (77%) of 1-(5-bromo-2-nitrophenyl)-ethanone as a solid. $^1$H NMR (400 MHz, d$_6$-DMSO): δ 8.05 (d, J=5 Hz, 1H), 8.04 (s, 1H), 7.96 (dd, J=9, 2 Hz, 1H), 2.57 (s, 3H).

34c) Ethyl 6-bromo-4-methyl-2-quinolinecarboxylate and 1-(2-amino-5-bromophenyl)ethanone

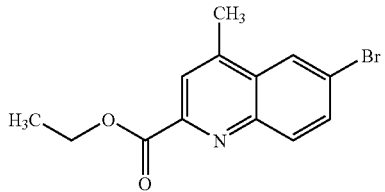

A 2.2 M solution of zinc(II)chloride (9.31 mL, 20.49 mmol) in diethyl ether was added to tin(II)chloride (3.88 g, 20.49 mmol) and activated 4 Å molecular sieve pellets (1.00 g) in ethanol (10 mL) under argon. Then, 1-(5-bromo-2-nitrophenyl)-ethanone (1.00 g, 4.10 mmol) and ethyl pyruvate (499.6 mg, 4.30 mmol) in ethanol (10 mL) were added to the reaction mixture via canula. The mixture was heated at 70° C. in an oil bath for three hours, then allowed to cool to room temperature, and carefully quenched with saturated sodium bicarbonate. Ethyl acetate was added and the mixture was filtered through Celite®. The filtrate was extracted with ethyl acetate and the organic layer was dried over anhydrous magnesium sulfate, then filtered and concentrated. The residue was purified by silica gel chromatography eluting with 1:6 ethyl acetate:hexanes to give 39.4 mg (3%) of ethyl 6-bromo-4-methyl-2-quinolinecarboxylate as a solid and 543.1 mg (62%) of 1-(5-bromo-2-aminophenyl)-ethanone as a solid.

Ethyl 6-bromo-4-methyl-2-quinolinecarboxylate $^1$H NMR (400 MHz, d$_6$-DMSO): δ 8.39 (d, J=2 Hz, 1H), 8.09 (d, J=9 Hz, 1H), 8.02 (s, 1H), 7.97 (dd, J=9, 2 Hz, 1H), 4.41 (q, J=7 Hz, 2H), 2.75 (s, 3H), 1.37 (t, J=7 Hz, 3H). ESI-LCMS m/z 294 (M+H)$^+$.

1-(2-Amino-5-bromophenyl)ethanone $^1$H NMR (400 MHz, d$_6$-DMSO): δ 7.82 (d, J=2 Hz, 1H), 7.35 (dd, J=7, 2 Hz, 1H), 7.31 (br s, 2H), 6.73 (d, J=9 Hz, 1H), 2.50 (s, 3H). ESI-LCMS m/z 213 (M+H)$^+$.

34d) 3-(2,6-Dichlorophenyl)-5-(1-methylethyl)-4-({[4-(4,4,5,5-tetramethyl-1,3,2-dioxaborolan-2-yl)phenyl]oxy}methyl)isoxazole

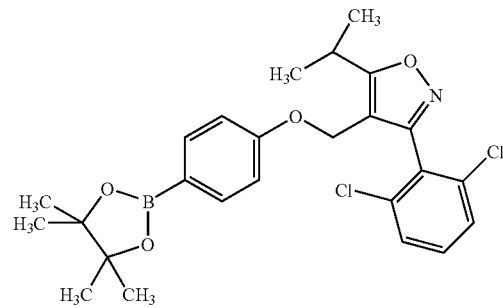

Cesium carbonate (1.96 g, 6.03 mmol) was added to 4-(4,4,5,5-tetramethyl-1,3,2-dioxaborolan-2-yl)-phenol (1.26 g, 5.74 mmol) and 4-(chloromethyl)-3-(2,6-dichlorophenyl)-5-(1-methylethyl)isoxazole (1.75 g, 5.74 mmol) in N,N-dimethylformamide (57 mL) at room temperature. The resulting suspension was heated for sixty-nine hours at 60° C. The reaction was cooled and concentrated to remove the N,N-dimethylformamide, then water was added and the reaction mixture was extracted with diethyl ether. The organic layer was dried over anhydrous magnesium sulfate, then filtered and concentrated. The residue was purified by silica gel chromatography eluting with 1:6 ethyl acetate:hexanes to give 2.24 g (80%) of 3-(2,6-dichlorophenyl)-5-(1-methylethyl)-4-({[4-(4,4,5,5-tetramethyl-1,3,2-dioxaborolan-2-yl)phenyl]oxy}methyl)isoxazole as an solid. $^1$H NMR (400 MHz, d$_6$-DMSO): δ 7.62-7.59 (m, 2H), 7.55-7.48 (m, 3H), 6.76 (d, J=9 Hz, 2H), 4.82 (s, 2H), 3.44 (septet, J=7 Hz, 1H), 1.31 (d, J=7 Hz, 6H), 1.24 (s, 12H). ESI-LCMS m/z 488 (M+H)$^+$.

34e) Ethyl 6-[4-({[3-(2,6-dichlorophenyl)-5-(1-methylethyl)-4-isoxazolyl]methyl}oxy)phenyl]-4-methyl-2-quinolinecarboxylate

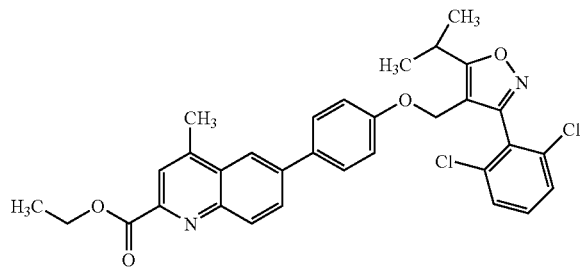

Palladium(II)acetate (1.2 mg, 5.4 μmol) was added to ethyl 6-bromo-4-methyl-2-quinolinecarboxylate (31.5 mg, 107.1 μmol), 3-(2,6-dichlorophenyl)-5-(1-methylethyl)-4-({[4-(4,4,5,5-tetramethyl-1,3,2-dioxaborolan-2-yl)phenyl]oxy}methyl)isoxazole (52.3 mg, 107.1 μmol), triphenylphosphine (2.8 mg, 10.7 μmol), and potassium phosphate (79.6 mg, 374.8 μmol). Then, dioxane (2.1 mL) was added to the mixture, followed by water (10.7 μL), and the reaction mixture was heated open to the atmosphere at 60° C. in an oil bath for 17 hours, then allowed to cool to room temperature. Water was added, followed by ethyl acetate, and the mixture was filtered through Celite®. The filtrate was extracted with ethyl acetate, and the organic layer was dried over anhydrous magnesium sulfate, then filtered and concentrated. The residue was purified by silica gel chromatography eluting with 1:2 ethyl acetate:hexanes to give 32.1 mg (52%) of ethyl 6-[4-({[3-(2,6-dichlorophenyl)-5-(1-methylethyl)-4-isoxazolyl]methyl}oxy)phenyl]-4-methyl-2-quinolinecarboxylate as a solid. $^1$H NMR (400 MHz, d$_6$-DMSO): δ 8.25 (d, J=2 Hz, 1H), 8.17 (d, J=9 Hz, 1H), 8.10 (dd, J=9, 2 Hz, 1H), 7.98 (s, 1H), 7.78 (d, J=9 Hz, 2H), 7.65-7.62 (m, 2H), 7.55 (dd, J=9, 7 Hz, 1H), 6.94 (d, J=9 Hz, 2H), 4.89 (s, 2H), 4.41 (q, J=7 Hz, 2H), 3.48 (septet, J=7 Hz, 1H), 2.82 (s, 3H), 1.38 (t, J=7 Hz, 3H), 1.35 (d, J=7 Hz, 6H). ESI-LCMS m/z 575 (M+H)$^+$.

34f) 6-[4-({[3-(2,6-Dichlorophenyl)-5-(1-methylethyl)-4-isoxazolyl]methyl}oxy)phenyl]-4-methyl-2-quinolinecarboxylic acid

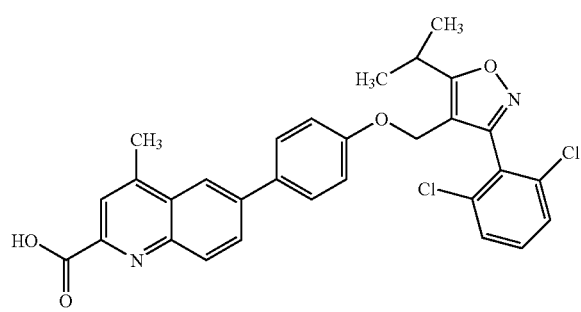

A 1 N solution of sodium hydroxide (93.1 μL, 93.1 μmol) was added to ethyl 6-[4-({[3-(2,6-dichlorophenyl)-5-(1-methylethyl)-4-isoxazolyl]methyl}oxy)phenyl]-4-methyl-2-quinolinecarboxylate (26.8 mg, 46.6 μmol) in tetrahydrofuran and methanol (1:1, 931.4 μL) and the mixture was heated in the microwave at 90° C. for 10 minutes. After cooling, the mixture was neutralized with 1 N hydrochloric acid (93.1 μL), water was added, and the reaction mixture was extracted with ethyl acetate. The organic layer was washed with brine, then dried over anhydrous magnesium sulfate, filtered and concentrated to give 23.1 mg (91%) of 6-[4-({[3-(2,6-dichlorophenyl)-5-(1-methylethyl)-4-isoxazolyl]methyl}oxy)phenyl]-4-methyl-2-quinolinecarboxylic acid as a solid. $^1$H NMR (400 MHz, d$_6$-DMSO): δ 13.29 (br s, 1H), 8.24 (d, J=2 Hz, 1H), 8.16 (d, J=9 Hz, 1H), 8.10 (dd, J=9, 2 Hz, 1H), 7.98 (s, 1H), 7.77 (d, J=9 Hz, 2H), 7.65-7.62 (m, 2H), 7.55 (dd, J=9, 7 Hz, 1H), 6.94 (d, J=9 Hz, 2H), 4.89 (s, 2H), 3.48 (septet, J=7 Hz, 1H), 2.81 (s, 3H), 1.35 (d, J=7 Hz, 6H). HRMS C$_{30}$H$_{24}$Cl$_2$N$_2$O$_4$ m/z 547.1191 (M+H)$^+_{Cal}$; 547.1199 (M+H)$^+_{Obs}$.

Example 35

6-[4-({[3-(2,6-Dichlorophenyl)-5-(1-methylethyl)-4-isoxazolyl]methyl}oxy)phenyl]-2-methyl-3-quinolinecarboxylic acid

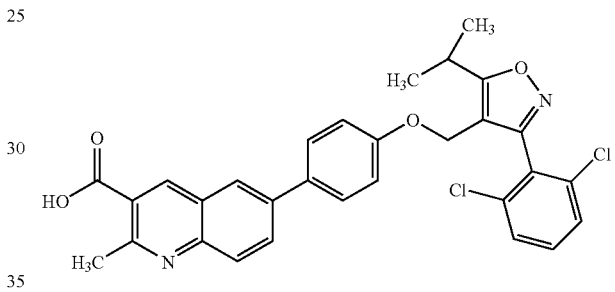

35a) Ethyl 6-bromo-2-methyl-3-quinolinecarboxylate

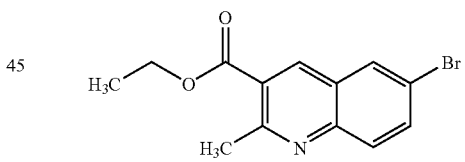

A 2.2 M solution of zinc(II)chloride (9.88 mL, 21.74 mmol) in diethyl ether was added to tin(II)chloride (4.12 g, 21.74 mmol) and activated 4 Å molecular sieve pellets (1.00 g) in ethanol (10 mL) under argon. Then, 5-bromo-2-nitrobenzaldehyde (1.00 g, 4.35 mmol) and ethyl 3-oxobutanoate (594.0 mg, 4.56 mmol) in ethanol (12 mL) were added to the reaction mixture via canula. The mixture was heated at 70° C. in an oil bath for three hours, then allowed to cool to room temperature, and carefully quenched with saturated sodium bicarbonate. Ethyl acetate was added and the mixture was filtered through Celite®. The filtrate was extracted with ethyl acetate and the organic layer was dried over anhydrous magnesium sulfate, then filtered and concentrated. The residue was purified by silica gel chromatography eluting with 1:6 ethyl acetate:hexanes to give 697.9 mg (55%) of ethyl 6-bromo-2-methyl-3-quinolinecarboxylate as a solid. $^1$H NMR (400 MHz, d$_6$-DMSO): δ 8.84 (s, 1H), 8.42 (d, J=2 Hz, 1H), 7.95 (dd, J=9, 2 Hz, 1H), 7.91 (d, J=9 Hz, 1H), 4.38 (q, J=7 Hz, 2H), 2.84 (s, 3H), 1.37 (t, J=7 Hz, 3H). ESI-LCMS m/z 294 (M+H)+.

35b) Ethyl 6-[4-({[3-(2,6-dichlorophenyl)-5-(1-methylethyl)-4-isoxazolyl]methyl}oxy)phenyl]-2-methyl-3-quinolinecarboxylate

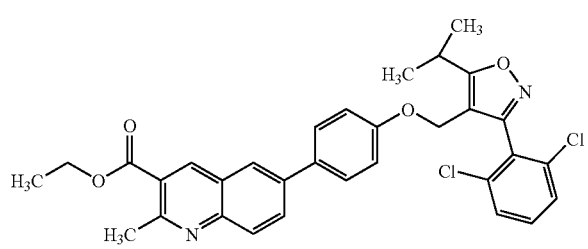

Palladium(II)acetate (1.2 mg, 5.3 µmol) was added to ethyl 6-bromo-2-methyl-3-quinolinecarboxylate (31.0 mg, 105.5 µmol), 3-(2,6-dichlorophenyl)-5-(1-methylethyl)-4-({[4-(4,4,5,5-tetramethyl-1,3,2-dioxaborolan-2-yl)phenyl]oxy}methyl)isoxazole (51.5 mg, 105.5 µmol), triphenylphosphine (2.7 mg, 10.5 µmol), and potassium phosphate (78.3 mg, 369.2 µmol). Then, dioxane (2.1 mL) was added to the mixture, followed by water (10.5 µL), and the reaction mixture was heated open to the atmosphere at 60° C. in an oil bath for 21 hours, then allowed to cool to room temperature. Water was added, followed by ethyl acetate, and the mixture was filtered through Celite®. The filtrate was extracted with ethyl acetate, and the organic layer was dried over anhydrous magnesium sulfate, then filtered and concentrated. The residue was purified by silica gel chromatography eluting with 3:7 ethyl acetate:hexanes to give 31.6 mg (52%) of ethyl 6-[4-({[3-(2,6-dichlorophenyl)-5-(1-methylethyl)-4-isoxazolyl]methyl}oxy)phenyl]-2-methyl-3-quinolinecarboxylate as a solid. $^{1}$H NMR (400 MHz, d$_6$-DMSO): δ 8.87 (s, 1H), 8.32 (d, J=2 Hz, 1H), 8.11 (dd, J=9, 2 Hz, 1H), 7.99 (d, J=9 Hz, 1H), 7.70 (d, J=9 Hz, 2H), 7.66-7.60 (m, 2H), 7.55 (dd, J=9, 7 Hz, 1H), 6.93 (d, J=9 Hz, 2H), 4.88 (s, 2H), 4.38 (q, J=7 Hz, 2H), 3.48 (septet, J=7 Hz, 1H), 2.85 (s, 3H), 1.38 (t, J=7 Hz, 3H), 1.34 (d, J=7 Hz, 6H). ESI-LCMS m/z 575 (M+H)+.

35c) 6-[4-({[3-(2,6-Dichlorophenyl)-5-(1-methylethyl)-4-isoxazolyl]methyl}oxy)phenyl]-2-methyl-3-quinolinecarboxylic acid

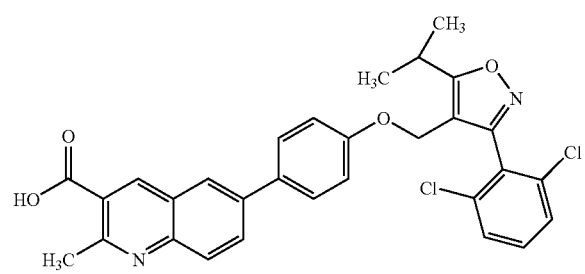

A 1 N solution of sodium hydroxide (92.8 µL, 92.8 µmol) was added to ethyl 6-[4-({[3-(2,6-dichlorophenyl)-5-(1-methylethyl)-4-isoxazolyl]methyl}oxy)phenyl]-2-methyl-3-quinolinecarboxylate (26.7 mg, 46.4 µmol) in tetrahydrofuran and methanol (1:1, 927.9 µL) and the mixture was heated in the microwave at 90° C. for 10 minutes. After cooling, the mixture was neutralized with 1 N hydrochloric acid (92.8 µL), water was added, and the reaction mixture was extracted with ethyl acetate. The organic layer was washed with brine, then dried over anhydrous magnesium sulfate, filtered and concentrated to give 25.1 mg (99%) of 6-[4-({[3-(2,6-dichlorophenyl)-5-(1-methylethyl)-4-isoxazolyl]methyl}oxy)phenyl]-2-methyl-3-quinolinecarboxylic acid as a solid. $^{1}$H NMR (400 MHz, d$_6$-DMSO): δ 13.31 (br s, 1H), 8.86 (s, 1H), 8.29 (d, J=2 Hz, 1H), 8.09 (dd, J=9, 2 Hz, 1H), 7.98 (d, J=9 Hz, 1H), 7.69 (d, J=9 Hz, 2H), 7.66-7.60 (m, 2H), 7.55 (dd, J=9, 7 Hz, 1H), 6.93 (d, J=9 Hz, 2H), 4.88 (s, 2H), 3.47 (septet, J=7 Hz, 1H), 2.86 (s, 3H), 1.34 (d, J=7 Hz, 6H). HRMS C$_{30}$H$_{24}$Cl$_2$N$_2$O$_4$ m/z 547.1191 (M+H)+$_{Cal}$; 547.1191 (M+H)+$_{Obs}$.

Example 36

6-[4-({[3-(2,6-Dichlorophenyl)-5-(1-methylethyl)-4-isoxazolyl]methyl}oxy)phenyl]-1-isoquinolinecarboxylic acid

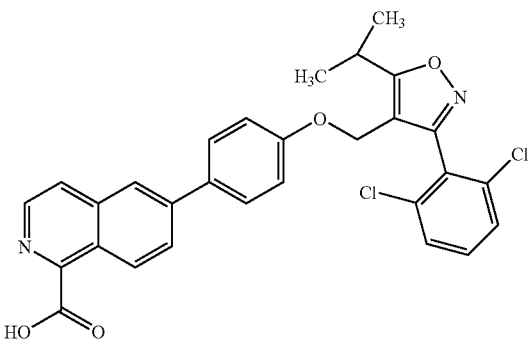

36a) N-[2-(3-Bromophenyl)ethyl]benzenesulfonamide

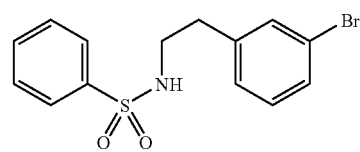

Benzenesulfonyl chloride (1.54 mL, 12.00 mmol) was added to [2-(3-bromophenyl)ethyl]amine (2.00 g, 10.00 mmol) and N,N-di-iso-propylethylamine (5.22 mL, 29.99 mmol) in dichloromethane (33 mL) at 0° C. under argon and the reaction was allowed to warm to room temperature and stirred for 16 hours. The dichloromethane was concentrated under vacuum; diethyl ether was then added, followed by 10% citric acid. The solution was extracted with diethyl ether and the organic layer was washed with saturated sodium bicarbonate, dried over anhydrous magnesium sulfate, then filtered and concentrated. The residue was purified by silica gel chromatography eluting with 1:4 ethyl acetate:hexanes to give 3.22 g (95%) of N-[2-(3-bromophenyl)ethyl]benzenesulfonamide as a solid. $^{1}$H NMR (400 MHz, d$_6$-DMSO): δ 7.77-7.73 (m, 2H), 7.70 (t, J=6 Hz, 1H), 7.62 (d, J=7 Hz, 1H), 7.57 (t, J=8 Hz, 2H), 7.40-7.34 (m, 2H), 7.22 (t, J=8 Hz, 1H), 7.15 (d, J=8 Hz, 1H), 2.96 (q, J=7 Hz, 2H), 2.67 (t, J=7 Hz, 2H). ESI-LCMS m/z 340 (M+H)⁺.

36b) Ethyl chloro(methylthio)acetate

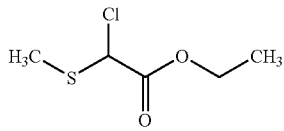

N-Chlorosuccinimide (5.97 g, 44.71 mmol) was added portionwise to ethyl (methylthio)acetate (6.00 g, 44.71 mmol) in carbon tetrachloride (30 mL) at 0° C. under argon and the reaction was allowed to warm to room temperature and stirred for 17 hours. The reaction mixture was filtered and the filtrate was concentrated under vacuum. The oil was purified by distillation to give 3.22 g (43%) of ethyl chloro(methylthio)acetate as an oil. $^1$H NMR (400 MHz, d$_6$-DMSO): δ 6.10 (s, 1H), 4.20 (q, J=7 Hz, 2H), 2.24 (s, 3H), 1.22 (t, J=7 Hz, 3H).

36c) Ethyl 6-bromo-2-(phenylsulfonyl)-1,2,3,4-tetrahydro-1-isoquinolinecarboxylate and Ethyl 8-bromo-2-(phenylsulfonyl)-1,2,3,4-tetrahydro-1-isoquinolinecarboxylate

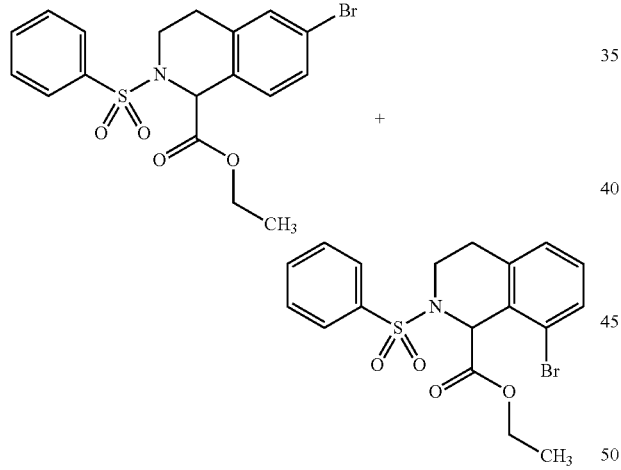

Tin(IV)chloride (6.67 mL of a 1 M solution in dichloromethane, 6.67 mmol) was added to N-[2-(3-bromophenyl)ethyl]benzenesulfonamide (1.08 g, 3.17 mmol) and ethyl chloro(methylthio)acetate (1.07 g, 6.35 mmol) in 1,2-dichloroethane (11 mL) under argon and the reaction was heated at reflux for 3 hours. After cooling, the mixture was poured into ice water and extracted with ethyl acetate. The organic layer was washed with saturated sodium bicarbonate and brine, dried over anhydrous magnesium sulfate, then filtered and concentrated. The residue was purified by silica gel chromatography eluting with 1:4 ethyl acetate:hexanes to give 1.07 g (79%) of ethyl 6-bromo-2-(phenylsulfonyl)-1,2,3,4-tetrahydro-1-isoquinolinecarboxylate and 255.6 mg (19%) of ethyl 8-bromo-2-(phenylsulfonyl)-1,2,3,4-tetrahydro-1-isoquinolinecarboxylate as oils.

Ethyl 6-bromo-2-(phenylsulfonyl)-1,2,3,4-tetrahydro-1-isoquinolinecarboxylate $^1$H NMR (400 MHz, d$_6$-DMSO): δ 7.81 (d, J=8 Hz, 2H), 7.64 (t, J=8 Hz, 1H), 7.55 (t, J=8 Hz, 2H), 7.43-7.37 (m, 2H), 7.33 (d, J=8 Hz, 1H), 5.56 (s, 1H), 4.03-3.86 (m, 2H), 3.74-3.56 (m, 2H), 2.84-2.64 (m, 2H), 1.06 (t, J=7 Hz, 3H). ESI-LCMS m/z 424 (M+H)⁺.

Ethyl 8-bromo-2-(phenylsulfonyl)-1,2,3,4-tetrahydro-1-isoquinolinecarboxylate $^1$H NMR (400 MHz, d$_6$-DMSO): δ 7.76 (d, J=8 Hz, 2H), 7.62 (t, J=8 Hz, 1H), 7.53 (t, J=8 Hz, 2H), 7.48 (d, J=8 Hz, 1H), 7.19-7.12 (m, 2H), 5.73 (s, 1H), 4.06-3.92 (m, 2H), 3.74-3.66 (m, 1H), 3.48-3.40 (m, 1H), 2.80-2.74 (m, 2H), 1.07 (t, J=7 Hz, 3H). ESI-LCMS m/z 424 (M+H)⁺.

36d) Ethyl 6-bromo-1-isoquinolinecarboxylate

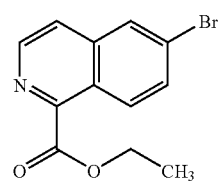

1,8-Diazabicyclo[5.4.0]undec-7-ene (762.3 µL, 5.10 mmol) was added to ethyl 6-bromo-2-(phenylsulfonyl)-1,2,3,4-tetrahydro-1-isoquinolinecarboxylate (1.03 g, 2.43 mmol) in toluene (12 mL) under argon and the reaction was stirred for 18 hours. Water was added and the mixture was extracted with ethyl acetate. The organic layer was washed with saturated sodium bicarbonate, dried over anhydrous magnesium sulfate, then filtered and concentrated. The residue was purified by silica gel chromatography eluting with 1:3 ethyl acetate:hexanes to give 400.6 mg (59%) of ethyl 6-bromo-1-isoquinolinecarboxylate as a solid. $^1$H NMR (400 MHz, d$_6$-DMSO): δ 8.63 (d, J=6 Hz, 1H), 8.43 (d, J=2 Hz, 1H), 8.41 (d, J=10 Hz, 1H), 8.05 (d, J=6 Hz, 1H), 7.91 (dd, J=9, 2 Hz, 1H), 4.46 (q, J=7 Hz, 2H), 1.37 (t, J=7 Hz, 3H). ESI-LCMS m/z 280 (M+H)⁺.

36e) Ethyl 6-[4-({[3-(2,6-dichlorophenyl)-5-(1-methylethyl)-4-isoxazolyl]methyl}oxy)phenyl]-1-isoquinolinecarboxylate

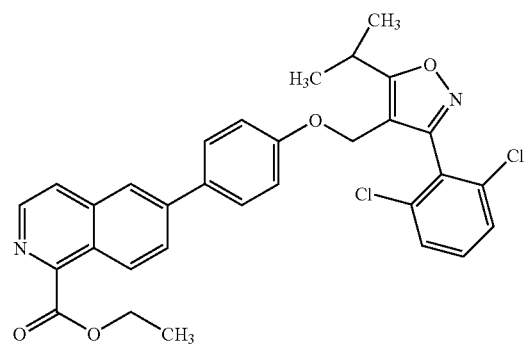

Palladium(II)acetate (2.5 mg, 11.2 μmol) was added to ethyl 6-bromo-1-isoquinolinecarboxylate (62.7 mg, 223.8 μmol), 3-(2,6-dichlorophenyl)-5-(1-methylethyl)-4-({[4-(4,4,5,5-tetramethyl-1,3,2-dioxaborolan-2-yl)phenyl]oxy}methyl)isoxazole (109.3 mg, 223.8 μmol), triphenylphosphine (5.9 mg, 22.4 μmol), and potassium phosphate (166.3 mg, 783.4 μmol). Then, dioxane (2.2 mL) was added to the mixture, followed by water (22.4 μL), and the reaction mixture was heated open to the atmosphere at 60° C. in an oil bath for 67 hours, then allowed to cool to room temperature. Water was added, followed by ethyl acetate, and the mixture was filtered through Celite®. The filtrate was extracted with ethyl acetate, and the organic layer was dried over anhydrous magnesium sulfate, then filtered and concentrated. The residue was purified by silica gel chromatography eluting with 2:3 ethyl acetate:hexanes to give 53.6 mg (43%) of ethyl 6-[4-({[3-(2,6-dichlorophenyl)-5-(1-methylethyl)-4-isoxazolyl]methyl}oxy)phenyl]-1-isoquinolinecarboxylate as an oil. $^1$H NMR (400 MHz, $d_6$-DMSO): δ 8.56 (d, J=5 Hz, 1H), 8.47 (d, J=9 Hz, 1H), 8.30 (s, 1H), 8.08-8.03 (m, 2H), 7.75 (d, J=9 Hz, 2H), 7.65-7.60 (m, 2H), 7.55 (dd, J=9, 7 Hz, 1H), 6.95 (d, J=9 Hz, 2H), 4.90 (s, 2H), 4.47 (q, J=7 Hz, 2H), 3.48 (septet, J=7 Hz, 1H), 1.38 (t, J=7 Hz, 3H), 1.34 (d, J=7 Hz, 6H). ESI-LCMS m/z 560 (M+H)$^+$.

36f) 6-[4-({[3-(2,6-Dichlorophenyl)-5-(1-methylethyl)-4-isoxazolyl]methyl}oxy)phenyl]-1-isoquinolinecarboxylic acid

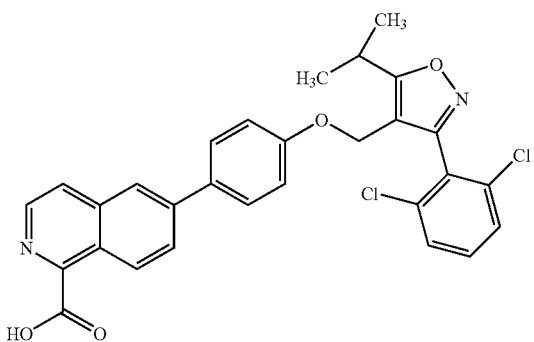

A 1 N solution of sodium hydroxide (156.4 μL, 156.4 μmol) was added to ethyl 6-[4-({[3-(2,6-dichlorophenyl)-5-(1-methylethyl)-4-isoxazolyl]methyl}oxy)phenyl]-1-isoquinolinecarboxylate (43.9 mg, 78.2 μmol) in tetrahydrofuran and methanol (1:1, 1.6 mL) and the mixture was heated in the microwave at 90° C. for 10 minutes. After cooling, the mixture was neutralized with 1 N hydrochloric acid (156.4 μL), water was added, and the reaction mixture was extracted with ethyl acetate. The organic layer was washed with brine, then dried over anhydrous magnesium sulfate, filtered and concentrated to give 19.9 mg (48%) of 6-[4-({[3-(2,6-dichlorophenyl)-5-(1-methylethyl)-4-isoxazolyl]methyl}oxy)phenyl]-1-isoquinolinecarboxylic acid as a solid. $^1$H NMR (400 MHz, $d_6$-DMSO): δ 13.64 (br s, 1H), 8.63 (d, J=9 Hz, 1H), 8.55 (d, J=6 Hz, 1H), 8.29 (s, 1H), 8.06 (m, 2H), 7.75 (d, J=9 Hz, 2H), 7.65-7.61 (m, 2H), 7.55 (dd, J=9, 7 Hz, 1H), 6.95 (d, J=9 Hz, 2H), 4.90 (s, 2H), 3.48 (septet, J=7 Hz, 1H), 1.34 (d, J=7 Hz, 6H). ESI-LCMS m/z 533 (M+H)$^+$.

Example 37

6-[4-({[3-(2,6-Dichlorophenyl)-5-(1-methylethyl)-4-isoxazolyl]methyl}oxy)phenyl]-4-methyl-2-quinazolinecarboxylic acid

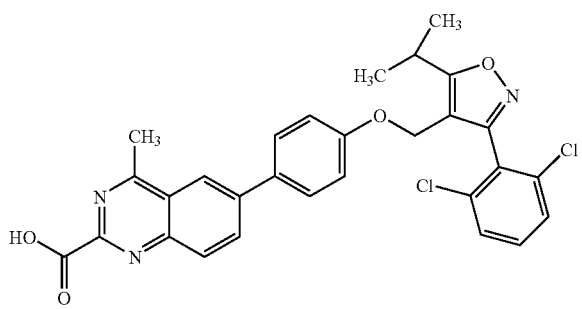

37a) Ethyl[(2-acetyl-4-bromophenyl)amino](oxo)acetate

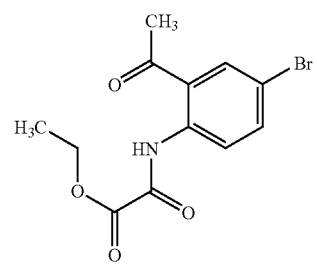

Ethyl chlorooxoacetate (352.7 μL, 3.15 mmol) was added to 1-(2-amino-5-bromophenyl)ethanone (519.8 mg, 2.43 mmol, Example 34c) and pyridine (589.1 μL, 7.28 mmol) in dichloromethane (8 mL) at 0° C. under argon and the reaction was allowed to warm to room temperature and stirred for 17 hours. Water was added, and the solution was extracted with diethyl ether. The organic layer was washed with 10% citric acid, then saturated sodium bicarbonate, dried over anhydrous magnesium sulfate, filtered, and concentrated. The residue was purified by silica gel chromatography eluting with 1:4 ethyl acetate:hexanes to give 648.7 mg (85%) of ethyl[(2-acetyl-4-bromophenyl)amino](oxo)acetate as a solid. $^1$H NMR (400 MHz, $d_6$-DMSO): δ 12.61 (s, 1H), 8.47 (d, J=9 Hz, 1H), 8.26 (d, J=2 Hz, 1H), 7.88 (dd, J=9, 2 Hz, 1H), 4.31 (q, J=7 Hz, 2H), 2.69 (s, 3H), 1.32 (t, J=7 Hz, 3H). ESI-LCMS m/z 314 (M+H)$^+$.

37b) Ethyl 6-bromo-4-methyl-2-quinazolinecarboxylate

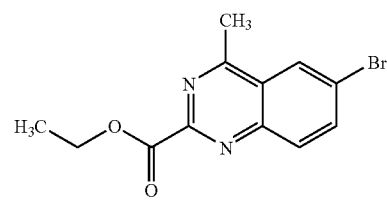

Ammonium acetate (400.0 mg, 5.19 mmol) was added to ethyl[(2-acetyl-4-bromophenyl)amino](oxo)acetate (163.0 mg, 518.9 μmol) in acetic acid (5.2 mL) at room temperature and the reaction was heated at reflux for 19 hours. The reaction mixture was concentrated, then water was added, and the solution was extracted with ethyl acetate. The organic layer was dried over anhydrous magnesium sulfate, filtered, and concentrated. The residue was purified by silica gel chromatography eluting with 2:3 ethyl acetate:hexanes to give 75.5 mg (49%) of ethyl 6-bromo-4-methyl-2-quinazolinecarboxylate as a solid. $^1$H NMR (400 MHz, $d_6$-DMSO): δ 8.63 (d, J=2 Hz, 1H), 8.21 (dd, J=9, 2 Hz, 1H), 8.07 (d, J=9 Hz, 1H), 4.41 (q, J=7 Hz, 2H), 2.97 (s, 3H), 1.35 (t, J=7 Hz, 3H). ESI-LCMS m/z 295 (M+H)$^+$.

37c) Ethyl 6-[4-({[3-(2,6-dichlorophenyl)-5-(1-methylethyl)-4-isoxazolyl]methyl}oxy)phenyl]-4-methyl-2-quinazolinecarboxylate

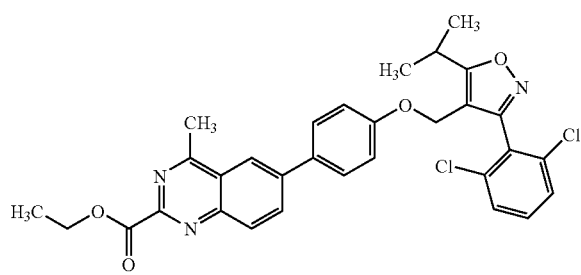

Palladium(II)acetate (2.7 mg, 12.1 μmol) was added to ethyl 6-bromo-4-methyl-2-quinazolinecarboxylate (71.1 mg, 240.9 μmol), 3-(2,6-dichlorophenyl)-5-(1-methylethyl)-4-({[4-(4,4,5,5-tetramethyl-1,3,2-dioxaborolan-2-yl)phenyl]oxy}methyl)isoxazole (176.4 mg, 361.4 μmol), triphenylphosphine (6.3 mg, 24.1 μmol), and potassium phosphate (179.0 mg, 843.2 μmol). Then, dioxane (2.4 mL) was added to the mixture, followed by water (24.1 μL), and the reaction mixture was heated open to the atmosphere at 60° C. in an oil bath for 14 hours, then allowed to cool to room temperature. Water was added, followed by ethyl acetate, and the mixture was filtered through Celite®. The filtrate was extracted with ethyl acetate, and the organic layer was dried over anhydrous magnesium sulfate, then filtered and concentrated. The residue was purified by silica gel chromatography eluting with 1:1 ethyl acetate:hexanes to give 126.2 mg (91%) of ethyl 6-[4-({[3-(2,6-dichlorophenyl)-5-(1-methylethyl)-4-isoxazolyl]methyl}oxy)phenyl]-4-methyl-2-quinazolinecarboxylate as a solid. $^1$H NMR (400 MHz, $d_6$-DMSO): δ 8.44 (d, J=2 Hz, 1H), 8.34 (dd, J=9, 2 Hz, 1H), 8.15 (d, J=9 Hz, 1H), 7.81 (d, J=9 Hz, 2H), 7.65-7.62 (m, 2H), 7.55 (dd, J=9, 7 Hz, 1H), 6.95 (d, J=9 Hz, 2H), 4.90 (s, 2H), 4.41 (q, J=7 Hz, 2H), 3.48 (septet, J=7 Hz, 1H), 3.03 (s, 3H), 1.36 (t, J=7 Hz, 3H), 1.35 (d, J=7 Hz, 6H). ESI-LCMS m/z 576 (M+H)$^+$.

37d) 6-[4-({[3-(2,6-Dichlorophenyl)-5-(1-methylethyl)-4-isoxazolyl]methyl}oxy)phenyl]-4-methyl-2-quinazolinecarboxylic acid

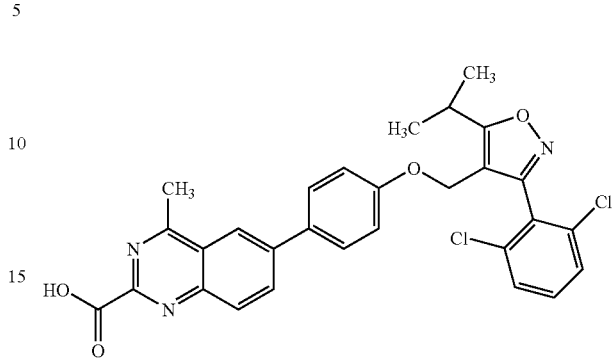

A 1 N solution of sodium hydroxide (384.4 μL, 384.4 μmol) was added to ethyl 6-[4-({[3-(2,6-dichlorophenyl)-5-(1-methylethyl)-4-isoxazolyl]methyl}oxy)phenyl]-4-methyl-2-quinazolinecarboxylate (110.8 mg, 192.2 μmol) in tetrahydrofuran and methanol (1:1, 1.9 mL) and the mixture was heated in the microwave at 90° C. for 10 minutes. After cooling, the mixture was neutralized with 1 N hydrochloric acid (384.4 μL), water added, and the reaction mixture was extracted with ethyl acetate. The organic layer was washed with brine, then dried over anhydrous magnesium sulfate, filtered and concentrated to give 104.0 mg (99%) of 6-[4-({[3-(2,6-dichlorophenyl)-5-(1-methylethyl)-4-isoxazolyl]methyl}oxy)phenyl]-4-methyl-2-quinazolinecarboxylic acid as a solid. $^1$H NMR (400 MHz, $d_6$-DMSO): δ 13.47 (br s, 1H), 8.43 (d, J=2 Hz, 1H), 8.33 (dd, J=9, 2 Hz, 1H), 8.12 (d, J=9 Hz, 1H), 7.81 (d, J=9 Hz, 2H), 7.65-7.62 (m, 2H), 7.55 (dd, J=9, 7 Hz, 1H), 6.95 (d, J=9 Hz, 2H), 4.90 (s, 2H), 3.48 (septet, J=7 Hz, 1H), 3.03 (s, 3H), 1.35 (d, J=7 Hz, 6H). ESI-LCMS m/z 548 (M+H)$^+$.

Example 38

6-[4-({[3-(2,6-Dichlorophenyl)-5-(1-methylethyl)-4-isoxazolyl]methyl}thio)phenyl]-2-quinolinecarboxylic acid

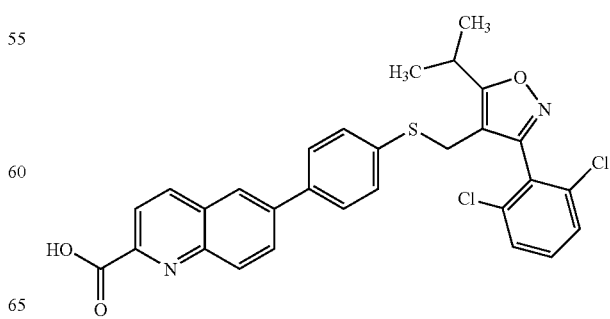

38a) [4-({[3-(2,6-Dichlorophenyl)-5-(1-methyl-ethyl)-4-isoxazolyl]methyl}thio)phenyl]boronic acid

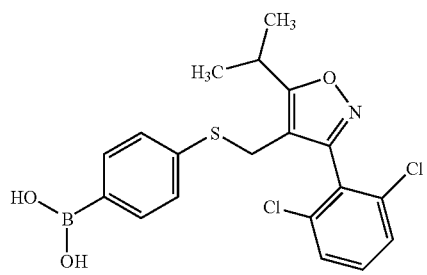

A mixture of 4-(chloromethyl)-3-(2,6-dichlorophenyl)-5-(1-methylethyl)isoxazole (152 mg, 0.5 mmol), cesium carbonate (489 mg, 1.5 mmol) and 4-mercaptophenyl boronic acid (75 mg, 0.5 mmol) in dimethylformamide (5 mL) was allowed to stir for 24 hours in a 60° C. oil bath. The mixture was diluted with ethyl acetate and washed with water. The organic layer was washed with brine, dried with magnesium sulfate, filtered and concentrated to yield 277 mg of crude [4-({[3-(2,6-dichlorophenyl)-5-(1-methylethyl)-4-isoxazolyl]methyl}thio)phenyl]boronic acid and dimethylformamide. $^1$H NMR (400 MHz, $d_6$-DMSO): δ 7.63-7.59 (m, 4H), 7.55-7.51 (m, 1H), 7.17 (d, J=8 Hz, 2H), 3.86 (s, 2H), 3.12 (septet, J=7 Hz, 1H), 1.13 (d, J=7 Hz, 6H).

38b) Ethyl 6-[4-({[3-(2,6-dichlorophenyl)-5-(1-methylethyl)-4-isoxazolyl]methyl}thio)phenyl]-2-quinolinecarboxylate

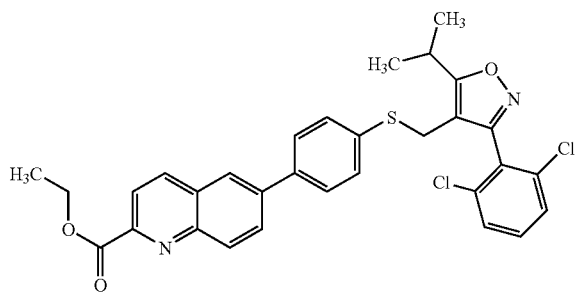

A mixture of crude [4-({[3-(2,6-dichlorophenyl)-5-(1-methylethyl)-4-isoxazolyl]methyl}thio)phenyl]boronic acid (76 mg, 0.18 mmol), ethyl 6-bromo-2-quinolinecarboxylate (42 mg, 0.15 mmol), tetrakis(triphenylphosphine)palladium (0) (7 mg, 0.0006 mmol) in 1,2-dimethoxyethane (0.8 mL), and 2 M sodium carbonate (0.65 mL) was heated in a 70° C. oil bath for 1.5 hours. The solution was partitioned between ethyl acetate and water. The organic layer was washed with brine, dried with magnesium sulfate filtered and concentrated. The residue was purified by silica gel chromatography (hexane to 2:5 ethyl acetate:hexanes gradient elution) to give 20 mg (22% as 0.4 ethyl acetate) of ethyl 6-[4-({[3-(2,6-dichlorophenyl)-5-(1-methylethyl)-4-isoxazolyl]methyl}thio)phenyl]-2-quinolinecarboxylate. $^1$H NMR (400 MHz, CDCl$_3$): δ 8.38-8.32 (m, 2H), 8.21 (d, J=9 Hz, 1H), 7.98 (s, 1H), 7.96 (d, J=2 Hz, 1H), 7.59 (d, J=8 Hz, 2H), 7.43-7.32 (m, 5H), 4.57 (q, J=7 Hz, 2H), 3.82 (s, 2H), 3.07 (septet, J=7 Hz, 1H), 1.50 (t, J=7 Hz, 3H), 1.27 (d, J=7 Hz, 6H).

38c) 6-[4-({[3-(2,6-Dichlorophenyl)-5-(1-methyl-ethyl)-4-isoxazolyl]methyl}thio)phenyl]-2-quinolinecarboxylic acid

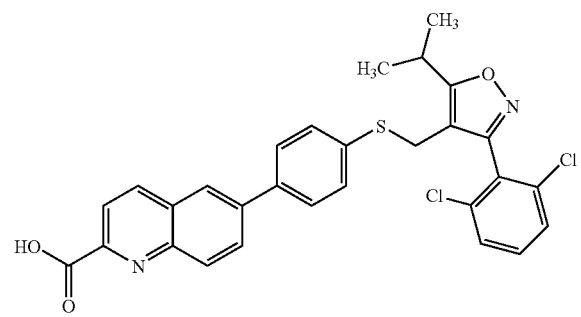

A solution of ethyl 6-[4-({[3-(2,6-dichlorophenyl)-5-(1-methylethyl)-4-isoxazolyl]methyl}thio)phenyl]-2-quinolinecarboxylate (20 mg, 0.033 mmol) in tetrahydrofuran (0.33 mL) was placed in a microwave reaction vial followed by ethanol (0.17 mL) and 1 N sodium hydroxide (0.050 mL). The tube was sealed then heated to 100° C. for ten minutes. The reaction mixture was then concentrated and the residue partitioned between tetrahydrofuran and brine. 1 N hydrochloric acid (0.050 mL) was added. The organic layer was separated and concentrated to yield 17 mg (94%) of 6-[4-({[3-(2,6-dichlorophenyl)-5-(1-methylethyl)-4-isoxazolyl]methyl}thio)phenyl]-2-quinolinecarboxylic acid as an orange solid. $^1$H NMR (400 MHz, $d_6$-DMSO): δ 8.57 (d, J=9 Hz, 1H), 8.35 (s, 1H), 8.20-8.10 (m, 3H), 7.76 (d, J=8 Hz, 2H), 7.63 (d, J=7 Hz, 2H), 7.58-7.7.54 (m, 1H), 7.42 (d, J=8 Hz, 2H), 3.95 (s, 2H), 3.24 (septet, J=7 Hz, 1H), 1.16 (d, J=7 Hz, 6H). HRMS (ESI) $C_{29}H_{22}Cl_2N_2O_3S$ calculated: 549.0806 $[M+H]^+$, found: 549.0813 $[M+H]^+$.

Example 39

6-[4-({[3-(2,6-Dichlorophenyl)-5-(1-methylethyl)-4-isoxazolyl]methyl}oxy)phenyl]-2-quinoxalinecarboxylic acid

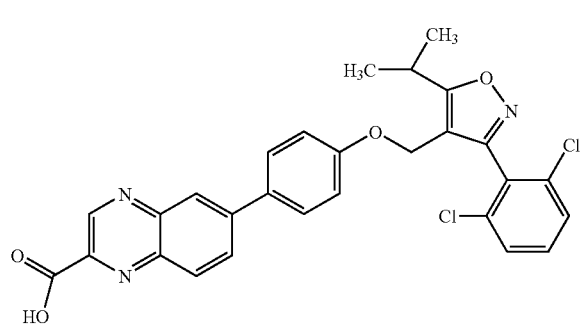

39a) Ethyl 6-bromo-2-quinoxalinecarboxylate

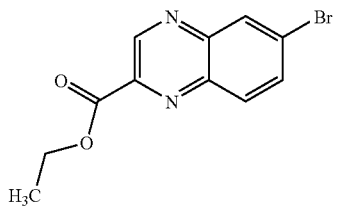

To a stirred solution of 4-bromo-o-phenylenediamine (3.1 g, 16.6 mmol) in 1-methyl-2-pyrrolidinone (150 mL) was added dropwise ethyl bromopyruvate at room temperature under nitrogen. After 20 hours, the reaction mixture was partitioned between water and diethyl ether. The organic phase was separated and the aqueous phase was extracted with diethyl ether twice more. The organic extracts were combined, washed twice with water, dried over magnesium sulfate, filtered, and the filtrate was concentrated to give an oil. The crude product was partially purified by flash chromatography over silica with dichloromethane to give a tan solid. The impure product was purified on a Chiralpak AS-H column with 95% carbon dioxide at 140 bar at 35° C. and 2 mL/min with 5% co-solvent (methanol:chloroform (80:20) to give 0.614 g (13%) of ethyl 6-bromo-2-quinoxalinecarboxylate as a tan solid. $^1$H NMR (CDCl$_3$, 400 MHz): δ 9.52 (s, 1H), 8.37 (d, J=2 Hz, 1H), 8.16 (d, J=9 Hz, 1H), 7.93 (dd, J=9, 2 Hz, 1H), 4.59 (quartet, J=7 Hz, 2H), 1.50 (t, J=7 Hz, 3H). ESI-LCMS m/z 281 (M+H)$^+$.

39b) Ethyl 6-[4-({[3-(2,6-dichlorophenyl)-5-(1-methylethyl)-4-isoxazolyl]methyl}oxy)phenyl]-2-quinoxalinecarboxylate

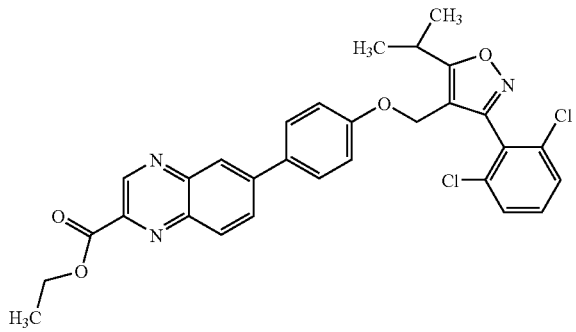

Ethyl 6-bromo-2-quinoxalinecarboxylate (0.108 g, 0.384 mmol), 3-(2,6-dichlorophenyl)-5-(1-methylethyl)-4-({[4-(4,4,5,5-tetramethyl-1,3,2-dioxaborolan-2-yl)phenyl]oxy}methyl)isoxazole (0.27 g, 0.553 mmol), potassium phosphate (0.256 g, 1.21 mmol), palladium(II)acetate (0.0088 g, 0.039 mmol), triphenylphosphine (0.013 g, 0.050 mmol), 1,4-dioxane (8 mL) and water (0.035 mL) were combined and heated at 60° C. with stirring overnight. After 20 hours, the reaction mixture was allowed to stand at room temperature. The reaction mixture was partitioned between water and ethyl acetate. The aqueous phase was separated and extracted a second time with ethyl acetate. The organic extracts were combined, washed with brine, dried over magnesium sulfate, filtered, and the filtrate was concentrated to give an oil. The crude product was purified by flash chromatography over silica with hexanes:ethyl acetate (100:0 to 50:50) to give a yellow solid. The solid was dissolved in dichloromethane and the solution was concentrated to give 0.12 g (56%) of ethyl 6-[4-({[3-(2,6-dichlorophenyl)-5-(1-methylethyl)-4-isoxazolyl]methyl}oxy)phenyl]-2-quinoxalinecarboxylate as a yellow amorphous solid. $^1$H NMR (CDCl$_3$, 400 MHz): δ 9.52 (s, 1H), 8.31 (d, J=9 Hz, 1H), 8.27 (d, J=2 Hz, 1H), 8.06 (dd, J=9, 2 Hz, 1H), 7.65 (d, J=9 Hz, 2H), 7.41 (m, 2H), 7.32 (dd, J=9, 7 Hz, 1H), 6.92 (d, J=9 Hz, 2H), 4.80 (s, 2H), 4.60 (quartet, J=7 Hz, 2H), 3.36 (septet, J=7 Hz, 1H), 1.51 (t, J=7 Hz, 3H), 1.44 (d, J=7 Hz, 6H). ESI-LCMS m/z 562 (M+H)$^+$.

39c) 6-[4-({[3-(2,6-Dichlorophenyl)-5-(1-methylethyl)-4-isoxazolyl]methyl}oxy)phenyl]-2-quinoxalinecarboxylic acid

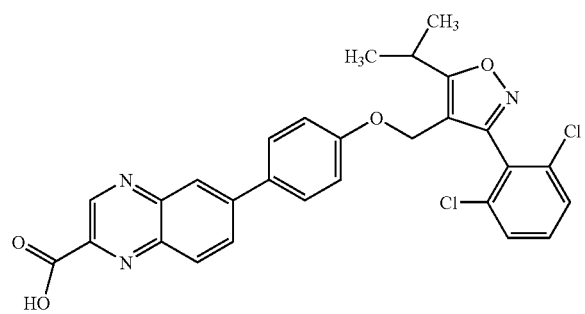

To a stirred solution of ethyl 6-[4-({[3-(2,6-dichlorophenyl)-5-(1-methylethyl)-4-isoxazolyl]methyl}oxy)phenyl]-2-quinoxalinecarboxylate (0.112 g, 0.20 mmol) in ethanol (5 mL) and tetrahydrofuran (5 mL) was added 1 N sodium hydroxide (0.21 mL, 0.21 mmol). The reaction mixture was stirred at room temperature under nitrogen for 3.5 hours. The solvent was removed in vacuo and water (5 mL) was added to the resulting solid. The pH of the aqueous mixture was adjusted to ~3 (litmus paper) with 1 N HCl. The acidic aqueous mixture was extracted with ethyl acetate. The aqueous phase was separated and extracted a second time with ethyl acetate. The aqueous phase was separated and found to contain product according to thin layer chromatography. The pH of the aqueous phase was adjusted to ~2 (litmus paper) with 1 N HCl. The acidic aqueous phase was combined with the aforementioned ethyl acetate extracts. The organic phase was separated, washed with water followed by brine, dried over magnesium sulfate, filtered, and the filtrate was concentrated to give a yellow solid which was dried under high vacuum at room temperature to give 0.095 g (89%) of 6-[4-({[3-(2,6-dichlorophenyl)-5-(1-methylethyl)-4-isoxazolyl]methyl}oxy)phenyl]-2-quinoxalinecarboxylic acid. $^1$H NMR (d$_6$-DMSO, 400 MHz): δ 13.89 (br s, 1H), 9.40 (s, 1H), 8.32 (s, 1H), 8.24 (m, 2H), 7.81 (d, J=9 Hz, 2H), 7.62 (m, 2H), 7.53 (dd, J=9, 7 Hz, 1H), 6.95 (d, J=9 Hz, 2H), 4.89 (s, 2H), 3.47 (septet, J=7 Hz, 1H), 1.33 (d, J=7 Hz, 6H). ESI-LCMS m/z 532 (M−H)$^-$.

Biological Example 40

FXR Cofactor Binding Assay

Determination of a ligand mediated cofactor peptide interaction to quantify ligand binding to the nuclear receptor Farnesoid X Receptor (FXR). The method measures the ability of putative ligands to modulate the interaction between the purified bacterial expressed FXRα ligand binding domain (LBD) and a synthetic biotinylated peptide based on residues 676-700 of steroid receptor coactivator-1 (SRC-1) (LXXLL-containing domain-2 where L is the amino acid leucine and X indicates any other amino acid (LCD2), 676-700). The sequence of the SRC-1 peptide used is as published in Iannone, M. A., et al., 2001 Cytometry 44:326-337 where the N-terminus was biotinylated (B) and the C-terminus was amidated. Detection of the associated complex was measured by time resolved fluorescence (TRF). The purified LBD of FXR was labeled with biotin then mixed with stoichiometric amounts of allophycocyanin (APC) labeled streptavidin (Molecular Probes). The biotinylated peptide was then mixed with a ½ stoichiometric amount of europium labeled streptavidin (Wallac Inc). Each was then blocked with a 5 fold excess of biotin and allowed to equilibrate for 15 min. Equimolar amounts of receptor and peptide were mixed together and were allowed to equilibrate for at least 30 min prior to the addition to either a variable or constant concentrations of the sample for which the affinity is to be determined. After equilibration, the time-resolved fluorescent signal was quantitated using a fluorescent plate reader. The affinity of the test compound was estimated from a plot of fluorescence versus concentration of test compound added.

A basal level of FXR: peptide formation is observed in the absence of added ligand. Ligands that promote the complex formation induce a concentration-dependent increase in time-resolved fluorescent signal. Compounds which bind equally well to both monomeric FXR and to the FXR: peptide complex would be expected to give no change in signal, whereas ligands which bind preferentially to the monomeric receptor would be expected to induce a concentration-dependent decrease in the observed signal.

Methods & Materials

Advance Preparation: Human Farnesoid X Receptor α Ligand Binding Domain

Human FXRα Ligand Binding Domain (FXRα LBD) was expressed in *E. coli* strain BL21 (DE3) as an amino-terminal polyhistidine tagged fusion protein. Expression was under the control of an isopropyl-β-D-thiogalactopyranoside (IPTG) inducible T7 promoter. DNA encoding this recombinant protein is subcloned into the pRSET-A expression vector (Invitrogen). The coding sequence of Human FXRα LBD was derived from Genbank accession number U 68233 (amino acids 237 to 472).

Ten-liter fermentation batches were grown in Rich $PO_4$ media with 0.1 mg/mL Ampicillin at 25° C. for 12 hours, cooled to 9° C. and held at that temperature for 36 hours to a density of $OD_{600}$=14. At this cell density, 0.25 mM IPTG is added and induction proceeded for 24 hours at 9° C., to a final $OD_{600}$=16. Cells are harvested by centrifugation (20 minutes, 3500× gravity, 4° C.), and concentrated cell slurries were stored in phosphate buffered saline (PBS) at −8° C.

Purification of Receptor Ligand Binding Domain

Routinely, 30-40 g cell paste (equivalent to 2-3 liters of the fermentation batch) was resuspended in 200-250 mL Tris buffered saline (TBS), pH 7.2 (25 mM Tris-hydroxymethylamino methane (Tris), 150 mM sodium chloride). Cells were lysed by passing 3 times through a French Press and cell debris was removed by centrifugation (30 minutes, 20,000× gravity, 4° C.). The cleared supernatant was filtered through course pre-filters, and TBS, pH 7.2, 500 mM imidazole was added to obtain a final imidazole concentration of 50 mM. This lysate was loaded onto a column (6×8 cm) packed with Sepharose [$Ni^{++}$ charged] Chelation resin (Pharmacia) and pre-equilibrated with TBS pH 7.2/50 mM imidazole. After washing to baseline absorbance with equilibration buffer, the column was washed with one column volume of TBS pH 7.2 containing 90 mM imidazole. FXRα LBD was eluted directly with 365 mM imidazole. Column fractions were pooled and dialyzed against TBS, pH 7.2, containing 0.5 mM EDTA and 5 mM DTT. The dialyzed protein sample was concentrated using Centri-prep 10 K (Amicon) and subjected to size exclusion, using a column (3×90 cm) packed with Sepharose S-75 resin (Pharmacia) pre-equilibrated with TBS, pH 7.2, containing 0.5 mM ethylene diamine tetraacetic acid (EDTA) and 5 mM dithiothreitol (DTT).

Biotinylation of FXR

Purified FXRα LBD was desalted/buffer exchanged using PD-10 gel filtration columns into PBS [100 mM $Na_2PO_4$, pH 7.2, 150 mM NaCl]. FXRα LBD was diluted to approximately 60 μM in PBS and five-fold molar excess of NHS-LC-Biotin (Pierce) is added in a minimal volume of PBS. This solution was incubated with gentle mixing for 30 minutes at room temperature. The biotinylation modification reaction was stopped by the addition of 2000× molar excess of Tris-HCl, pH 8. The modified FXRα LBD was dialyzed against 4 buffer changes, each of at least 50 volumes, PBS containing 5 mM DTT, 2 mM EDTA and 2% sucrose. The biotinylated FXRα LBD was then subjected to mass spectrometric analysis to reveal the extent of modification by the biotinylation reagent. In general, approximately 95% of the protein had at least a single site of biotinylation; and the overall extent of biotinylation followed a normal distribution of multiple sites, ranging from zero to four.

Preparation of Streptavidin-(Europium Chelate)-SRC1: Streptavdin-(APC)-FXR Complex Biotinylated SRC-1 (LCD2, 676-700) peptide and a ½ stoichiometric amount of streptavidin-conjugated europium chelate was incubated in assay buffer containing 10 mM DTT for at least 30 minutes. A second solution of stoichiometric amounts of biotinylated FXR and streptavidin-conjugated APC was incubated in assay buffer containing 10 mM DTT for at least 30 minutes. Each solution was then blocked with a 5 fold molar excess of biotin and allowed to equilibrate for at least 30 min. The labeled receptor and cofactor were mixed and again allowed to equilibrate for at least 30 min, added to the compound plate, utilizing e.g., a Titertek Multidrop 384.

Materials:
Assay Buffer: 50 mM 3-(N-morpholino)propanesulfonic acid (MOPS) pH 7.5, 50 mM NaF, 50 μM 3-[(3-cholamidopropyl)-demethylammonio]-1-propanesulfonate (CHAPS), 0.1 mg/ml Fraction 5 fatty acid free bovine serum albumin (BSA), 1 mM ethylenediaminetetraacetic acid (EDTA). Solid DTT is added to the assay buffer to a final concentration of 10 mM just before use in the assay.BSA, fatty acid free
DTT
NaF
Europium labeled Streptavidin: (Wallac CR28-100)
384 well Plates Methods:
Experimental Details:
Test compounds and controls were serial diluted in DMSO and 0.1 μL at the desired concentration were added to a 384 well plate.

To each well to be assayed a previously prepared solution of FXR-APC and Europium labeled SRC1 was added to 0.1 μL of test compound and controls for a final assay volume of 10 μL.

The plates were incubated for at least 1 hour at room temperature and the fluorescent signal determined in a Fluorescence Reader in a time resolved mode utilizing e.g., a Wallac Viewlux Imager or Wallac Victor Multilabel counter.

Data Reduction:

For each concentration of test compound, the results of each test well was expressed as % of control, C, calculated according to eq. 1.

$$C = 100 * \frac{F_{sample} - F_{basal}}{F_{std} - F_{basal}} \quad (1)$$

where $F_{sample}$ is the signal observed in a particular sample well, $F_{total}$ is the signal observed in the presence of control inhibitor and $F_{basal}$ is the count rate observed in the presence of no ligand. The values used for $F_{std}$ and $F_{basal}$ are averages of the corresponding control wells included on every plate. The results are reported in Table 1 below. In Table 1, + indicates a $pEC_{50}$ of 5-5.99; ++ indicates a $pEC_{50}$ 6-6.99 and +++ indicates a $pEC_{50}$ greater than 7.

TABLE 1

| Example | Activity ($pEC_{50}$) |
|---|---|
| 1g | ++ |
| 1h | ++ |
| 1i | ++ |
| 2 | ++ |
| 3 | ++ |
| 4 | ++ |
| 5 | ++ |
| 6 | ++ |
| 7 | ++ |
| 8 | ++ |
| 9 | ++ |
| 10 | ++ |
| 11 | ++ |
| 12 | ++ |
| 13 | ++ |
| 14 | ++ |
| 15 | ++ |
| 16 | ++ |
| 17 | ++ |
| 18 | ++ |
| 19 | ++ |
| 20 | ++ |
| 21 | ++ |
| 22 | ++ |
| 23 | ++ |
| 24 | + |
| 25 | ++ |
| 26 | ++ |
| 27 | + |
| 28 | ++ |
| 29 | ++ |
| 30 | ++ |
| 31 | ++ |
| 32 | ++ |
| 33 | ++ |
| 34 | +++ |
| 35 | ++ |
| 36 | ++ |
| 37 | ++ |

TABLE 1-continued

| Example | Activity ($pEC_{50}$) |
|---|---|
| 38 | ++ |
| 39 | ++ |

Example 41

The Effects of FXR Agonists on Diet Induced Obese Mice

Methods: Male 20 to 25 g C57BL mice (Charles River, Indianapolis, Ind.) were housed at 72° F. and 50% relative humidity with a 12 h light and dark cycle and fed with standard rodent chow (Purina 5001, Harlan Teklad, Indianapolis, Ind.) or a high-fat diet (TD93075, Harlan Teklad, Indianapolis, Ind.) for eight weeks. After three weeks, mice on high-fat diet were randomized to vehicle or treatment groups based on fasting glucose and body weight. Starting from the fifth week, mice were given either vehicle or the compound in Example 1 (10, 30 and 100 mg/kg) or the compound in Example 5 (10, 30, 100 mg/kg) twice a day orally. Mice on the standard rodent chow were also given vehicle as a control. Body composition was measured using the quantitative magnetic resonance (QMR) method before and at the end of compound treatment. At the end of the study (fourth week of compound treatment), blood samples were taken from inferior vena cava and tissue samples were collected for further analysis. Serum chemistry levels were measured using the Instrumentation Laboratory Ilab600™ clinical chemistry analyzer (Instrumentation Laboratory, Boston, Mass.).

Results: The compound in Example 1 and the compound in Example 5 decreased body fat mass, serum glucose, insulin, cholesterol, triglyceride, NEFA, and glycerol in high-fat diet fed obese mice.

That which is claimed is:

1. 6-[4-({[3-(2,6-Dichlorophenyl)-5-(1-methylethyl)-4-isoxazolyl]methyl}oxy)phenyl]-2-quinolinecarboxylic acid or a pharmaceutically acceptable salt thereof.

2. 6-[4-({[3-(2,6-Dichlorophenyl)-5-(1-methylethyl)-4-isoxazolyl]methyl}oxy)phenyl]-2-quinolinecarboxylic acid.

3. 6-[4-({[3-(2,6-Dichlorophenyl)-5-(1-methylethyl)-4-isoxazolyl]methyl}oxy)phenyl]-2-quinolinecarboxylic acid potassium salt.

4. A pharmaceutical composition comprising 6-[4-({[3-(2,6-dichlorophenyl)-5-(1-methylethyl)-4-isoxazolyl]methyl}oxy)phenyl]-2-quinolinecarboxylic acid or a pharmaceutically acceptable salt thereof and a pharmaceutically acceptable carrier or diluent.

5. A pharmaceutical composition of claim 4 which comprises 6-[4-({[3-(2,6-dichlorophenyl)-5-(1-methylethyl)-4-isoxazolyl]methyl}oxy)phenyl]-2-quinolinecarboxylic acid.

6. A pharmaceutical composition of claim 4 which comprises 6-[4-({[3-(2,6-dichlorophenyl)-5-(1-methylethyl)-4-isoxazolyl]methyl}oxy)phenyl]-2-quinolinecarboxylic acid potassium salt.

* * * * *